United States Patent
Ma et al.

(10) Patent No.: US 11,631,820 B2
(45) Date of Patent: Apr. 18, 2023

(54) ORGANIC COMPOUND, ELECTRONIC COMPONENT, AND ELECTRONIC DEVICE

(71) Applicant: SHAANXI LIGHTE OPTOELECTRONICS MATERIAL CO., LTD., Xi'an (CN)

(72) Inventors: Tiantian Ma, Xi'an (CN); Lei Yang, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 124 days.

(21) Appl. No.: 17/624,192

(22) PCT Filed: Sep. 28, 2020

(86) PCT No.: PCT/CN2020/118497
§ 371 (c)(1),
(2) Date: Dec. 30, 2021

(87) PCT Pub. No.: WO2021/135456
PCT Pub. Date: Jul. 8, 2021

(65) Prior Publication Data
US 2022/0223800 A1 Jul. 14, 2022

(30) Foreign Application Priority Data

Dec. 31, 2019 (CN) .......... 201911417529.2
Aug. 12, 2020 (CN) .......... 202010807416.X

(51) Int. Cl.
*H01L 51/00* (2006.01)
*C07D 209/94* (2006.01)
(Continued)

(52) U.S. Cl.
CPC ........ *H01L 51/0072* (2013.01); *C07D 209/94* (2013.01); *C07D 401/14* (2013.01);
(Continued)

(58) Field of Classification Search
CPC ............. H01L 51/0072; H01L 51/0052; H01L 51/0067; H01L 51/0071; H01L 51/0073;
(Continued)

(56) References Cited

U.S. PATENT DOCUMENTS

| | | |
|---|---|---|
| 10,985,324 B2 | 4/2021 | Ma et al. |
| 2014/0364625 A1 | 12/2014 | Ahn et al. |
| 2015/0115205 A1 | 4/2015 | Kang et al. |

FOREIGN PATENT DOCUMENTS

| | | |
|---|---|---|
| CN | 103703003 A | 4/2014 |
| CN | 104136440 A | 11/2014 |

(Continued)

OTHER PUBLICATIONS

The World Intellectual Property Organization (WIPO) International Search Report for PCT /CN2020/118497 dated Dec. 31, 2020 6 Pages (with translation).

(Continued)

*Primary Examiner* — Shane Fang
(74) *Attorney, Agent, or Firm* — Anova Law Group, PLLC

(57) ABSTRACT

An organic compound represently by Chemical formula 1 and Chemical formula 2, an electronic component, and an electronic device. The two * in Chemical formula 2 are attached to any two adjacent * of the four * in Chemical formula 1 to form a fused ring. The organic compound can (Continued)

improve the electron transport performance of the electronic component.

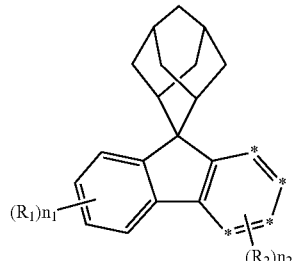

Chemical formula 1

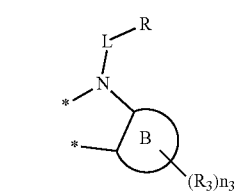

Chemical formula 2

13 Claims, 2 Drawing Sheets

(51) Int. Cl.
| | |
|---|---|
| *C07D 401/14* | (2006.01) |
| *C07D 403/04* | (2006.01) |
| *C07D 403/10* | (2006.01) |
| *C07D 405/10* | (2006.01) |
| *C07D 495/04* | (2006.01) |
| *C09K 11/06* | (2006.01) |
| *H01L 51/50* | (2006.01) |

(52) U.S. Cl.
CPC ......... *C07D 403/04* (2013.01); *C07D 403/10* (2013.01); *C07D 405/10* (2013.01); *C07D 495/04* (2013.01); *C09K 11/06* (2013.01); *H01L 51/0052* (2013.01); *H01L 51/0067* (2013.01); *H01L 51/0071* (2013.01); *H01L 51/0073* (2013.01); *C09K 2211/1018* (2013.01); *H01L 51/5012* (2013.01)

(58) Field of Classification Search
CPC . H01L 51/5012; C07D 209/94; C07D 401/14; C07D 403/04; C07D 403/10; C07D 405/10; C07D 495/04; C09K 11/06; C09K 2211/1018
See application file for complete search history.

(56) References Cited

FOREIGN PATENT DOCUMENTS

| | | |
|---|---|---|
| CN | 104271582 A | 1/2015 |
| CN | 107459466 A | 12/2017 |
| CN | 110128279 A | 8/2019 |
| CN | 110467536 A | 11/2019 |
| WO | 2011136520 A1 | 11/2011 |
| WO | 2013109045 A1 | 7/2013 |
| WO | 2013122402 A1 | 8/2013 |
| WO | WO 2020080872 * 10/2018 ............. C07F 5/027 |

OTHER PUBLICATIONS

China National Intellectual Property Administration Notification of the first Office Action for CN 202010807416.X dated Jun. 11, 2021 14 pages (with translation).

* cited by examiner

ORGANIC COMPOUND, ELECTRONIC COMPONENT, AND ELECTRONIC DEVICE

CROSS REFERENCE TO RELATED APPLICATIONS

The present application is a national phase entry under 35 U.S.C. § 371 of International Application No. PCT/CN2020/118497, filed on Sep. 28, 2020, which claims priority to and benefits of Chinese Patent Application CN201911417529.2 filed on Dec. 31, 2019 and entitled "ORGANIC COMPOUND, ELECTRONIC COMPONENT, AND ELECTRONIC DEVICE" and Chinese Patent Application CN202010807416.X filed on Aug. 12, 2020 and entitled "ORGANIC COMPOUND, ELECTRONIC COMPONENT, AND ELECTRONIC DEVICE". The content of all of the above patent applications is incorporated herein by reference in their entirety as part of the present application.

TECHNICAL FIELD

The present application relates to the technical field of organic materials, and in particular to an organic compound, an electronic component, and an electronic device.

BACKGROUND

Organic electroluminescent devices (OELDs), as a new generation of display technology, have the advantages of ultra-low thickness, self-luminescence, wide viewing angle, fast response, high luminous efficiency, prominent temperature adaptability, simple production process, low driving voltage, low energy consumption, and the like. OELDs have been widely used in industries such as flat panel display, flexible display, solid-state lighting, automotive display, and the like.

Organic electroluminescent device generally includes an anode, a cathode, and an organic material layer arranged between the two. The organic material layer usually has a multi-layer structure composed of different materials, which can improve the luminance, efficiency, and life span of the organic electroluminescent device. The organic material layer may be composed of a hole injection layer (HIL), a hole transport layer (HTL), a light-emitting layer (EML), an electron transport layer (ETL), an electron injection layer (EIL), and the like. In a structure of an organic electroluminescent device, when a voltage is applied between two electrodes, holes and electrons are injected into an organic material layer from an anode and a cathode respectively, injected holes and injected electrons combine to form excitons, and light emission is achieved when these excitons return to a ground state.

For existing organic electroluminescent device, the main issues are the life span and efficiency. As a display area increases, the driving voltage increases, and the demands for luminous efficiency and power efficiency are also increasing. Therefore, it is necessary to continue to develop new materials to further improve the performance of the organic electroluminescent device.

The information disclosed in the background art is merely intended to facilitate the comprehension to the background of the present disclosure, and thus may include information that does not constitute the prior art known to those ordinary skilled in the art.

SUMMARY

The present disclosure is intended to provide an organic compound, an electronic component, and an electronic device to improve the performance of organic electroluminescent device.

To achieve the objective of the present disclosure, the present disclosure adopts the following technical solutions:

A first aspect of the present disclosure provides an organic compound having structures shown in Chemical formula 1 and Chemical formula 2:

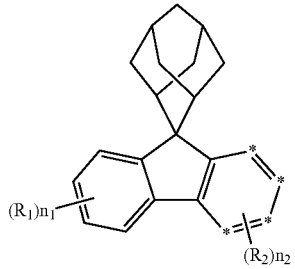

Chemical formula 1

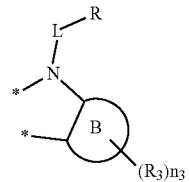

Chemical formula 2

Chemical formula 1 Chemical formula 2 wherein the two * in Chemical formula 2 are attached to any two adjacent * of the four * in Chemical formula 1 to form a fused ring;

Ring B is a benzene ring or a fused aromatic ring with 10 to 14 carbon atoms forming ring;

L is selected from a single bond, a substituted or unsubstituted alkylene with 1 to 20 carbon atoms, a substituted or unsubstituted arylene with 6 to 30 carbon atoms, a substituted or unsubstituted heteroarylene with 3 to 30 carbon atoms, or a substituted or unsubstituted cycloalkylene with 3 to 20 carbon atoms;

R is selected from a substituted or unsubstituted alkyl with 1 to 20 carbon atoms, a substituted or unsubstituted aryl with 6 to 30 carbon atoms, a substituted or unsubstituted heteroaryl with 3 to 30 carbon atoms, or a substituted or unsubstituted cycloalkyl with 3 to 20 carbon atoms;

$R_1$, $R_2$, and $R_3$ are the same or different, and are respectively independently selected from hydrogen, deuterium, a cyano, a halogen, a substituted or unsubstituted alkyl with 1 to 20 carbon atoms, a substituted or unsubstituted aryl with 6 to 30 carbon atoms, a substituted or unsubstituted heteroaryl with 3 to 30 carbon atoms, or a substituted or unsubstituted cycloalkyl with 3 to 20 carbon atoms;

$n_t$ is the number of substituents $R_t$, where t is any integer from 1 to 3; when t is 1, $n_t$ is selected from 1, 2, 3, or 4; when t is 2, $n_t$ is selected from 1 or 2; when t is 3, $n_t$ is selected from 1, 2, 3, 4, 5, 6, 7, or 8; and when $n_t$ is greater than 1, any two substituents $R_t$ are the same or different.

A second aspect of the present disclosure provides an electronic component, comprising an anode and a cathode arranged oppositely, and a functional layer arranged between the anode and the cathode, where the functional layer includes the organic compound described above.

A third aspect of the present disclosure provides an electronic device, comprising the electronic component described above.

BRIEF DESCRIPTION OF THE DRAWINGS

The above and other features and advantages of the present disclosure will become more apparent by describing exemplary embodiments thereof in detail with reference to the accompanying drawings.

REFERENCE NUMERALS OF MAIN ELEMENTS IN THE FIGURES

Figure 1:
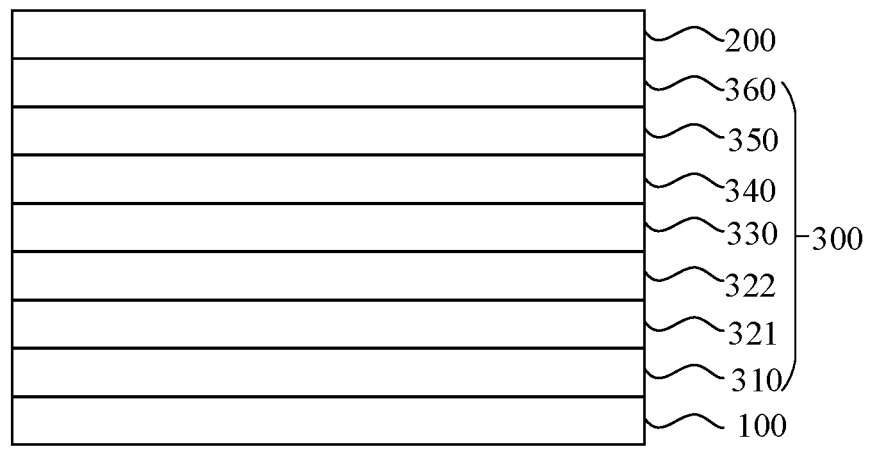
FIG. 1 is a schematic structure diagram of an organic electroluminescent device according to an embodiment of the present disclosure.
Figure 2:
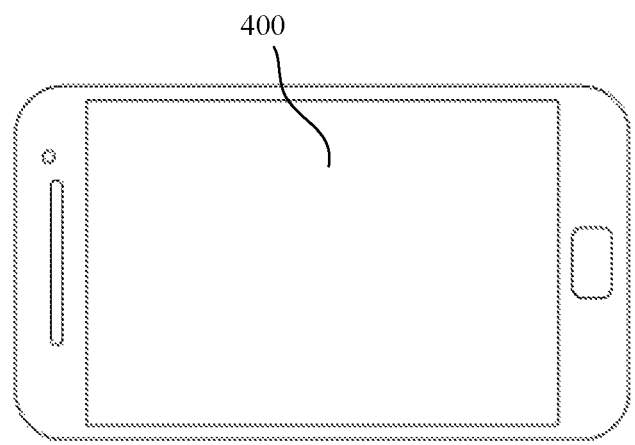
FIG. 2 is a schematic structure diagram of an electronic device according to an embodiment of the present disclosure.

Anode 100; Hole injection layer 310; Hole transport layer 321; Electron blocking layer 322; Organic electroluminescent layer 330; Hole blocking layer 340; Electron transport layer 350; Electron injection layer 360; Cathode 200; Electronic device 400.

DETAILED DESCRIPTION

Exemplary embodiments will be described below comprehensively with reference to the accompanying drawings. However, the exemplary embodiments can be implemented in various forms and should not be construed as being limited to examples described herein. On the contrary, these embodiments are provided such that the present disclosure is comprehensive and complete and the concept of the exemplary embodiments is fully conveyed to those skilled in the art. The described features, structures, or characteristics may be incorporated into one or more embodiments in any suitable manner. In the following description, many specific details are provided to give a full understanding of the embodiments of the present disclosure.

In the figures, the thickness of regions and layers may be exaggerated for clarity. The same reference numerals in the figures indicate the same or similar structures, and thus their detailed descriptions will be omitted.

An embodiment of the present disclosure provides an organic compound having structures shown in Chemical formula 1 and Chemical formula 2:

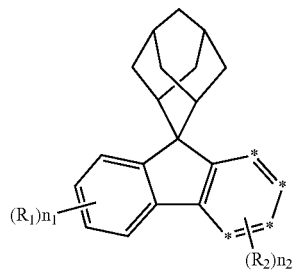

Chemical formula 1

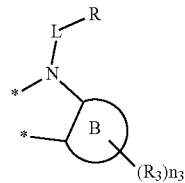

Chemical formula 2 wherein the two * in Chemical formula 2 are attached to any two adjacent * of the four * in Chemical formula 1 to form a fused ring;

Ring B is a benzene ring or a fused aromatic ring with 10 to 14 carbon atoms forming ring;

L is selected from a single bond, a substituted or unsubstituted alkylene with 1 to 20 carbon atoms, a substituted or unsubstituted arylene with 6 to 30 carbon atoms, a substituted or unsubstituted heteroarylene with 3 to 30 carbon atoms, or a substituted or unsubstituted cycloalkylene with 3 to 20 carbon atoms;

R is selected from a substituted or unsubstituted alkyl with 1 to 20 carbon atoms, a substituted or unsubstituted aryl with 6 to 30 carbon atoms, a substituted or unsubstituted heteroaryl with 3 to 30 carbon atoms, or a substituted or unsubstituted cycloalkyl with 3 to 20 carbon atoms;

$R_1$, $R_2$, and $R_3$ are the same or different, and are respectively independently selected from hydrogen, deuterium, a cyano, a halogen, a substituted or unsubstituted alkyl with 1 to 20 carbon atoms, a substituted or unsubstituted aryl with 6 to 30 carbon atoms, a substituted or unsubstituted heteroaryl with 3 to 30 carbon atoms, or a substituted or unsubstituted cycloalkyl with 3 to 20 carbon atoms;

$n_t$ is the number of substituents $R_t$, where t is any integer from 1 to 3; when t is 1, $n_t$ is selected from 1, 2, 3, or 4; when t is 2, $n_t$ is selected from 1 or 2; when t is 3, $n_t$ is selected from 1, 2, 3, 4, 5, 6, 7, or 8; and when $n_t$ is greater than 1, any two substituents $R_t$ are the same or different.

In the present disclosure, if it is not specifically indicated that a group is substituted, the group is unsubstituted.

In the present disclosure, the used description manners such as "each . . . is independently", " . . . are respectively independently" and " . . . are independently selected from" can be used interchangeably, and should be understood in a broad sense, which can mean that, in different groups, specific options expressed by the same symbols do not affect each other; or in the same group, specific options expressed by the same symbols do not affect each other. For example,
"

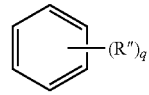

formula Q-1

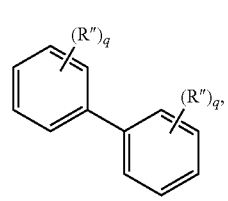

formula Q-2 where q is independently 0, 1, 2, or 3 and each R'' are independently selected from hydrogen, deuterium, fluorine, or chlorine", which means that, in formula Q-1, there are q substituents R" on the benzene ring, each R" can be the same or different, and options for each R" do not affect each other; and in formula Q-2, there are q substituents R" on each benzene ring of the biphenyl, the numbers q of substituents R" on the two benzene rings can be the same or different, each R" can be the same or different, and options for each R" do not affect each other.

In the present disclosure, the term "substituted or unsubstituted" means that a functional group described after the term may have or may not have a substituent (hereinafter, for ease of description, substituents are collectively referred to as Rc). For example, the "substituted or unsubstituted aryl" refers to Rc-substituted aryl or unsubstituted aryl. Where the above-mentioned substituent Rc can be selected from deuterium, a halogen, a cyano, a heteroaryl with 3 to 20 carbon atoms, an aryl with 6 to 20 carbon atoms, a trialkylsilyl with 3 to 12 carbon atoms, a triarylsilyl with 18 to 30 carbon atoms, an alkyl with 1 to 10 carbon atoms, a haloalkyl with 1 to 10 carbon atoms, an alkenyl with 2 to 6 carbon atoms, an alkynyl with 2 to 6 carbon atoms, a cycloalkyl with 3 to 10 carbon atoms, a heterocycloalkyl with 2 to 10 carbon atoms, a cycloalkenyl with 5 to 10 carbon atoms, a heterocycloalkenyl with 4 to 10 carbon atoms, an alkoxy with 1 to 10 carbon atoms, an alkylthio with 1 to 10 carbon atoms, an aryloxy with 6 to 18 carbon atoms, an arylthio with 6 to 18 carbon atoms, a phosphinoxy with 6 to 18 carbon atoms, an alkylsulfonyl with 6 to 18 carbon atoms, a trialkylphosphino with 3 to 18 carbon atoms, or a trialkylboron with 3 to 18 carbon atoms.

The connection of Chemical formula 2 to Chemical formula 1 at different positions can form different structures. Specifically, the organic compound of the present disclosure may be any one of Chemical formula A, Chemical formula B, Chemical formula C, Chemical formula D, Chemical formula E, and Chemical formula F:

A

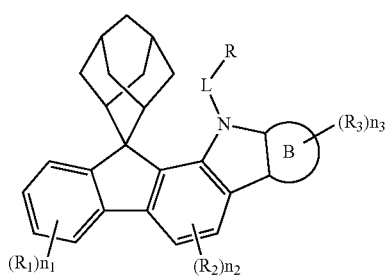

B

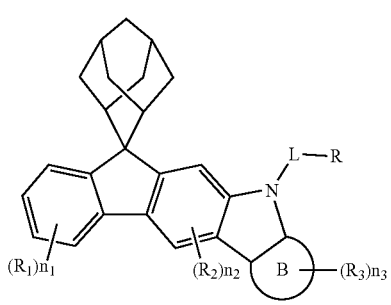

C

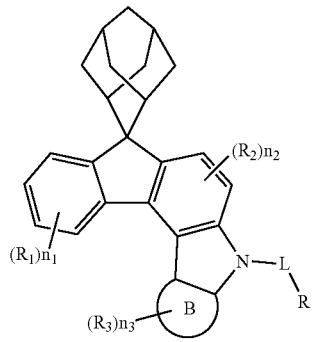

D

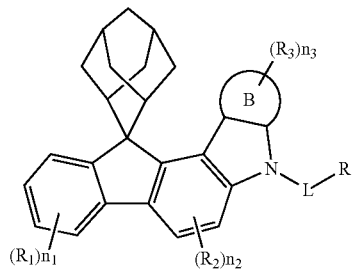

E

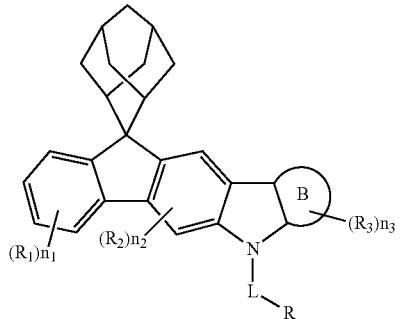

F

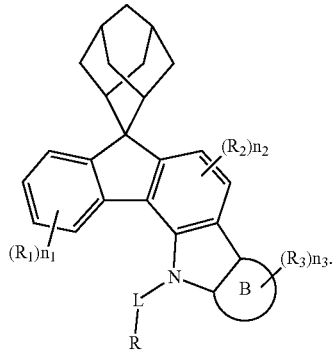

In the present disclosure, a planar structure formed by fusing spiro(adamantyl-fluorenyl) with indolyl is adopted as a core structure, which has high rigidity, high hole mobility, and high first-triplet energy level; and electron-rich/electron-deficient aryl or heteroaryl is introduced through modification of indole nitrogen to form a molecular structure suitable for a host material of an organic electroluminescent layer in an organic electroluminescent device. When the organic compound is used to one of a single-component bipolar host material and a two-component mixed host material, it can enhance the efficiency and life span of the organic electroluminescent device. In particular, when adamantyl is combined with a fused planar structure in a spiro mode, the intermolecular stacking can be effectively reduced to reduce the crystallization property of the material, thereby the life span of the device is improved.

In the present disclosure, the number of carbon atoms of Ring B, L, R, $R_1$, $R_2$, and $R_3$ refers to the number of all carbon atoms. For example, if L is selected from a substituted arylene with 10 carbon atoms, the number of all carbon atoms in the arylene and substituents thereof is 10; and if Ring B is selected from a substituted aryl with 10 carbon atoms, the number of all carbon atoms in the aryl and substituents thereof is 10.

In the present disclosure, unless otherwise specifically defined, the term "hetero" means that a functional group includes at least one heteroatom such as B, N, O, S, Si, Se, P, and the like, and the rest atoms are carbon and hydrogen. Unsubstituted alkyl may be saturated alkyl without any double or triple bonds.

In the present disclosure, the "alkyl" may include linear alkyl or branched alkyl. The alkyl may have 1 to 20 carbon atoms. In the present disclosure, a numerical range such as "1 to 20" refers to each integer in a given range. For example, "alkyl with 1 to 20 carbon atoms" refers to alkyl with 1, 2, 3, 4, 5, 6, 7, 8, 9, 10, 11, 12, 13, 14, 15, 16, 17, 18, 19, or 20 carbon atoms. The alkyl may also be a medium-sized alkyl with 1 to 10 carbon atoms. The alkyl may also be a lower alkyl with 1 to 6 carbon atoms. In addition, the alkyl may be a substituted or unsubstituted alkyl with 1 to 5 carbon atoms. Specific examples of alkyl with 1 to 5 carbon atoms include, but are not limited to methyl, ethyl, n-propyl, isopropyl, n-butyl, isobutyl, tert-butyl, n-pentyl, isopentyl, or neopentyl.

In the present disclosure, the term "alkenyl" refers to hydrocarbyl with one or more double bonds in a linear or branched hydrocarbon chain. The alkenyl group may be unsubstituted or substituted. The alkenyl may have 2 to 6 carbon atoms. A numerical range such as "2 to 6" in the present disclosure refers to each integer in a given range. For example, "alkenyl with 2 to 6 carbon atoms" refers to alkenyl with 2, 3, 4, 5, or 6 carbon atoms. For example, the alkenyl may be vinyl.

In the present disclosure, the term "cycloalkyl" refers to saturated hydrocarbyl with an alicyclic structure, including monocyclic and fused-ring structures. The cycloalkyl may have 3 to 10 carbon atoms, and a numerical range such as "3 to 10" refers to each integer in a given range. For example, "cycloalkyl with 3 to 10 carbon atoms" refers to cycloalkyl with 3, 4, 5, 6, 7, 8, 9, or 10 carbon atoms. The cycloalkyl may be a small ring, a common ring, or a large ring with 3 to 10 carbon atoms. The cycloalkyl may have a monocyclic system (with only one ring), a bicyclic system (with two rings), or a polycyclic system (with three or more rings). The cycloalkyl may also have a spiro-ring system (with two rings sharing one carbon atom), a fused ring system (with two rings sharing two carbon atoms), and a bridged ring system (with two rings sharing three or more carbon atoms). In addition, the cycloalkyl may be substituted or unsubstituted.

In the present disclosure, the term "aryl" refers to any functional group or substituent derived from an aromatic ring. The aryl may refer to a monocyclic aryl or a polycyclic aryl. In other words, the aryl may refer a monocyclic aryl, a fused-ring aryl, two or more monocyclic aryls conjugated through carbon-carbon bonds, a monocyclic aryl and a fused-ring aryl conjugated through carbon-carbon bonds, and two or more fused-ring aryls conjugated through carbon-carbon bonds. That is, two or more aromatic groups conjugated through carbon-carbon bonds can also be regarded as the aryl of the present disclosure. The aryl does not include heteroatoms such as B, N, O, S, Se, Si, P, and the like. For example, in the present disclosure, biphenyl, terphenyl, and the like belong aryl. Examples of aryl include phenyl, naphthyl, fluorenyl, anthracenyl, phenanthryl, biphenyl, terphenyl, tetraphenyl, pentaphenyl, hexaphenyl, benzo[9,10]phenanthryl, pyrenyl, benzofluoranthenyl, chrysenyl, and the like, but are not limited thereto.

In the present disclosure, substituted aryl refers to aryl in which one or more hydrogen atoms are substituted by other groups. For example, at least one hydrogen atom of the aryl is substituted by deuterium, F, Cl, I, CN, hydroxyl, amino, branched alkyl, linear alkyl, cycloalkyl, alkoxy, alkylamine, alkylthio or other groups. Specific examples of heteroaryl-substituted aryl include, but are not limited to, dibenzofuranyl-substituted phenyl, dibenzothienyl-substituted phenyl, pyridyl-substituted phenyl, and the like. Specific examples of aryl-substituted aryl include, but are not limited to, phenyl-substituted naphthyl, phenyl-substituted phenanthryl, naphthyl-substituted phenyl, phenyl-substituted anthracenyl, and the like. It should be appreciated that the number of carbon atoms in substituted aryl refers to the total number of carbon atoms in the aryl and substituents thereof. For example, substituted aryl with 20 carbon atoms means that the total number of carbon atoms in the aryl and substituents thereof is 20. For example, 9,9-dimethylfluorenyl is a substituted aryl with 15 carbon atoms.

In the present disclosure, the heteroaryl may be heteroaryl with at least one from B, O, N, P, Si, Se, or S as a heteroatom. The heteroaryl can be monocyclic heteroaryl or polycyclic heteroaryl. In other words, the heteroaryl may refer to a single aromatic ring system or multiple aromatic ring systems conjugated through carbon-carbon bonds, where any one of aromatic ring system is an aromatic monocyclic ring or an aromatic fused ring. For example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolinyl, indolyl, carbazolyl, N-arylcarbazolyl, N-heteroarylcarbazolyl, N-alkylcarbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, dibenzosilyl, dibenzofuranyl, phenyl-substituted dibenzofuranyl, and dibenzofuranyl-substituted phenyl, but is not limited thereto. Where the thienyl, furyl, phenanthrolinyl, and the like are heteroaryl with a single aromatic ring system; and N-arylcarbazolyl, N-heteroarylcarbazolyl, phenyl-substituted dibenzofuranyl, and the like are heteroaryl with multiple aromatic ring systems conjugated through carbon-carbon bonds.

In the present disclosure, the explanation of aryl can be applied to arylene; the explanation of heteroaryl can be applied to heteroarylene; the explanation of alkyl can be applied to alkylene; and the explanation of cycloalkyl can be applied to cycloalkylene.

In the present disclosure, a ring system formed by n atoms is an n-membered ring. For example, phenyl is 6-membered aryl. A 6-10 membered aromatic ring refers to benzene ring, indene ring, naphthalene ring, and the like.

In the present disclosure, a non-positional bond refers to a single bond "*—$\xi$—" extending from a ring system, which means that one end of the bond can be connected to any position in the ring system through which the bond penetrates, and the other end is connected to the remaining part in the compound molecule.

For example, as shown in the following formula (f), the naphthyl represented by the formula (f) is connected to the other position in the molecule through two non-positional bonds that penetrate through the bicyclic ring, which indicates any possible connection modes shown in formula (f-1) to formula (f-10).

(f)

(f-1)

(f-2)

(f-3)

(f-4)

(f-5)

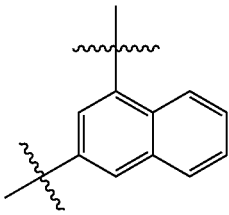
(f-6)

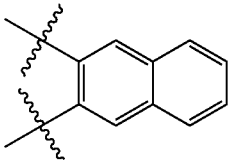
(f-7)

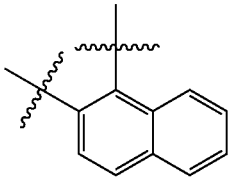
(f-8)

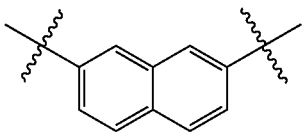
(f-9)

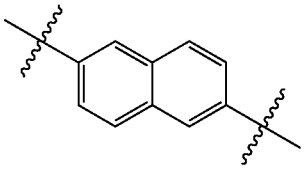
(f-10)

For example, as shown in the following formula (X'), the phenanthryl represented by the formula (X') is connected to the other position in the molecule through a non-positional bond extending from the middle of a benzene ring at a side, which indicates any possible connection modes shown in formula (X'-1) to formula (X'-4).

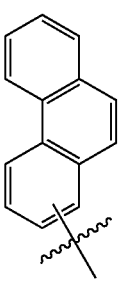
(X')

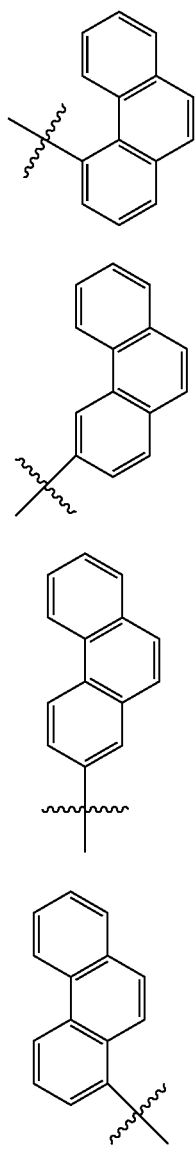

(X'-1)

(X'-2)

(X'-3)

(X'-4)

In the present disclosure, a non-positional substituent refers to a substituent connected through a single bond extending from the center of a ring system, which means that the substituent can be connected to any possible position in the ring system. For example, as shown in the following formula (Y), the substituent R represented by the formula (Y) is connected to a quinoline ring through a non-positional bond, which indicates any possible connection modes shown in formula (Y-1) to formula (Y-7).

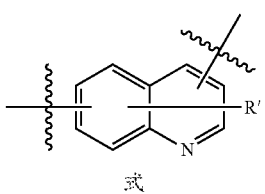

(Y)

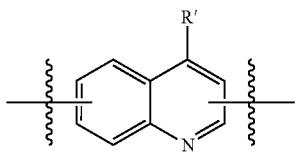

(Y-1)

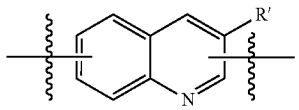

(Y-2)

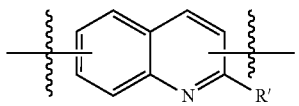

(Y-3)

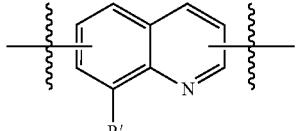

(Y-4)

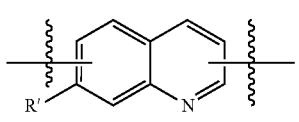

(Y-5)

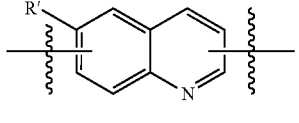

(Y-6)

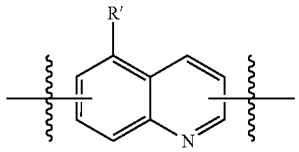

(Y-7)

The non-positional bond or non-positional substitution mentioned hereinafter has the same meaning, which will not be repeated hereinafter.

In the present disclosure, the halogen can be, for example, fluorine, chlorine, bromine, or iodine.

In the present disclosure, specific examples of trialkylsilyl include, but are not limited to, trimethylsilyl, triethylsilyl and the like.

In the present disclosure, specific examples of triarylsilyl include, but are not limited to, triphenylsilyl and the like.

Substituents of L, R, $R_1$, $R_2$, and $R_3$ may be the same or different, and may be respectively independently selected from deuterium; a fluorine; a chlorine; a bromine; a cyano; an alkyl with 1 to 5 carbon atoms; an alkenyl with 2 to 6 carbon atoms; a haloalkyl with 1 to 12 carbon atoms; a cycloalkyl with 3 to 10 carbon atoms; an aryl with 6 to 12 carbon atoms that is optionally substituted by 0, 1, 2, or 3 substituents selected from deuterium, a fluorine, a chlorine, a bromine, a cyano, or an alkyl; a heteroaryl with 6 to 12 carbon atoms; a trialkylsilyl with 3 to 12 carbon atoms; or an arylsilyl with 6 to 18 carbon atoms; optionally, when there are two substituents on the same atom in L, R, $R_1$, $R_2$, and $R_3$, the two substituents may be connected with each other to form a 5 to 18 membered aliphatic ring or a 5 to 18 membered aromatic ring with the atom commonly connected to the two.

Optionally, the Chemical formula 2 of the present disclosure may be selected from any one of Chemical formula 2-1, Chemical formula 2-2, Chemical formula 2-3, and Chemical formula 2-4:

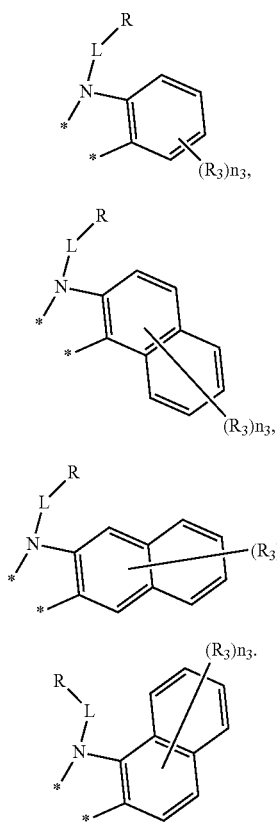

Specifically, Ring B may be a benzene ring or a naphthalene ring.

According to an embodiment of the present disclosure, L is selected from a single bond, a substituted or unsubstituted arylene with 6 to 15 carbon atoms, or a substituted or unsubstituted heteroarylene with 3 to 20 carbon atoms.

According to an embodiment of the present disclosure, R is selected from a substituted or unsubstituted alkyl with 1 to 5 carbon atoms, a substituted or unsubstituted aryl with 6 to 20 carbon atoms, or a substituted or unsubstituted heteroaryl with 3 to 20 carbon atoms; and $R_1$, $R_2$, and $R_3$ may be the same or different, and may be respectively independently selected from hydrogen, deuterium, a cyano, a fluorine, a substituted or unsubstituted alkyl with 1 to 5 carbon atoms, a substituted or unsubstituted aryl with 6 to 20 carbon atoms, or a substituted or unsubstituted heteroaryl with 3 to 20 carbon atoms.

According to an embodiment of the present disclosure, the substituent of L is selected from deuterium, a halogen, a cyano, an alkyl with 1 to 4 carbon atoms, an aryl with 6 to 12 carbon atoms, or a heteroaryl with 3 to 12 carbon atoms.

According to an embodiment of the present disclosure, the substituent of L is selected from deuterium, a fluorine, a cyano, a methyl, an ethyl, an isopropyl, a tert-butyl, a phenyl, a naphthyl, a biphenyl, a pyridyl, a carbazolyl, a dibenzofuranyl, or a dibenzothienyl.

According to an embodiment of the present disclosure, substituents of R, $R_1$, $R_2$ and $R_3$ are the same or different, and are each independently selected from deuterium; a halogen; a cyano; an alkyl with 1 to 4 carbon atoms; an aryl with 6 to 12 carbon atoms that is substituted by a substituent selected from deuterium, a fluorine, a cyano, a methyl, an ethyl, an isopropyl, or a tert-butyl or unsubstituted; a heteroaryl with 3 to 12 carbon atoms; a vinyl; an allyl; a trifluoromethyl; or a trimethylsilyl.

According to an embodiment of the present disclosure, substituents of R, $R_1$, $R_2$ and $R_3$ are the same or different, and are each independently selected from deuterium, a fluorine, a cyano, a methyl, an ethyl, an isopropyl, a tert-butyl, a phenyl, a deuterium-substituted phenyl, a fluorine-substituted phenyl, a cyano-substituted phenyl, an allyl, a naphthyl, a biphenyl, a pyridyl, a pyrimidinyl, a carbazolyl, a dibenzofuranyl, a dibenzothienyl, a vinyl, a trifluoromethyl, or a trimethylsilyl.

According to another embodiment of the present disclosure, L is selected from the group consisting of a single bond and groups shown in Chemical formula j-1 to Chemical formula j-14:

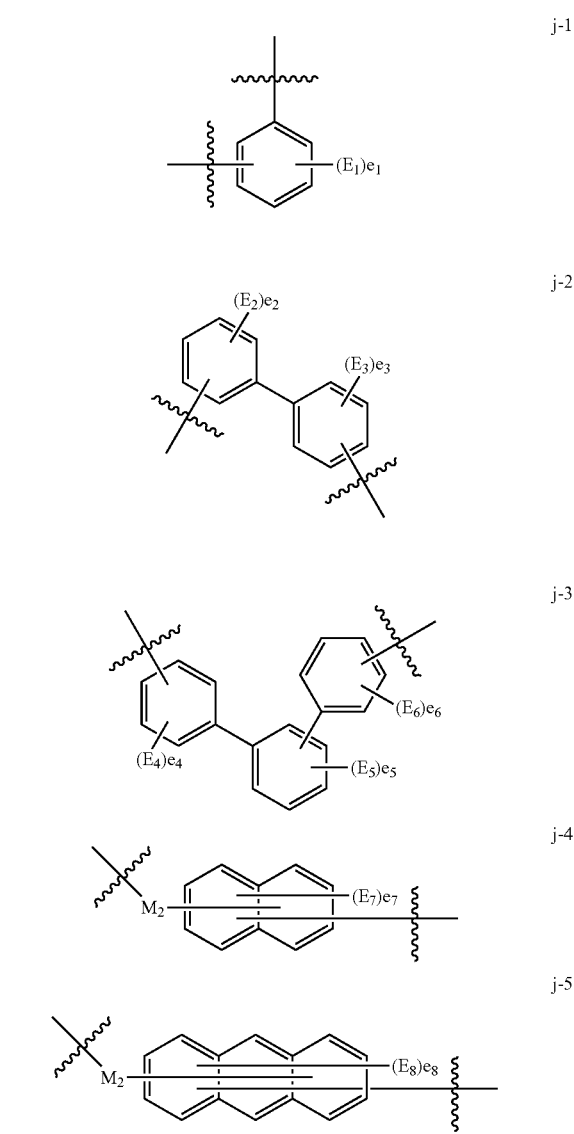

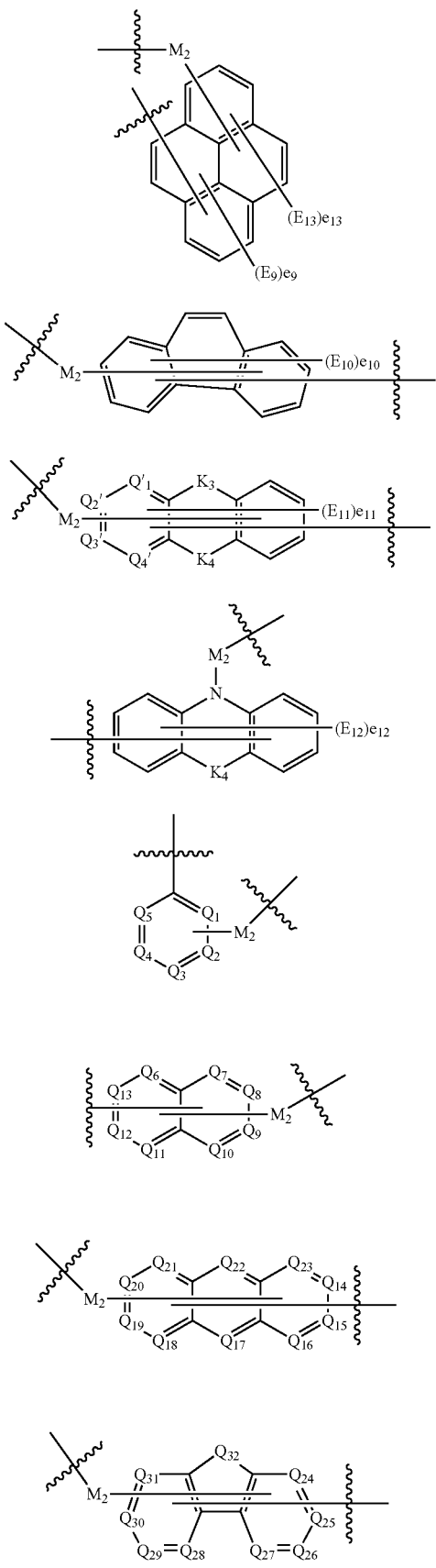

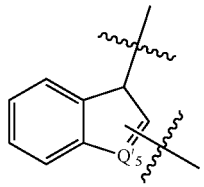

where M₂ is selected from a single bond or

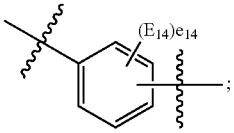

$Q_1$ to $Q_5$ and $Q'_1$ to $Q'_5$ are each independently selected from N or $C(F_5)$, and at least one of $Q_1$ to $Q_5$ is N; when two or more of $Q_1$ to $Q_5$ are $C(F_5)$, any two $F_5$ groups are the same or different; and when two or more of $Q'_1$ to $Q'_4$ are $C(F_5)$, any two $F_5$ groups are the same or different;

$Q_6$ to $Q_{13}$ are each independently selected from N or $C(F_6)$, and at least one of $Q_6$ to $Q_{13}$ is N; and when two or more of $Q_6$ to $Q_{13}$ are $C(F_6)$, any two $F_6$ groups are the same or different;

$Q_{14}$ to $Q_{23}$ are each independently selected from N or $C(F_7)$, and at least one of $Q_{14}$ to $Q_{23}$ is N; and when two or more of $Q_{14}$ to $Q_{23}$ are $C(F_7)$, any two $F_7$ groups are the same or different;

$Q_{24}$ to $Q_{32}$ are each independently selected from N or $C(F_8)$, and at least one of $Q_{24}$ to $Q_{32}$ is N; and when two or more of $Q_{24}$ to $Q_{32}$ are $C(F_8)$, any two $F_8$ groups are the same or different;

$E_1$ to $E_{14}$ and $F_5$ to $F_8$ are each independently selected from hydrogen, deuterium, a fluorine, a chlorine, a bromine, a cyano, a heteroaryl with 3 to 20 carbon atoms, an aryl with 6 to 20 carbon atoms, a trialkylsilyl with 3 to 12 carbon atoms, an arylsilyl with 8 to 12 carbon atoms, an alkyl with 1 to 10 carbon atoms, a haloalkyl with 1 to 10 carbon atoms, an alkenyl with 2 to 6 carbon atoms, an alkynyl with 2 to 6 carbon atoms, a cycloalkyl with 3 to 10 carbon atoms, a heterocycloalkyl with 2 to 10 carbon atoms, a cycloalkenyl with 5 to 10 carbon atoms, a heterocycloalkenyl with 4 to 10 carbon atoms, an alkoxy with 1 to 10 carbon atoms, an alkylamine with 1 to 10 carbon atoms, an alkylthio with 1 to 10 carbon atoms, an aryloxy with 6 to 18 carbon atoms, an arylamino with 6 to 18 carbon atoms, an arylthio with 6 to 18 carbon atoms, a phosphinoxy with 6 to 18 carbon atoms, an alkylsulfonyl with 6 to 18 carbon atoms, a trialkylphosphino with 3 to 18 carbon atoms, or a trialkylboron with 3 to 18 carbon atoms, where when any one of $E_1$ to $E_{14}$ is independently selected from a aryl with 6 to 20 carbon atoms, $E_1$ to $E_3$ and $E_{14}$ are not aryl;

$e_r$ is the number of substituents $E_r$, and r is any integer from 1 to 14; when r is selected from 1, 2, 3, 4, 5, 6, 9, 13, or 14, $e_r$ is selected from 1, 2, 3, and 4; when r is selected from 7 or 11, $e_r$ is selected from 1, 2, 3, 4, 5, or 6; when r is 12, $e_r$ is selected from 1, 2, 3, 4, 5, 6, or 7; when r is selected from 8 or 10, $e_r$ is selected from 1, 2, 3, 4, 5, 6, 7, or 8; and when $e_r$ is greater than 1, any two $E_r$ groups are the same or different;

$K_3$ is selected from O, S, Se, $N(E_{15})$, $C(E_{16}E_{17})$, or $Si(E_{18}E_{19})$, where $E_{15}$ to $E_{19}$ are each independently selected from: an aryl with 6 to 20 carbon atoms, a heteroaryl with 3 to 20 carbon atoms, an alkyl with 1 to 10 carbon atoms, an alkenyl with 2 to 6 carbon atoms, an alkynyl with 2 to 6 carbon atoms, a cycloalkyl with 3 to 10 carbon atoms, a heterocycloalkyl with 2 to 10 carbon atoms, a cycloalkenyl with 5 to 10 carbon atoms, or a heterocycloalkenyl with 4 to 10 carbon atoms; or $E_{16}$ and $E_{17}$ are connected with each other to form a ring with an atom commonly connected to $E_{16}$ and $E_{17}$; or $E_{18}$ and $E_{19}$ are connected with each other to form a ring with an atom commonly connected to $E_{18}$ and $E_{19}$. It should be noted that, in $K_3$, $E_{16}$ and $E_{17}$ or $E_{18}$ and $E_{19}$ may be connected with each other to form a saturated or unsaturated ring with an atom commonly connected to them, or may exist independently of each other. For example, when $E_{16}$ and $E_{17}$ form a ring and $E_{18}$ and $E_{19}$ form a ring, the ring may be a 5-membered ring such as

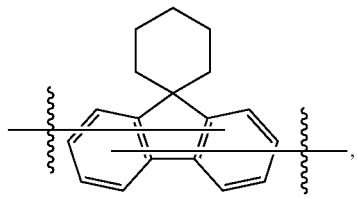

a 6-membered ring such as

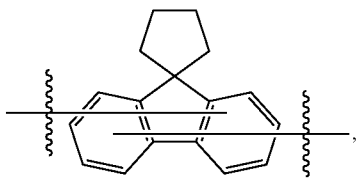

or a 13-membered ring such as

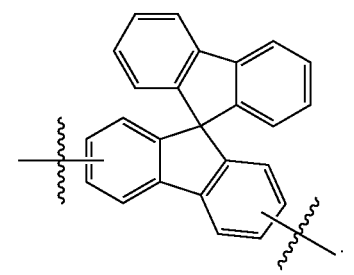

Of course, $E_{16}$ and $E_{17}$ or $E_{18}$ and $E_{19}$ may also form a ring with another number of carbon atoms forming ring, which will not be listed here. The present disclosure has no specific limitation on the number of carbon atoms forming ring in the ring.

$K_4$ is selected from a single bond, O, S, Se, $N(E_{20})$, $C(E_{21}E_{22})$, or $Si(E_{23}E_{24})$, where $E_{20}$ to $E_{24}$ are each independently selected from: an aryl with 6 to 20 carbon atoms, a heteroaryl with 3 to 20 carbon atoms, an alkyl with 1 to 10 carbon atoms, an alkenyl with 2 to 6 carbon atoms, an alkynyl with 2 to 6 carbon atoms, a cycloalkyl with 3 to 10 carbon atoms, a heterocycloalkyl with 2 to 10 carbon atoms, a cycloalkenyl with 5 to 10 carbon atoms, or a heterocycloalkenyl with 4 to 10 carbon atoms; or $E_{21}$ and $E_{22}$ are connected with each other to form a ring with an atom commonly connected to $E_{21}$ and $E_{22}$; or $E_{23}$ and $E_{24}$ are connected with each other to form a ring with an atom commonly connected to $E_{23}$ and Ea. The present disclosure has no specific limitation on the number of carbon atoms forming ring in a ring formed by $E_{21}$ and $E_{22}$ or $E_{23}$ and $E_{24}$. The number of carbon atoms forming ring in a ring formed by $E_{21}$ and $E_{22}$ or $E_{23}$ and $E_{24}$ is defined as the same as that in the ring formed by $E_{16}$ and $E_{17}$, which will not be repeated here.

Optionally, L is selected from the group consisting of a single bond and a group shown in chemical formula j-15:

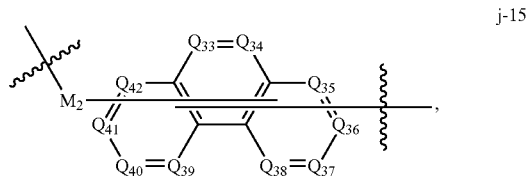

where $Q_{33}$ to $Q_{42}$ are each independently selected from N or $C(F_9)$, and at least one of $Q_{33}$ to $Q_{42}$ is N; and when two or more of $Q_{33}$ to $Q_{42}$ are $C(F_9)$, any two $F_9$ groups are the same or different; and $F_9$ is each independently selected from hydrogen, deuterium, a fluorine, a chlorine, a bromine, a cyano, a heteroaryl with 3 to 20 carbon atoms, an aryl with 6 to 20 carbon atoms, a trialkylsilyl with 3 to 12 carbon atoms, an arylsilyl with 8 to 12 carbon atoms, an alkyl with 1 to 10 carbon atoms, a haloalkyl with 1 to 10 carbon atoms, an alkenyl with 2 to 6 carbon atoms, an alkynyl with 2 to 6 carbon atoms, a cycloalkyl with 3 to 10 carbon atoms, a heterocycloalkyl with 2 to 10 carbon atoms, a cycloalkenyl with 5 to 10 carbon atoms, a heterocycloalkenyl with 4 to 10 carbon atoms, an alkoxy with 1 to 10 carbon atoms, an alkylamine with 1 to 10 carbon atoms, an alkylthio with 1 to 10 carbon atoms, an aryloxy with 6 to 18 carbon atoms, an arylamine with 6 to 18 carbon atoms, an arylthio with 6 to 18 carbon atoms, a phosphinoxy with 6 to 18 carbon atoms, an alkylsulfonyl with 6 to 18 carbon atoms, a trialkylphosphino with 3 to 18 carbon atoms, or a trialkylboron with 3 to 18 carbon atoms.

Optionally, L is selected from the group consisting of a single bond and the following groups:

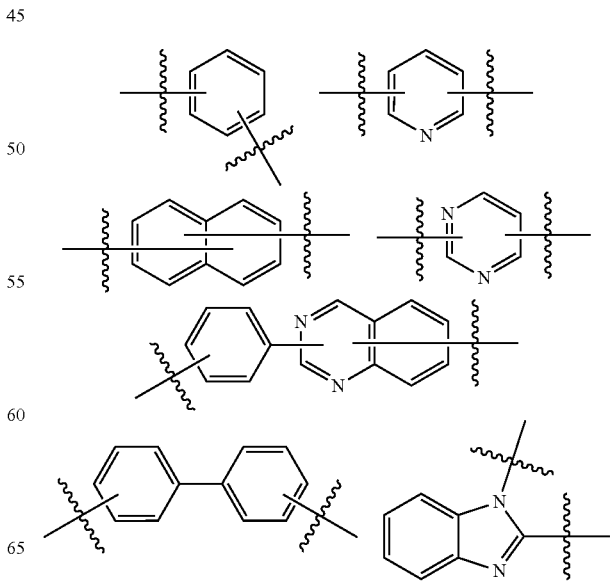

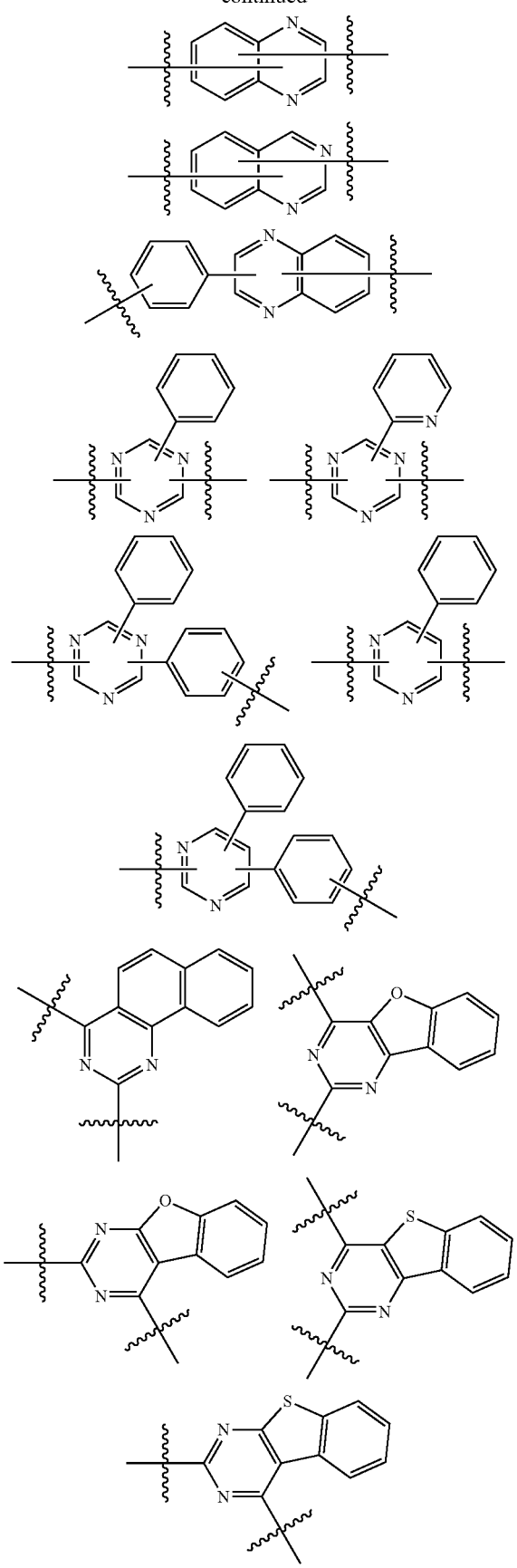
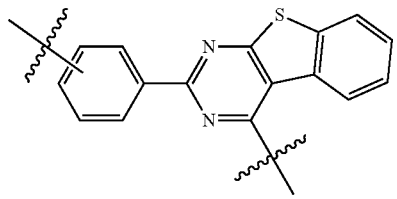
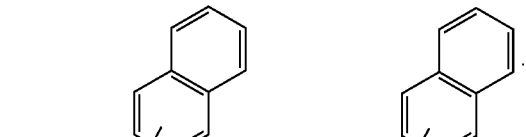
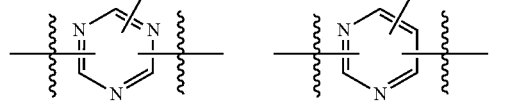
Further preferably, L is selected from the group consisting of a single bond and the following groups:
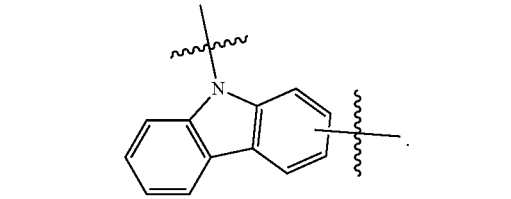
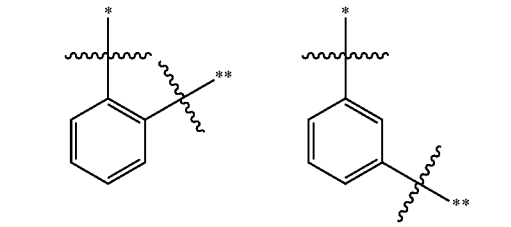
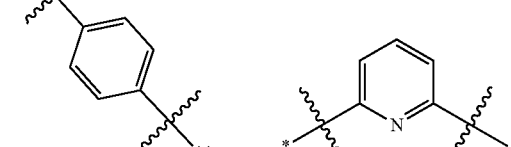
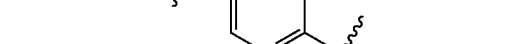

-continued
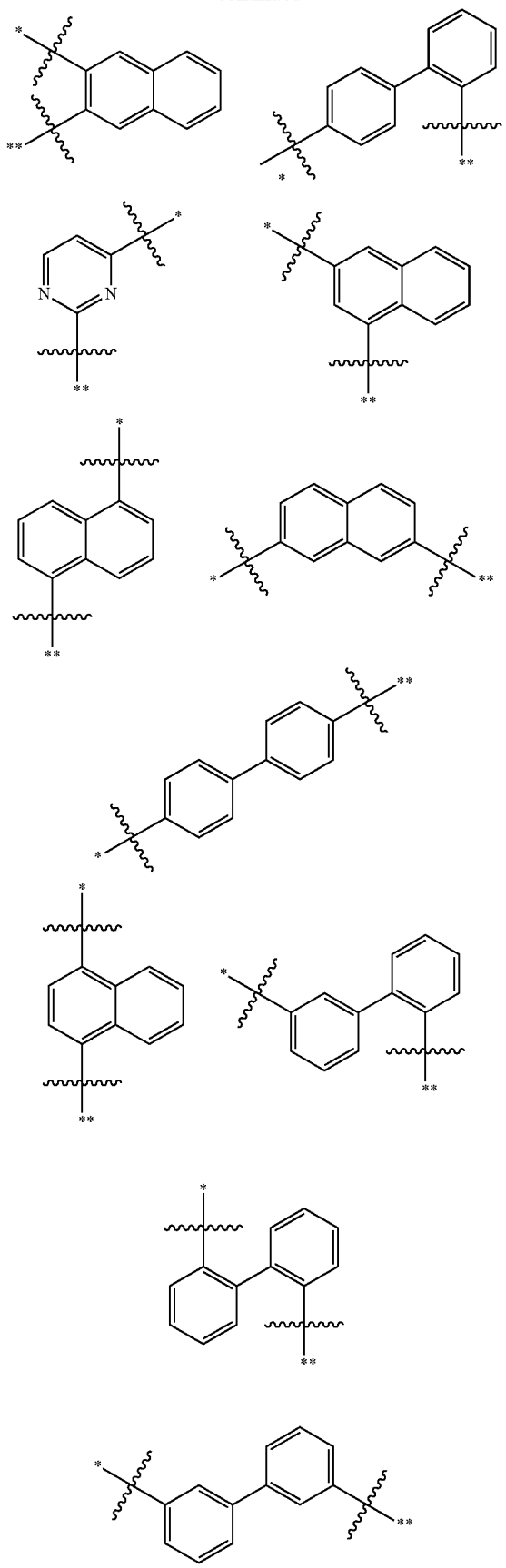
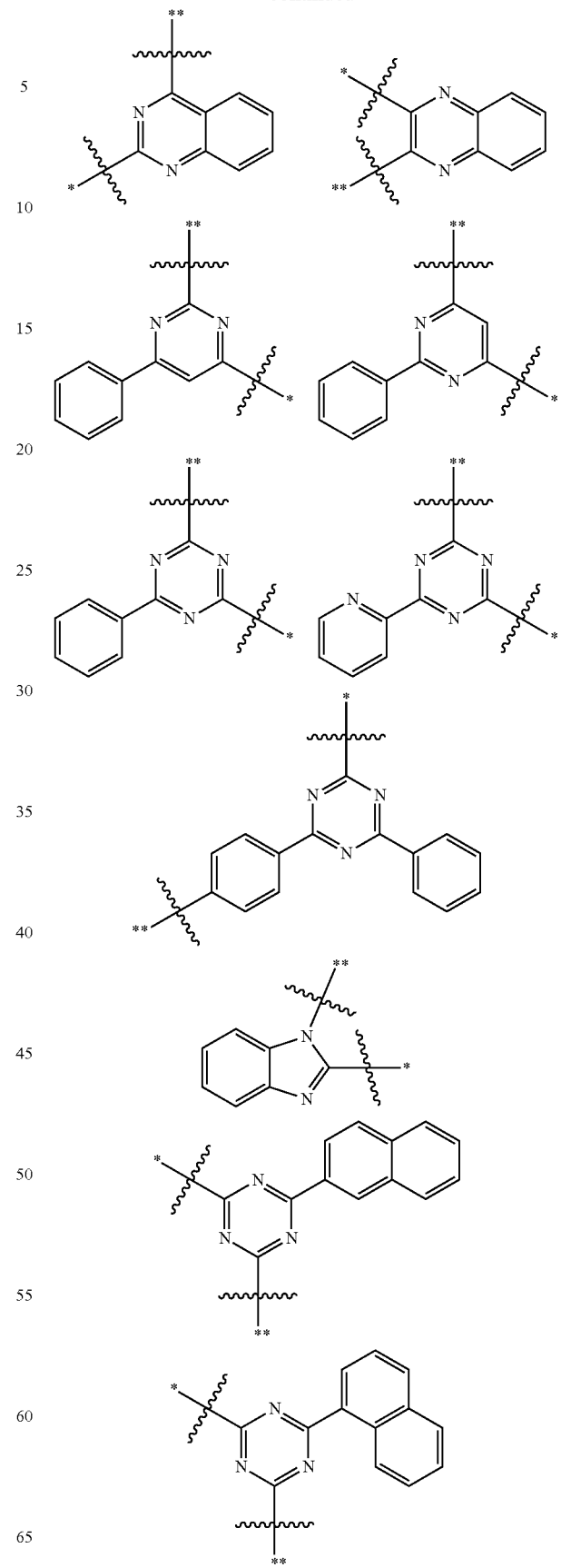

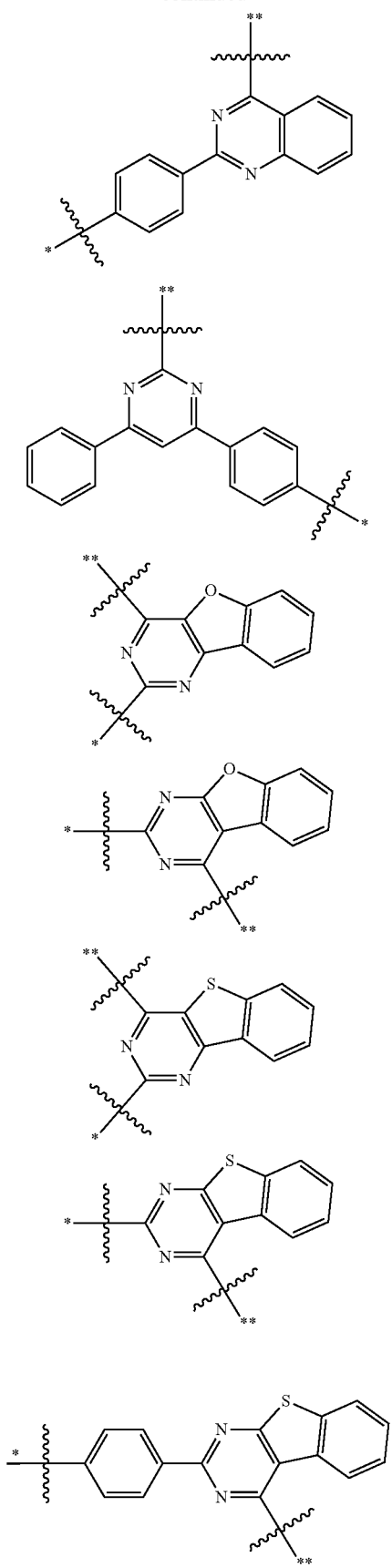
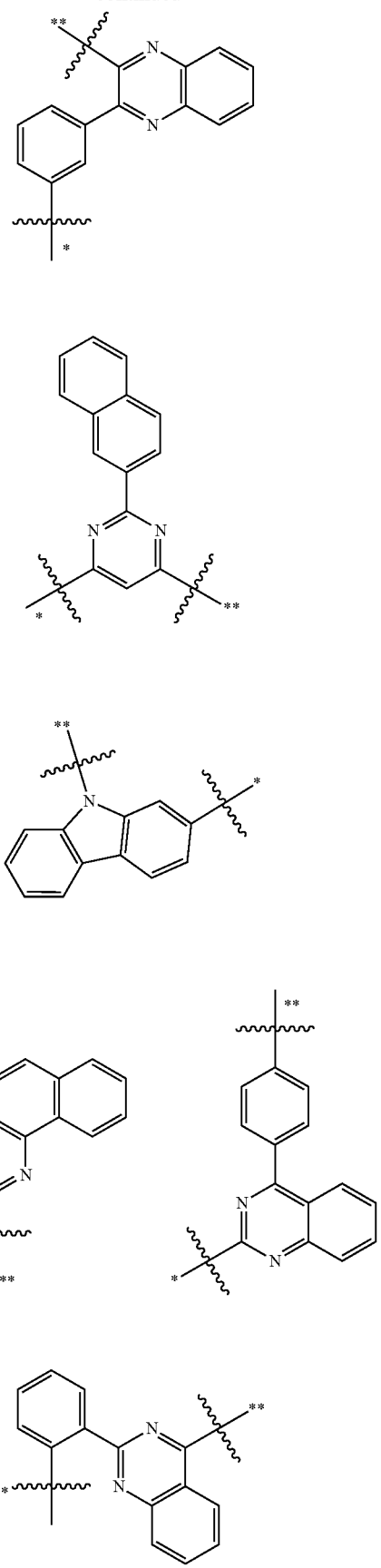

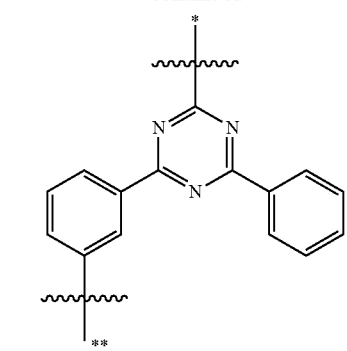

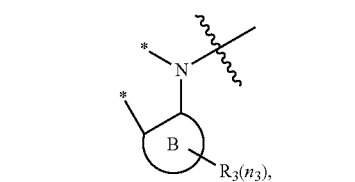

where * represents a point connected with and ** represents a point connected with R.

According to another embodiment of the present disclosure, L is selected from the group consisting of a single bond and the following groups:

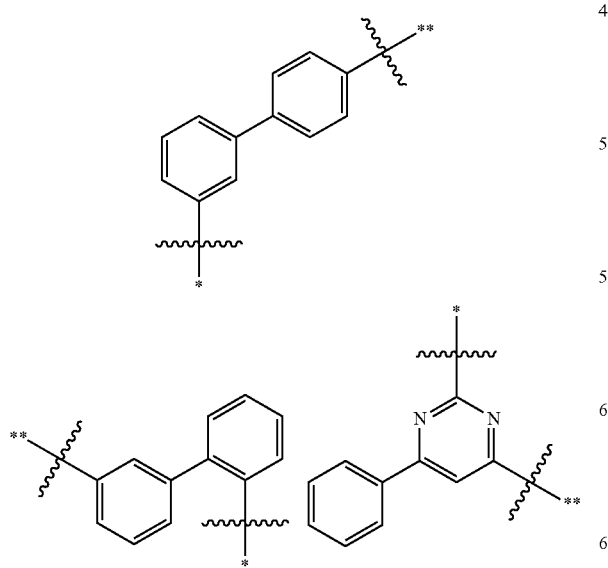

where * represents a point connected with and ** represents a point connected with R.

According to another embodiment of the present disclosure, R is selected from the group consisting of a substituted or unsubstituted alkyl with 1 to 10 carbon atoms and groups shown in Chemical formula i-1 to Chemical formula i-15; and $R_1$, $R_2$, and $R_3$ are selected from the group consisting of hydrogen, deuterium, a cyano, a halogen, a substituted or unsubstituted alkyl with 1 to 10 carbon atoms, and groups shown in Chemical formula i-1 to Chemical formula i-15:

i-1

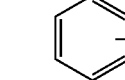

i-2

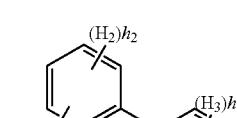

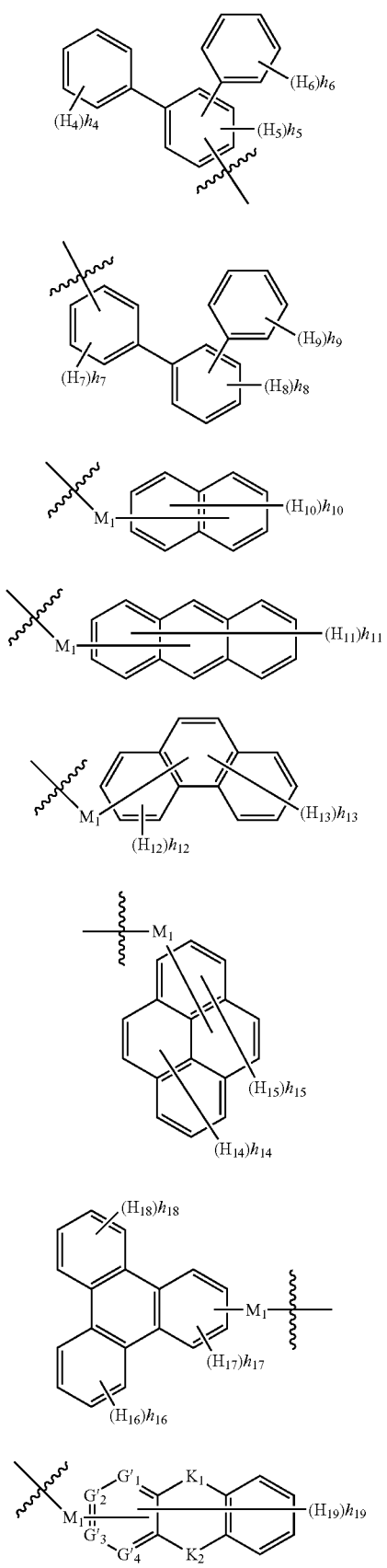
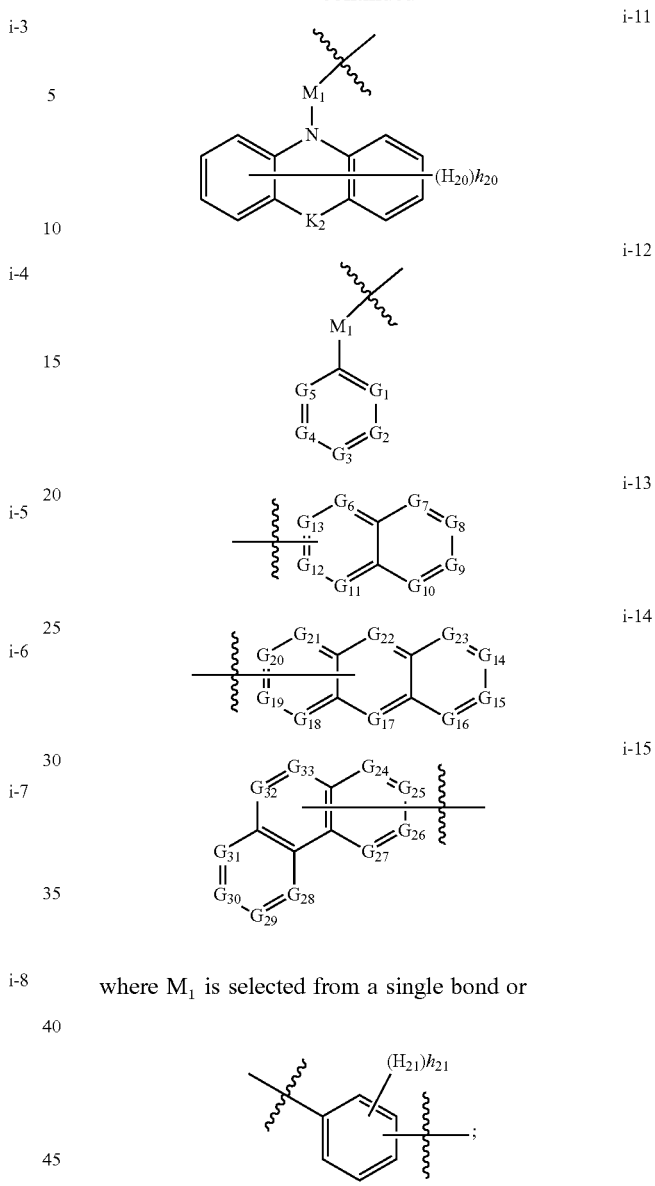

where $M_1$ is selected from a single bond or $G_1$ to $G_5$ and $G'_1$ to $G'_4$ are each independently selected from N or $C(F_1)$, and at least one of $G_1$ to $G_5$ is N; when two or more of $G_1$ to $G_5$ are $C(F_1)$, any two $F_1$ groups are the same or different; and when two or more of $G'_1$ to $G'_4$ are $C(F_1)$, any two $F_1$ groups are the same or different;

$G_6$ to $G_{13}$ are each independently selected from N or $C(F_2)$, and at least one of $G_6$ to $G_{13}$ is N; and when two or more of $G_6$ to $G_{13}$ are $C(F_2)$, any two $F_2$ groups are the same or different;

$G_{14}$ to $G_{23}$ are each independently selected from N or $C(F_3)$, and at least one of $G_{14}$ to $G_{23}$ is N; and when two or more of $G_{14}$ to $G_{23}$ are $C(F_3)$, any two $F_3$ groups are the same or different;

$G_{24}$ to $G_{33}$ are each independently selected from N or $C(F_4)$, and at least one of $G_{24}$ to $G_{33}$ is N; and when two or more of $G_{24}$ to $G_{33}$ are $C(F_4)$, any two $F_4$ groups are the same or different;

$H_1$ to $H_{21}$ and $F_1$ to $F_4$ are each independently selected from: hydrogen, deuterium, a fluorine, a chlorine, a bromine, a cyano, an aryl with 6 to 20 carbon atoms, a heteroaryl with 3 to 20 carbon atoms, a trialkylsilyl with 3 to 12 carbon atoms, an arylsilyl with 8 to 12 carbon atoms, an alkyl with 1 to 10 carbon atoms, a haloalkyl with 1 to 10 carbon atoms, an alkenyl with 2 to 6 carbon atoms, an alkynyl with 2 to 6 carbon atoms, a cycloalkyl with 3 to 10 carbon atoms, a heterocycloalkyl with 2 to 10 carbon atoms, a cycloalkenyl with 5 to 10 carbon atoms, a heterocycloalkenyl with 4 to 10 carbon atoms, an alkoxy with 1 to 10 carbon atoms, an alkylamine with 1 to 10 carbon atoms, an alkylthio with 1 to 10 carbon atoms, an aryloxy with 6 to 18 carbon atoms, an arylamino with 6 to 18 carbon atoms, an arylthio with 6 to 18 carbon atoms, a phosphinoxy with 6 to 18 carbon atoms, an alkylsulfonyl with 6 to 18 carbon atoms, a trialkylphosphino with 3 to 18 carbon atoms, or a trialkylboron with 3 to 18 carbon atoms, where when any one of $H_4$ to $H_{20}$ is independently an aryl with 6 to 20 carbon atoms, $H_1$ to $H_3$ and $H_{21}$ are not aryl;

$h_k$ is the number of substituents $H_k$, and k is any integer from 1 to 21, when k is selected from 5 or 17, $h_k$ is selected from 1, 2, or 3; when k is selected from 2, 7, 8, 12, 15, 16, 18, or 21, $h_k$ is selected from 1, 2, 3, or 4; when k is selected from 1, 3, 4, 6, 9, or 14, $h_k$ is selected from 1, 2, 3, 4, or 5; when k is 13, $h_k$ is selected from 1, 2, 3, 4, 5, or 6; when k is selected from 10 or 19, $h_k$ is selected from 1, 2, 3, 4, 5, 6, or 7; when k is 20, $h_k$ is selected from 1, 2, 3, 4, 5, 6, 7, or 8; when k is 11, $h_k$ is selected from 1, 2, 3, 4, 5, 6, 7, 8, or 9; and when $h_k$ is greater than 1, any two $H_k$ groups are the same or different;

$K_1$ is selected from O, S, Se, $N(H_{22})$, $C(H_{23}H_{24})$, or $Si(H_{25}H_{26})$, where $H_{22}$ to $H_{26}$ are each independently selected from: an aryl with 6 to 20 carbon atoms, a heteroaryl with 3 to 20 carbon atoms, an alkyl with 1 to 10 carbon atoms, an alkenyl with 2 to 6 carbon atoms, an alkynyl with 2 to 6 carbon atoms, a cycloalkyl with 3 to 10 carbon atoms, a heterocycloalkyl with 2 to 10 carbon atoms, a cycloalkenyl with 5 to 10 carbon atoms, or a heterocycloalkenyl with 4 to 10 carbon atoms; or $H_{23}$ and $H_{24}$ are connected with each other to form a ring with an atom commonly connected to $H_{23}$ and $H_{24}$; or $H_{25}$ and $H_{26}$ are connected with each other to form a ring with an atom commonly connected to $H_{25}$ and $H_{26}$. It should be noted that, in $K_1$, $H_{23}$ and $H_{24}$ or $H_{25}$ and $H_{26}$ may be connected with each other to form a saturated or unsaturated ring with an atom commonly connected to them, or may exist independently of each other. For example, when $H_{23}$ and $H_{24}$ form a ring and $H_{25}$ and $H_{26}$ form a ring, the ring may be a 5-membered ring such as

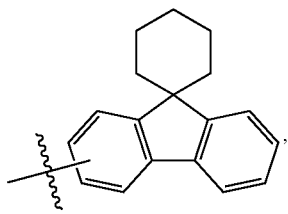

a 6-membered ring such as

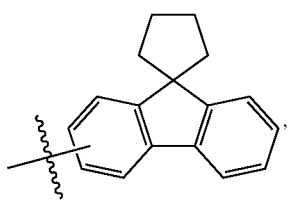

or a 13-membered ring such as

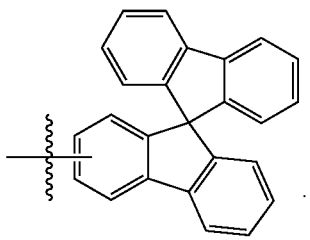

Of course, $H_{23}$ and $H_{24}$ or $H_{25}$ and $H_{26}$ may also form a ring with another number of carbon atoms forming ring, which will not be listed here. The present disclosure has no specific limitation on the number of carbon atoms forming ring in the ring.

$K_2$ is selected from a single bond, O, S, Se, $N(H_{27})$, $C(H_{28}H_{29})$, or $Si(H_{30}H_{31})$, where $H_{27}$ to $H_{31}$ are each independently selected from: an aryl with 6 to 20 carbon atoms, a heteroaryl with 3 to 20 carbon atoms, an alkyl with 1 to 10 carbon atoms, an alkenyl with 2 to 6 carbon atoms, an alkynyl with 2 to 6 carbon atoms, a cycloalkyl with 3 to 10 carbon atoms, a heterocycloalkyl with 2 to 10 carbon atoms, a cycloalkenyl with 5 to 10 carbon atoms, or a heterocycloalkenyl with 4 to 10 carbon atoms; or $H_{28}$ and $H_{29}$ are connected with each other to form a ring with an atom commonly connected to $H_{28}$ and $H_{29}$; or $H_{30}$ and $H_{31}$ are connected with each other to form a ring with an atom commonly connected to $H_{30}$ and $H_{31}$. The number of carbon atoms forming ring in a ring formed by $H_{28}$ and $H_{29}$ or $H_{30}$ and $H_{31}$ is defined as the same as that in the ring formed by $H_{23}$ and $H_{24}$, which will not be repeated here.

Optionally, R is selected from a substituted or unsubstituted alkyl with 1 to 5 carbon atoms or a substituted or unsubstituted W; and $R_1$, $R_2$, and $R_3$ are selected from hydrogen, deuterium, a cyano, a fluorine, a substituted or unsubstituted alkyl with 1 to 5 carbon atoms, or a substituted or unsubstituted W; the unsubstituted W may be selected from the group consisting of the following groups:

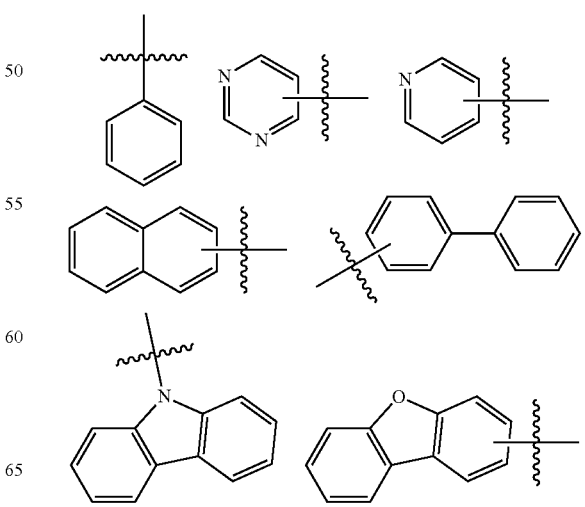

-continued

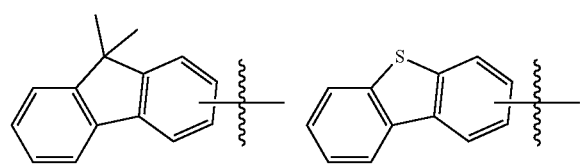
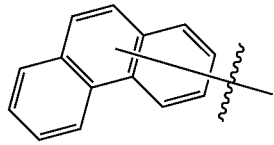
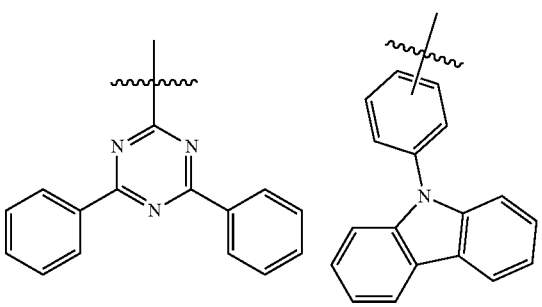
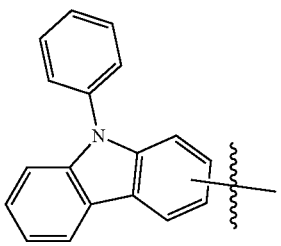

when W is substituted, the substituents of W may be selected from hydrogen, deuterium, a fluorine, a chlorine, a cyano, a trimethylsilyl, an alkyl with 1 to 5 carbon atoms, a haloalkyl with 1 to 4 carbon atoms, an aryl with 6 to 12 carbon atoms, an alkenyl with 2 to 4 carbon atoms, or a heteroaryl with 3 to 12 carbon atoms; and when W is substituted by a plurality of substituents, the plurality of substituents is the same or different.

Optionally, R is selected from the group consisting of an alkyl with 1 to 5 carbon atoms and the following groups:

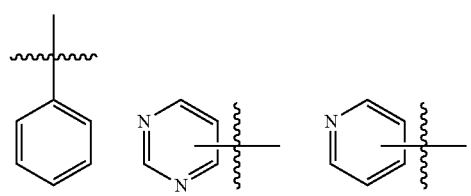
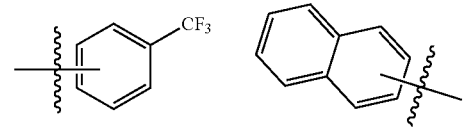
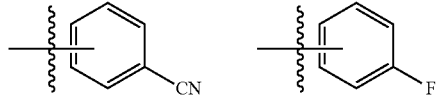

-continued

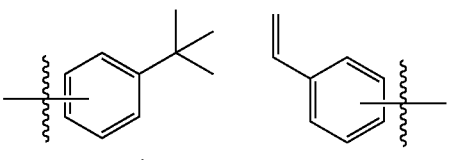
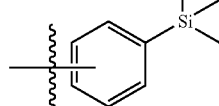
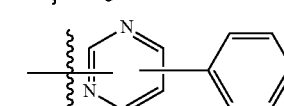
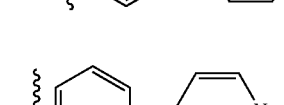
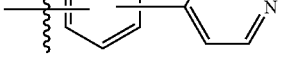
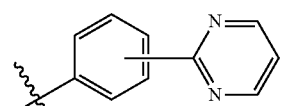
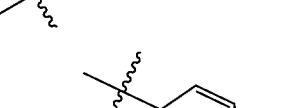
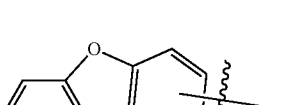
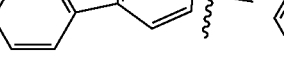
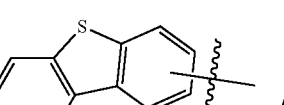
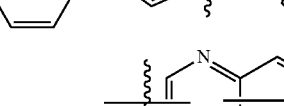
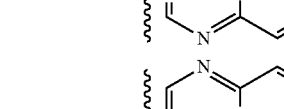
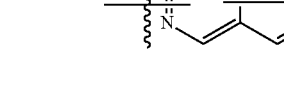
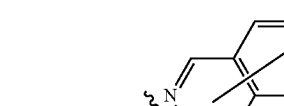

-continued
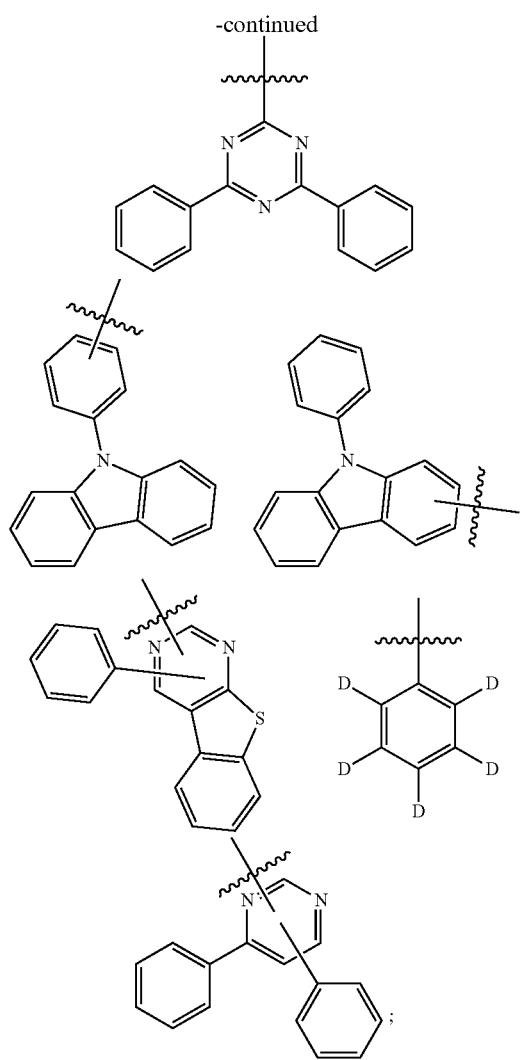
and
R₁, R₂, and R₃ are selected from the group consisting of hydrogen, deuterium, a cyano, a fluorine, an alkyl with 1 to 5 carbon atoms, and the following groups:
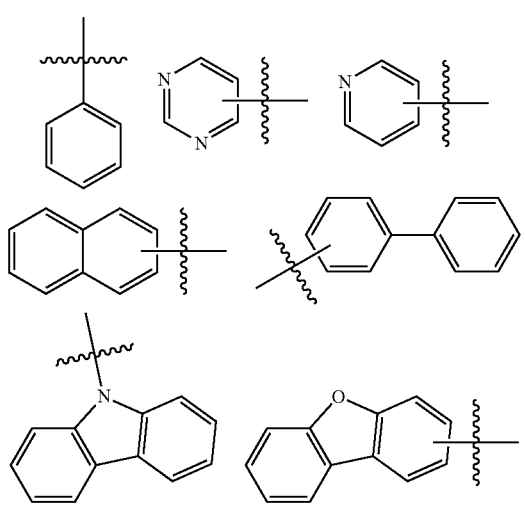
-continued
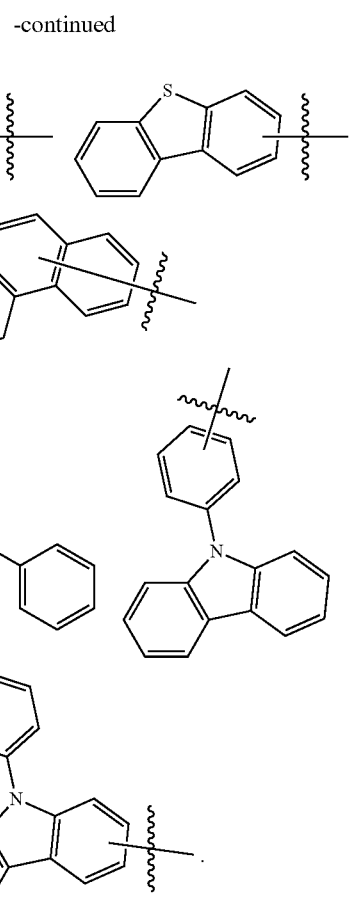
Optionally, R is selected from the group consisting of an alkyl with 1 to 5 carbon atoms and the following groups:
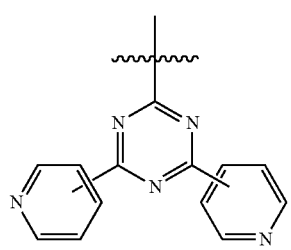
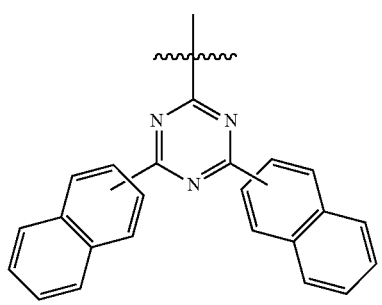

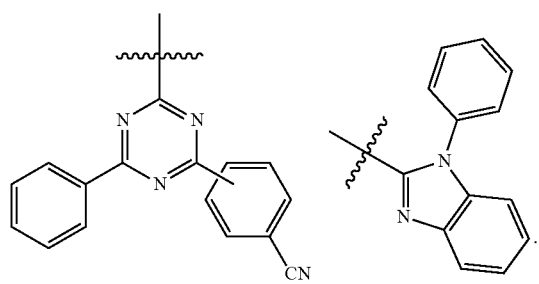
Optionally, R is selected from the group consisting of a methyl, an ethyl, an isopropyl, a tert-butyl, and the following groups:
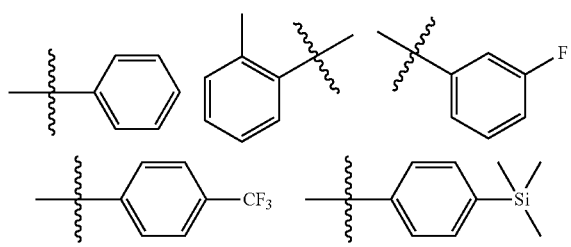
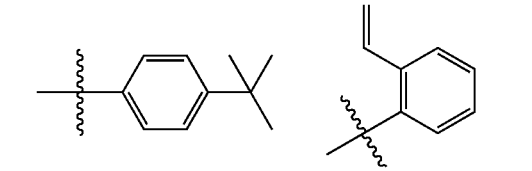
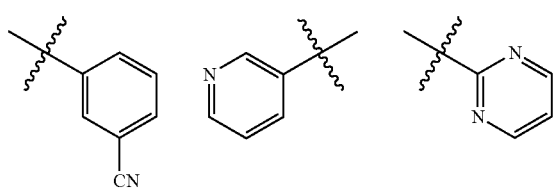
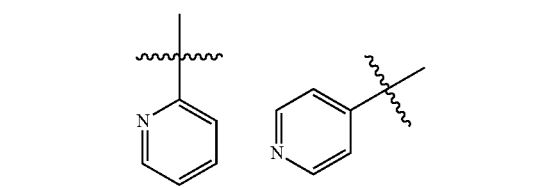
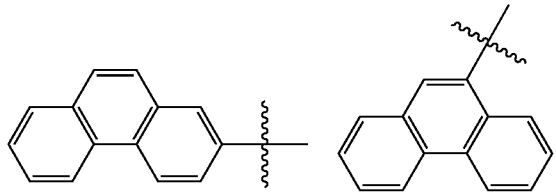
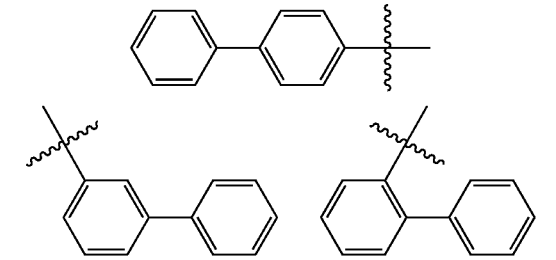
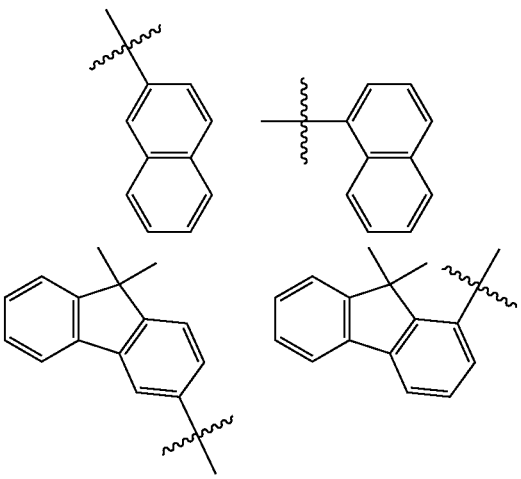
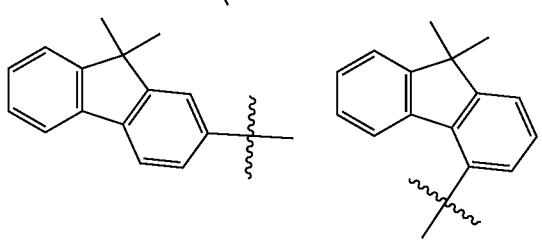
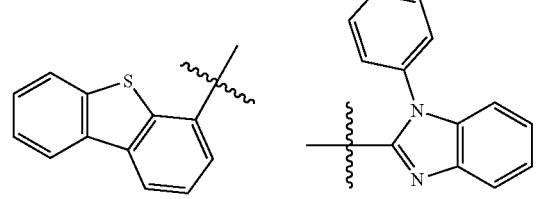
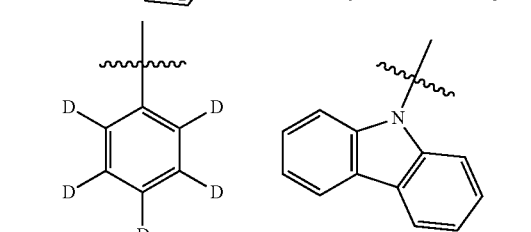
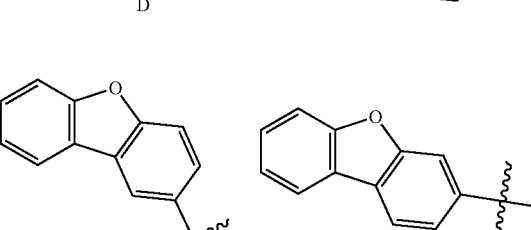
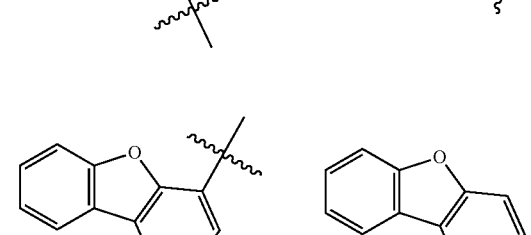

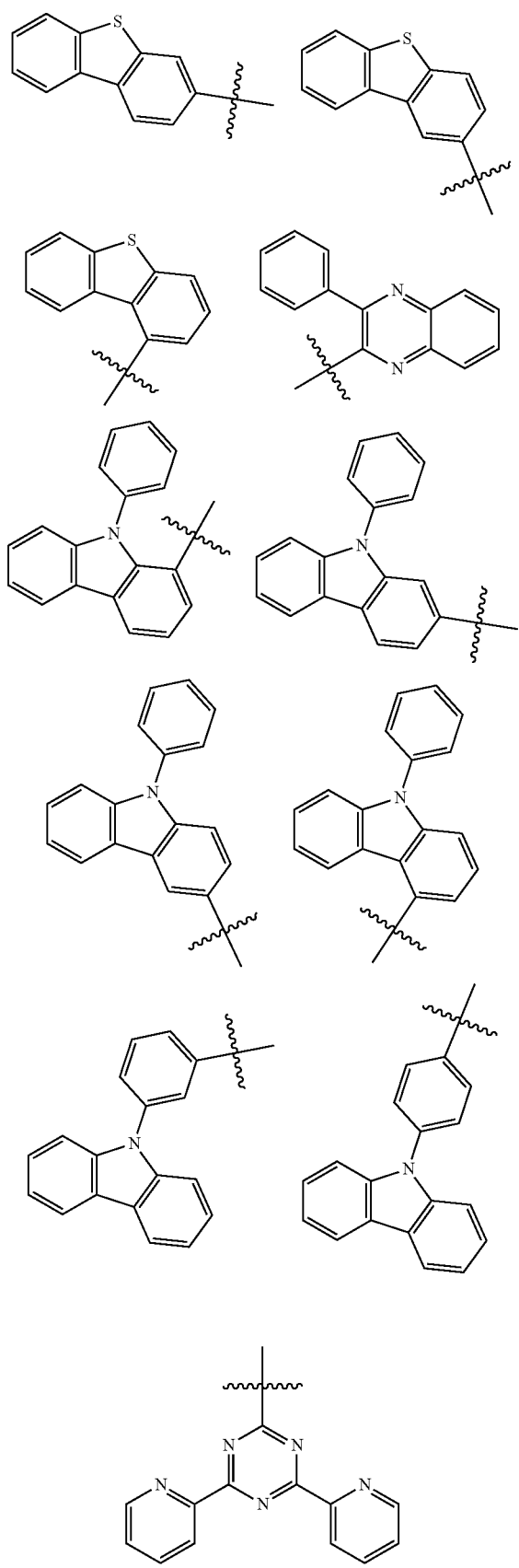
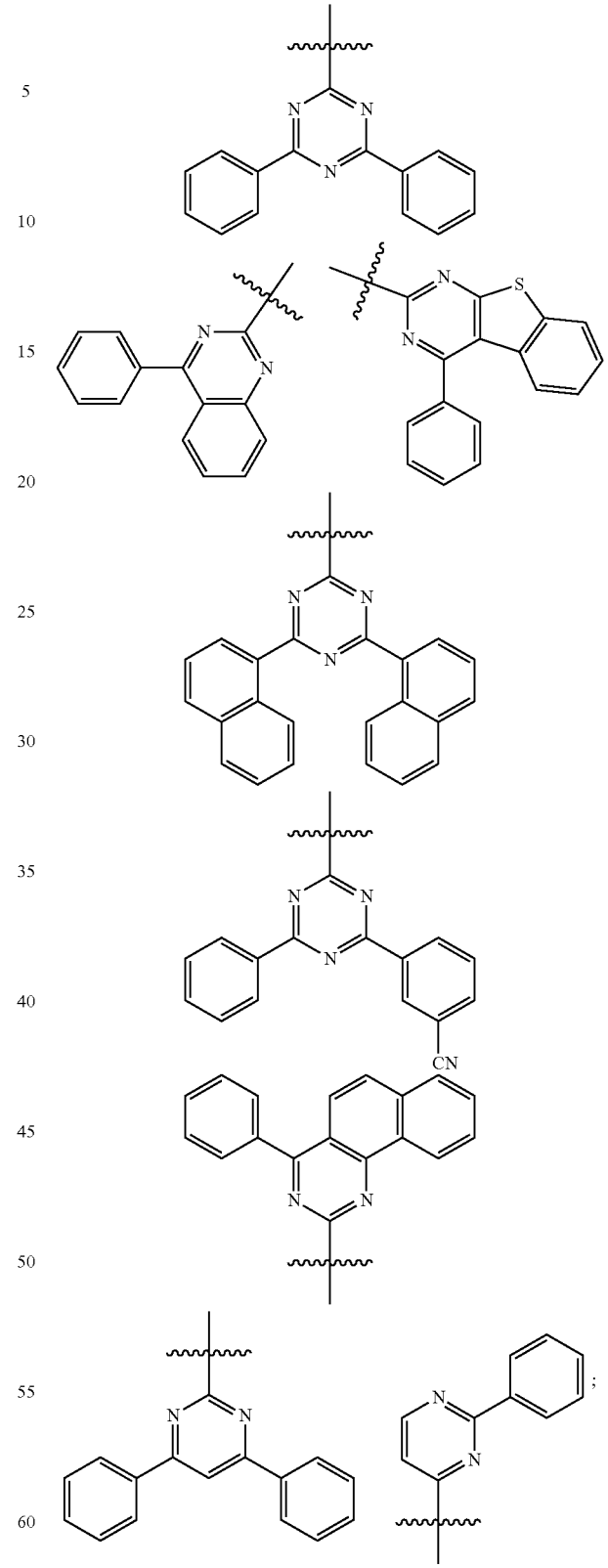
and
R₁, R₂, and R₃ are selected from the group consisting of hydrogen, deuterium, a fluorine, a cyano, a methyl, an ethyl, an isopropyl, a tert-butyl, and the following groups:

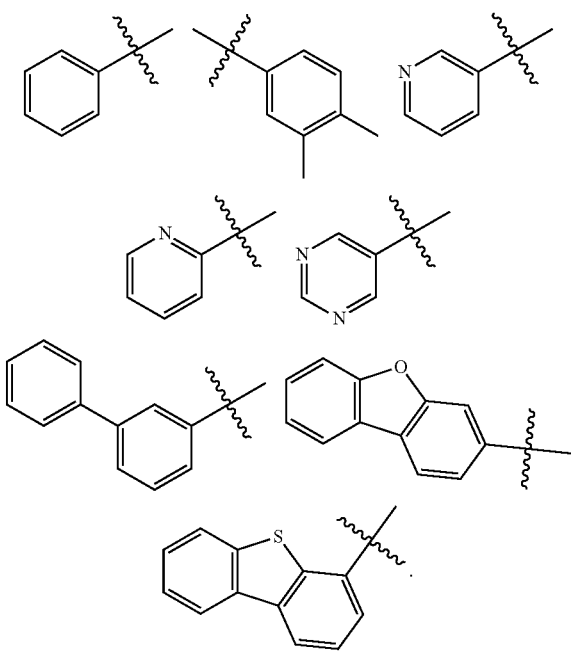
Optionally, the organic compound of the present disclosure may be selected from the group consisting of the following compounds:
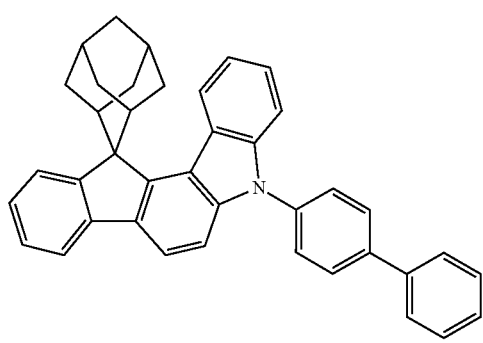
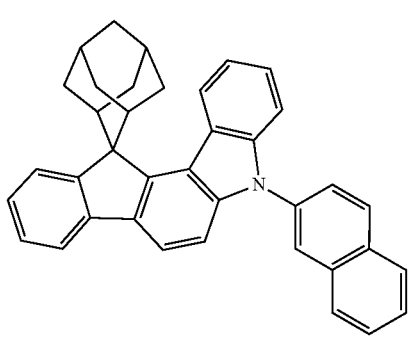
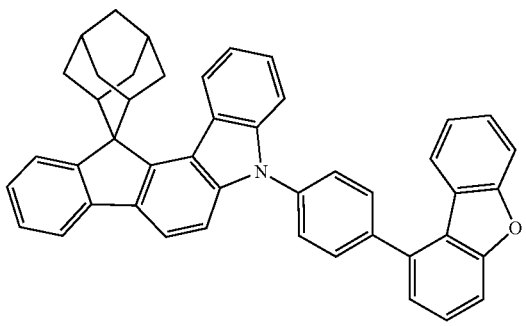
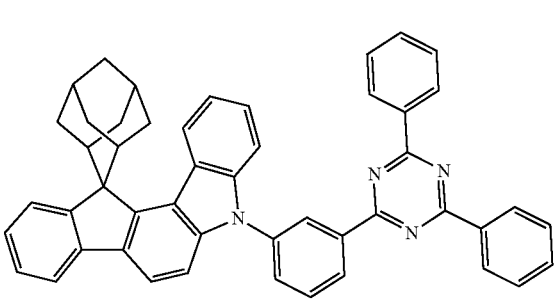
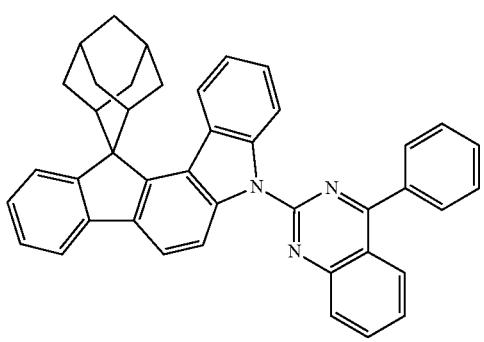
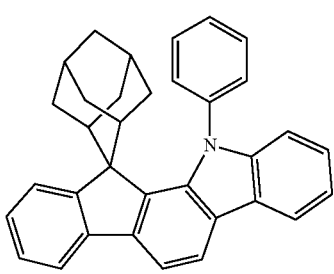
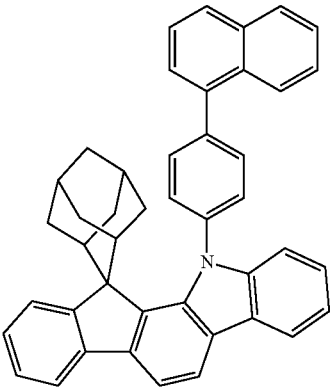

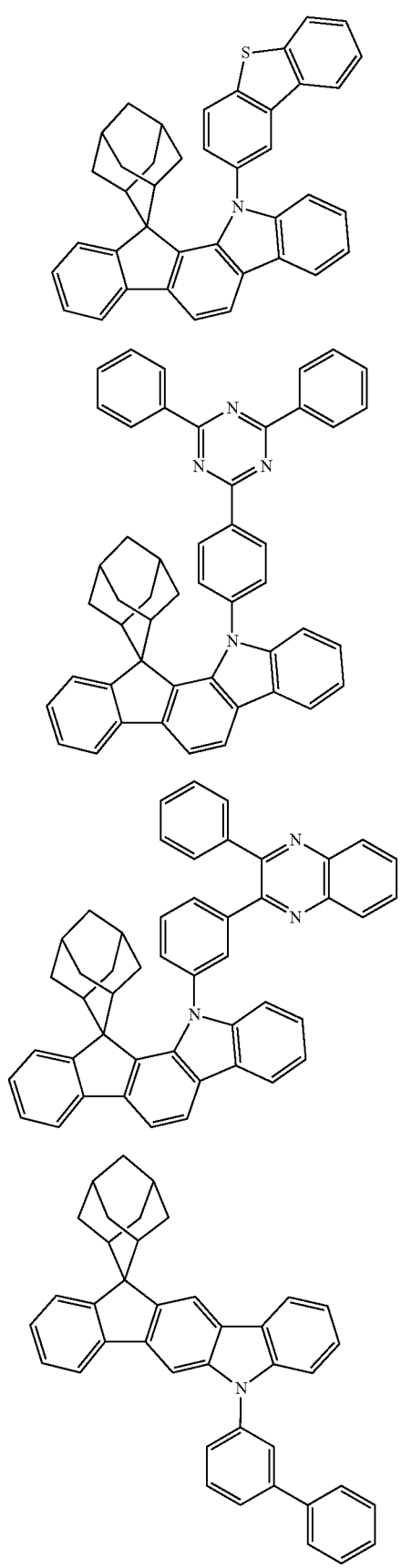
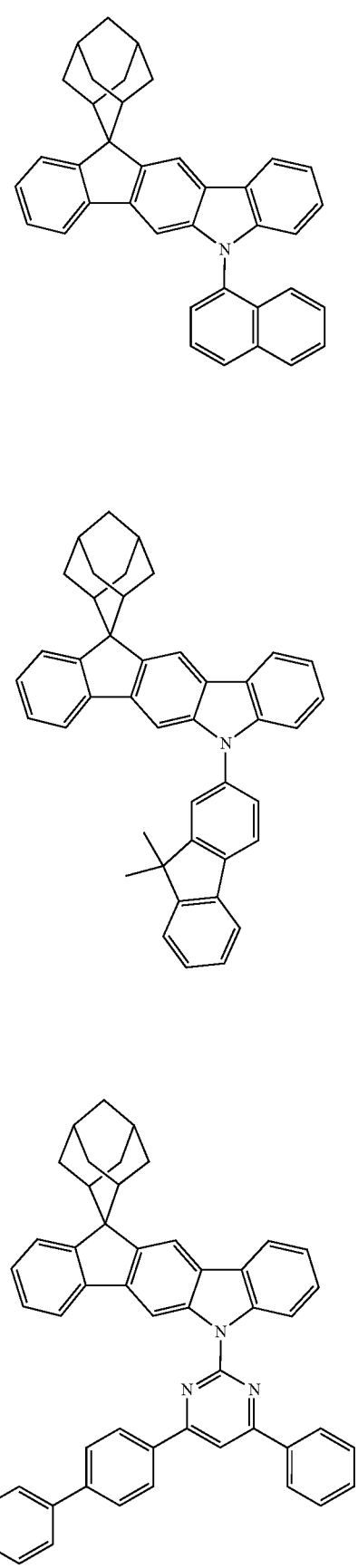

15
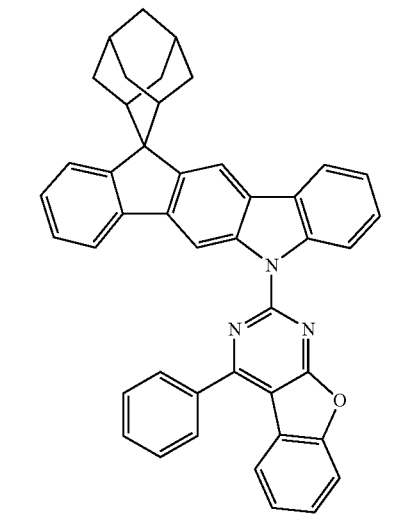
16
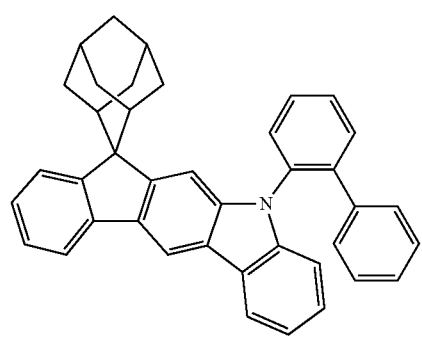
17
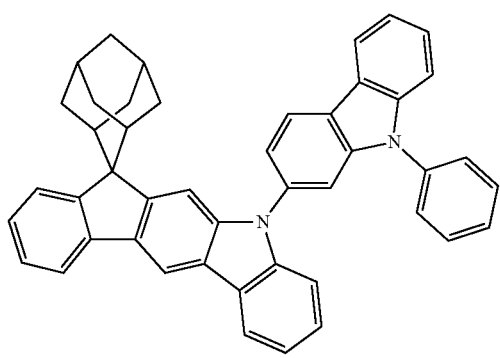
18
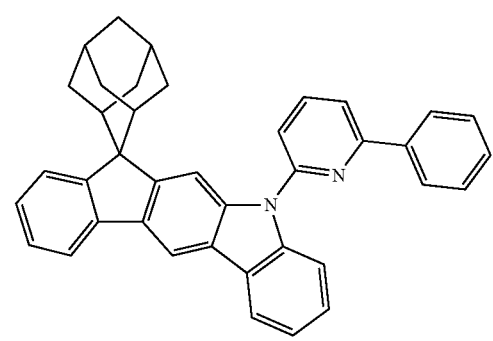
19
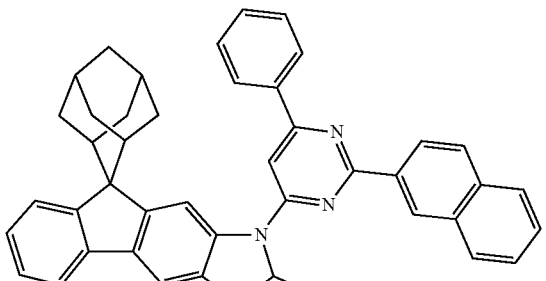
20
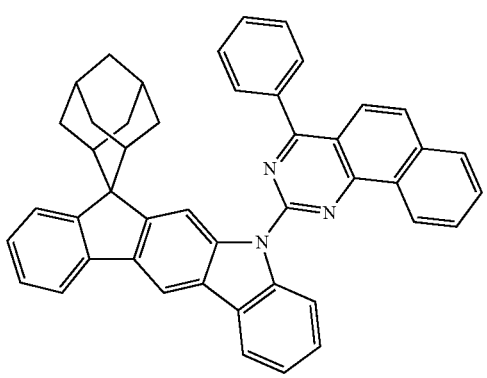
21
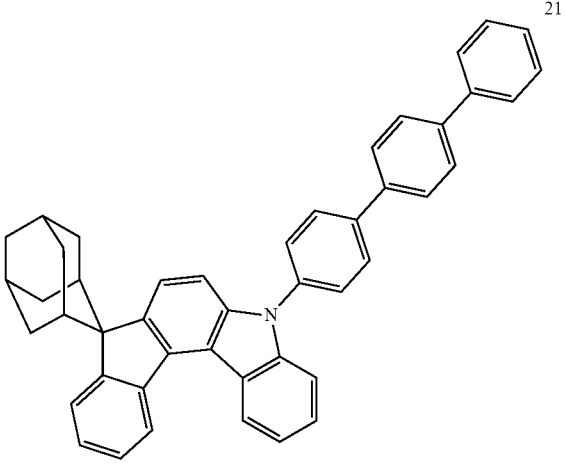
22
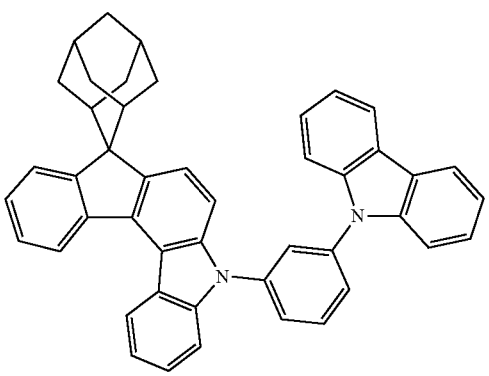

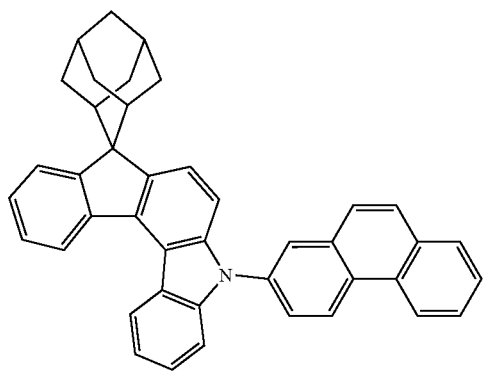
23
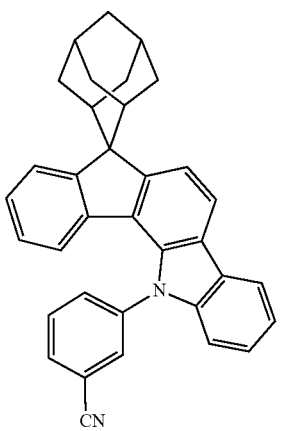
26
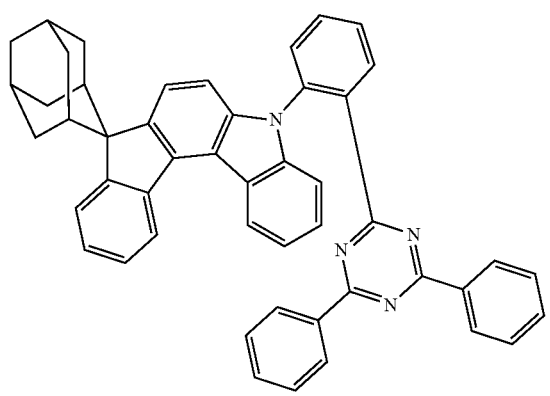
24
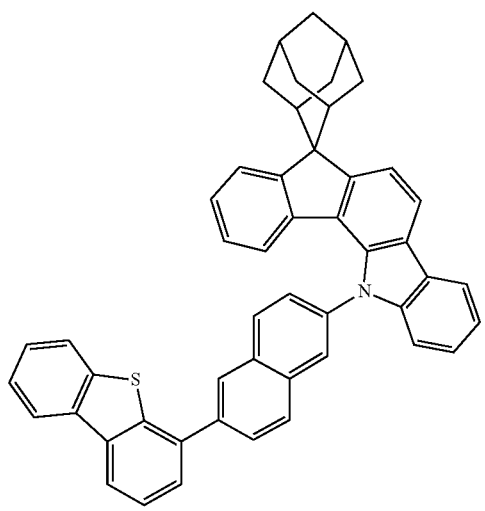
27
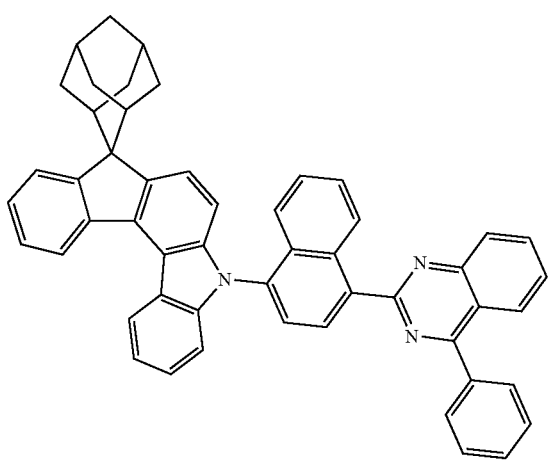
25
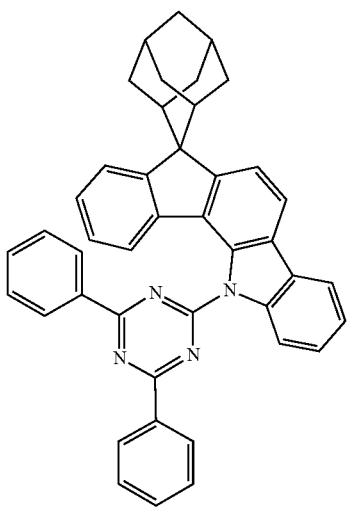
28

29
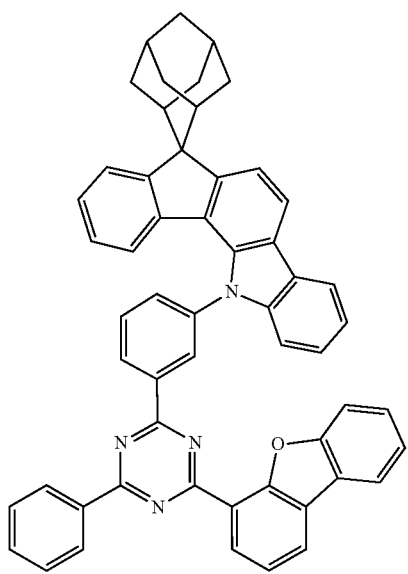
30
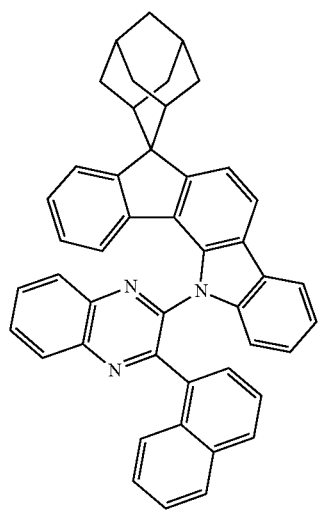
31
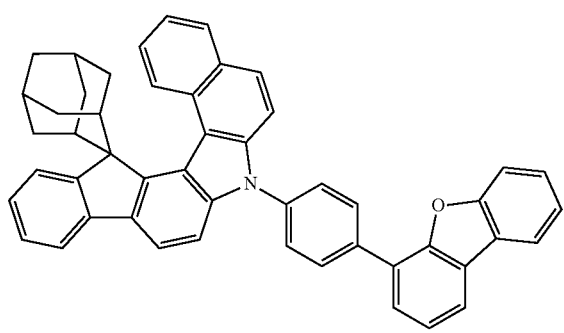
32
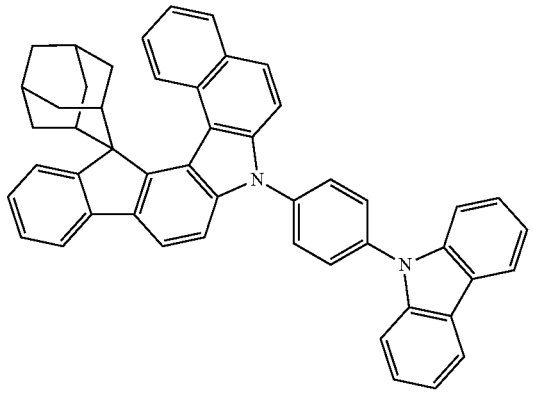
33
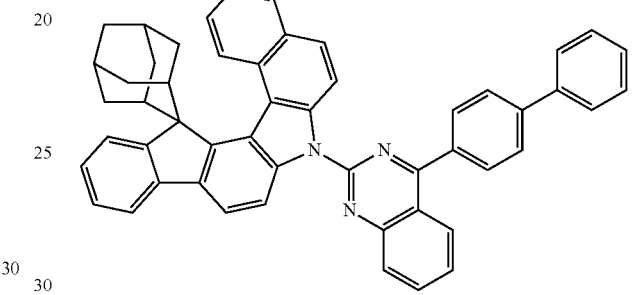
34
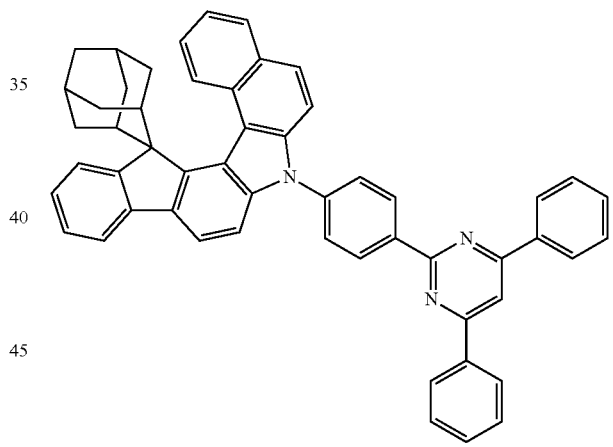
35
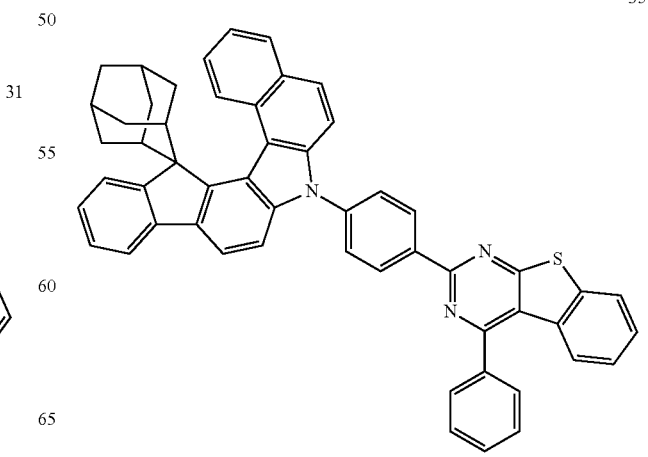

36
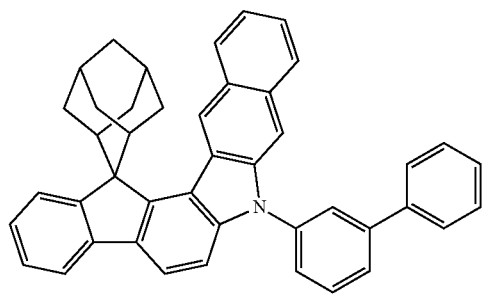
37
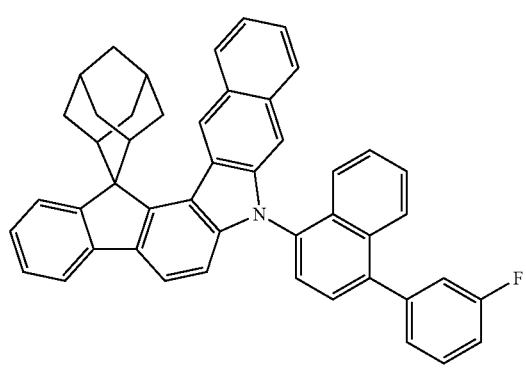
38
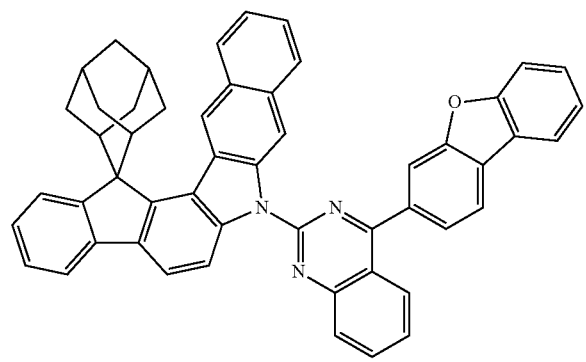
39
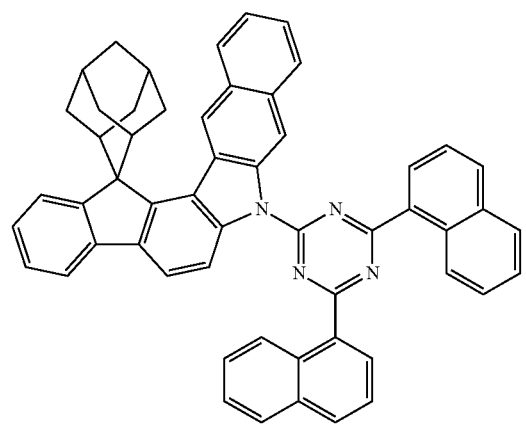
40
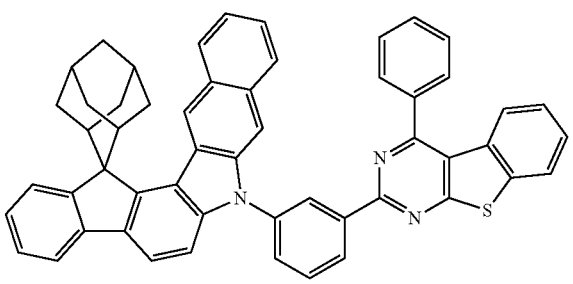
41
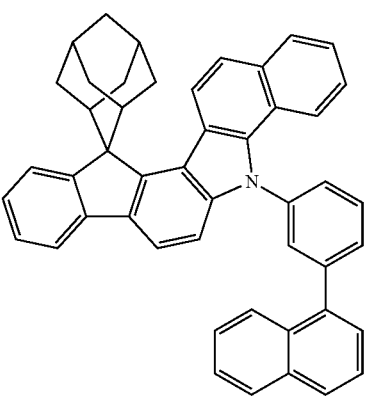
42
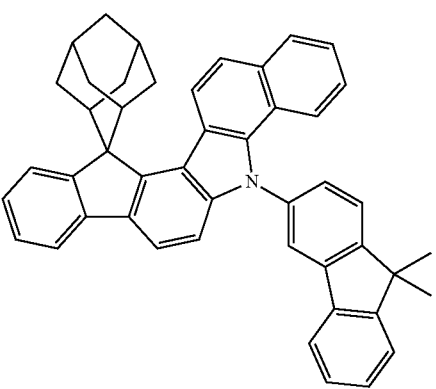
43
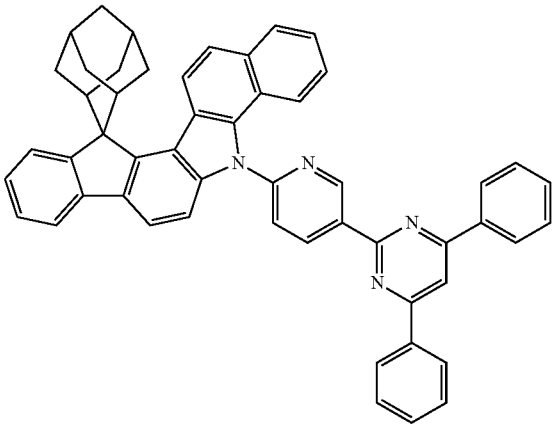

44
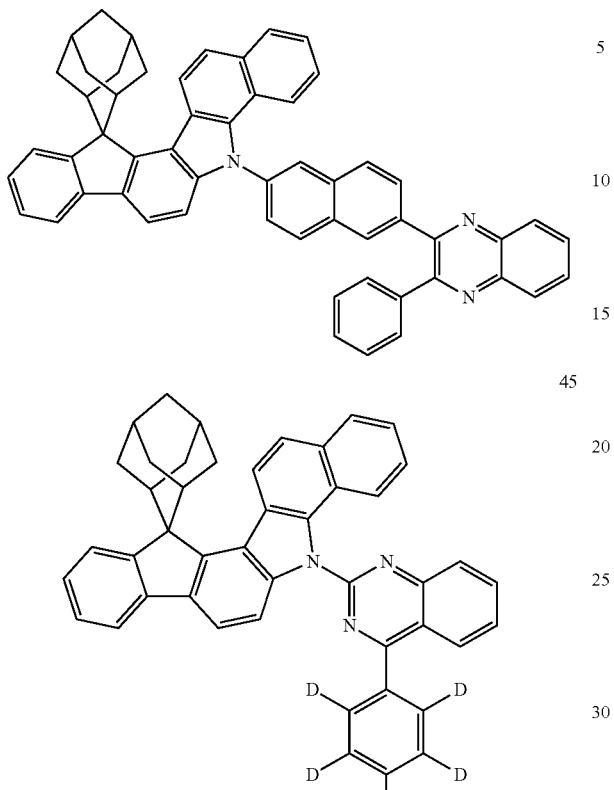
45
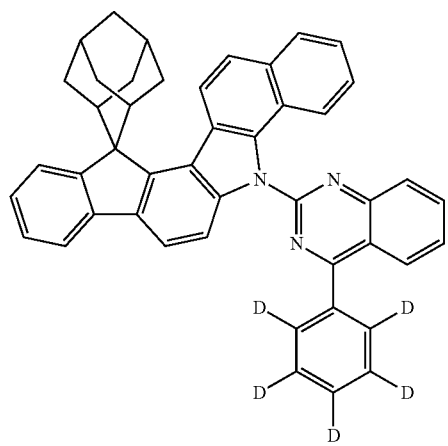
46
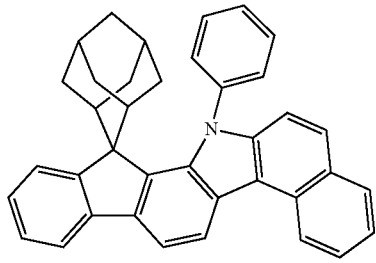
47
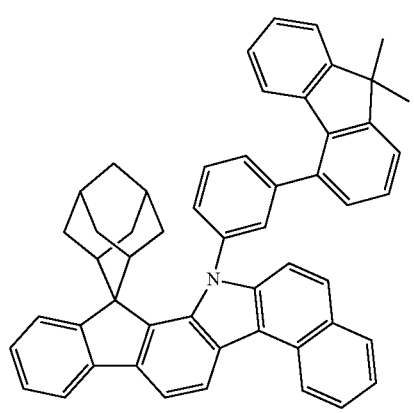
48
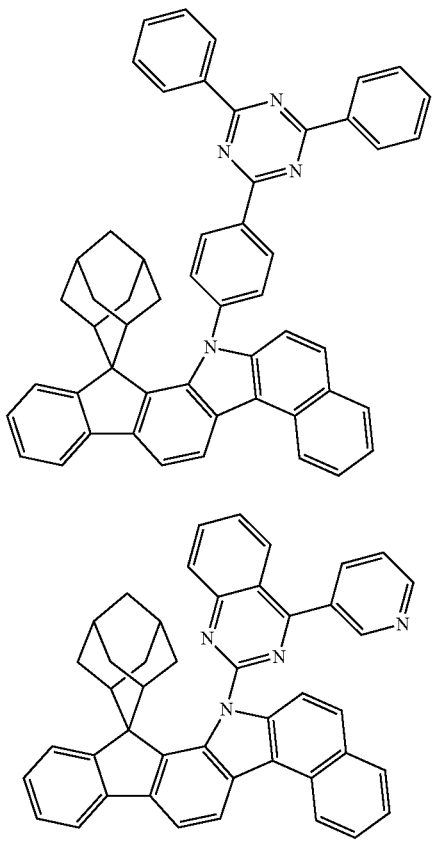
49
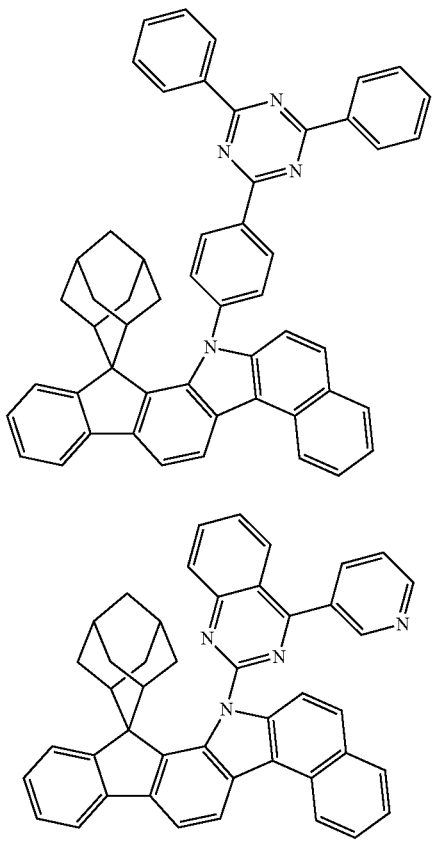
50
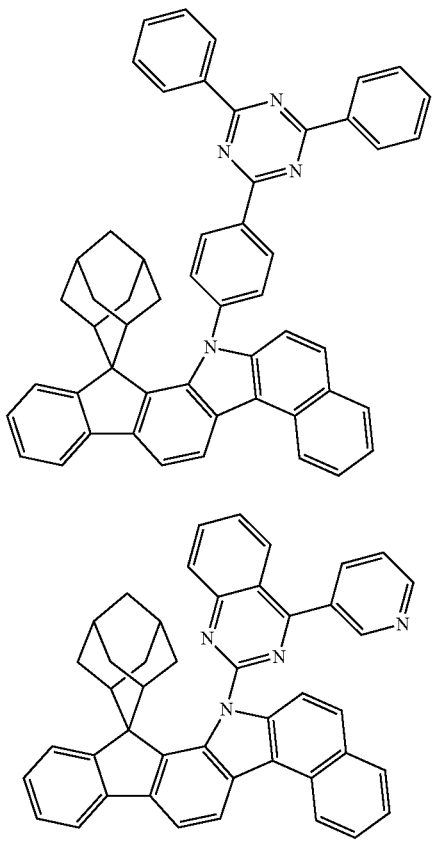
51
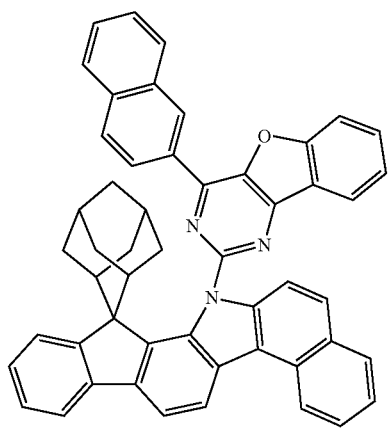

US 11,631,820 B2
53
-continued
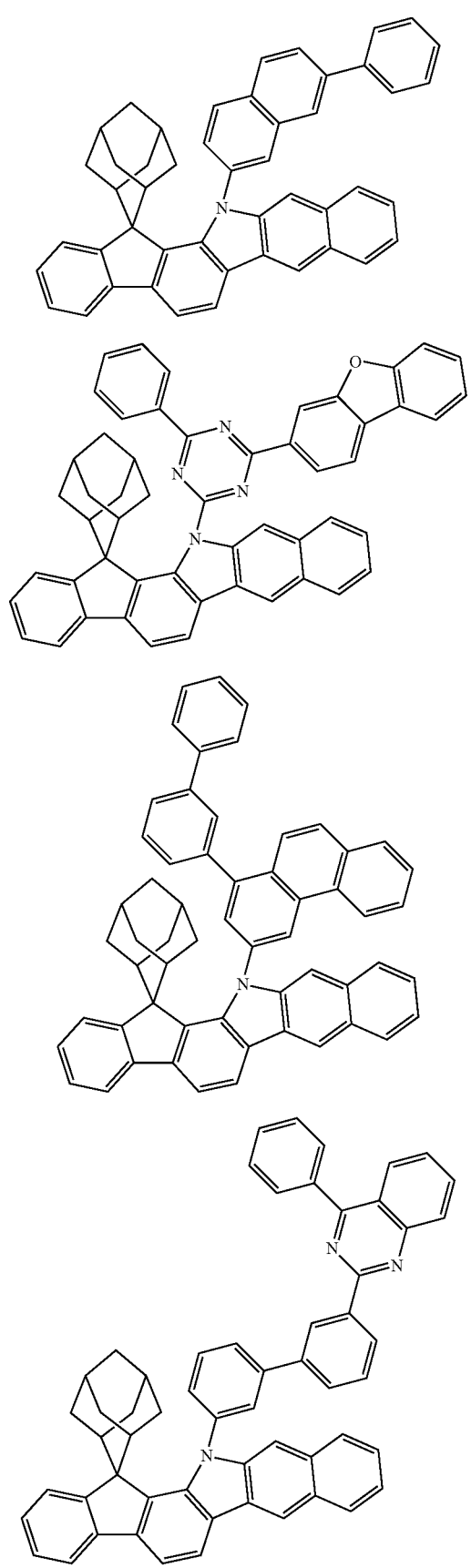
54
-continued
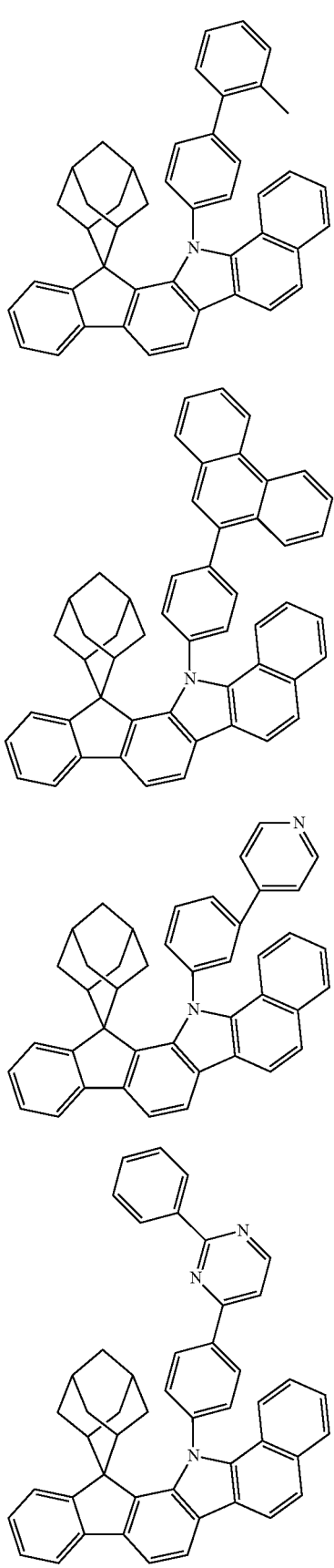

60
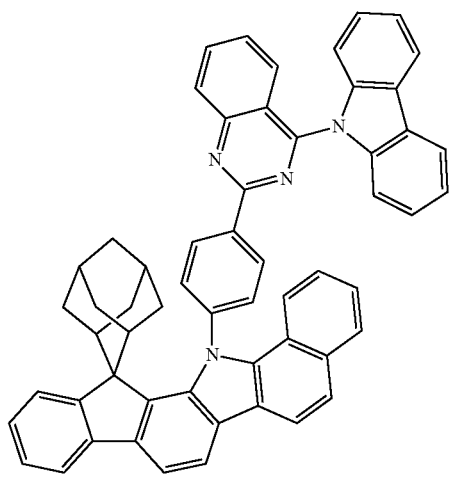
61
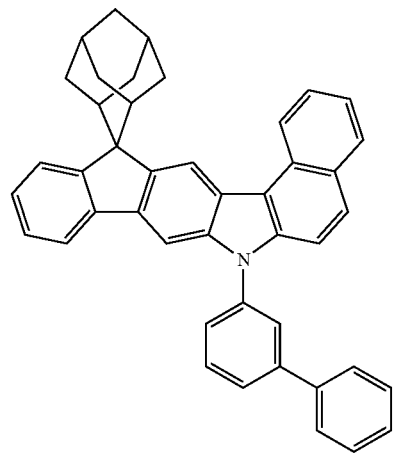
62
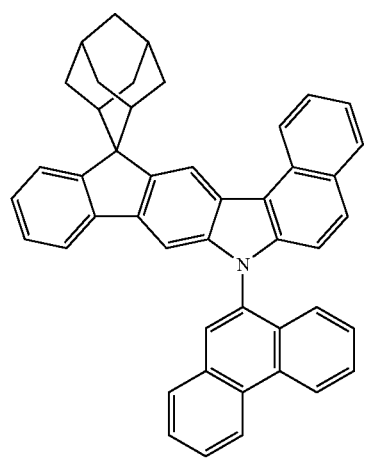
63
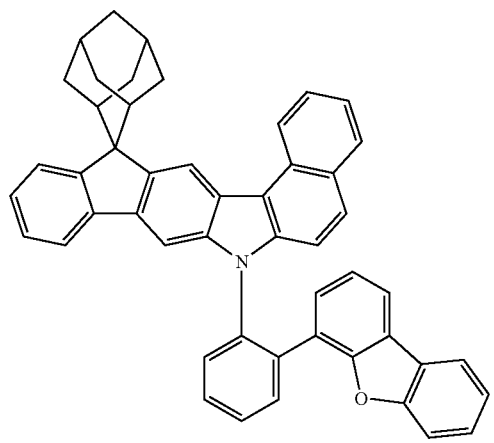
64
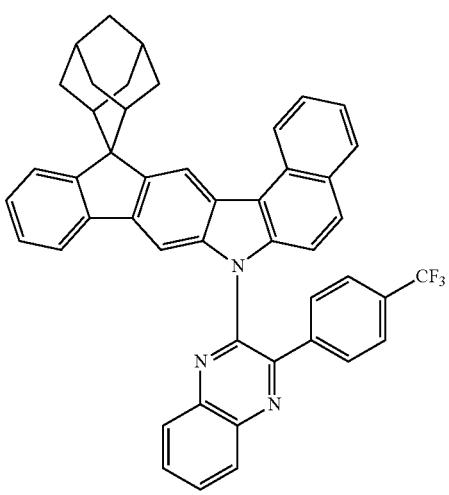
65
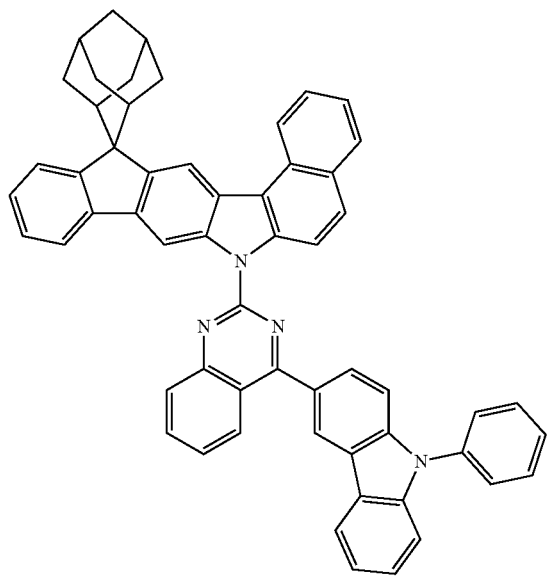

66
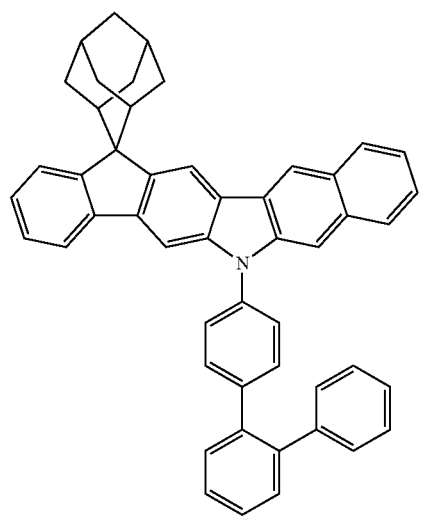
67
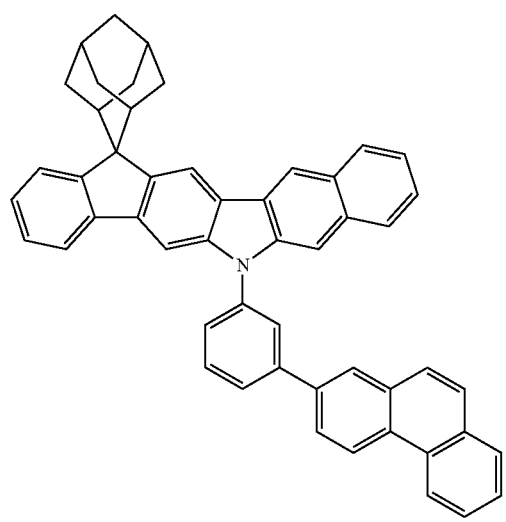
68
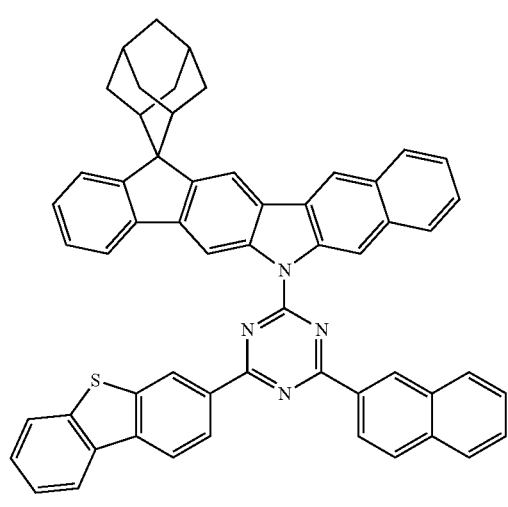
69
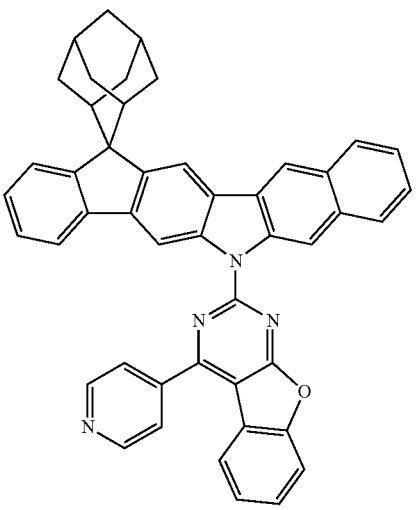
70
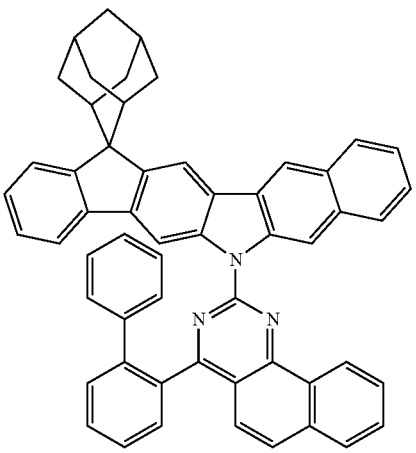
71
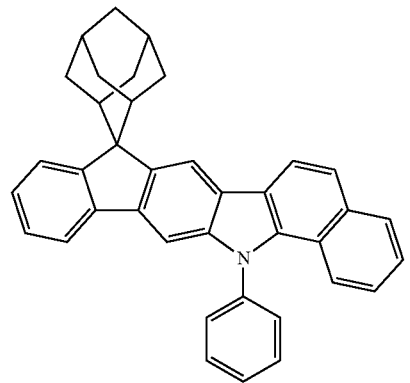

72
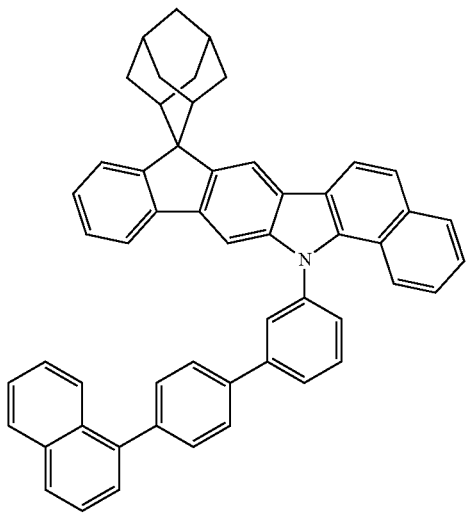
73
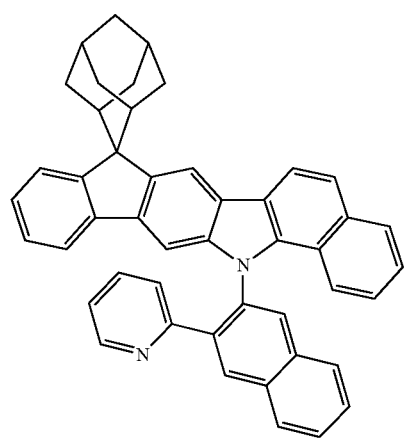
74
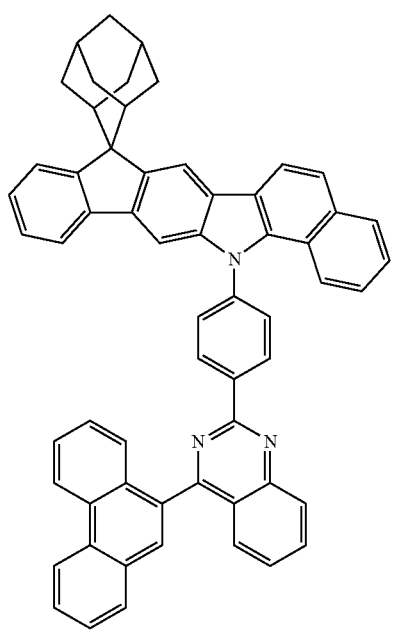
75
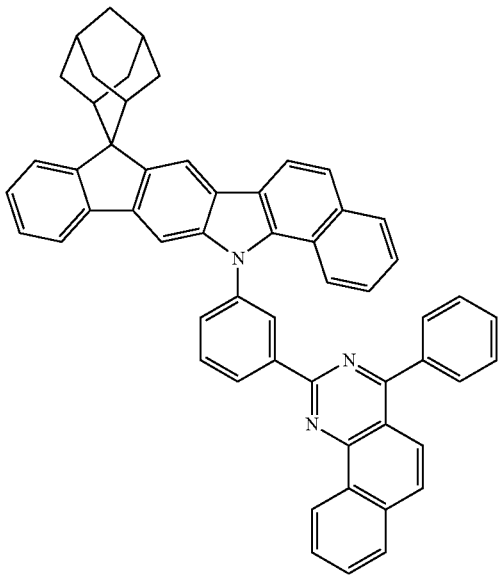
76
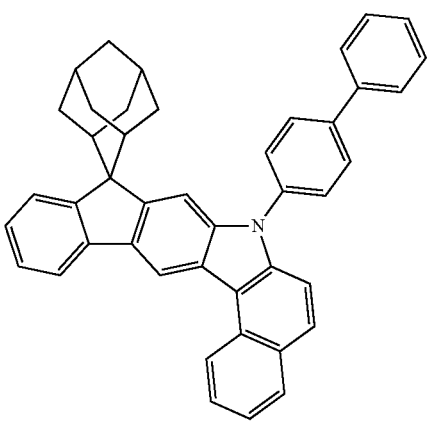
77
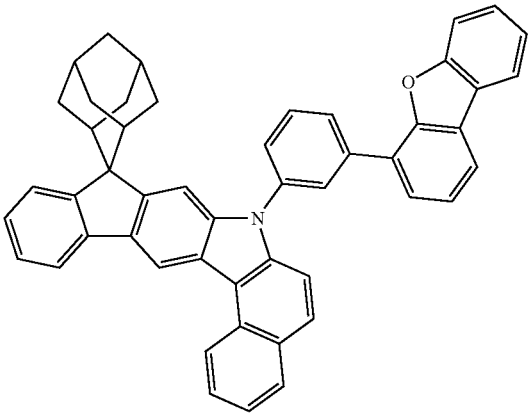

78
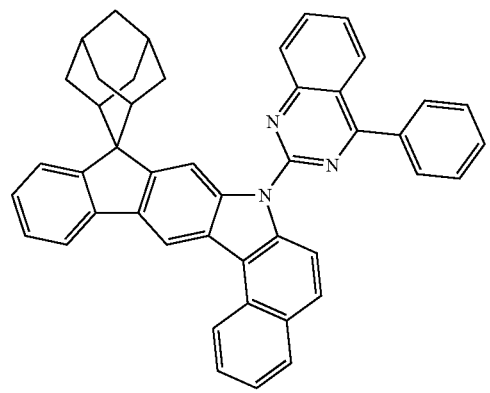
79
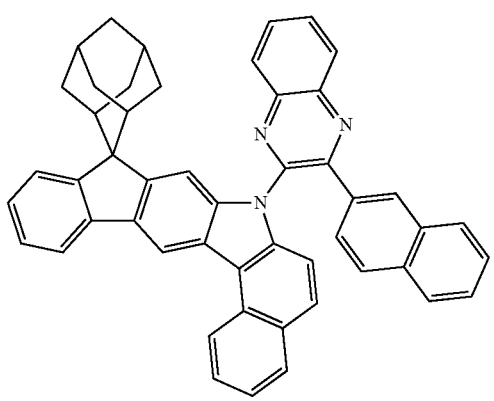
80
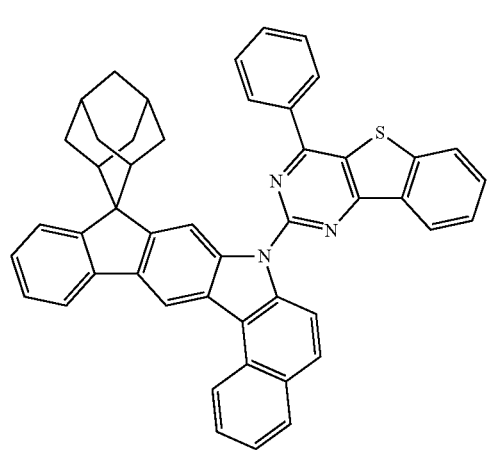
81
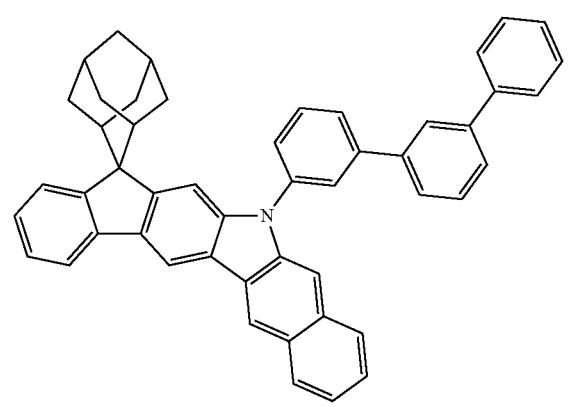
82
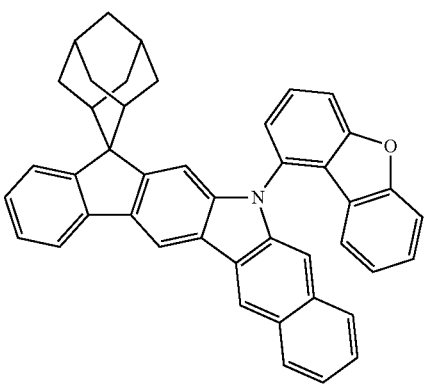
83
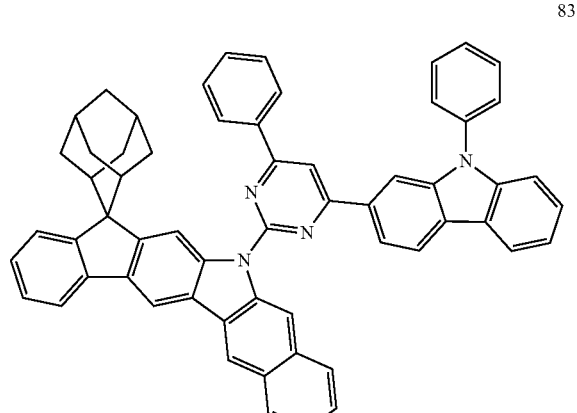
84
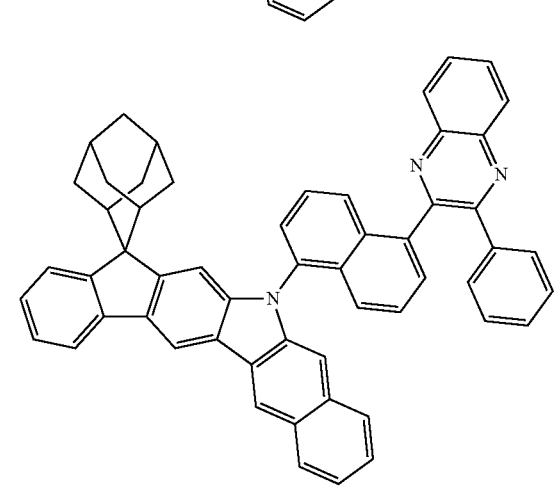
85
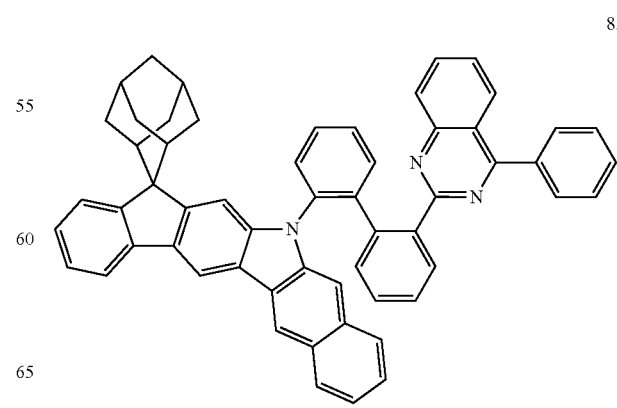

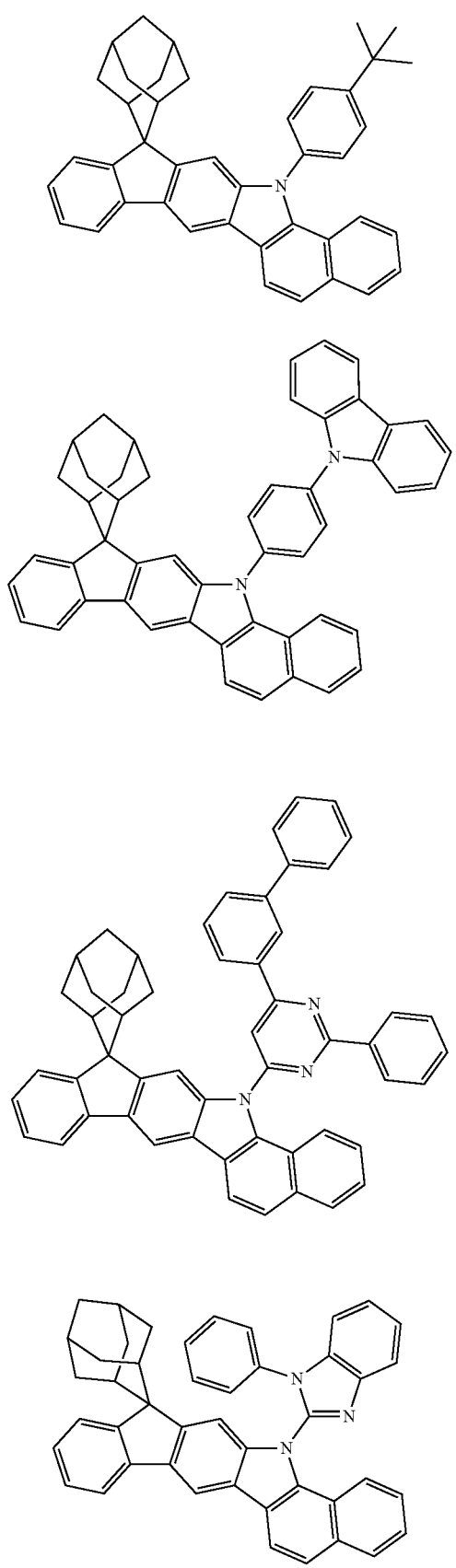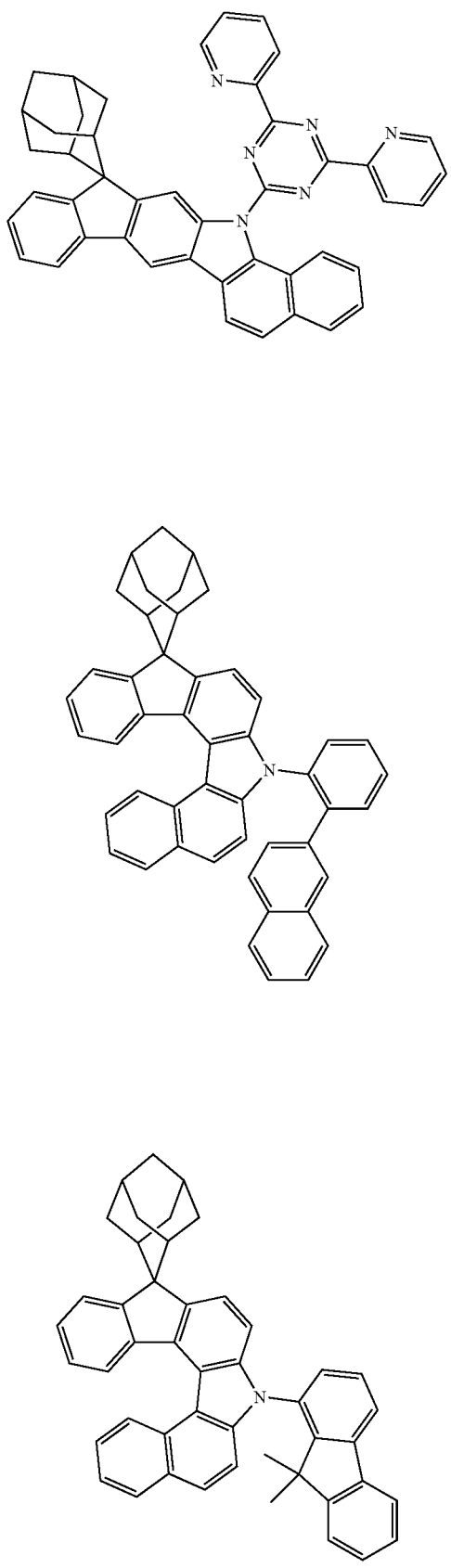

93
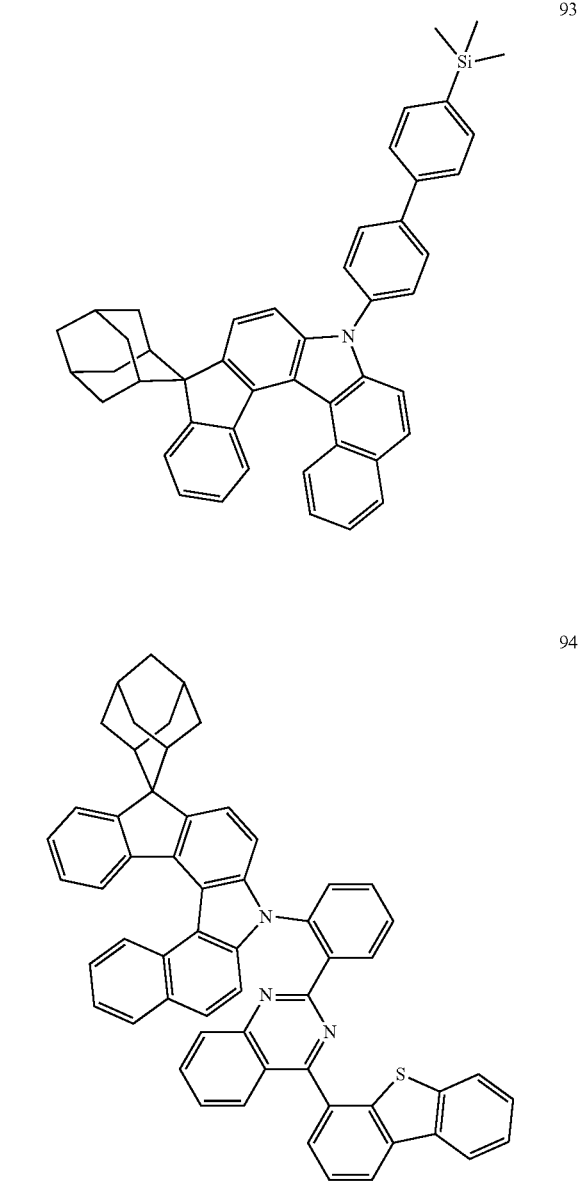
94
96
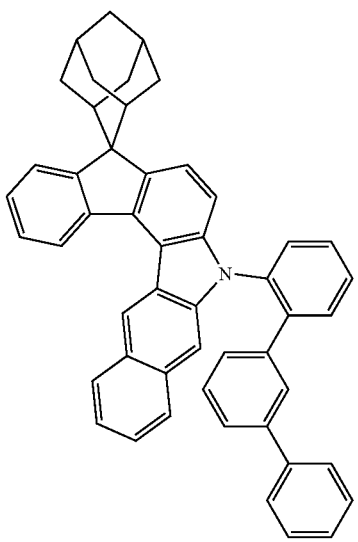
97
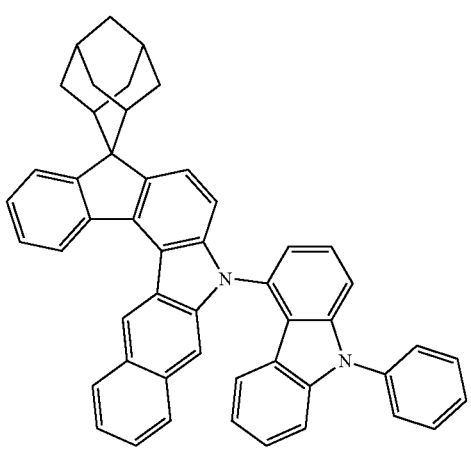
95
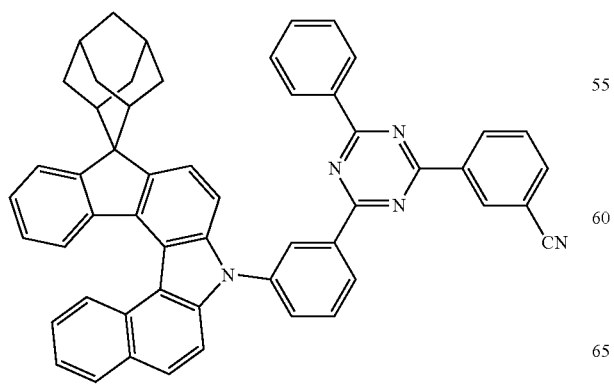
98
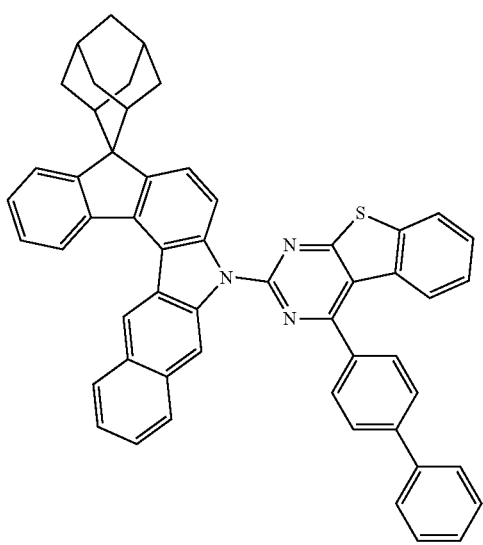

99
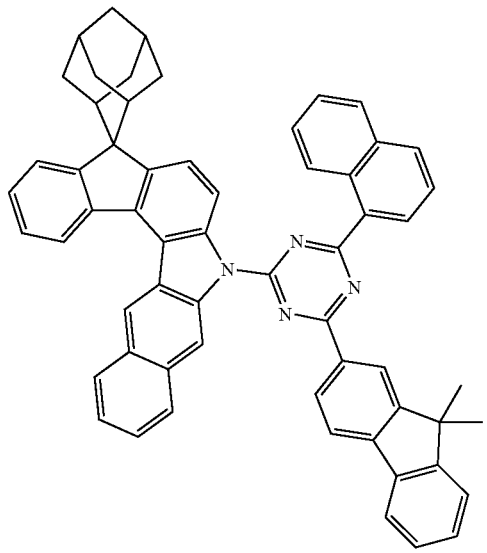
100
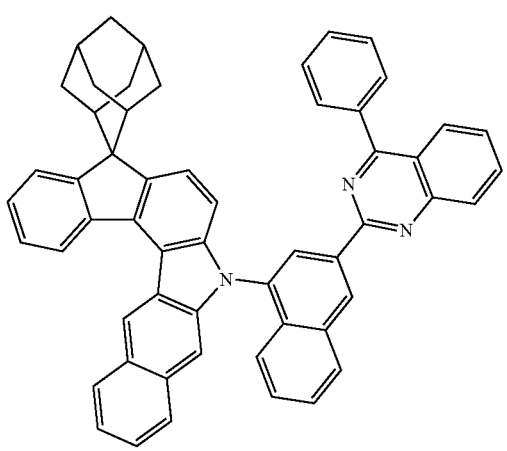
101
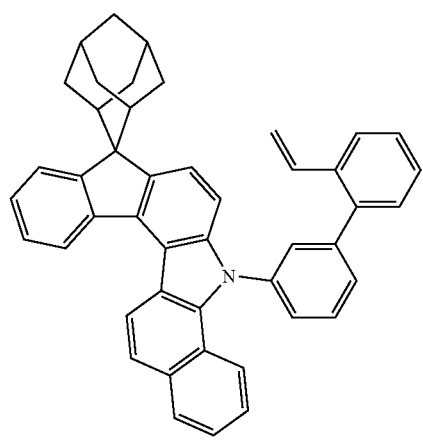
102
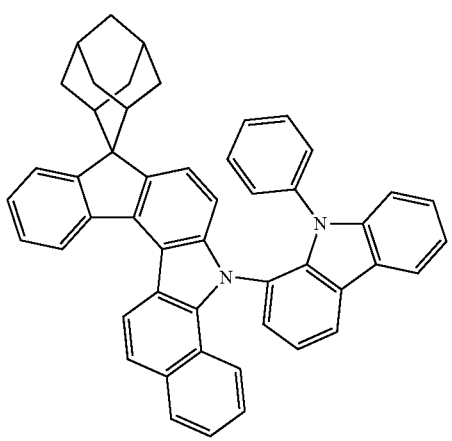
103
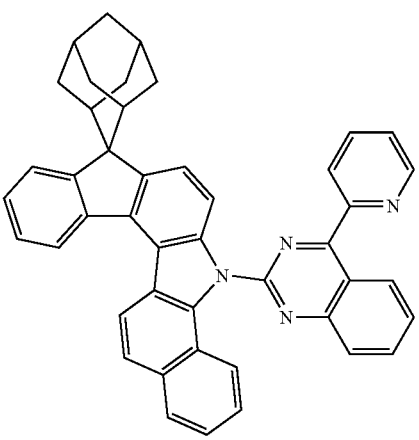
104
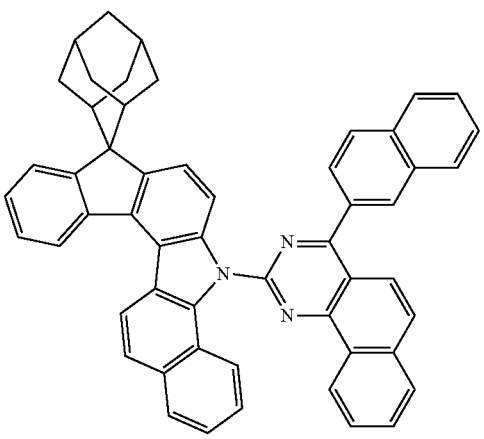

105
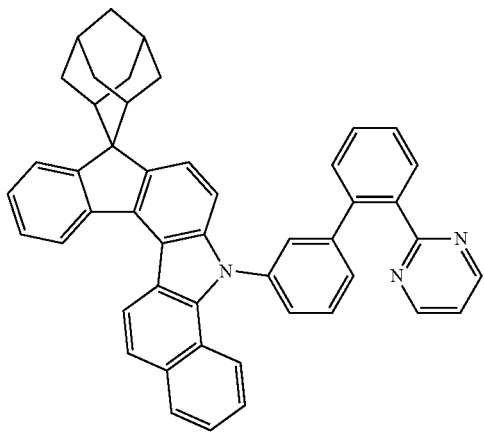
106
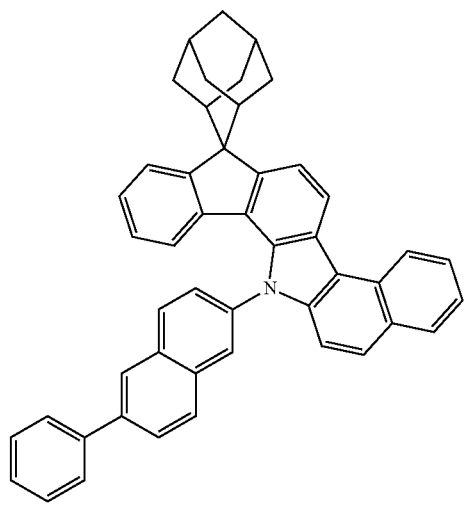
107
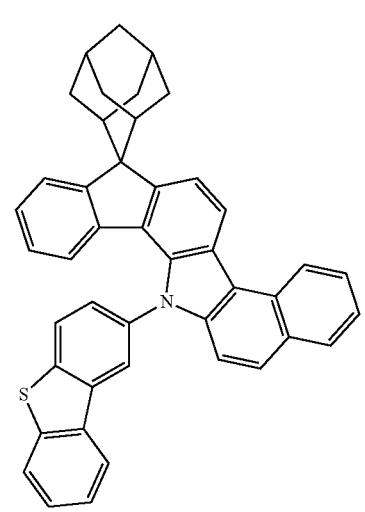
108
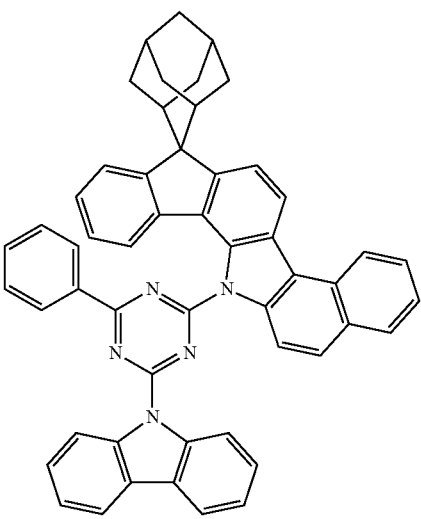
109
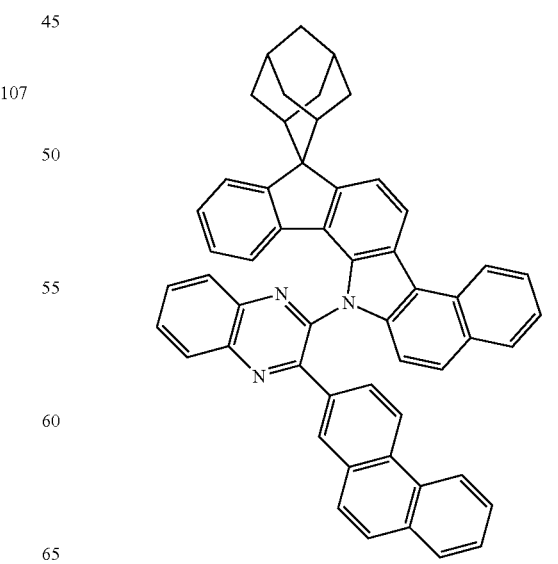
110

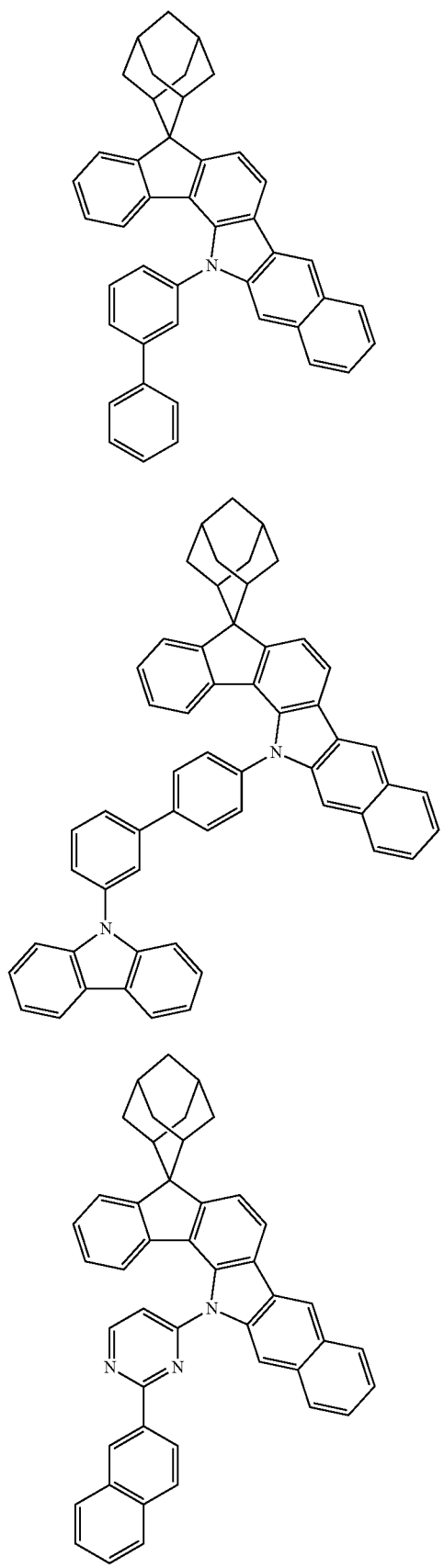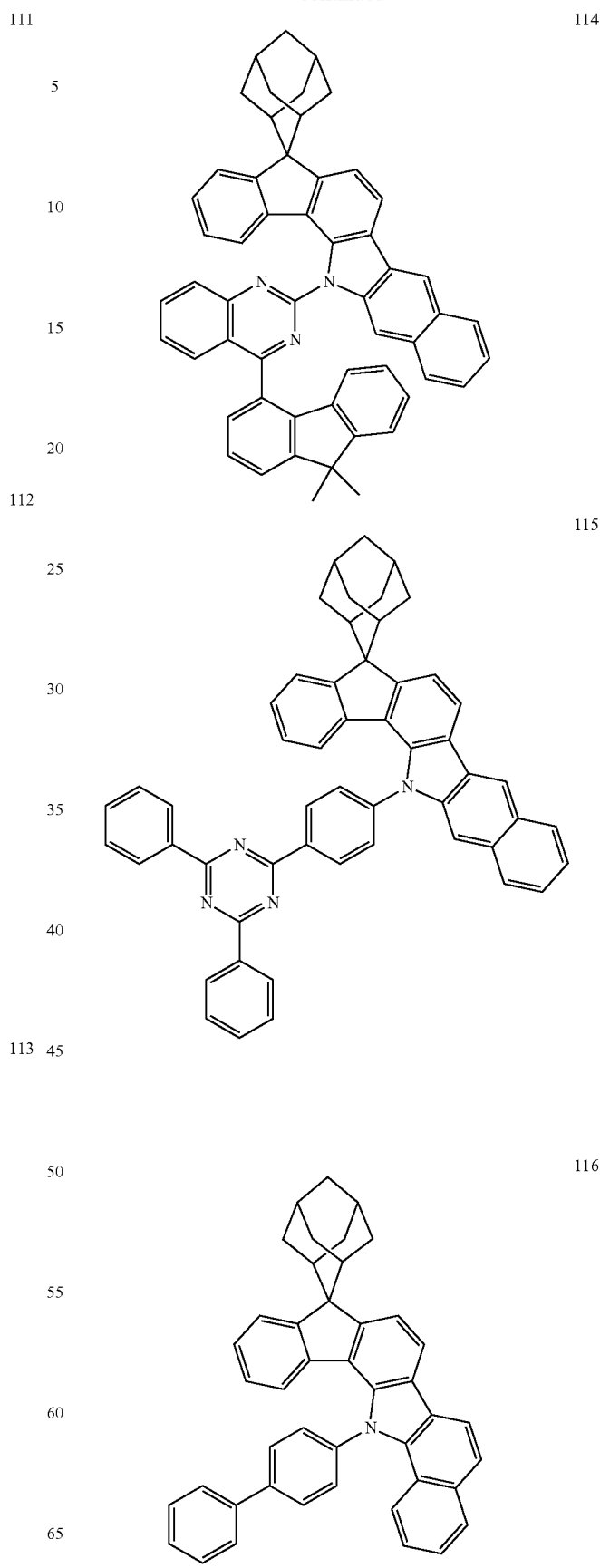

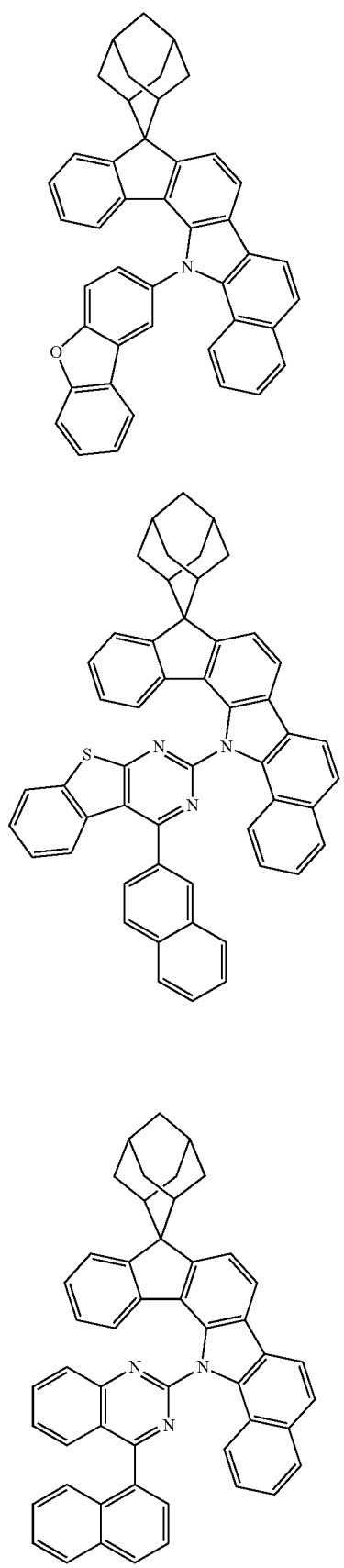
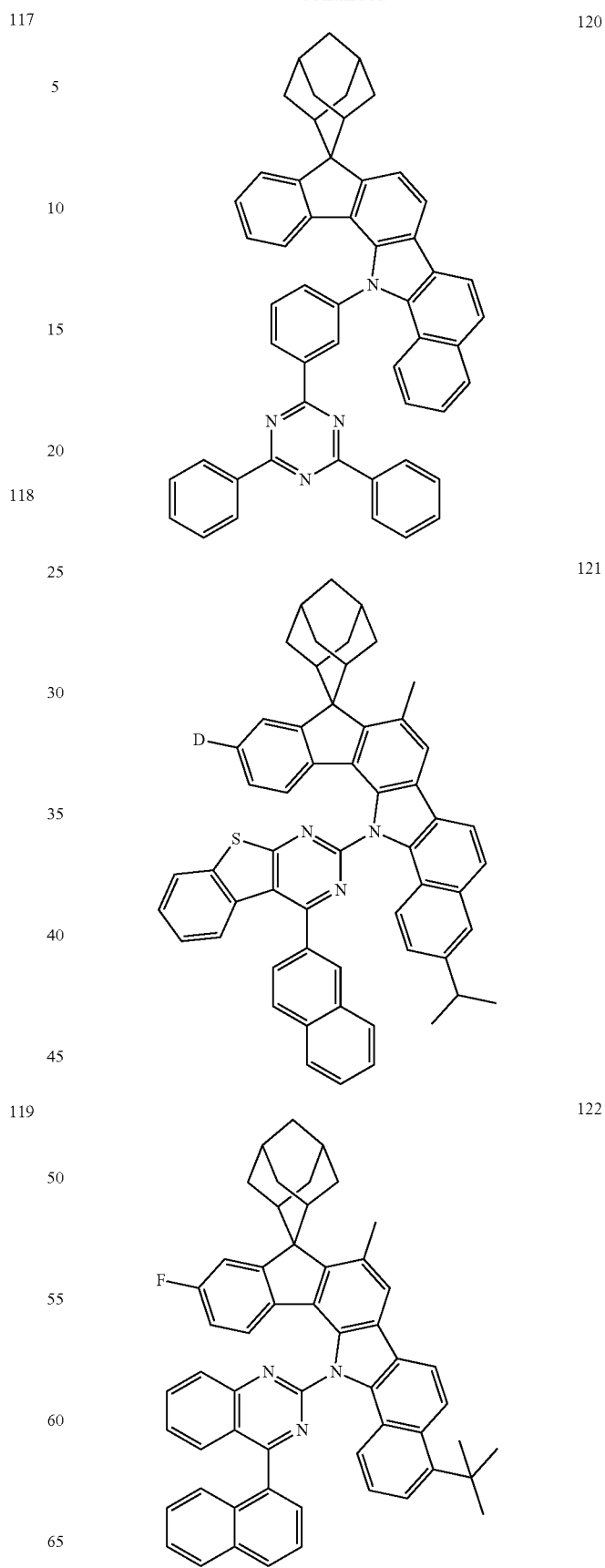

123
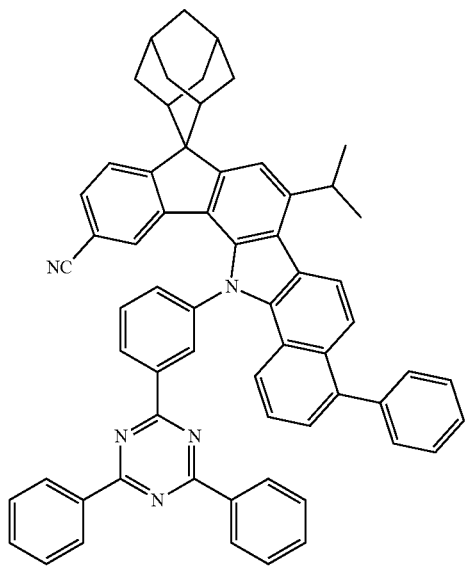
125
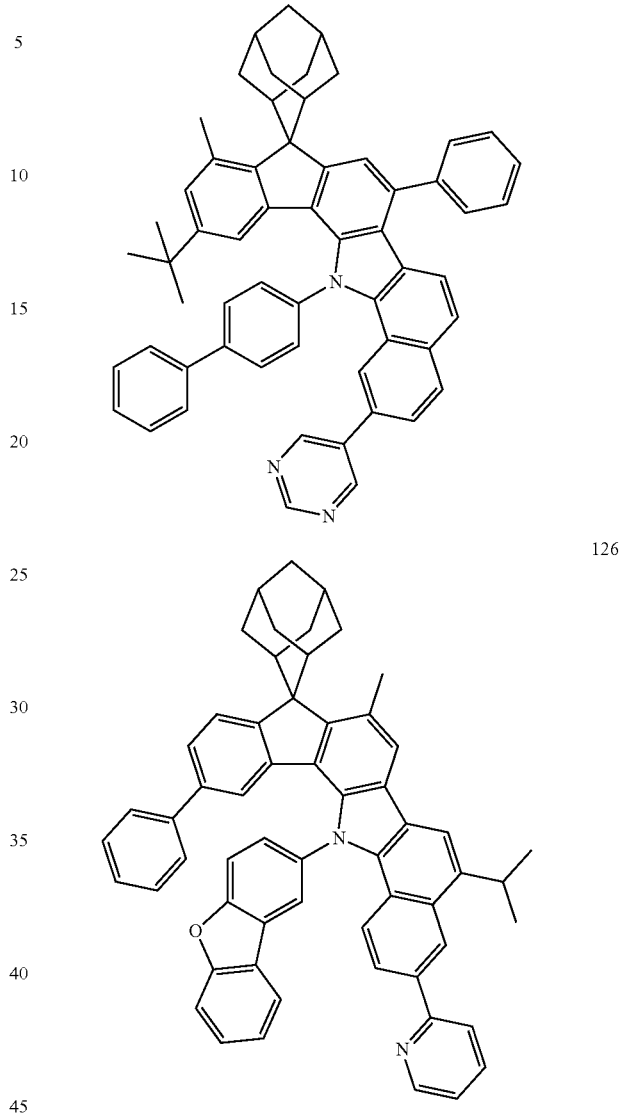
126
124
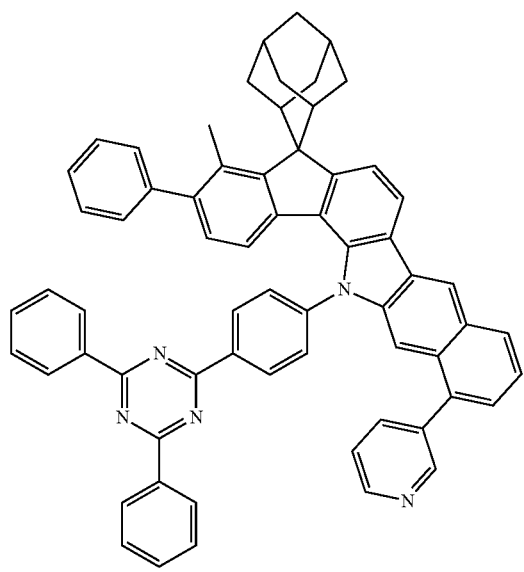
127
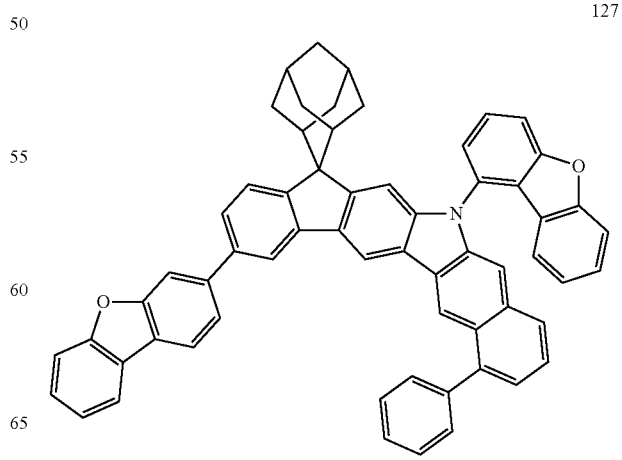

128
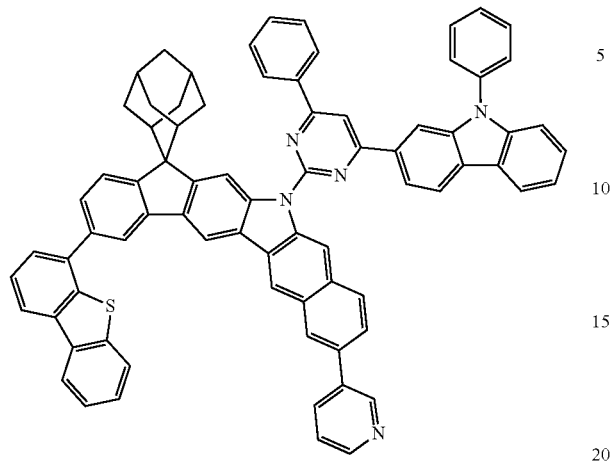
129
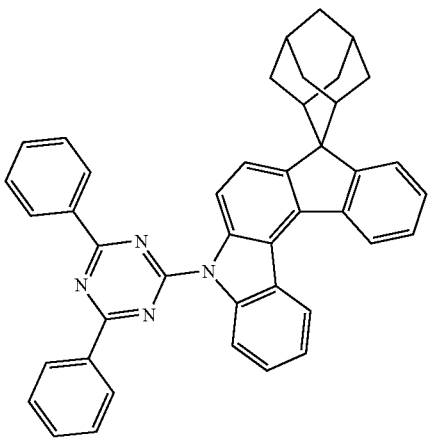
130
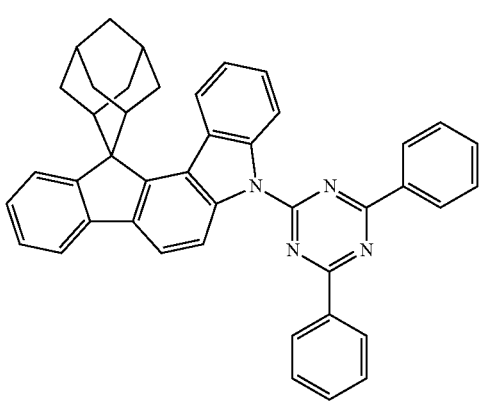
131
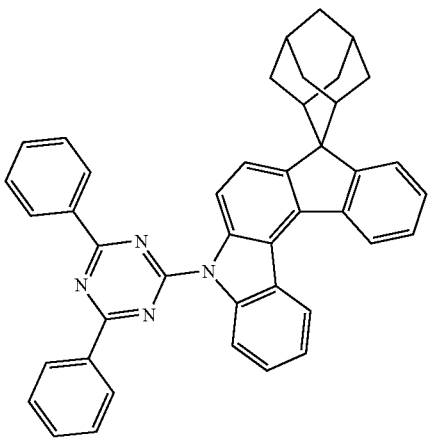
132
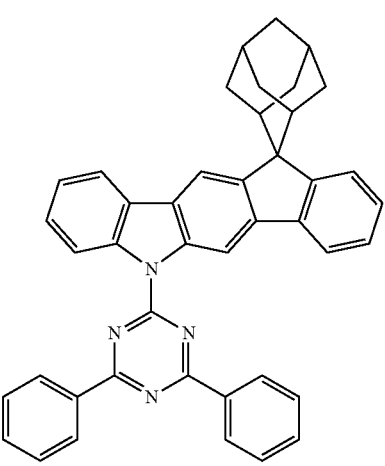
133
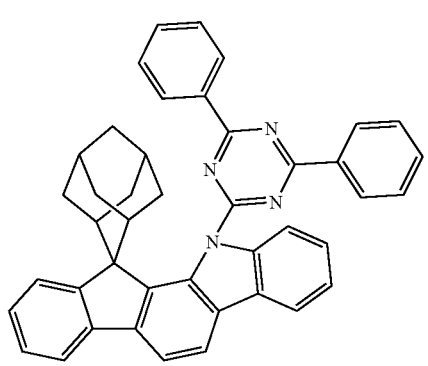
134
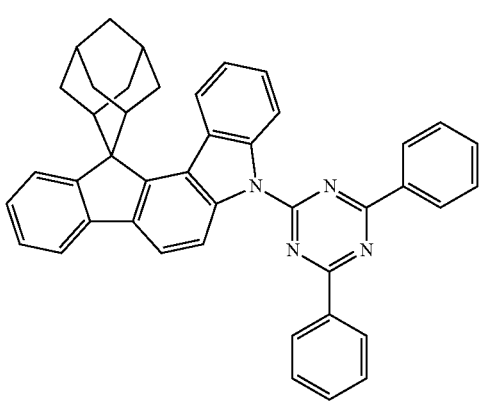

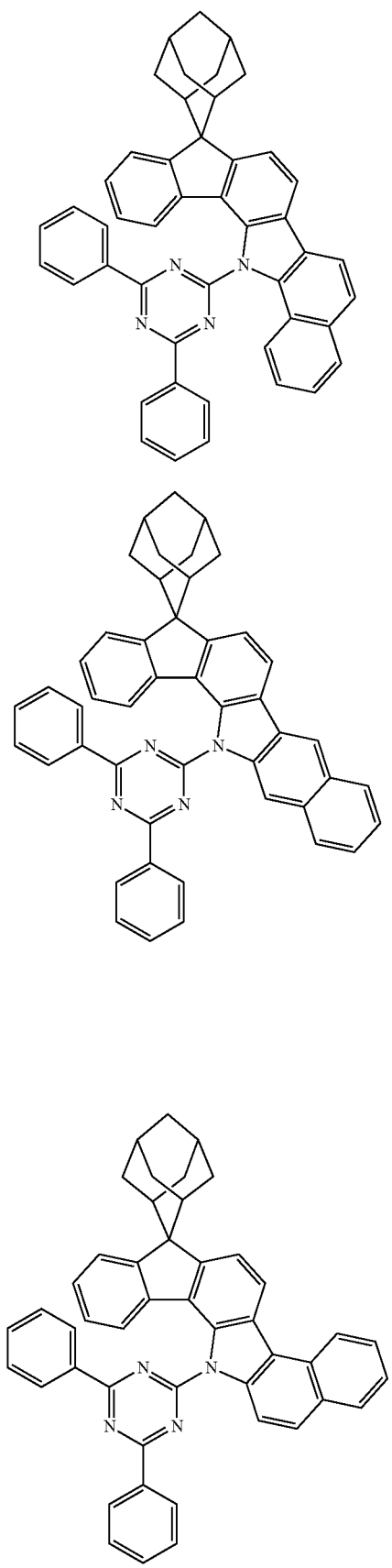
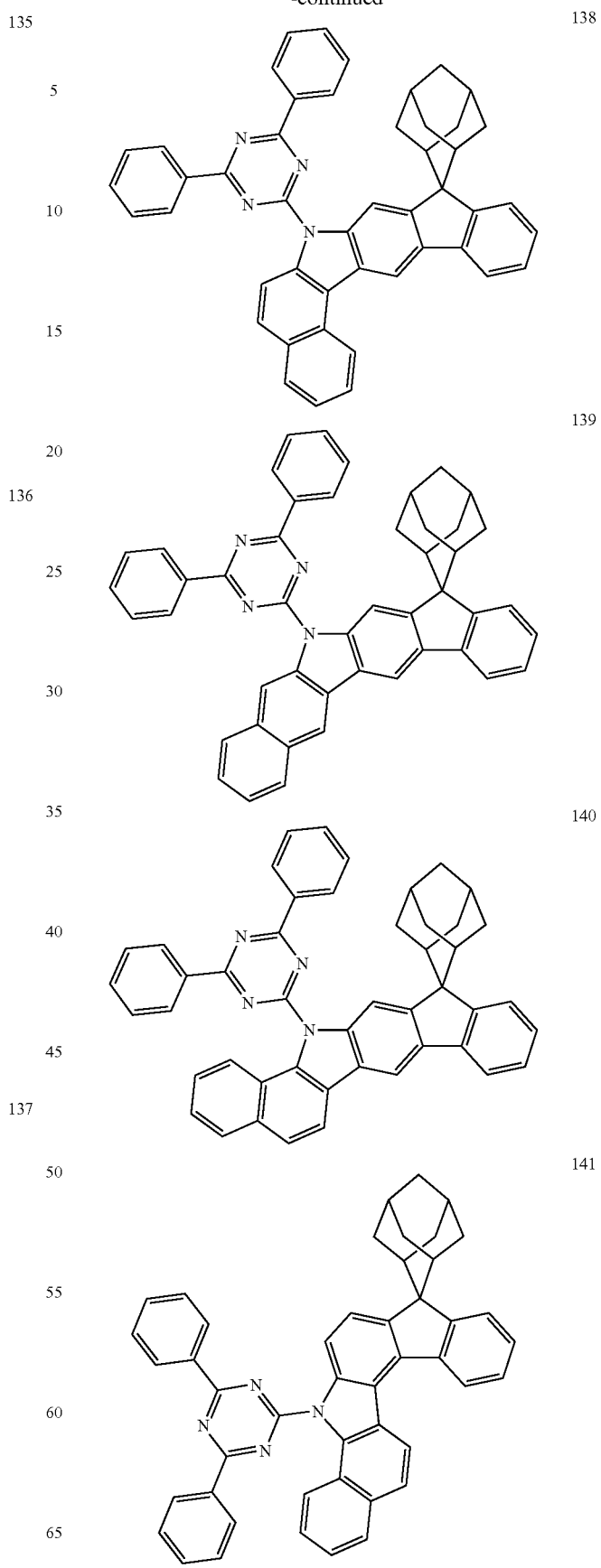

142
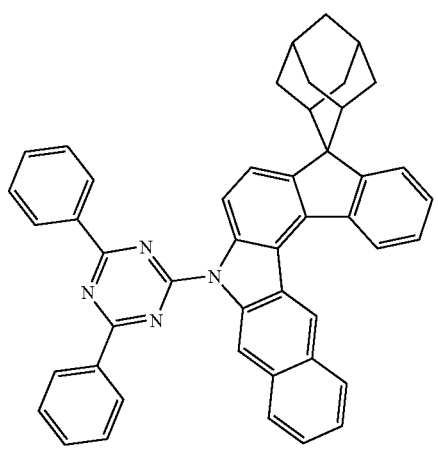
143
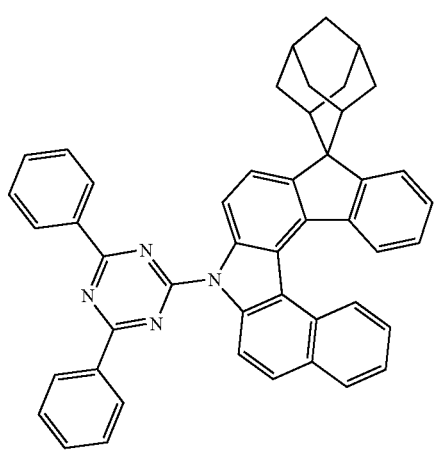
144
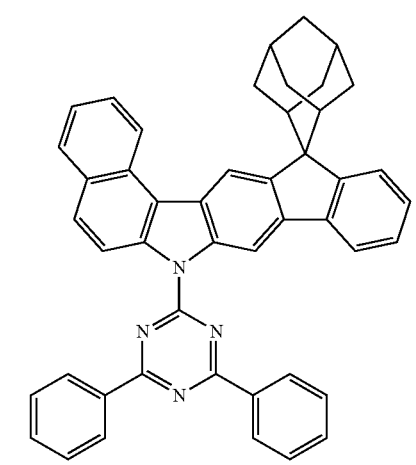
145
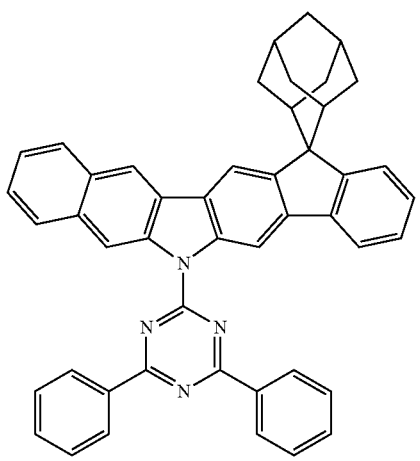
146
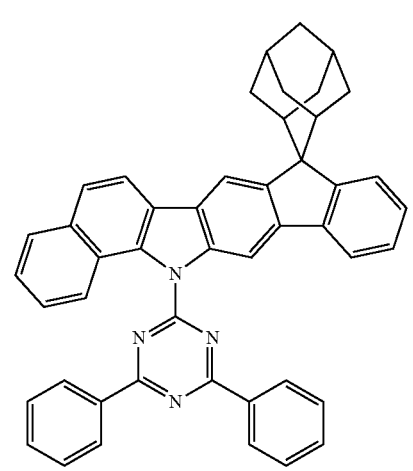
147
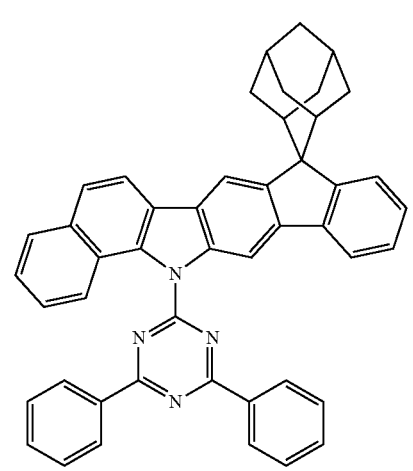
148
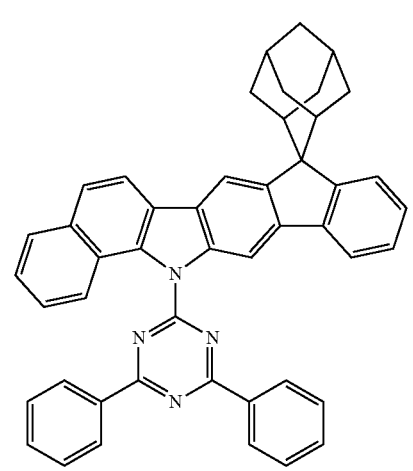

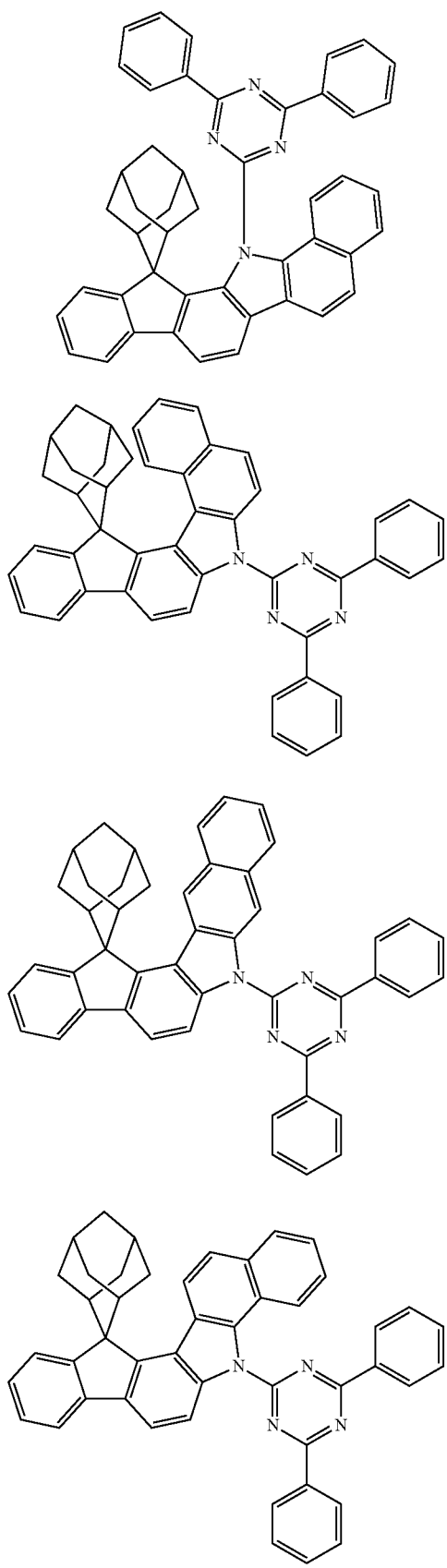
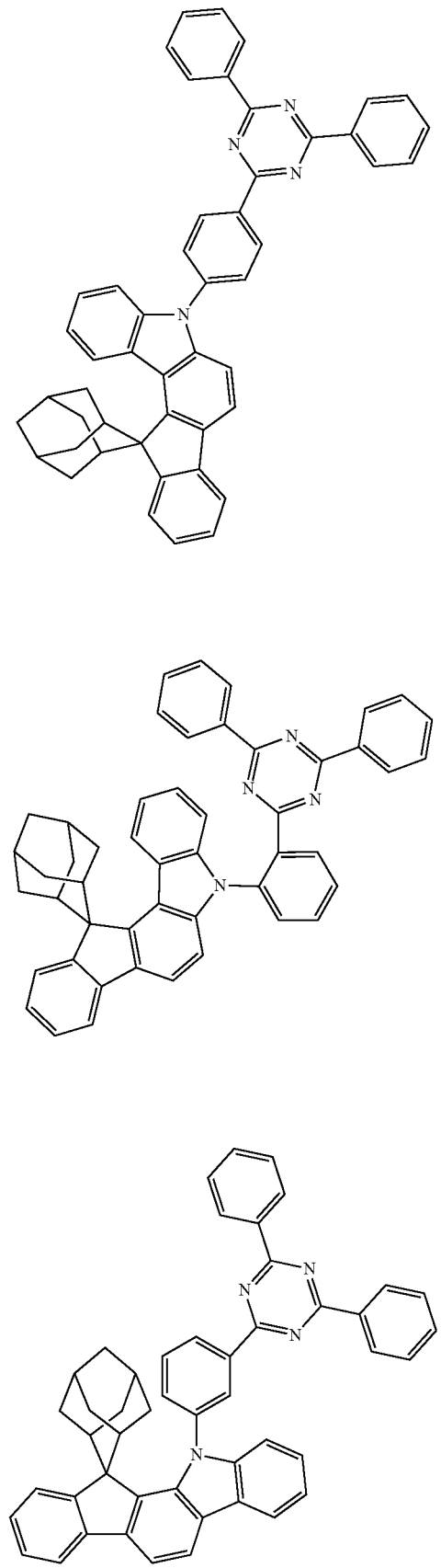

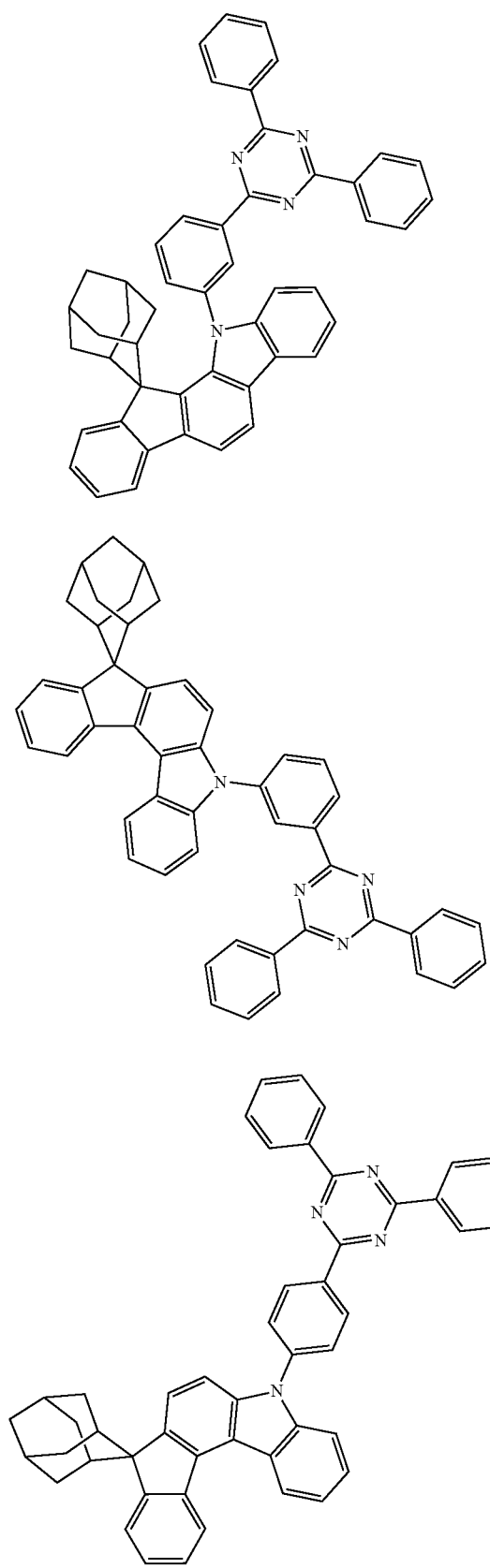

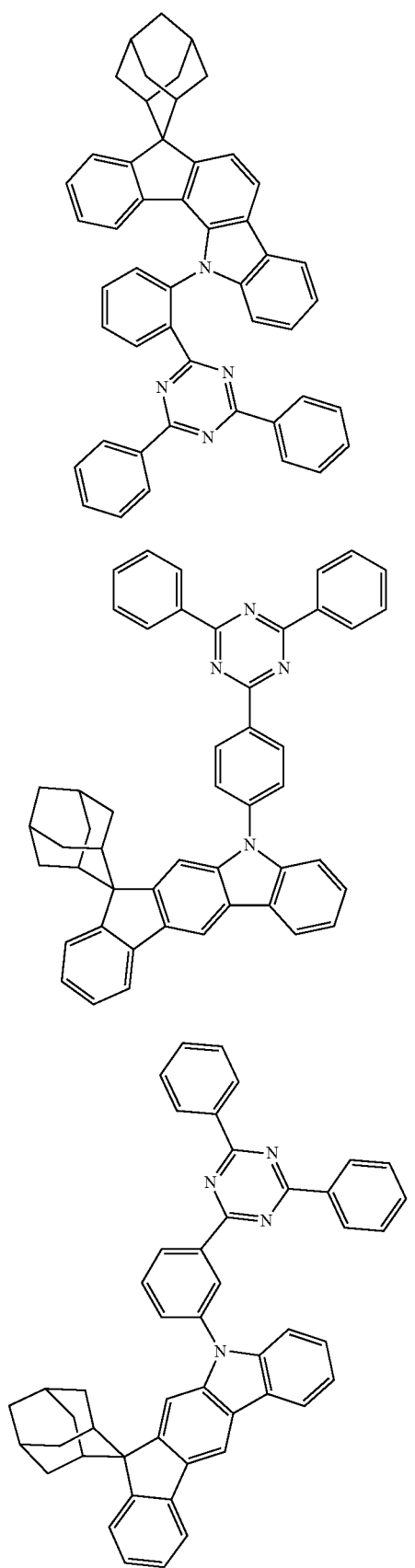
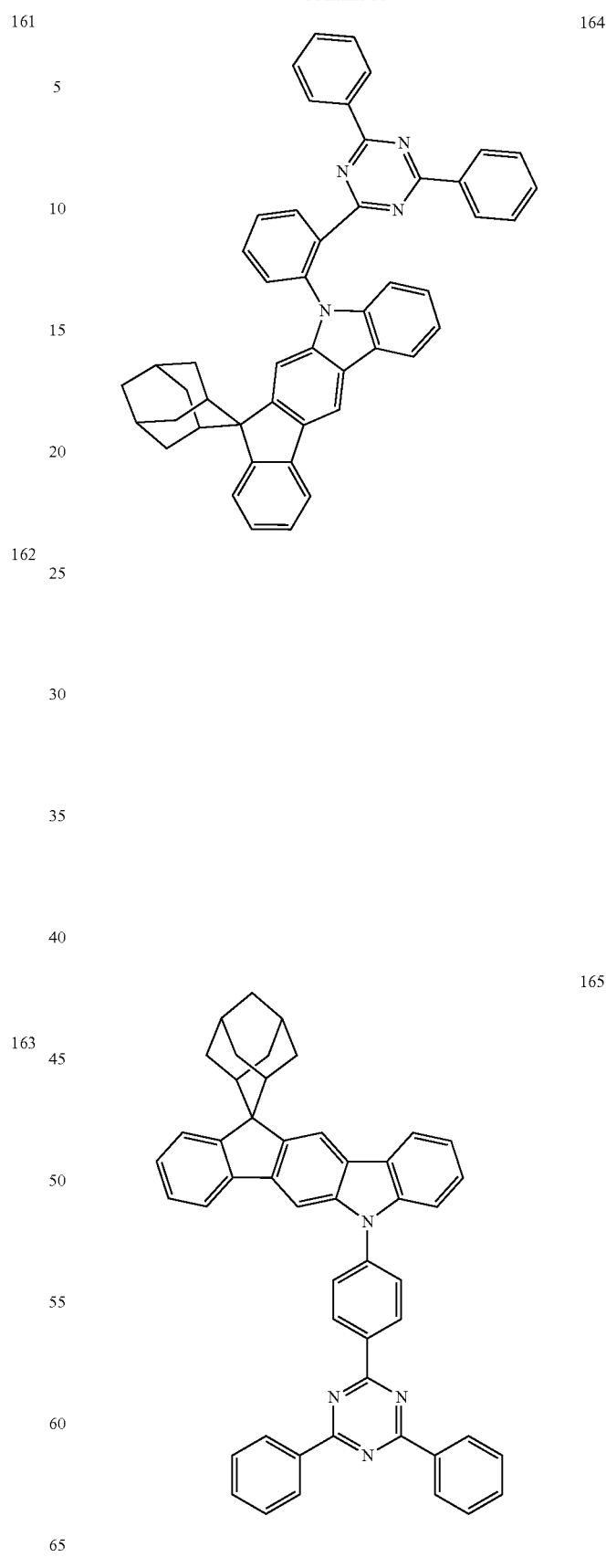

166

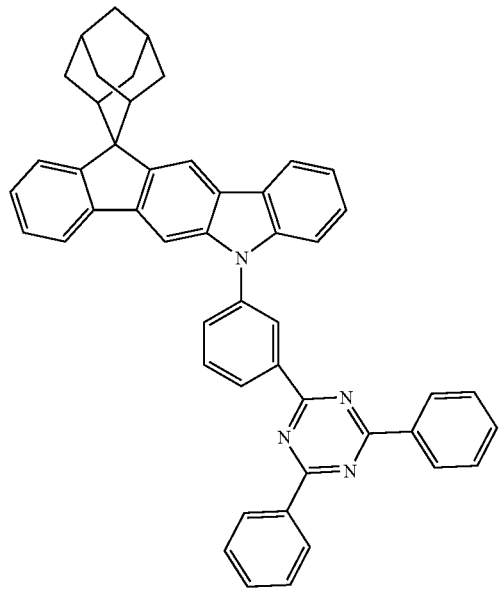

167

168

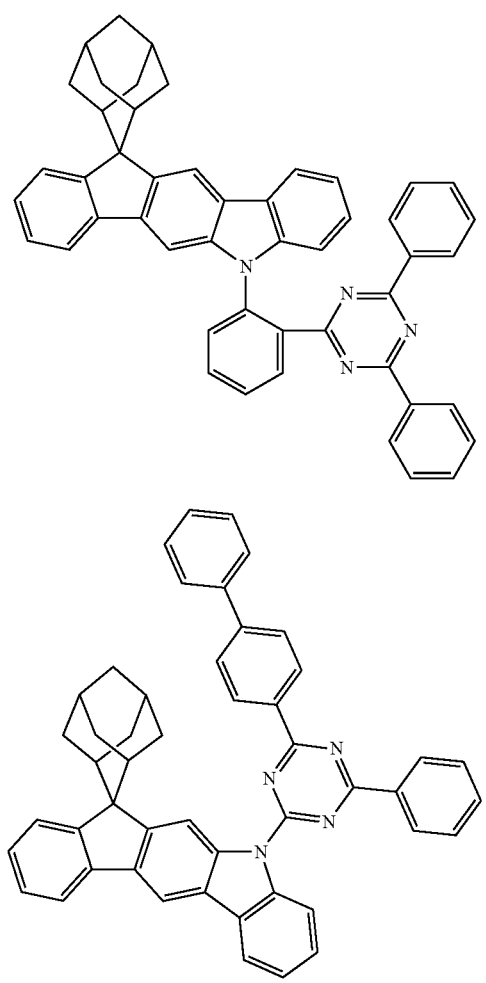

169

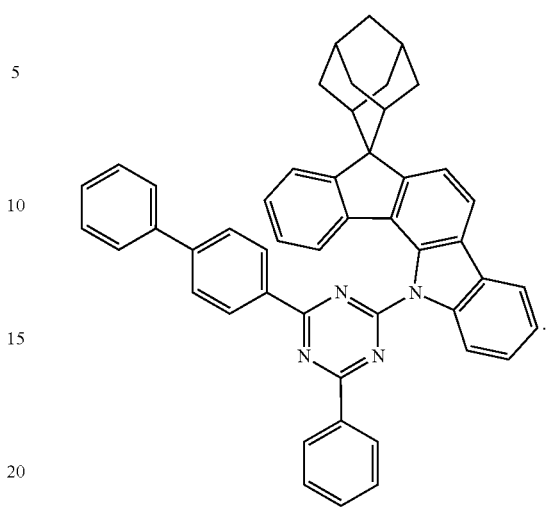

The following synthesis examples and examples are used to further illustrate and explain the content of the present disclosure.

Generally, the organic compound of the present disclosure can be prepared by the method described in the present disclosure. Unless otherwise specified, substituent symbols mentioned in the present disclosure have the same meanings as the substituent symbols in Chemical formula 1. Those skilled in the art will recognize that the chemical reactions described in the present disclosure can be used to appropriately prepare many other compounds of the present disclosure, and other methods for preparing the organic compounds of the present disclosure are considered to be within the scope of the present disclosure. For example, those skilled in the art can synthesize other organic compounds of the present disclosure with reference to or by appropriately modifying the preparation methods provided in the present disclosure, such as with the help of appropriate protecting groups, using other known reagents, and modifying reaction conditions, and the like, in addition to those described in the present disclosure.

In the synthesis examples described below, unless otherwise stated, temperatures are expressed in Celsius (° C.).

The compounds in the present disclosure were synthesized by the following methods:

Synthesis of Intermediate a-1

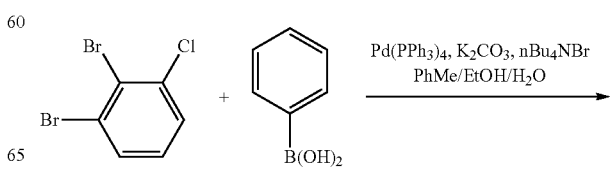

-continued

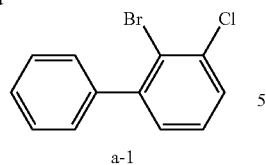

a-1

1,2-dibromo-3-chlorobenzene (80.0 g, 298.7 mmol), phenylboronic acid (36.5 g, 298.7 mmol), tetrakis(triphenylphosphine)palladium (6.9 g, 6.0 mmol), potassium carbonate (103.2 g, 746.7 mmol), and tetrabutylammonium bromide (19.2 g, 59.7 mmol) were added to a flask, then a mixed solvent of toluene (600 mL), ethanol (150 mL), and water (150 mL) was added, and under nitrogen protection, a reaction system was heated to 80° C. and stirred at the temperature for 18 h; then a resulting reaction solution was cooled to room temperature, the stirring was stopped, and the reaction solution was washed with water; a resulting organic phase was separated out, dried with anhydrous magnesium sulfate, and subjected to solvent removal under reduced pressure to obtain a crude product; and the crude product was purified through silica gel column chromatography with dichloromethane/n-heptane as a mobile phase to obtain Intermediate a-1 as a white solid (42.0 g, yield: 53%).

Intermediate b-1 and Intermediate c-1 were synthesized by a method the same as the synthesis method of Intermediate a-1, except that Reactant A in Table 1 below was used instead of 1,2-dibromo-3-chlorobenzene:

-continued

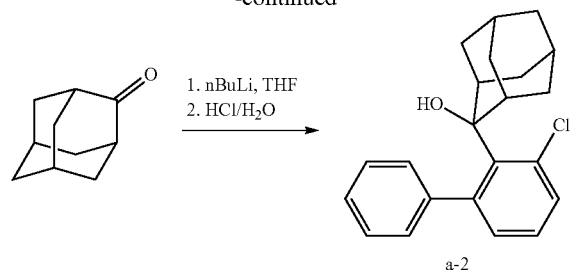

a-2

Under nitrogen protection, Intermediate a-1 (42.0 g, 157.9 mmol) and tetrahydrofuran (300 mL) were added to a flask, and a resulting mixture was cooled to −78° C.; a solution of n-butyl lithium in THF (2.5 M) (95 mL, 236.9 mmol) was added dropwise under stirring, and a resulting mixture was stirred for 1 h at the temperature; a solution of adamantanone (19.0 g, 126.3 mmol) in tetrahydrofuran (100 mL) was added dropwise at −78° C., and a resulting mixture was incubated for 1 h, then warmed to room temperature, and stirred for 24 h; a solution of hydrochloric acid (12 M) (26.3 mL, 315.8 mmol) in water (100 mL) was added to a resulting reaction solution, and a resulting mixture was stirred for 1 h, and then allowed to be separated into layers; a resulting

TABLE 1

| Intermediate No. | Reactant A | Structure | Yield |
|---|---|---|---|
| b-1 | ![](Br, I, Cl on benzene) | ![](Br, Cl on biphenyl) | 66% |
| c-1 | ![](Br, I, Cl on benzene) | ![](Br, Cl on biphenyl) | 40% |

Synthesis of Intermediate a-2

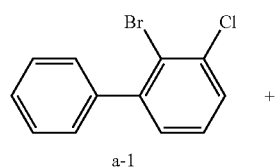

a-1
+ organic phase was washed with water until neutral, dried with anhydrous magnesium sulfate, and subjected to solvent removal under reduced pressure to obtain a crude product; and the crude product was purified through silica gel column chromatography using an ethyl acetate/n-heptane system to obtain Intermediate a-2 as a white solid (25.8 g, yield: 48%).

Intermediate b-2 and Intermediate c-2 were synthesized by a method the same as the synthesis method of Intermediate a-2, except that Reactant A in Table 2 below was used instead of Intermediate a-1:

TABLE 2

| Intermediate No. | Reactant A | Structure | Yield |
|---|---|---|---|
| b-2 | (2-bromo-4-chlorobiphenyl) | (adamantyl-C(OH)-biphenyl-Cl) | 78% |
| c-2 | (2-bromo-2'-chlorobiphenyl) | (adamantyl-C(OH)-biphenyl-Cl) | 69% |

Synthesis of Intermediate a-3

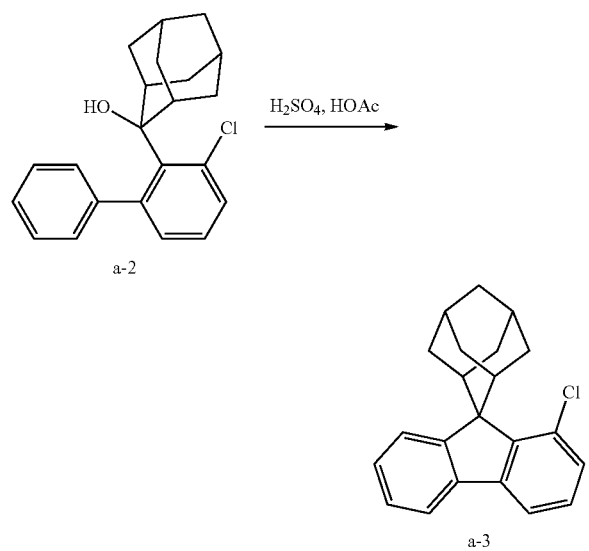

Intermediate a-2 (25.8 g, 76.3 mmol) and glacial acetic acid (300 mL) were added to a flask, then under nitrogen protection, stirred at room temperature, a solution of concentrated sulfuric acid (98%) (0.8 mL, 15.3 mmol) in acetic acid (20 mL) was slowly added dropwise, and a reaction system was heated to 80° C. and stirred for 2 h; then a resulting reaction solution was cooled to room temperature and filtered to obtain a filter cake, and the filter cake was rinsed with water and ethanol and then dried to obtain a crude product; and the crude product was purified through silica gel column chromatography using a dichloromethane/n-heptane system to obtain Intermediate a-3 as a white solid (20.4 g, yield: 84%).

Intermediate b-3 and Intermediate c-3 were synthesized by a method the same as the synthesis method of Intermediate a-3, except that Reactant A in Table 3 below was used instead of Intermediate a-2:

TABLE 3

| Intermediate No. | Reactant A | Structure | Yield |
|---|---|---|---|
| b-3 | (adamantyl-C(OH)-biphenyl-Cl) | (adamantyl-fluorene-Cl) | 83% |

TABLE 3-continued

| Intermediate No. | Reactant A | Structure | Yield |
|---|---|---|---|
| c-3 | 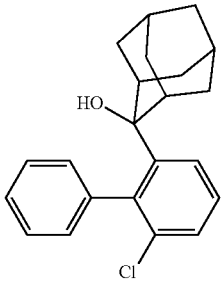 [SMILES: CC1CC2CCC(O)(c3cccc(Cl)c3-c3ccccc3)C(C1)C2] | 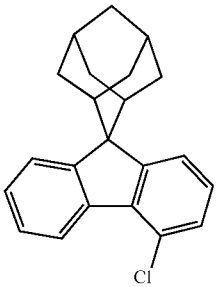 [SMILES: CC1CC2CCC3(c4ccccc4-c4c(Cl)cccc43)C(C1)C2] | 77% |

Synthesis of Intermediate a-4

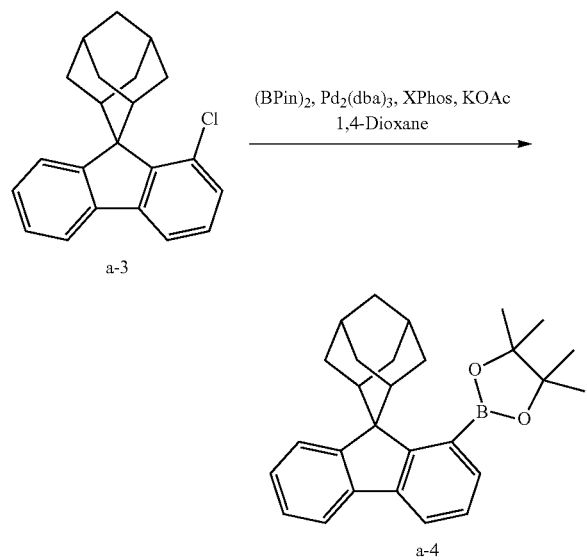

Intermediate a-3 (20.4 g, 63.7 mmol), bis(pinacolato)diboron (19.4 g, 76.5 mmol), tris(dibenzylideneacetone)dipalladium (0.6 g, 0.6 mmol), 2-dicyclohexylphosphino-2',4',6'-triisopropylbiphenyl (0.6 g, 1.3 mmol), potassium acetate (12.5 g, 127.4 mmol), and 1,4-dioxane (150 mL) were added to a flask, and a reaction system was heated to 100° C. and stirred under nitrogen protection to allow a reaction under reflux for 16 h; a resulting reaction solution was cooled to room temperature, then dichloromethane and water were added, and a resulting mixture was allowed to be separated into layers; a resulting organic phase was washed with water, dried with anhydrous magnesium sulfate, and then subjected to solvent removal under reduced pressure to obtain a crude product; and the crude product was purified through silica gel column chromatography using a dichloromethane/n-heptane system to obtain Intermediate a-4 as a white solid (13.3 g, yield: 51%).

Intermediate b-4 and Intermediate c-4 were synthesized by a method the same as the synthesis method of Intermediate a-4, except that Reactant A in Table 4 below was used instead of Intermediate a-3:

TABLE 4

| Intermediate No. | Reactant A | Structure | Yield |
|---|---|---|---|
| b-4 | 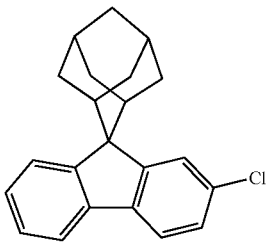 [SMILES: CC1CC2CCC3(c4ccccc4-c4ccc(Cl)cc43)C(C1)C2] | 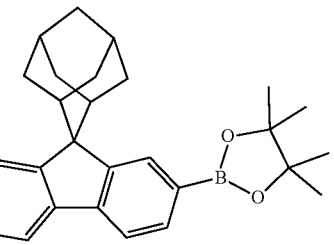 | 80% |

TABLE 4-continued

| Intermediate No. | Reactant A | Structure | Yield |
|---|---|---|---|
| c-4 | (adamantyl-fluorene-Cl structure) | (adamantyl-fluorene-Bpin structure) | 64% |

Synthesis of Intermediate a-i

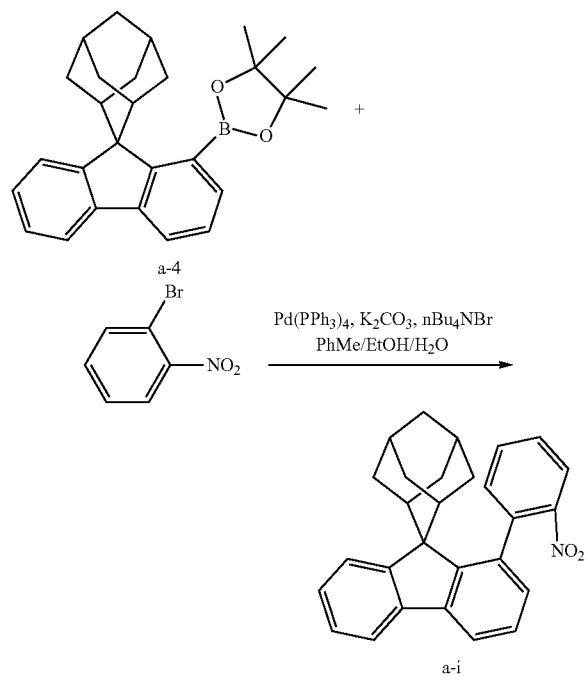

Intermediate a-4 (13.3 g, 32.3 mmol), 2-nitrobromobenzene (7.1 g, 35.5 mmol), tetrakis(triphenylphosphine)palladium (0.7 g, 0.6 mmol), potassium carbonate (11.1 g, 80.7 mmol), and tetrabutylammonium bromide (2.1 g, 6.5 mmol) were added to a flask, then a mixed solvent of toluene (80 mL), ethanol (20 mL), and water (20 mL) was added, and a reaction system was heated to 80° C. and stirred at the temperature for 24 h under nitrogen protection; a resulting reaction solution was cooled to room temperature, then the stirring was stopped, and the reaction solution was washed with water; a resulting organic phase was separated out, dried with anhydrous magnesium sulfate, and subjected to solvent removal under reduced pressure to obtain a crude product; and the crude product was purified through silica gel column chromatography with dichloromethane/n-heptane as a mobile phase to obtain Intermediate a-i as a white solid (9.0 g, yield: 69%).

Intermediates shown in Table 5 below were synthesized by a method the same as the synthesis method of Intermediate a-i, except that Reactant A in Table 5 was used instead of Intermediate a-4 and Reactant B in Table 5 was used instead of 2-nitrobromobenzene:

TABLE 5

| Intermediate No. | Reactant A | Reactant B |
|---|---|---|
| b-i | (adamantyl-fluorene-Bpin structure) | (2-bromonitrobenzene) |

TABLE 5-continued
| | | |
|---|---|---|
| c-i | 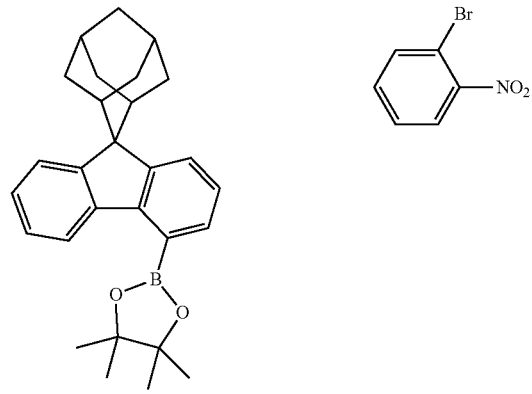 | |
| a-ii | 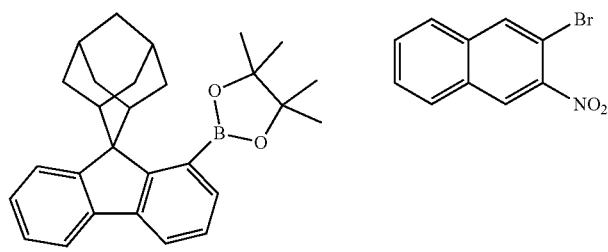 | |
| c-ii | 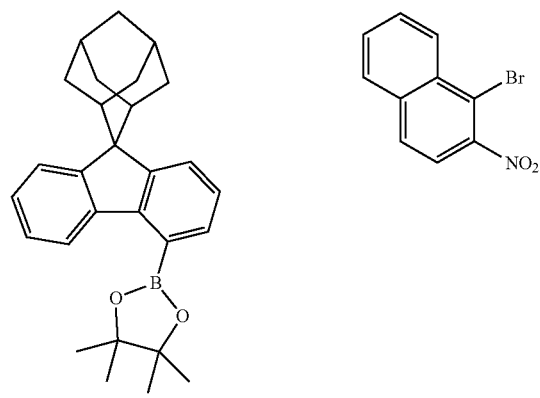 | |
| a-iii | 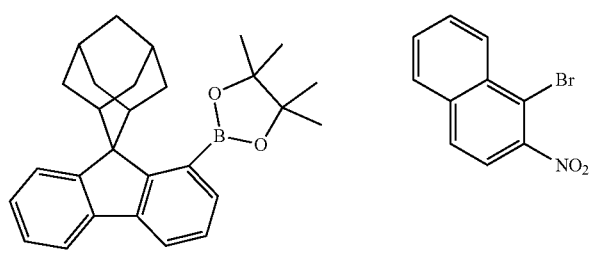 | |
| b-ii | 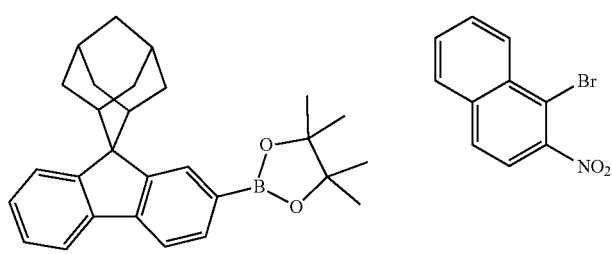 | |

TABLE 5-continued
| | | |
|---|---|---|
| b-iii | 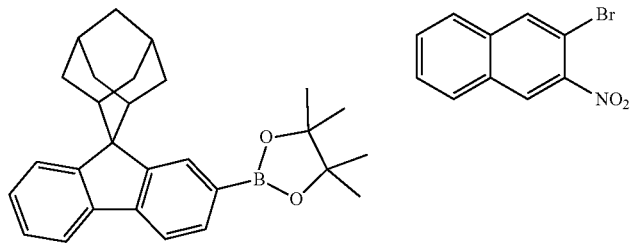 | |
| c-iii | 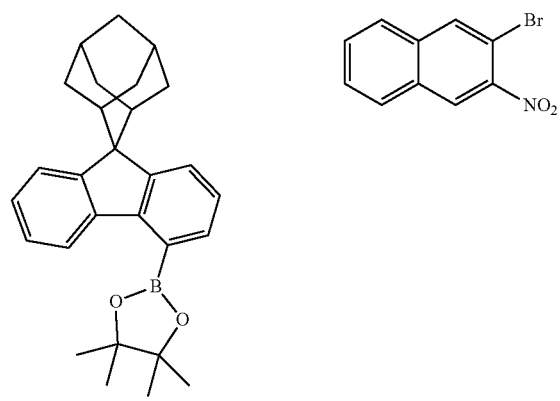 | |
| c-iv | 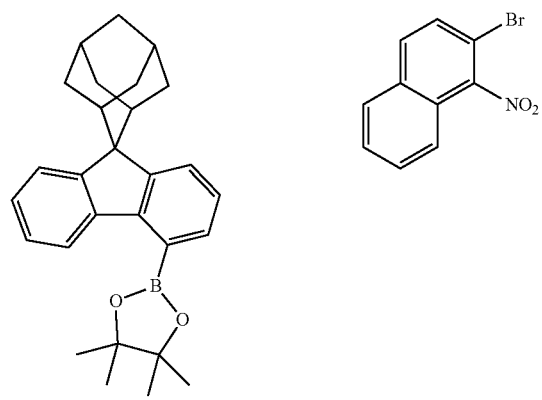 | |
| Intermediate No. | Structure | Yield |
|---|---|---|
| b-i | 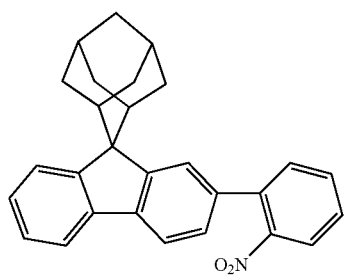 [SMILES: CC1CC2CCC3(c4ccccc4-c4ccc(-c5ccccc5[N+](=O)[O-])cc43)C(C1)C2] | 77% |

TABLE 5-continued
| | | |
|---|---|---|
| c-i | 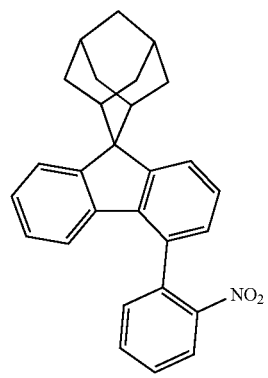 [SMILES: CC1CC2CCC3(c4ccccc4-c4c(-c5ccccc5[N+](=O)[O-])cccc43)C(C1)C2] | 52% |
| a-ii | 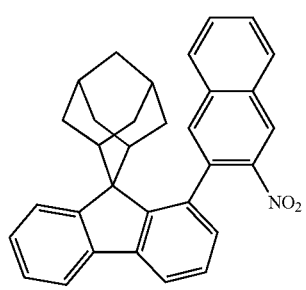 [SMILES: CC1CC2CCC3(c4ccccc4-c4cccc(-c5cc6ccccc6cc5[N+](=O)[O-])c43)C(C1)C2] | 40% |
| c-ii | 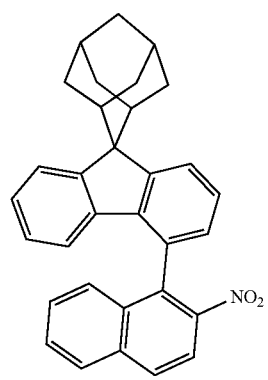 [SMILES: CC1CC2CCC3(c4ccccc4-c4c(-c5c([N+](=O)[O-])ccc6ccccc56)cccc43)C(C1)C2] | 63% |
| a-iii | 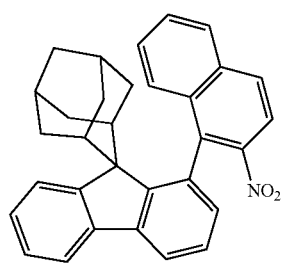 [SMILES: CC1CC2CCC3(c4ccccc4-c4cccc(-c5c([N+](=O)[O-])ccc6ccccc56)c43)C(C1)C2] | 56% |
| b-ii | 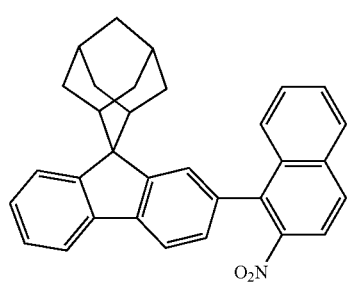 [SMILES: CC1CC2CCC3(c4ccccc4-c4ccc(-c5c([N+](=O)[O-])ccc6ccccc56)cc43)C(C1)C2] | 83% |

TABLE 5-continued
| | | |
|---|---|---|
| b-iii | 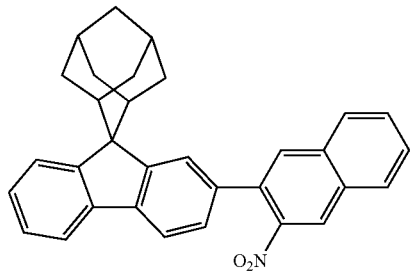 [SMILES: CC1CC2CCC3(c4ccccc4-c4ccc(-c5cc6ccccc6cc5[N+](=O)[O-])cc43)C(C1)C2] | 70% |
| c-iii | 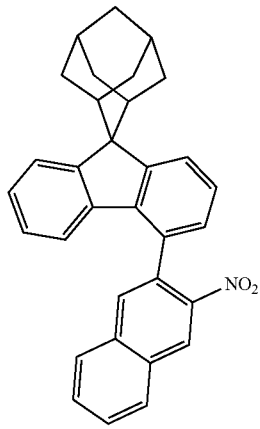 [SMILES: CC1CC2CCC3(c4ccccc4-c4c(-c5cc6ccccc6cc5[N+](=O)[O-])cccc43)C(C1)C2] | 64% |
| c-iv | 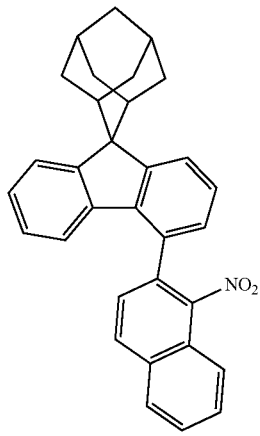 [SMILES: CC1CC2CCC3(c4ccccc4-c4c(-c5ccc6ccccc6c5[N+](=O)[O-])cccc43)C(C1)C2] | 67% |
Synthesis of Intermediate b-iv
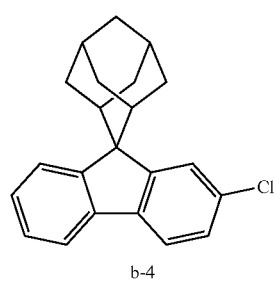
-continued
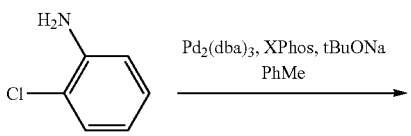

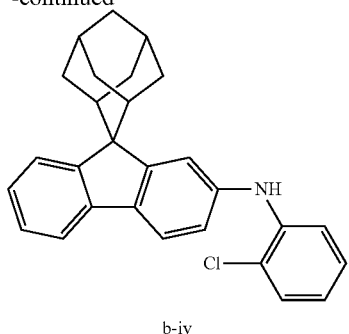

b-iv

Intermediate b-4 (7.6 g, 23.7 mmol), 2-chloroaniline (3.2 g, 24.9 mmol), tris(dibenzylideneacetone)dipalladium (0.2 g, 0.2 mmol), 2-dicyclohexylphosphino-2',4',6'-triisopropy- lbiphenyl (0.2 g, 0.5 mmol), sodium tert-butoxide (3.4 g, 35.6 mmol), and toluene (50 mL) were added to a flask, and a reaction system was heated to 105° C. and stirred under nitrogen protection to allow a reaction under reflux for 4 h; a resulting reaction solution was cooled to room temperature, then washed with water, and allowed to be separated into layers; a resulting organic phase was washed with water, dried with anhydrous magnesium sulfate, and then subjected to solvent removal under reduced pressure to obtain a crude product; and the crude product was purified through silica gel column chromatography using a dichloromethane/n-heptane system to obtain Intermediate b-iv as a white solid (7.7 g, yield: 79%).

Intermediates shown in Table 6 below were synthesized by a method the same as the synthesis method of Intermediate b-iv, except that Reactant A in the table 6 was used instead of Intermediate b-4 and Reactant B was used instead of 2-chloroaniline:

TABLE 6

| Intermediate No. | Reactant A | Reactant B |
| --- | --- | --- |
| a-iv | | |
| a-v | | |
| b-v | | |
| b-vi | | |

TABLE 6-continued
| | | |
|---|---|---|
| c-v | 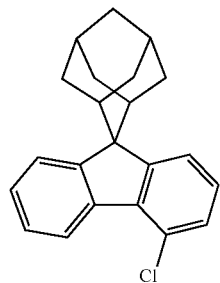 [SMILES: CC1CC2CCC3(c4ccccc4-c4c(Cl)cccc43)C(C1)C2] | 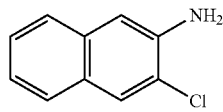 [SMILES: Nc1cc2ccccc2cc1Cl] |
| c-vi | 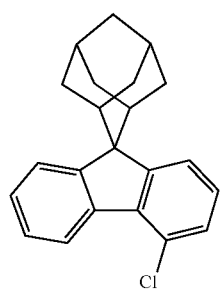 [SMILES: CC1CC2CCC3(c4ccccc4-c4c(Cl)cccc43)C(C1)C2] | 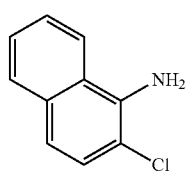 [SMILES: Nc1c(Cl)ccc2ccccc12] |
| a-vi | 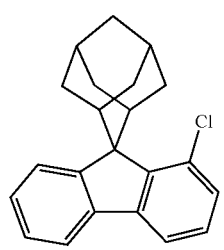 [SMILES: CC1CC2CCC3(c4ccccc4-c4cccc(Cl)c43)C(C1)C2] | 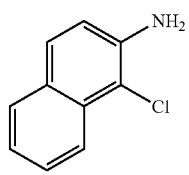 [SMILES: Nc1ccc2ccccc2c1Cl] |
| b-vii | 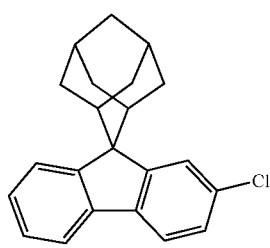 [SMILES: CC1CC2CCC3(c4ccccc4-c4ccc(Cl)cc43)C(C1)C2] | 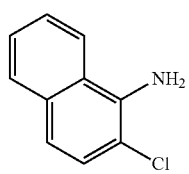 [SMILES: Nc1c(Cl)ccc2ccccc12] |
| c-vii | 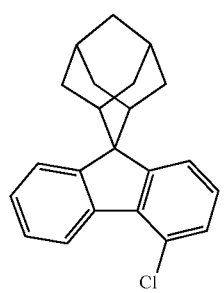 [SMILES: CC1CC2CCC3(c4ccccc4-c4c(Cl)cccc43)C(C1)C2] | 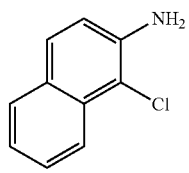 [SMILES: Nc1ccc2ccccc2c1Cl] |

TABLE 6-continued
| | | |
|---|---|---|
| c-viii | 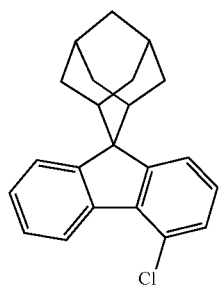 [SMILES: CC1CC2CCC3(c4ccccc4-c4c(Cl)cccc43)C(C1)C2] | 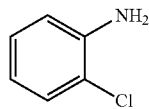 |
| b-viii | 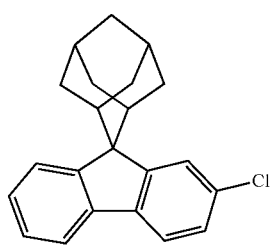 [SMILES: CC1CC2CCC3(c4ccccc4-c4ccc(Cl)cc43)C(C1)C2] | 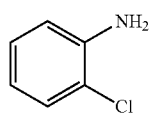 |
| Intermediate No. | Structure | Yield |
|---|---|---|
| a-iv | 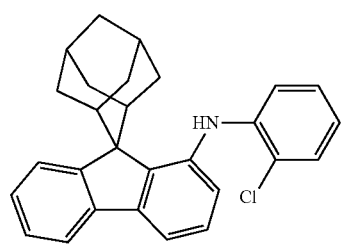 [SMILES: CC1CC2CCC3(c4ccccc4-c4cccc(Nc5ccccc5Cl)c43)C(C1)C2] | 60% |
| a-v | 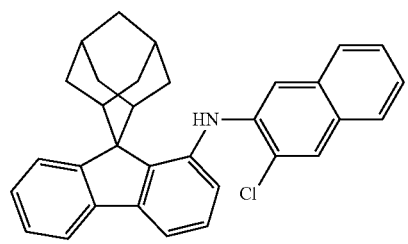 [SMILES: CC1CC2CCC3(c4ccccc4-c4cccc(Nc5cc6ccccc6cc5Cl)c43)C(C1)C2] | 53% |
| b-v | 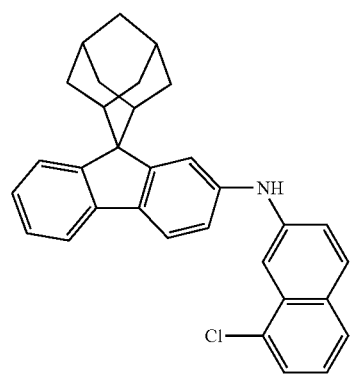 [SMILES: CC1CC2CCC3(c4ccccc4-c4ccc(Nc5ccc6cccc(Cl)c6c5)cc43)C(C1)C2] | 72% |

TABLE 6-continued
| b-vi | 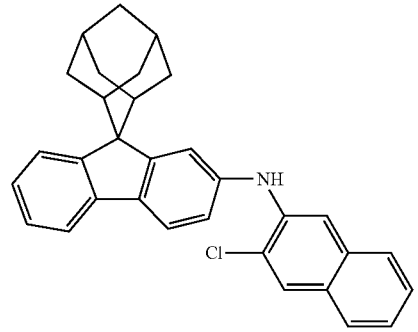 [SMILES: CC1CC2CCC3(c4ccccc4-c4ccc(Nc5cc6ccccc6cc5Cl)cc43)C(C1)C2] | 84% |
| c-v | 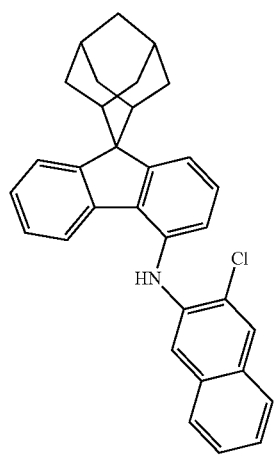 [SMILES: CC1CC2CCC3(c4ccccc4-c4c(Nc5cc6ccccc6cc5Cl)cccc43)C(C1)C2] | 67% |
| c-vi | 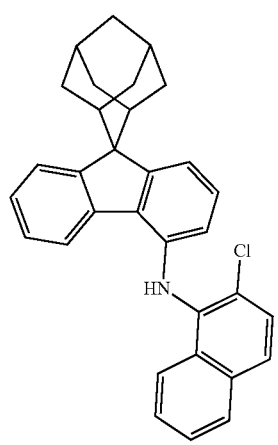 [SMILES: CC1CC2CCC3(c4ccccc4-c4c(Nc5c(Cl)ccc6ccccc56)cccc43)C(C1)C2] | 59% |
| a-vi | 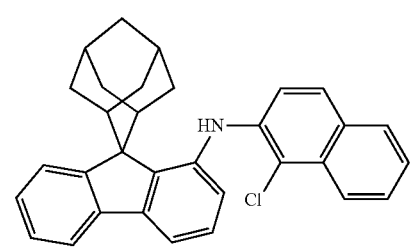 [SMILES: CC1CC2CCC3(c4ccccc4-c4cccc(Nc5ccc6ccccc6c5Cl)c43)C(C1)C2] | 38% |

TABLE 6-continued
| | | |
|---|---|---|
| b-vii | 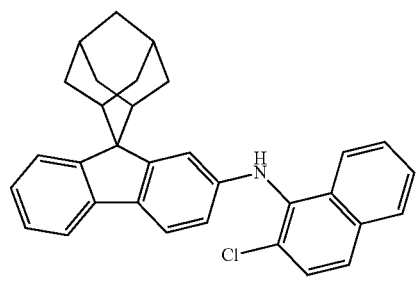 [SMILES: CC1CC2CCC3(c4ccccc4-c4ccc(Nc5c(Cl)ccc6ccccc56)cc43)C(C1)C2] | 61% |
| c-vii | 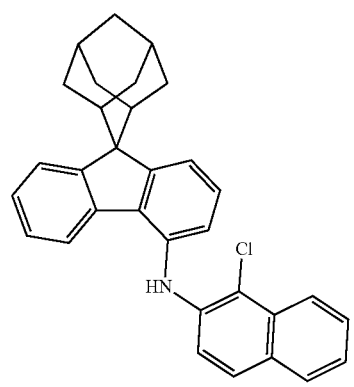 [SMILES: CC1CC2CCC3(c4ccccc4-c4c(Nc5ccc6ccccc6c5Cl)cccc43)C(C1)C2] | 70% |
| c-viii | 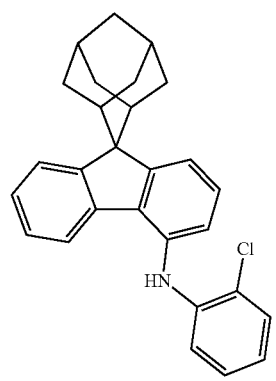 [SMILES: CC1CC2CCC3(c4ccccc4-c4c(Nc5ccccc5Cl)cccc43)C(C1)C2] | 63% |
| b-viii | 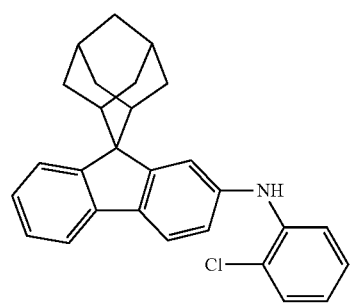 [SMILES: CC1CC2CCC3(c4ccccc4-c4ccc(Nc5ccccc5Cl)cc43)C(C1)C2] | 44% |

Synthesis of Intermediate A

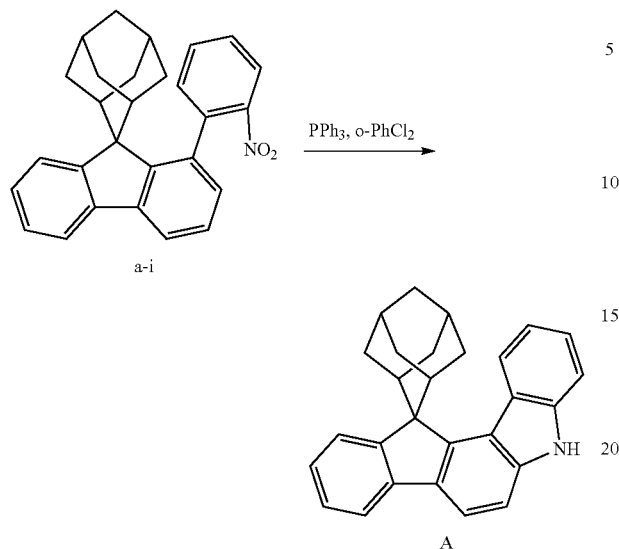

Intermediate a-i (9.0 g, 22.1 mmol), triphenylphosphine (14.5 g, 55.3 mmol), and o-dichlorobenzene (100 mL) were added to a flask, and a reaction system was heated to 175° C. and stirred for 18 h under nitrogen protection; a resulting reaction solution was cooled to room temperature, then washed with water, and allowed to be separated into layers; a resulting organic phase was washed with water, dried with anhydrous magnesium sulfate, and then subjected to solvent removal under high temperature and reduced pressure to obtain a crude product; and the crude product was purified through silica gel column chromatography using an ethyl acetate/n-heptane system to obtain Intermediate A as a white solid (7.5 g, yield: 90%).

Intermediates shown in Table 7 below were synthesized by a method the same as the synthesis method of Intermediate A, except that Reactant A in Table 7 was used instead of Intermediate a-i:

TABLE 7

| Intermediate No. | Reactant A | Structure | Yield |
|---|---|---|---|
| B | | 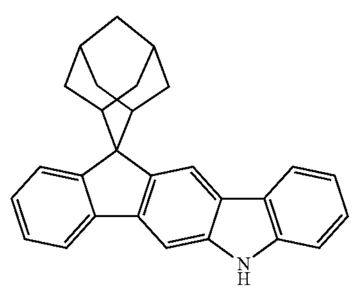 [SMILES: CC1CC2CCC3(c4ccccc4-c4cc5[nH]c6ccccc6c5cc43)C(C1)C2] | 93% |
| C | | 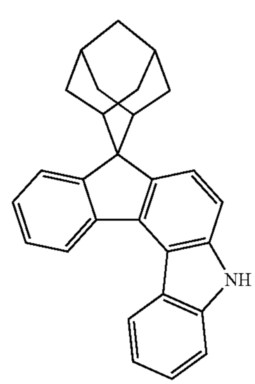 [SMILES: CC1CC2CCC3(c4ccccc4-c4c3ccc3[nH]c5ccccc5c43)C(C1)C2] | 85% |

TABLE 7-continued

| Intermediate No. | Reactant A | Structure | Yield |
| --- | --- | --- | --- |
| D | | 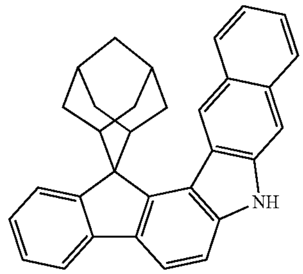 [SMILES: CC1CC2CCC3(c4ccccc4-c4ccc5[nH]c6cc7ccccc7cc6c5c43)C(C1)C2] | 75% |
| E | | 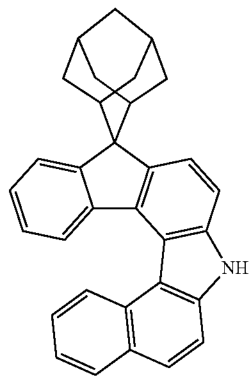 [SMILES: CC1CC2CCC3(c4ccccc4-c4c3ccc3[nH]c5ccc6ccccc6c5c43)C(C1)C2] | 87% |
| F | | 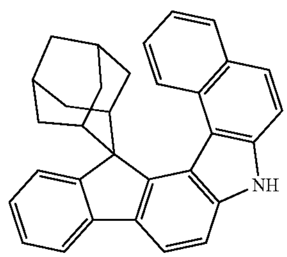 [SMILES: CC1CC2CCC3(c4ccccc4-c4ccc5[nH]c6ccc7ccccc7c6c5c43)C(C1)C2] | 78% |
| G | | 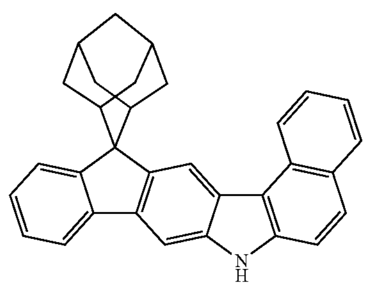 [SMILES: CC1CC2CCC3(c4ccccc4-c4cc5[nH]c6ccc7ccccc7c6c5cc43)C(C1)C2] | 92% |
| H | | 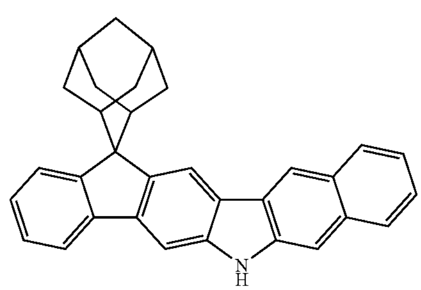 [SMILES: CC1CC2CCC3(c4ccccc4-c4cc5[nH]c6cc7ccccc7cc6c5cc43)C(C1)C2] | 84% |

TABLE 7-continued
| Intermediate No. | Reactant A | Structure | Yield |
|---|---|---|---|
| I | | 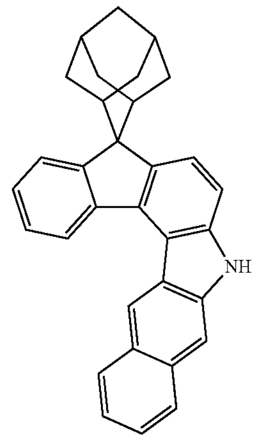 [SMILES: CC1CC2CCC3(c4ccccc4-c4c3ccc3[nH]c5cc6ccccc6cc5c43)C(C1)C2] | 77% |
| J | | 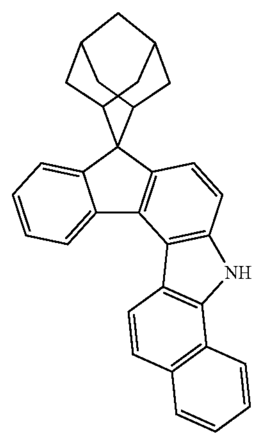 [SMILES: CC1CC2CCC3(c4ccccc4-c4c3ccc3[nH]c5c6ccccc6ccc5c43)C(C1)C2] | 64% |
Synthesis of Intermediate K
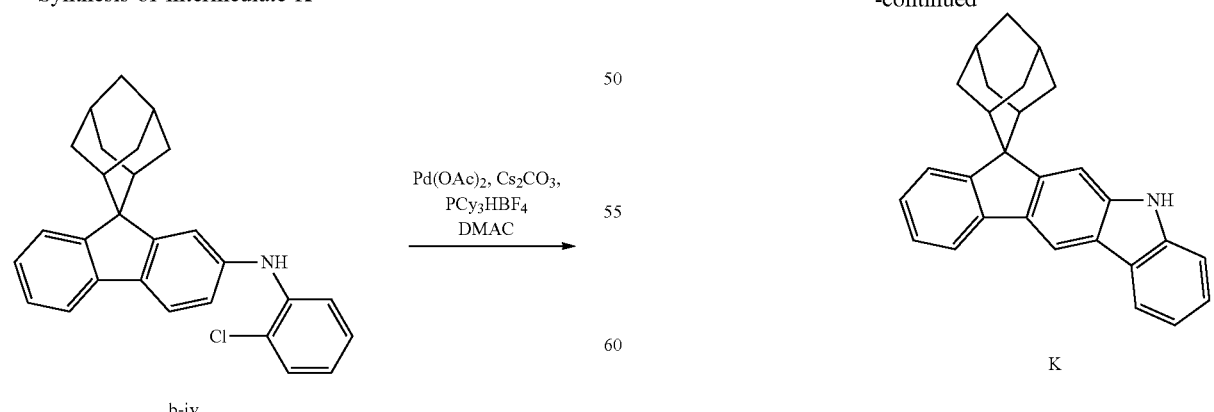
Intermediate b-iv (7.7 g, 18.7 mmol), palladium acetate (2.1 g, 9.4 mmol), cesium carbonate (24.4 g, 74.9 mmol), tricyclohexylphosphine tetrafluoroborate (6.9 g, 18.7 mmol), and dimethylacetamide (70 mL) were added to a flask, and a reaction system was heated to 160° C. and stirred for 12 h under nitrogen protection; a resulting reaction solution was cooled to room temperature, dichloromethane (300 mL) was added, and then washed with a large amount of water; a resulting organic phase was dried with anhydrous magnesium sulfate, and then subjected to solvent removal under reduced pressure to obtain a crude product; and the crude product was purified through silica gel column chromatography using a dichloromethane/n-heptane system to obtain Intermediate K as a white solid (6.0 g, yield: 85%).

Intermediates shown in Table 8 below were synthesized by a method the same as the synthesis method of Intermediate K, except that Reactant A in Table 8 was used instead of Intermediate b-iv:

TABLE 8

| Intermediate No. | Reactant A | Structure | Yield |
|---|---|---|---|
| L | | 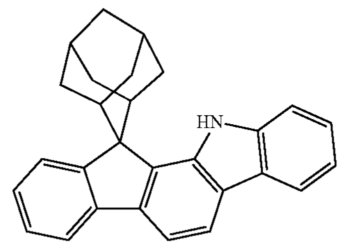 [SMILES: CC1CC2CCC3(c4ccccc4-c4ccc5c([nH]c6ccccc65)c43)C(C1)C2] | 78% |
| M | | 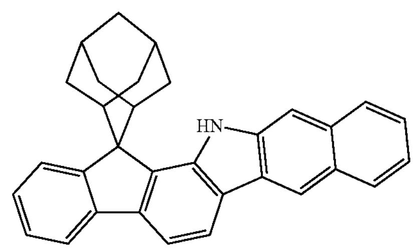 [SMILES: CC1CC2CCC3(c4ccccc4-c4ccc5c([nH]c6cc7ccccc7cc65)c43)C(C1)C2] | 77% |
| N | | 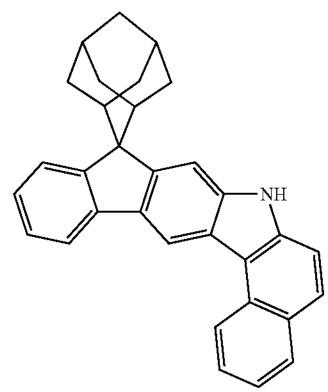 [SMILES: CC1CC2CCC3(c4ccccc4-c4cc5c(cc43)[nH]c3ccc4ccccc4c35)C(C1)C2] | 82% |
| O | | 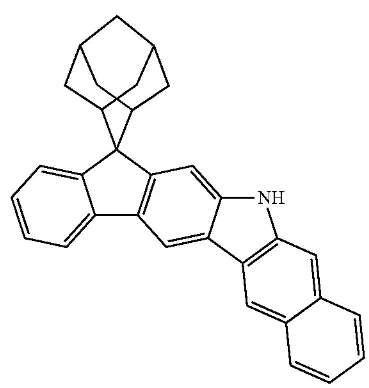 [SMILES: CC1CC2CCC3(c4ccccc4-c4cc5c(cc43)[nH]c3cc4ccccc4cc35)C(C1)C2] | 84% |

TABLE 8-continued
| Intermediate No. | Reactant A | Structure | Yield |
|---|---|---|---|
| P | 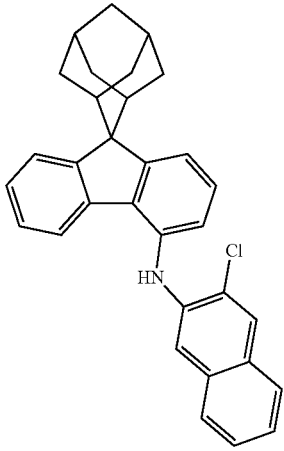 [SMILES: CC1CC2CCC3(c4ccccc4-c4c(Nc5cc6ccccc6cc5Cl)cccc43)C(C1)C2] | 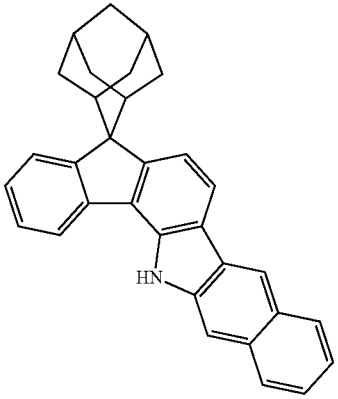 [SMILES: CC1CC2CCC3(c4ccccc4-c4c3ccc3c4[nH]c4cc5ccccc5cc43)C(C1)C2] | 69% |
| Q | 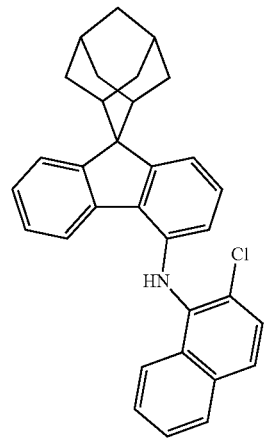 [SMILES: CC1CC2CCC3(c4ccccc4-c4c(Nc5c(Cl)ccc6ccccc56)cccc43)C(C1)C2] | 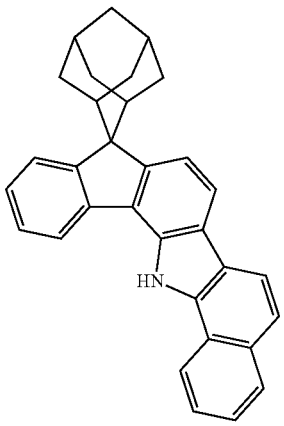 [SMILES: CC1CC2CCC3(c4ccccc4-c4c3ccc3c4[nH]c4c5ccccc5ccc34)C(C1)C2] | 86% |
| R | 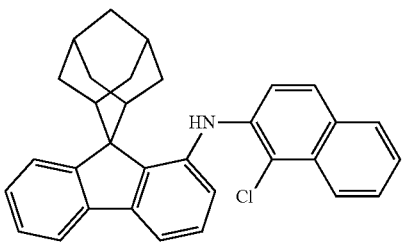 | 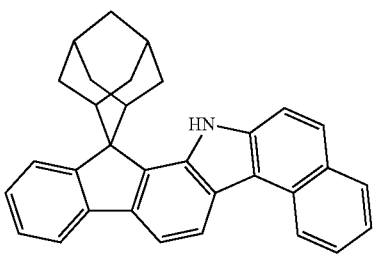 | 77% |
| S | 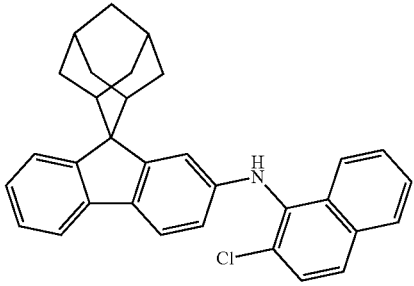 [SMILES: CC1CC2CCC3(c4ccccc4-c4ccc(Nc5c(Cl)ccc6ccccc56)cc43)C(C1)C2] | 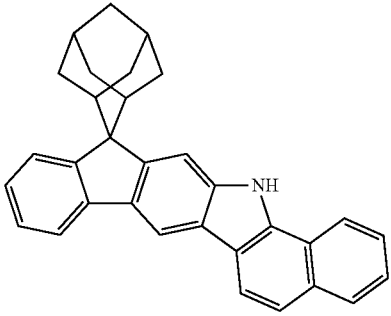 [SMILES: CC1CC2CCC3(c4ccccc4-c4cc5c(cc43)[nH]c3c4ccccc4ccc53)C(C1)C2] | 70% |

TABLE 8-continued
| Intermediate No. | Reactant A | Structure | Yield |
|---|---|---|---|
| T | | 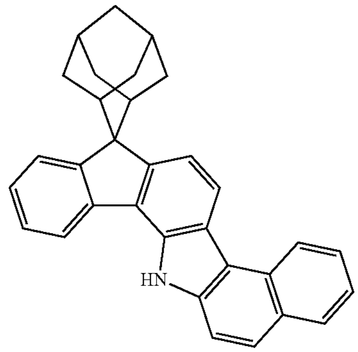 [SMILES: CC1CC2CCC3(c4ccccc4-c4c3ccc3c4[nH]c4ccc5ccccc5c43)C(C1)C2] | 65% |
| U | | 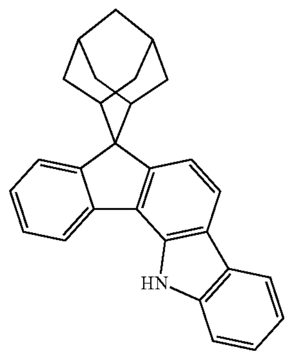 [SMILES: CC1CC2CCC3(c4ccccc4-c4c3ccc3c4[nH]c4ccccc43)C(C1)C2] | 53% |
| V | | 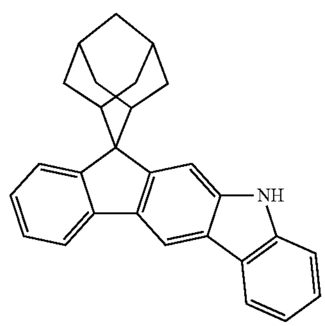 [SMILES: CC1CC2CCC3(c4ccccc4-c4cc5c(cc43)[nH]c3ccccc35)C(C1)C2] | 69% |
Synthesis of Compound 1
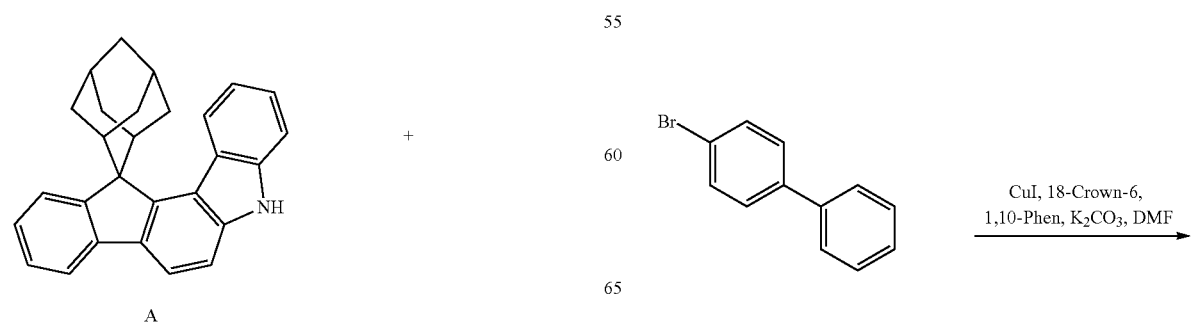
-continued -continued

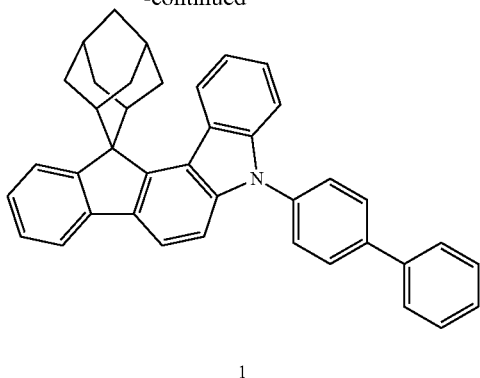

1

Intermediate A (7.5 g, 20.2 mmol), 4-bromobiphenyl (4.9 g, 21.0 mmol), cuprous iodide (0.8 g, 4.0 mmol), potassium carbonate (6.1 g, 43.9 mmol), 1,10-phenanthroline (1.4 g, 8.0 mmol), 18-crown-6-ether (0.5 g, 2.0 mmol), and dimethylformamide (50 mL) were added to a flask, and a reaction system was heated to 145° C. and stirred for 12 h under nitrogen protection; a resulting reaction solution was cooled to room temperature, dichloromethane (100 mL) and water were added, and a resulting mixture was allowed to be separated into layers; a resulting organic phase was washed with water, dried with anhydrous magnesium sulfate, and subjected to solvent removal under reduced pressure to obtain a crude product; and the crude product was first purified through silica gel column chromatography using a dichloromethane/n-heptane system, and then purified through recrystallization using a toluene/n-heptane system to obtain Compound 1 as a white solid (5.5 g, yield: 52%).

Compounds shown in Table 9 below were synthesized by a method the same as the synthesis method of Compound 1, except that Reactant A in Table 9 was used instead of Intermediate A and Reactant B was used instead of 4-bromobiphenyl:

TABLE 9

| Compound No. | Reactant A | Reactant B |
|---|---|---|
| 9 | | |
| 13 | | |
| 24 | | |

TABLE 9-continued
40 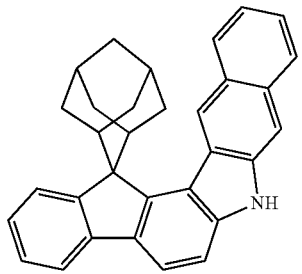 [SMILES: CC1CC2CCC3(c4ccccc4-c4ccc5[nH]c6cc7ccccc7cc6c5c43)C(C1)C2] 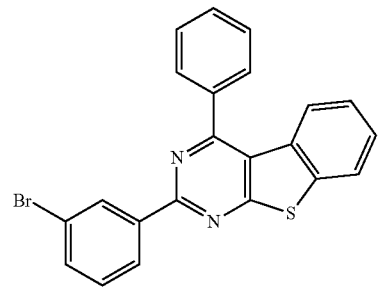 [SMILES: Brc1cccc(-c2nc(-c3ccccc3)c3c(n2)sc2ccccc23)c1]
52 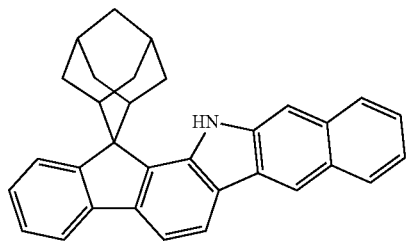 [SMILES: CC1CC2CCC3(c4ccccc4-c4ccc5c([nH]c6cc7ccccc7cc65)c43)C(C1)C2] 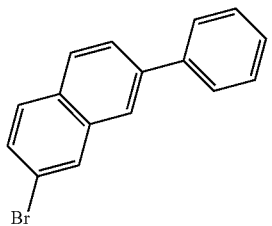 [SMILES: Brc1ccc2ccc(-c3ccccc3)cc2c1]
77 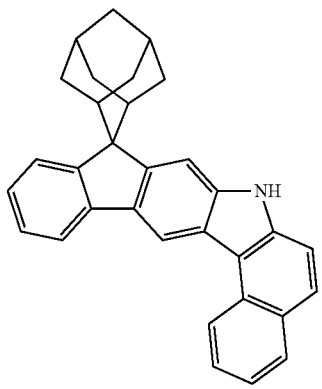 [SMILES: CC1CC2CCC3(c4ccccc4-c4cc5c(cc43)[nH]c3ccc4ccccc4c35)C(C1)C2] 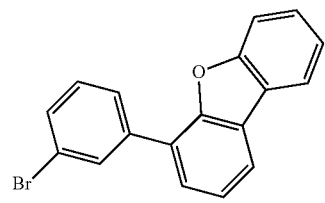 [SMILES: Brc1cccc(-c2cccc3c2oc2ccccc23)c1]
84 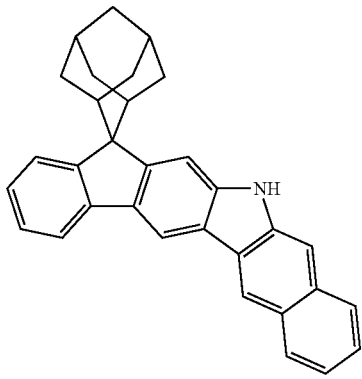 [SMILES: CC1CC2CCC3(c4ccccc4-c4cc5c(cc43)[nH]c3cc4ccccc4cc35)C(C1)C2] 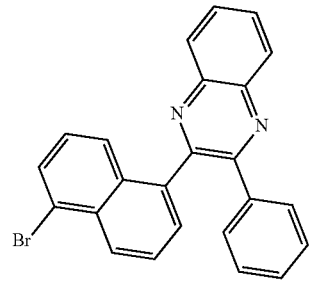 [SMILES: Brc1cccc2c(-c3nc4ccccc4nc3-c3ccccc3)cccc12]

TABLE 9-continued
| | | |
|---|---|---|
| 95 | 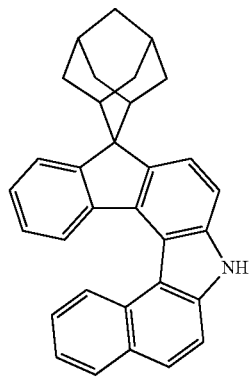 [SMILES: CC1CC2CCC3(c4ccccc4-c4c3ccc3[nH]c5ccc6ccccc6c5c43)C(C1)C2] | 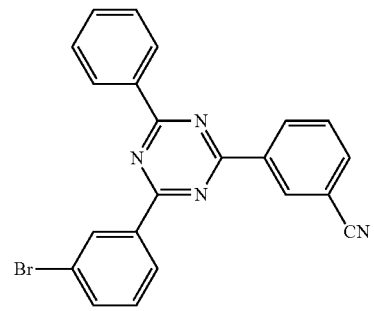 [SMILES: N#Cc1cccc(-c2nc(-c3ccccc3)nc(-c3cccc(Br)c3)n2)c1] |
| 112 | 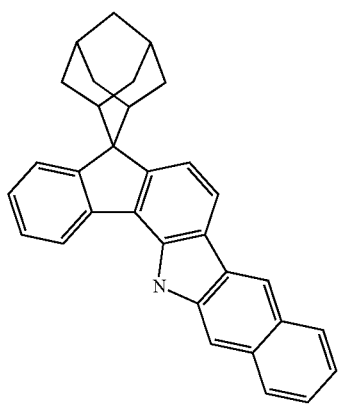 [SMILES: CC1CC2CCC3(c4ccccc4-c4c3ccc3c4[nH]c4cc5ccccc5cc43)C(C1)C2] | 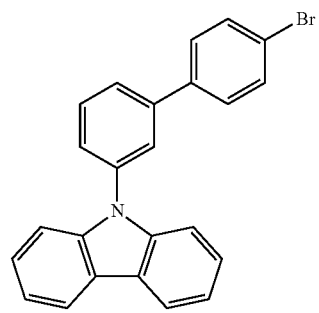 [SMILES: Brc1ccc(-c2cccc(-n3c4ccccc4c4ccccc43)c2)cc1] |
| 120 | 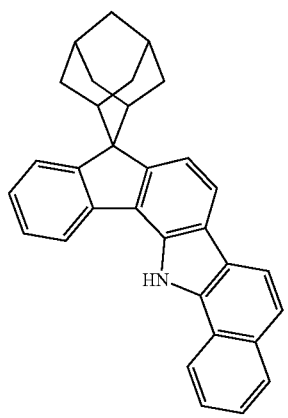 [SMILES: CC1CC2CCC3(c4ccccc4-c4c3ccc3c4[nH]c4c5ccccc5ccc34)C(C1)C2] | 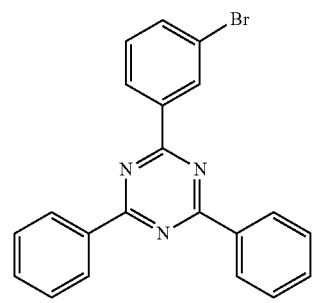 [SMILES: Brc1cccc(-c2nc(-c3ccccc3)nc(-c3ccccc3)n2)c1] |

TABLE 9-continued

| Compound No. | Structure | Yield |
|---|---|---|
| 9 | 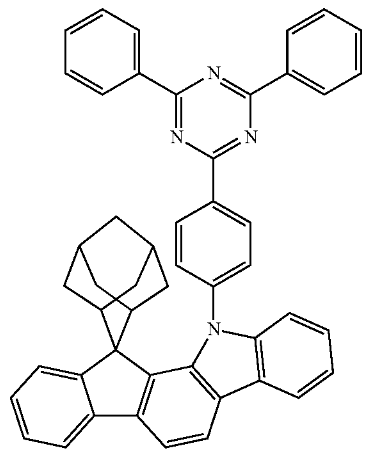 [SMILES: CC1CC2CCC3(c4ccccc4-c4ccc5c6ccccc6n(-c6ccc(-c7nc(-c8ccccc8)nc(-c8ccccc8)n7)cc6)c5c43)C(C1)C2] | 30% |
| 13 | 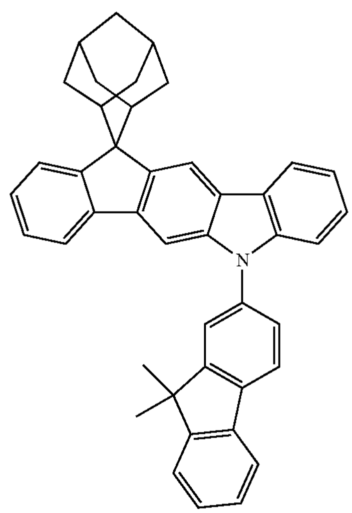 [SMILES: CC1CC2CCC3(c4ccccc4-c4cc5c(cc43)c3ccccc3n5-c3ccc4c(c3)C(C)(C)c3ccccc3-4)C(C1)C2] | 68% |
| 24 | 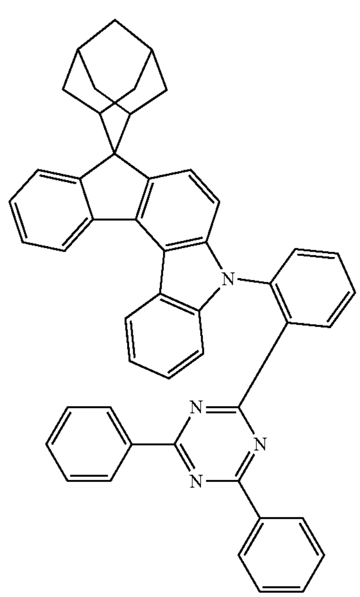 [SMILES: CC1CC2CCC3(c4ccccc4-c4c3ccc3c4c4ccccc4n3-c3ccccc3-c3nc(-c4ccccc4)nc(-c4ccccc4)n3)C(C1)C2] | 59% |

TABLE 9-continued
| 40 | 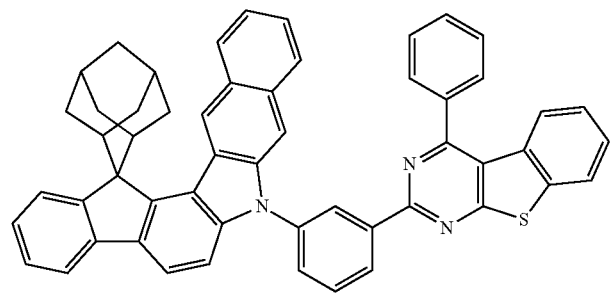 [SMILES: CC1CC2CCC3(c4ccccc4-c4ccc5c(c43)c3cc4ccccc4cc3n5-c3cccc(-c4nc(-c5ccccc5)c5c(n4)sc4ccccc45)c3)C(C1)C2] | 76% |
| 52 | 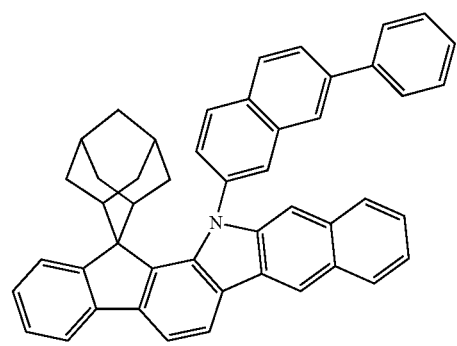 [SMILES: CC1CC2CCC3(c4ccccc4-c4ccc5c6cc7ccccc7cc6n(-c6ccc7ccc(-c8ccccc8)cc7c6)c5c43)C(C1)C2] | 45% |
| 77 | 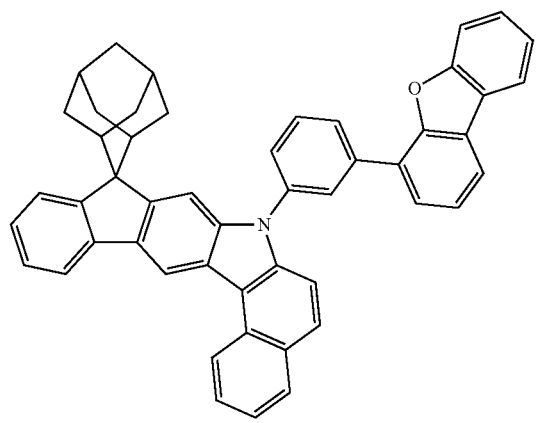 [SMILES: CC1CC2CCC3(c4ccccc4-c4cc5c6c7ccccc7ccc6n(-c6cccc(-c7cccc8c7oc7ccccc78)c6)c5cc43)C(C1)C2] | 77% |
| 84 | 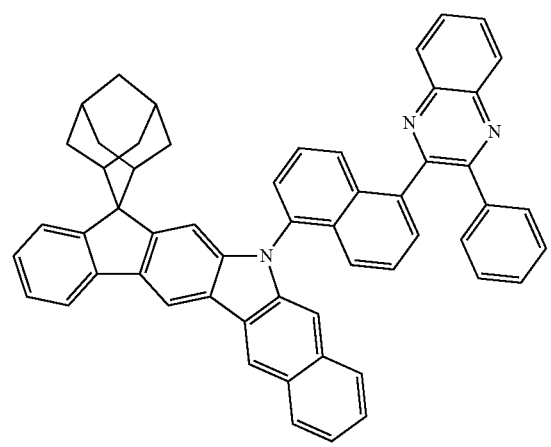 [SMILES: CC1CC2CCC3(c4ccccc4-c4cc5c6cc7ccccc7cc6n(-c6cccc7c(-c8nc9ccccc9nc8-c8ccccc8)cccc67)c5cc43)C(C1)C2] | 50% |

TABLE 9-continued
| 95 | 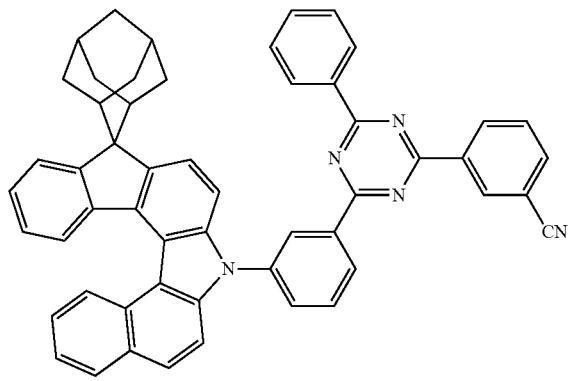 [SMILES: CC1CC2CCC3(c4ccccc4-c4c3ccc3c4c4c5ccccc5ccc4n3-c3cccc(-c4nc(-c5ccccc5)nc(-c5cccc(C#N)c5)n4)c3)C(C1)C2] | 62% |
| 112 | 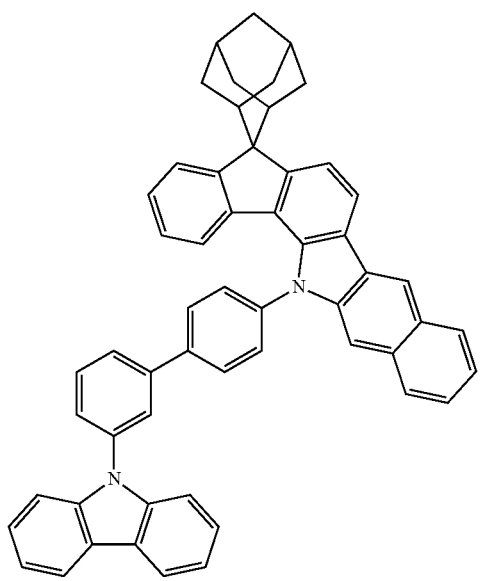 [SMILES: CC1CC2CCC3(c4ccccc4-c4c3ccc3c5cc6ccccc6cc5n(-c5ccc(-c6cccc(-n7c8ccccc8c8ccccc87)c6)cc5)c43)C(C1)C2] | 54% |
| 120 | 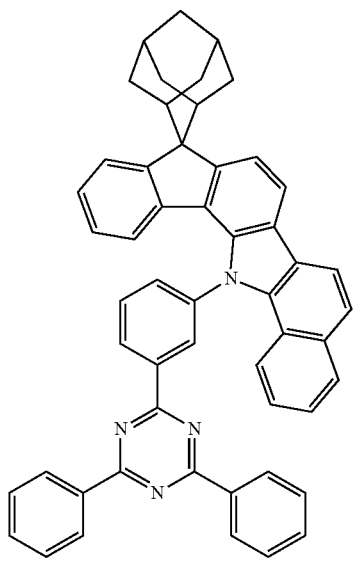 [SMILES: CC1CC2CCC3(c4ccccc4-c4c3ccc3c5ccc6ccccc6c5n(-c5cccc(-c6nc(-c7ccccc7)nc(-c7ccccc7)n6)c5)c43)C(C1)C2] | 39% |

Synthesis of Compound 20

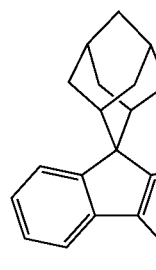

K

+

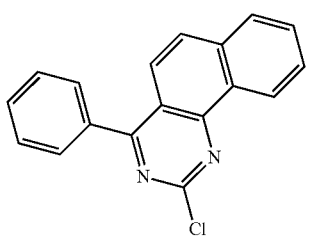

→ DMAP,Cs₂CO₃, DMSO →

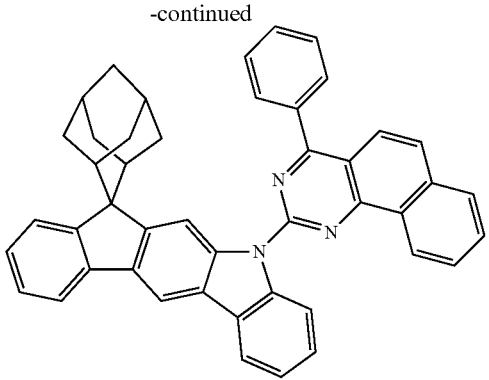

20

Intermediate K (6.0 g, 16.0 mmol), 2-chloro-4-phenyl-benzo[h]quinazoline (4.9 g, 16.8 mmol), 4-dimethylamino-pyridine (1.0 g, 8.0 mmol), cesium carbonate (5.2 g, 16.0 mmol), and dimethyl sulfoxide (80 mL) were added to a round-bottom flask, and a reaction system was stirred and heated to 100° C. under nitrogen protection to allow a reaction for 16 h; after the reaction was completed, a resulting reaction solution was cooled to room temperature and filtered to obtain a filter cake; the filter cake was rinsed with water and ethanol, and dried to obtain a crude product; and the crude product was purified through recrystallization using toluene to obtain Compound 20 as a yellow solid (5.1 g, yield: 51%).

Compounds shown in Table 10 below were synthesized by a method the same as the synthesis method of Compound 20, except that Reactant A in Table 10 was used instead of Intermediate K and Reactant B in Table 10 was used instead of 2-chloro-4-phenylbenzo[h] quinazoline:

TABLE 10

| Compound No. | Reactant A | Reactant B | Structure | Yield |
|---|---|---|---|---|
| 28 | (structure) | (structure) | (structure) | 44% |

TABLE 10-continued

| Compound No. | Reactant A | Reactant B | Structure | Yield |
|---|---|---|---|---|
| 33 | | | 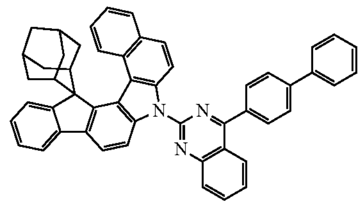 [SMILES: CC1CC2CCC3(c4ccccc4-c4ccc5c(c43)c3c4ccccc4ccc3n5-c3nc(-c4ccc(-c5ccccc5)cc4)c4ccccc4n3)C(C1)C2] | 66% |
| 50 | | | 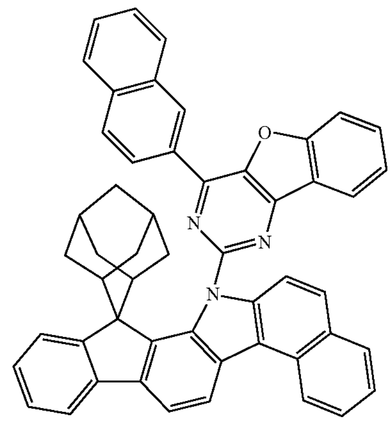 [SMILES: CC1CC2CCC3(c4ccccc4-c4ccc5c6c7ccccc7ccc6n(-c6nc(-c7ccc8ccccc8c7)c7oc8ccccc8c7n6)c5c43)C(C1)C2] | 37% |
| 64 | | | 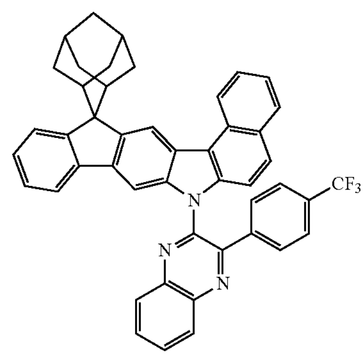 [SMILES: CC1CC2CCC3(c4ccccc4-c4cc5c(cc43)c3c4ccccc4ccc3n5-c3nc4ccccc4nc3-c3ccc(C(F)(F)F)cc3)C(C1)C2] | 50% |
| 69 | | | 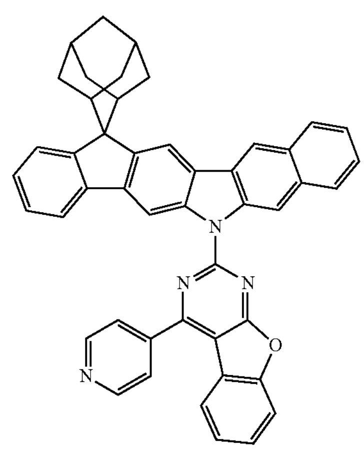 [SMILES: CC1CC2CCC3(c4ccccc4-c4cc5c(cc43)c3cc4ccccc4cc3n5-c3nc(-c4ccncc4)c4c(n3)oc3ccccc34)C(C1)C2] | 71% |

TABLE 10-continued

| Compound No. | Reactant A | Reactant B | Structure | Yield |
|---|---|---|---|---|
| 89 | | | 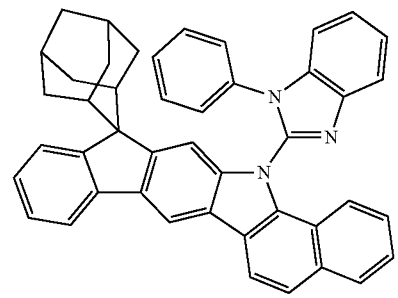 [SMILES: CC1CC2CCC3(c4ccccc4-c4cc5c6ccc7ccccc7c6n(-c6nc7ccccc7n6-c6ccccc6)c5cc43)C(C1)C2] | 48% |
| 98 | | | 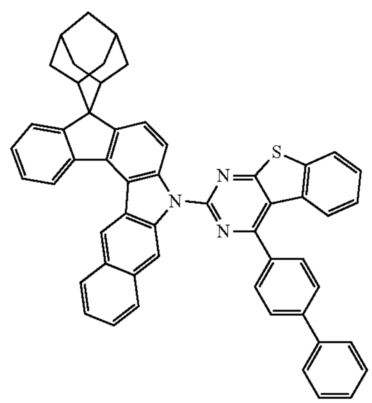 [SMILES: CC1CC2CCC3(c4ccccc4-c4c3ccc3c4c4cc5ccccc5cc4n3-c3nc(-c4ccc(-c5ccccc5)cc4)c4c(n3)sc3ccccc34)C(C1)C2] | 63% |
| 104 | | | 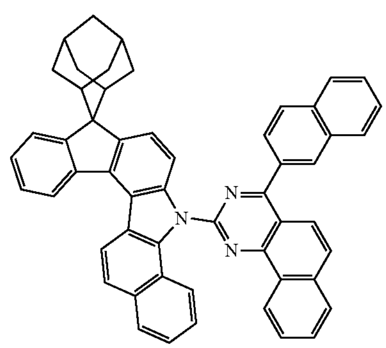 [SMILES: CC1CC2CCC3(c4ccccc4-c4c3ccc3c4c4ccc5ccccc5c4n3-c3nc(-c4ccc5ccccc5c4)c4ccc5ccccc5c4n3)C(C1)C2] | 48% |

TABLE 10-continued

| Compound No. | Reactant A | Reactant B | Structure | Yield |
|---|---|---|---|---|
| 108 | | | 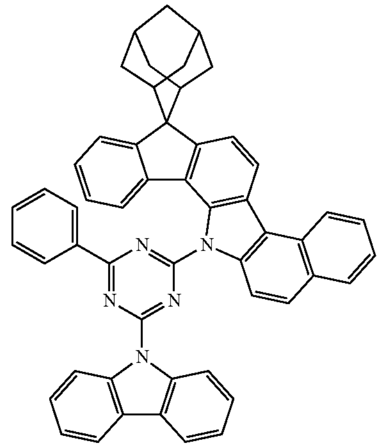 [SMILES: CC1CC2CCC3(c4ccccc4-c4c3ccc3c5c6ccccc6ccc5n(-c5nc(-c6ccccc6)nc(-n6c7ccccc7c7ccccc76)n5)c43)C(C1)C2] | 40% |
| 130 | | | 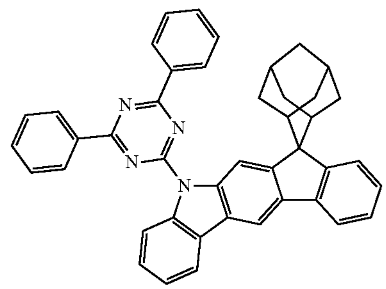 [SMILES: CC1CC2CCC3(c4ccccc4-c4cc5c6ccccc6n(-c6nc(-c7ccccc7)nc(-c7ccccc7)n6)c5cc43)C(C1)C2] | 55% |
| 132 | | | 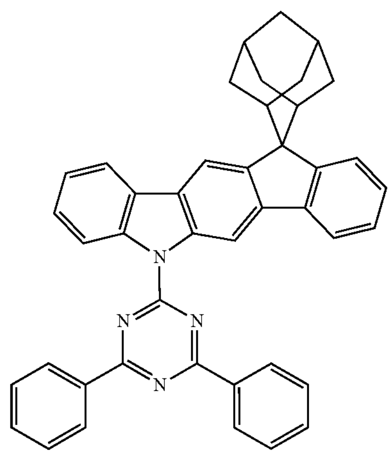 [SMILES: CC1CC2CCC3(c4ccccc4-c4cc5c(cc43)c3ccccc3n5-c3nc(-c4ccccc4)nc(-c4ccccc4)n3)C(C1)C2] | 39% |

The above compounds were subjected to mass spectrometry (MS) analysis, and obtained data were shown in Table 11 below:

TABLE 11

| | | | |
|---|---|---|---|
| Compound 1 | m/z = 528.3[M + H]$^+$ | Compound 120 | m/z = 733.3[M + H]$^+$ |
| Compound 9 | m/z = 683.3[M + H]$^+$ | Compound 20 | m/z = 630.3[M + H]$^+$ |
| Compound 13 | m/z = 568.3[M + H]$^+$ | Compound 33 | m/z = 706.3[M + H]$^+$ |
| Compound 24 | m/z = 683.3[M + H]$^+$ | Compound 50 | m/z = 720.3[M + H]$^+$ |
| Compound 40 | m/z = 762.3[M + H]$^+$ | Compound 64 | m/z = 698.3[M + H]$^+$ |
| Compound 52 | m/z = 628.3[M + H]$^+$ | Compound 69 | m/z = 671.3[M + H]$^+$ |
| Compound 77 | m/z = 668.3[M + H]$^+$ | Compound 89 | m/z = 618.3[M + H]$^+$ |
| Compound 84 | m/z = 756.3[M + H]$^+$ | Compound 98 | m/z = 762.3[M + H]$^+$ |

TABLE 11-continued

| Compound 95 | m/z = 758.3[M + H]⁺ | Compound 104 | m/z = 730.3[M + H]⁺ |
|---|---|---|---|
| Compound 112 | m/z = 743.3[M + H]⁺ | Compound 108 | m/z = 746.3[M + H]⁺ |
| Compound 28 | m/z = 607.3[M + H]⁺ | Compound 130 | m/z = 607.3[M + H]⁺ |
| Compound 132 | m/z = 607.3[M + H]⁺ | | |

H nuclear magnetic resonance data of Compound 28:

$^1$H-NMR (CD$_2$Cl$_2$, 400 MHz): 9.03 (d, 1H), 8.39 (d, 1H), 8.32 (br, 4H), 8.20 (d, 1H), 8.12 (d, 1H), 8.03 (d, 1H), 7.61 (t, 1H), 7.55 (t, 2H), 7.49 (t, 1H), 7.43 (t, 4H), 7.03 (t, 1H), 6.97 (d, 1H), 6.90 (t, 1H), 3.14 (d, 4H), 2.31 (d, 2H), 2.10 (s, 2H), 1.96 (t, 4H), 1.87 (s, 2H).

H nuclear magnetic resonance data of Compound 130:

$^1$H NMR (CD$_2$Cl$_2$, 400 MHz): 9.76 (s, 1H), 9.00 (d, 1H), 8.76 (d, 4H), 8.44 (s, 1H), 8.18-8.15 (m, 2H), 7.96 (d, 1H), 7.68 (t, 2H), 7.63-7.58 (m, 5H), 7.47-7.42 (m, 2H), 7.31 (t, 1H), 3.21 (d, 2H), 2.99 (d, 2H), 2.21 (s, 1H), 1.96-1.94 (m, 3H), 1.83-1.79 (m, 4H), 1.86 (s, 2H).

H nuclear magnetic resonance data of Compound 132:

$^1$H NMR (CD$_2$Cl$_2$, 400 MHz): 9.64 (s, 1H), 9.21 (d, 1H), 8.84 (d, 4H), 8.76 (s, 1H), 8.19-8.16 (m, 2H), 8.01 (d, 1H), 7.73-7.67 (m, 6H), 7.61 (t, 1H), 7.48-7.45 (m, 2H), 7.35 (t, 1H), 3.14 (d, 2H), 3.00 (d, 2H), 2.37 (s, 1H), 2.26 (s, 1H), 2.08 (s, 2H), 1.93-1.86 (m, 4H), 1.68 (s, 2H).

The present disclosure also provides an electronic component to realize photoelectric conversion. The electronic component includes an anode and a cathode arranged oppositely, and a functional layer arranged between the anode and the cathode, where the functional layer includes the organic compound of the present disclosure.

The electronic component of the present disclosure may be, for example, an organic electroluminescent device or a photoelectric conversion device.

According to an embodiment, the electronic component may be an organic electroluminescent device. The organic electroluminescent device may be, for example, a red organic electroluminescent device or a green organic electroluminescent device.

As shown in FIG. 1, the organic electroluminescent device includes an anode 100 and a cathode 200 arranged oppositely, and a functional layer 300 arranged between the anode 100 and the cathode 200, where the functional layer 300 includes the organic compound provided in the present disclosure.

Optionally, the functional layer 300 may include an organic electroluminescent layer 330, and the organic electroluminescent layer 330 may include the organic compound provided in the present disclosure.

In an embodiment of the present disclosure, the organic electroluminescent device may include an anode 100, a hole injection layer 310, a hole transport layer 321, an electron blocking layer 322, an organic electroluminescent layer 330 (as an energy conversion layer), an electron transport layer 350, an electron injection layer 360, and a cathode 200 that are successively stacked. The organic compound provided in the present disclosure can be used for an organic electroluminescent layer 330 of an organic electroluminescent device to effectively improve the life span of the organic electroluminescent device.

Optionally, the anode 100 may includes the following anode material, which may be preferably a material with a large work function that facilitates the injection of holes into the functional layer. Specific examples of the anode material may include: metals, such as nickel, platinum, vanadium, chromium, copper, zinc, and gold or alloys thereof; metal oxides, such as zinc oxide, indium oxide, indium tin oxide (ITO), and indium zinc oxide (IZO); a combination of a metal and an oxide, such as ZnO:Al or SnO$_2$:Sb; or conductive polymers, such as poly(3-methylthiophene), poly[3,4-(ethylene-1,2-dioxy)thiophene] (PEDT), polypyrrole, and polyaniline; but are not limited thereto. Preferably, a transparent electrode with indium tin oxide (ITO) may be adopted as the anode.

Optionally, the hole transport layer 321 may include one or more hole transport materials, and the hole transport materials may be selected from carbazole polymers, carbazole-connected triarylamine compounds, and other compounds, which is not particularly limited in the present disclosure. For example, the hole transport layer 321 may include Compound HT-01 or Compound HT-03.

Optionally, the electron blocking layer 322 may include one or more electron blocking materials, and the electron blocking materials may be selected from carbazole polymers and other compounds, which is not particularly limited in the present disclosure. For example, the electron blocking layer 322 may include Compound HT-02, Compound HT-04, or Compound HT-05.

Optionally, the organic electroluminescent layer 330 may be composed of a host material and a guest material, and the compound of the present disclosure may be used as the host material. Holes injected into the organic electroluminescent layer 330 and electrons injected into the organic electroluminescent layer 330 can recombine in the organic electroluminescent layer 330 to form excitons, the excitons transfer energy to the host material, and then the host material transfers energy to the guest material, such that the guest material can emit light.

The guest material of the organic electroluminescent layer 330 may be a compound with a condensed aryl ring or a derivative thereof, a compound with a heteroaryl ring or a derivative thereof, an aromatic amine derivative, or other materials, which is not particularly limited in the present disclosure. In an embodiment of the present disclosure, the guest material of the organic electroluminescent layer 330 may be Ir(piq)$_2$(acac) or Ir(ppy)$_3$.

Optionally, the cathode 200 includes the following cathode material, which may be a material with a small work function that facilitates the injection of electrons into the functional layer. Specific examples of the cathode material may include: metals such as magnesium, calcium, sodium, potassium, titanium, indium, yttrium, lithium, gadolinium, aluminum, silver, tin, and lead or alloys thereof; or multilayer materials such as LiF/Al, Liq/Al, LiO$_2$/Al, LiF/Ca, LiF/Al, and BaF$_2$/Ca; but are not limited thereto. Preferably, a metal electrode with silver and magnesium may be adopted as the cathode.

Optionally, as shown in FIG. 1, a hole injection layer 310 may be further provided between the anode 100 and the first hole transport layer 321 to enhance the ability to inject holes into the first hole transport layer 321. The hole injection layer 310 material can be selected from a benzidine derivative, a starburst arylamine compound, a phthalocyanine derivative, or other materials, which is not particularly limited in the present disclosure. In an embodiment of the present disclosure, the hole injection layer 310 may be composed of F4-TCNQ.

Optionally, as shown in FIG. 1, an electron injection layer 360 may be further provided between the cathode 200 and the electron transport layer 350 to enhance the ability to inject electrons into the electron transport layer 350. The electron injection layer 360 may include an inorganic material such as an alkali metal sulfide and an alkali metal halide, or may include a complex of an alkali metal and an organic substance. In an embodiment of the present disclosure, the electron injection layer 360 may include ytterbium (Yb).

Optionally, a hole blocking layer 340 may also be provided between the organic electroluminescent layer 330 and the electron transport layer 350.

An embodiment of the present disclosure also provides an electronic device, including any one of the electronic components described in the embodiments of the above-mentioned electronic component. Since the electronic device has the electronic component described in any one of embodiments of the above-mentioned electronic component, the electronic device has the same beneficial effects as the electronic component, which will not be repeated in the present disclosure.

Figure 3:
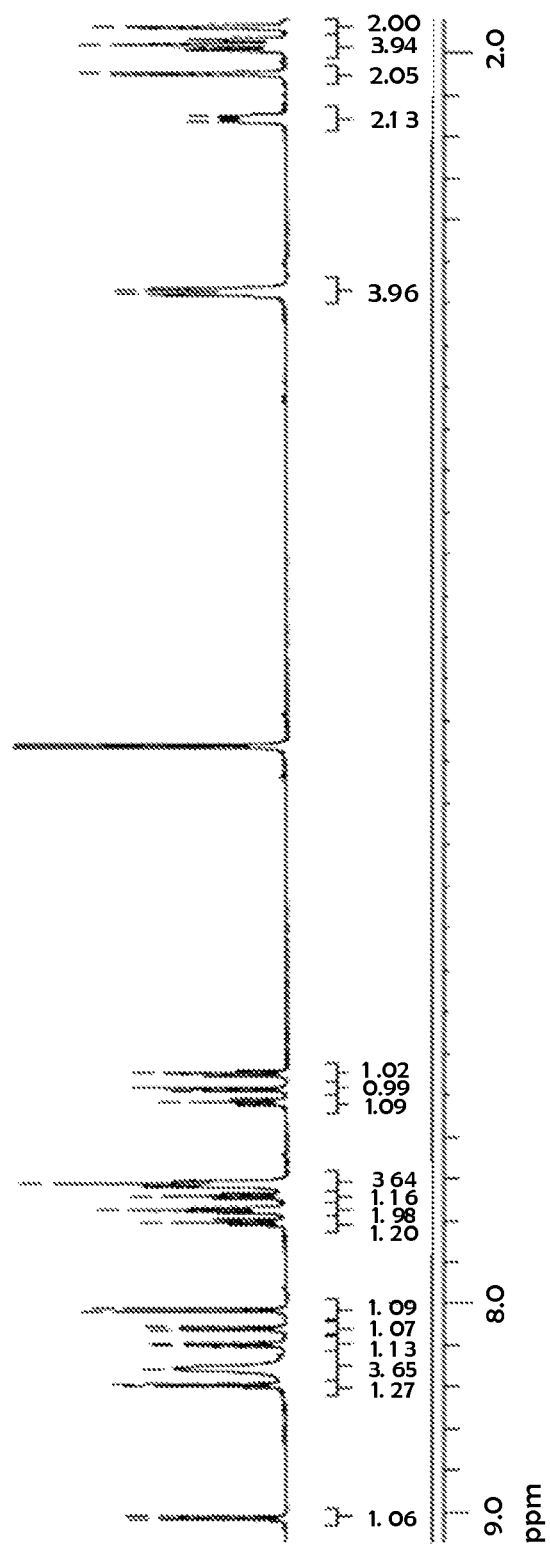
FIG. 3 is a nuclear magnetic resonance spectrum of Compound 28 according to one embodiment of the present disclosure.

For example, as shown in FIG. 3, the present disclosure provides an electronic device 400 including any one of the organic electroluminescent devices described in the embodiments of the above-mentioned organic electroluminescent device. The electronic device 400 may be a display device, a lighting device, an optical communication device, or other types of electronic device, including but not limited to computer screen, mobile phone screen, television set, electronic paper, emergency light, and optical module. Since the electronic device 400 has any one of the organic electroluminescent devices described in the embodiments of the above-mentioned organic electroluminescent device, the electronic device has the same beneficial effects as the organic electroluminescent device, which will not be repeated in the present disclosure.

Preparation and Performance Evaluation of Organic Electroluminescent Devices

Example 1: Green Organic Electroluminescent Device

An anode was produced by the following process: An ITO substrate (manufactured by Corning) with a thickness of 1,500 Å was cut into a size of 40 mm (length)×40 mm (width)×0.7 mm (thickness), then the substrate was processed through photolithography into an experimental substrate with cathode, anode, and insulating layer patterns, and the experimental substrate was subjected to a surface treatment with ultraviolet (UV)-ozone and $O_2$:$N_2$ plasma to increase a work function of the anode (experimental substrate) and remove scums.

F4-TCNQ was vacuum-deposited on the experimental substrate (anode) to form a hole injection layer (HIL) with a thickness of 100 Å. HT-01 was vapor-deposited on the hole injection layer to form a first hole transport layer with a thickness of 800 Å.

HT-02 was vacuum-deposited on the first hole transport layer to form a second hole transport layer with a thickness of 300 Å.

Compound 1, GHn1, and Ir(ppy)$_3$ were co-deposited on the second hole transport layer in a ratio of 50%:45%:5% to form a green organic electroluminescent layer (EML) with a thickness of 400 Å.

ET-01 and LiQ were mixed in a weight ratio of 1:1 and then vapor-deposited on the green organic electroluminescent layer to form an electron transport layer with a thickness of 300 Å, then LiQ was vapor-deposited on the electron transport layer to form an electron injection layer (EIL) with a thickness of 10 Å, and magnesium (Mg) and silver (Ag) were mixed in a ratio of 1:9 and then vacuum-deposited on the electron injection layer to form a cathode with a thickness of 105 Å.

In addition, CP-1 with a thickness of 650 Å was vapor-deposited on the cathode to form an organic capping layer (CPL), thereby completing the preparation of the organic electroluminescent device.

Examples 2 to 8

Organic electroluminescent devices were prepared by the same method as in Example 1, except that mixed components shown in Table 13 below were used instead of the mixed component in Example 1 when an organic electroluminescent layer was formed.

Comparative Examples 1 to 3

Organic electroluminescent devices were prepared by the same method as in Example 1, except that mixed components shown in Table 13 below were used instead of the mixed component in Example 1 when an organic electroluminescent layer was formed.

Structures of the materials used in the above examples and comparative examples were shown in Table 12 below:

TABLE 12

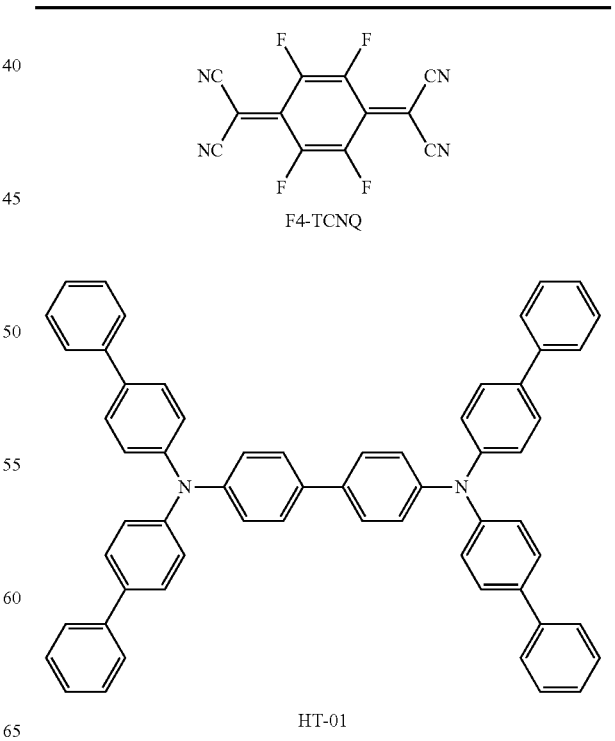

F4-TCNQ

HT-01

TABLE 12-continued
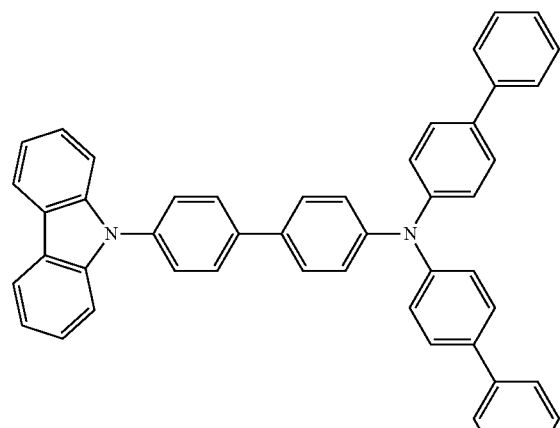
HT-02
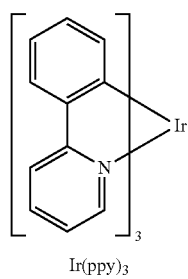
Ir(ppy)₃
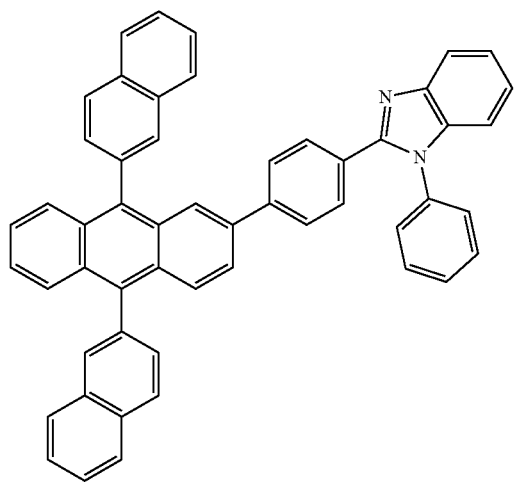
ET-01
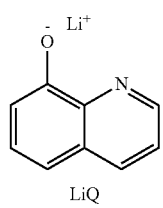
LiQ
TABLE 12-continued
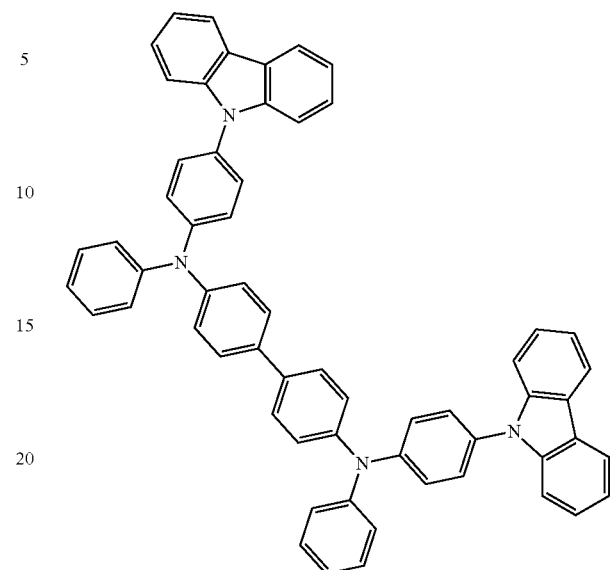
CP-1
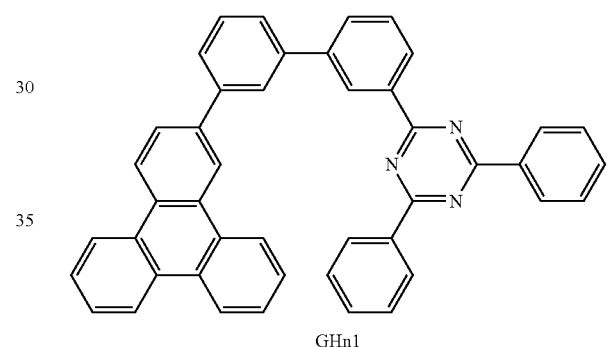
GHn1
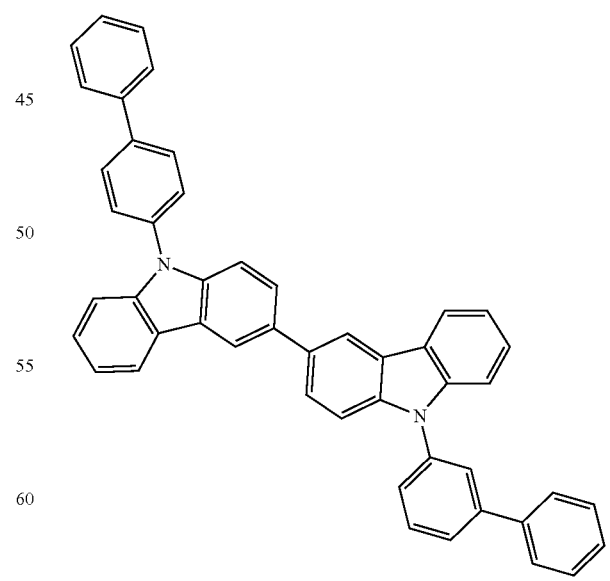
GHp1

TABLE 12-continued

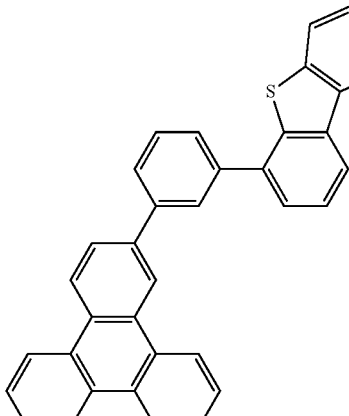

Compound A

TABLE 12-continued

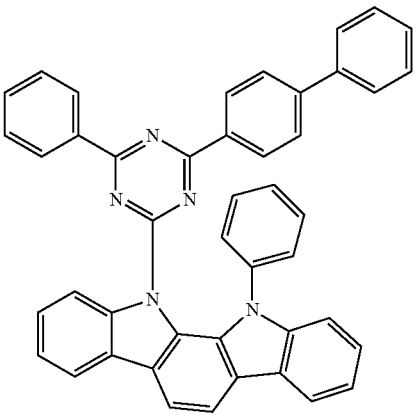

Compound C

The organic electroluminescent layers prepared above were subjected to performance analysis at 20 mA/cm$^2$, and results were shown in Table 13 below:

TABLE 13

| Example No. | EML:three materials = 50%:45%:5% | Driving voltage (V) | Current efficiency (Cd/A) | Power efficiency (lm/W) | Chromaticity coordinate CIEx, CIEy | External quantum efficiency (EQE) (%) | T95 life span (h) |
|---|---|---|---|---|---|---|---|
| Example 1 | Compound 1:GHn1:Ir(ppy)$_3$ | 3.82 | 78.4 | 64.5 | 0.22, 0.73 | 18.8 | 216 |
| Example 2 | Compound 13:GHn1:Ir(ppy)$_3$ | 3.69 | 78.2 | 66.6 | 0.22, 0.73 | 18.8 | 238 |
| Example 3 | GHp1:Compound 9:Ir(ppy)$_3$ | 3.80 | 72.9 | 60.3 | 0.22, 0.73 | 17.5 | 232 |
| Example 4 | GHp1:Compound 20:Ir(ppy)$_3$ | 3.89 | 79.3 | 64.0 | 0.22, 0.73 | 19.0 | 237 |
| Example 5 | GHp1:Compound 24:Ir(ppy)$_3$ | 3.67 | 71.5 | 61.2 | 0.22, 0.73 | 17.1 | 240 |
| Example 6 | GHp1:Compound 28:Ir(ppy)$_3$ | 3.82 | 75.3 | 61.9 | 0.22, 0.73 | 18.1 | 240 |
| Example 7 | GHp1:Compound 130:Ir(ppy)$_3$ | 3.77 | 76.0 | 63.3 | 0.22, 0.73 | 18.2 | 229 |
| Example 8 | GHp1:Compound 132:Ir(ppy)$_3$ | 3.81 | 74.9 | 61.7 | 0.22, 0.73 | 17.9 | 233 |
| Comparative Example 1 | Compound A:GHn1:Ir(ppy)$_3$ | 3.77 | 77.8 | 64.9 | 0.22, 0.73 | 18.7 | 135 |
| Comparative Example 2 | Compound B:GHn1:Ir(ppy)$_3$ | 3.80 | 73.2 | 60.5 | 0.22, 0.73 | 17.6 | 152 |
| Comparative Example 3 | GHp1:Compound C:Ir(ppy)$_3$ | 3.89 | 77.6 | 62.7 | 0.22, 0.73 | 18.6 | 140 |

TABLE 12-continued

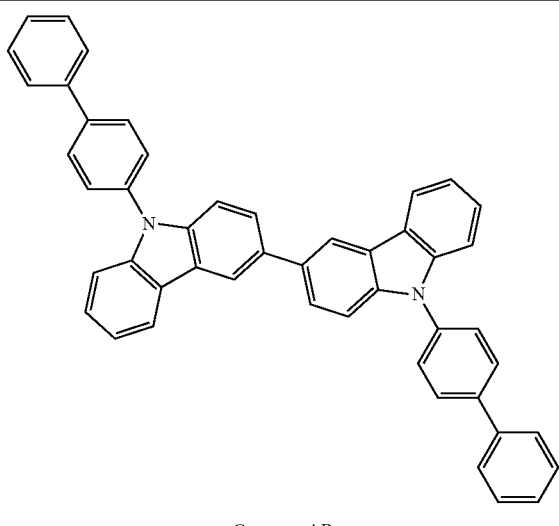

Compound B

With reference to Table 13, it can be seen that, compared with the organic electroluminescent layers of Comparative Examples 1 to 3, Examples 1 to 8 using the compound of the present disclosure as the mixed host material for the green light-emitting layer have a life span extended by at least 42% under similar driving voltage and luminous efficiency.

Therefore, when the novel compound of the present disclosure is used to produce a green organic electroluminescent device, it can effectively extend the life span and improve the luminous efficiency to a certain extent of the organic electroluminescent device.

Example 9: Red Organic Electroluminescent Device

An anode was produced by the following process: An ITO substrate (manufactured by Corning) with a thickness of 1,500 Å was cut into a size of 40 mm (length)×40 mm (width)×0.7 mm (thickness), then the substrate was processed through photolithography into an experimental substrate with cathode, anode, and insulating layer patterns, and the experimental substrate was subjected to a surface treatment with ultraviolet (UV)-ozone and $O_2$:$N_2$ plasma to increase a work function of the anode (experimental substrate) and remove scums.

F4-TCNQ was vacuum-deposited on the experimental substrate (anode) to form a hole injection layer (HIL) with a thickness of 100 Å. HT-03 was vapor-deposited on the hole injection layer to form a first hole transport layer with a thickness of 800 Å.

HT-04 was vacuum-deposited on the first hole transport layer to form a second hole transport layer with a thickness of 850 Å.

Compound 40 and Ir(piq)$_2$ (acac) were co-deposited on the second hole transport layer in a ratio of 95%:5% to form a red organic electroluminescent layer (EML) with a thickness of 350 Å.

ET-02 and LiQ were mixed in a weight ratio of 1:1 and then vapor-deposited on the red organic electroluminescent layer to form an electron transport layer with a thickness of 300 Å, then LiQ was vapor-deposited on the electron transport layer to form an electron injection layer with a thickness of 10 Å, and magnesium (Mg) and silver (Ag) were mixed in a ratio of 1:9 and then vacuum-deposited on the electron injection layer to form a cathode with a thickness of 105 Å.

In addition, CP-1 with a thickness of 650 Å was vapor-deposited on the cathode to form an organic capping layer (CPL), thereby completing the preparation of the organic electroluminescent device.

Examples 10 to 17

Organic electroluminescent devices were produced by the same method as in Example 9, except that Compounds shown in Table 15 below were used instead of Compound 40 when an organic electroluminescent layer was formed.

Comparative Example 4

An organic electroluminescent device was produced by the same method as in Example 9, except that BAlq was used instead of Compound 40 when an organic electroluminescent layer was formed.

Comparative Example 5

An organic electroluminescent device was produced by the same method as in Example 9, except that Compound D was used instead of Compound 40 when an organic electroluminescent layer was formed.

Structures of the materials used in the above examples and comparative examples were shown in Table 14 below:

TABLE 14

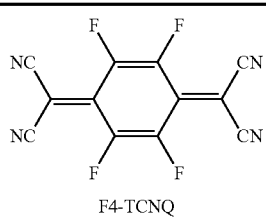

F4-TCNQ

TABLE 14-continued

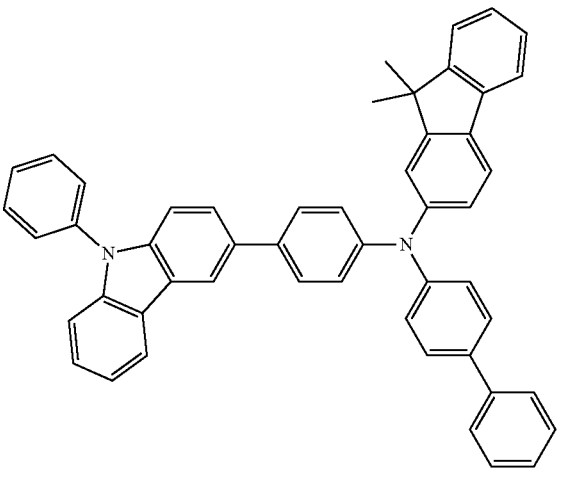

HT-03

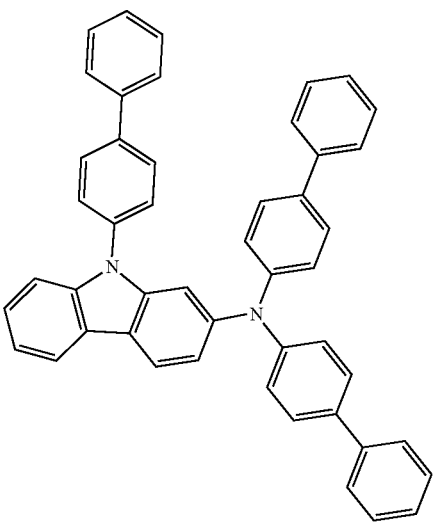

HT-04

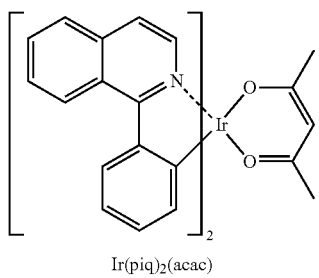

Ir(piq)$_2$(acac)

TABLE 14-continued

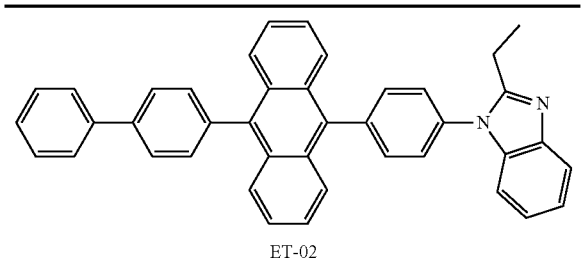
ET-02

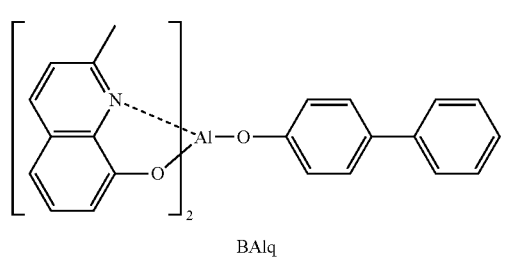
BAlq

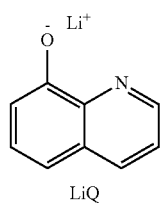
LiQ

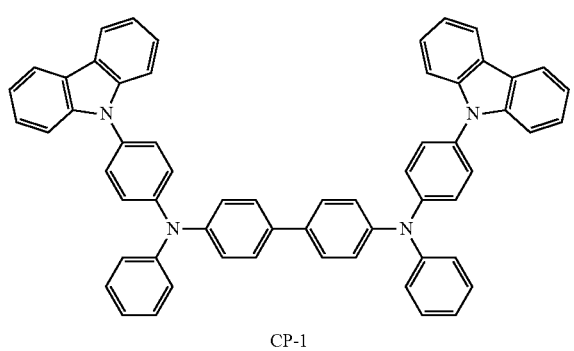 [SMILES: c1ccc(N(c2ccc(-c3ccc(N(c4ccccc4)c4ccc(-n5c6ccccc6c6ccccc65)cc4)cc3)cc2)c2ccc(-n3c4ccccc4c4ccccc43)cc2)cc1 ; "CP-1"]
CP-1

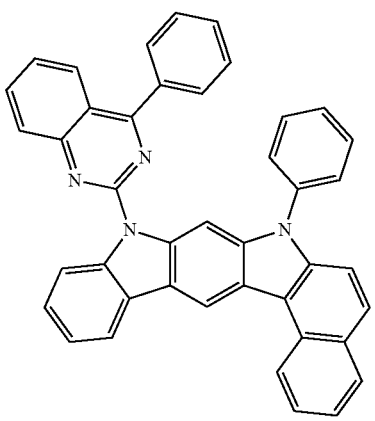
Compound D

The organic electroluminescent devices produced above were subjected to performance analysis at 20 mA/cm$^2$, and results were shown in Table 15 below:

TABLE 15

| Example No. | EML:compound: Ir(piq)$_2$acac = 95%:5% | Driving voltage (V) | Current efficiency (Cd/A) | Power efficiency (lm/W) | Chromaticity coordinate CIEx, CIEy | External quantum efficiency (EQE) (%) | T95 life span (h) |
|---|---|---|---|---|---|---|---|
| Example 9 | Compound 40 | 3.61 | 38.9 | 33.8 | 0.68, 0.32 | 26.4 | 430 |
| Example 10 | Compound 33 | 3.52 | 38.9 | 34.7 | 0.68, 0.32 | 26.4 | 443 |
| Example 11 | Compound 50 | 3.64 | 41.7 | 36.0 | 0.68, 0.32 | 28.4 | 400 |
| Example 12 | Compound 64 | 3.55 | 38.2 | 33.8 | 0.68, 0.32 | 26.0 | 473 |
| Example 13 | Compound 69 | 3.72 | 41.0 | 34.6 | 0.68, 0.32 | 27.9 | 384 |
| Example 14 | Compound 84 | 3.53 | 40.9 | 36.4 | 0.68, 0.32 | 27.8 | 395 |
| Example 15 | Compound 89 | 3.71 | 38.7 | 32.8 | 0.68, 0.32 | 26.3 | 452 |
| Example 16 | Compound 98 | 3.64 | 39.5 | 34.1 | 0.68, 0.32 | 26.9 | 445 |
| Example 17 | Compound 104 | 3.61 | 38.9 | 33.8 | 0.68, 0.32 | 26.4 | 430 |
| Comparative Example 4 | BAlq | 4.49 | 33.0 | 23.1 | 0.68, 0.32 | 22.4 | 388 |
| Comparative Example 5 | Compound D | 3.73 | 33.1 | 27.8 | 0.68, 0.32 | 22.5 | 207 |

With reference to Table 15, it can be seen that, compared with the organic electroluminescent device of Comparative Example 4, the organic electroluminescent devices of Examples 9 to 17 using the compound of the present disclosure in the host material for a red light-emitting layer have a driving voltage reduced by at least 17% and a luminous efficiency increased by at least 15%; and compared with the organic electroluminescent layer of Comparative Example 5, the organic electroluminescent layers of Examples 9 to 17 have a luminous efficiency increased by at least 15% and a life span increased by a certain extent.

Therefore, when the novel compound of the present disclosure is used to prepare a red organic electroluminescent device, it can effectively improve the efficiency and the life span of the organic electroluminescent device.

Example 18: Red Organic Electroluminescent Device

An anode was produced by the following process: An ITO substrate (manufactured by Corning) with a thickness of 1,500 Å was cut into a size of 40 mm (length)×40 mm (width)×0.7 mm (thickness), then the substrate was processed through photolithography into an experimental substrate with cathode, anode, and insulating layer patterns, and the experimental substrate was subjected to a surface treatment with ultraviolet (UV)-ozone and $O_2:N_2$ plasma to increase a work function of the anode (experimental substrate) and remove scums.

F4-TCNQ was vacuum-deposited on the experimental substrate (anode) to form a hole injection layer (HIL) with a thickness of 100 Å. HT-03 was vapor-deposited on the hole injection layer to form a first hole transport layer with a thickness of 800 Å.

HT-05 was vacuum-deposited on the first hole transport layer to form a second hole transport layer with a thickness of 900 Å.

Compound 52, RHn1, and Ir(piq)$_2$(acac) were co-deposited on the second hole transport layer in a ratio of 50%: 45%:5% to form a red organic electroluminescent layer (EML) with a thickness of 300 Å.

ET-03 and LiQ were mixed in a weight ratio of 2:1 and then vapor-deposited on the organic electroluminescent layer to form an electron transport layer with a thickness of 300 Å, then LiQ was vapor-deposited on the electron transport layer to form an electron injection layer with a thickness of 10 Å, and magnesium (Mg) and silver (Ag) were mixed in a ratio of 1:9 and then vacuum-deposited on the electron injection layer to form a cathode with a thickness of 105 Å.

In addition, CP-1 with a thickness of 650 Å was vapor-deposited on the cathode to form an organic capping layer (CPL), thereby completing the preparation of the organic electroluminescent device.

Examples 19 to 23

Organic electroluminescent devices were produced by the same method as in Example 18, except that mixed components shown in Table 17 below were used instead of the mixed component in Example 18 when an organic electroluminescent layer was formed.

Comparative Examples 6 to 7

Organic electroluminescent devices were produced by the same method as in Example 18, except that mixed components shown in Table 17 below were used instead of the mixed component in Example 18 when an organic electroluminescent layer was formed.

Structures of the materials used in the above examples and comparative examples were shown in Table 16 below:

TABLE 16

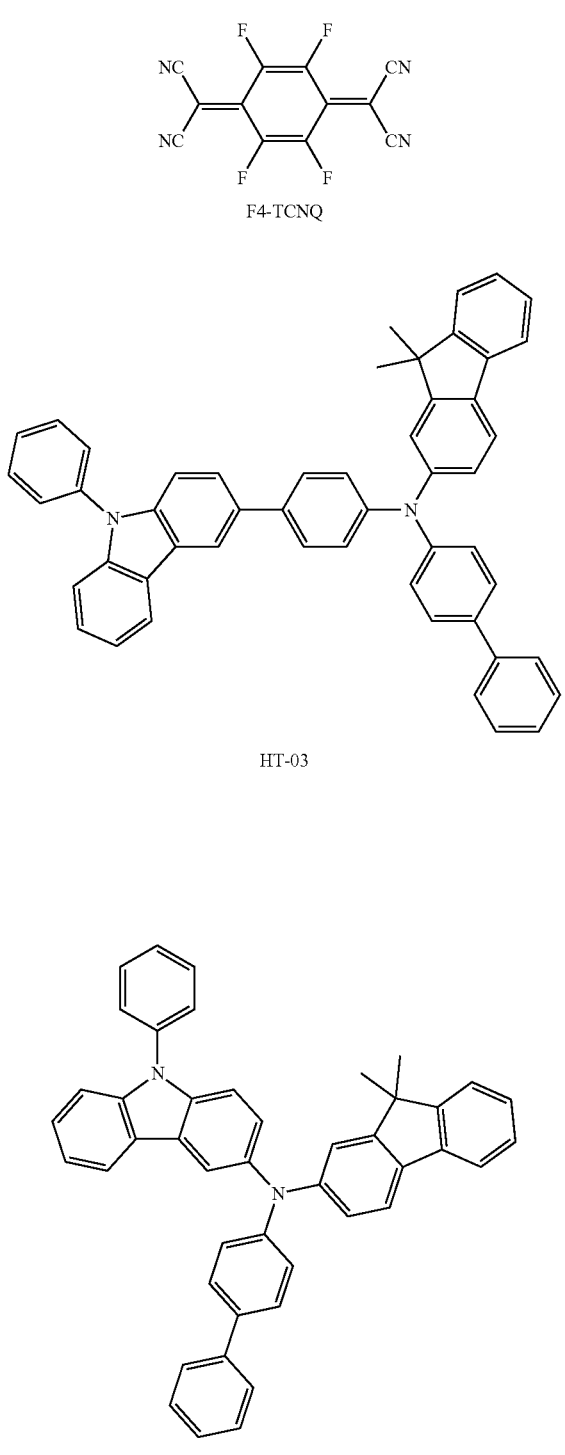

TABLE 16-continued
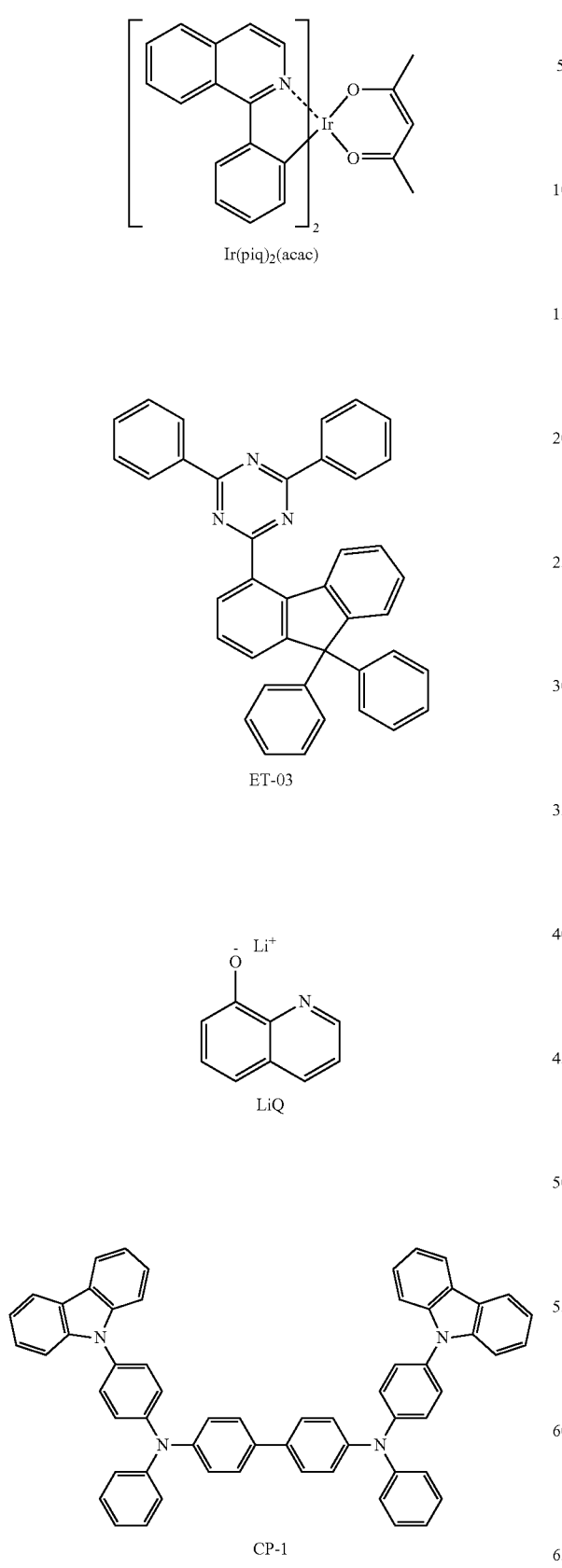
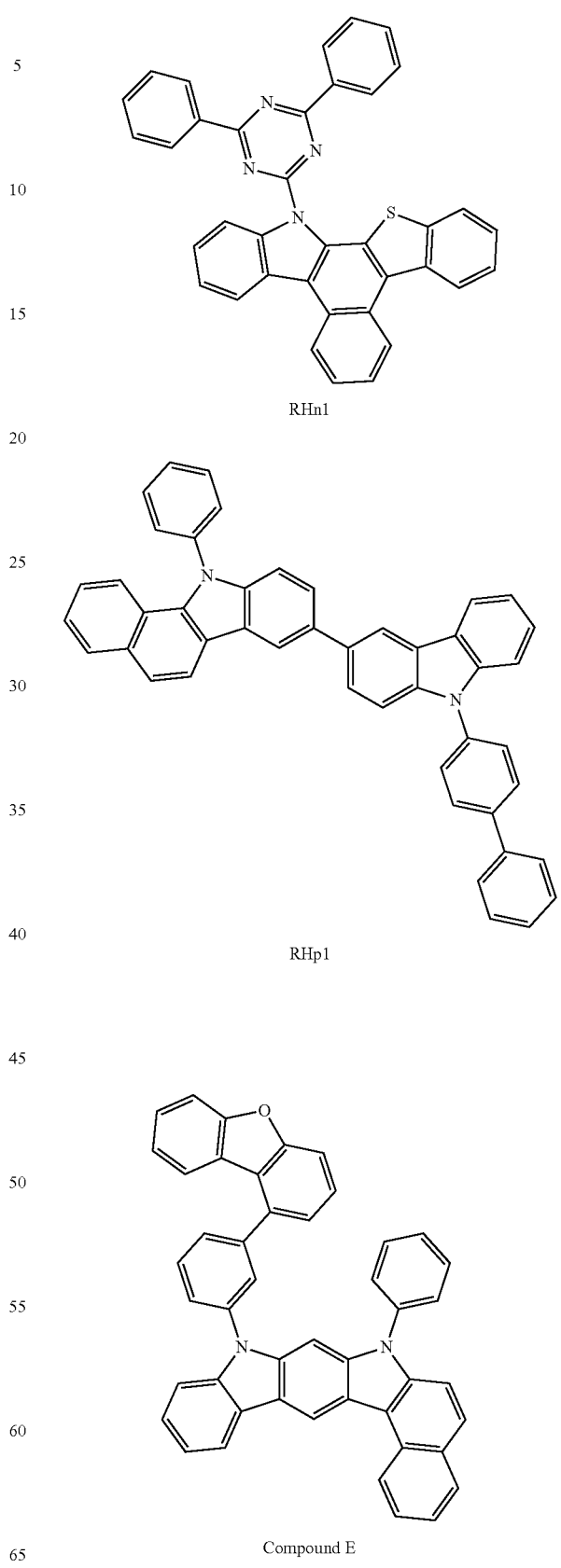

TABLE 16-continued

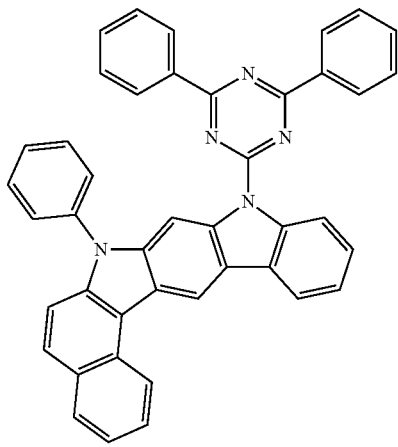

Compound F

The organic electroluminescent devices produced above were subjected to performance analysis at 20 mA/cm², and results were shown in Table 17 below:

TABLE 17

| Example No. | EML 50%:45%:5% | Driving voltage (V) | Current efficiency (Cd/A) | Power efficiency (lm/W) | Chromaticity coordinate CIEx, CIEy | External quantum efficiency (EQE) (%) | T95 life span (h) |
|---|---|---|---|---|---|---|---|
| Example 18 | Compound 52:RHn1:Ir(piq)₂ (acac) | 3.49 | 46.2 | 41.6 | 0.68, 0.32 | 31.4 | 352 |
| Example 19 | Compound 77:RHn1:Ir(piq)₂ (acac) | 3.44 | 44.1 | 40.3 | 0.68, 0.32 | 30.0 | 355 |
| Example 20 | Compound 112:RHn1:Ir(piq)₂ (acac) | 3.58 | 46.3 | 40.6 | 0.68, 0.32 | 31.5 | 389 |
| Example 21 | RHp1:Compound 95:Ir(piq)₂ (acac) | 3.58 | 44.6 | 39.1 | 0.68, 0.32 | 30.3 | 326 |
| Example 22 | RHp1:Compound 108:Ir(piq)₂ (acac) | 3.41 | 44.9 | 41.4 | 0.68, 0.32 | 30.5 | 391 |
| Example 23 | RHp1:Compound 120:Ir(piq)₂ (acac) | 3.56 | 45.2 | 39.9 | 0.68, 0.32 | 30.8 | 335 |
| Comparative Example 6 | Compound E:RHn1:IR(piq)₂ (acac) | 3.53 | 46.7 | 41.6 | 0.68, 0.32 | 31.8 | 227 |
| Comparative Example 7 | RHp1:Compound F:Ir(piq)₂ (acac) | 3.46 | 45.5 | 41.3 | 0.68, 0.32 | 31.0 | 282 |

With reference to Table 17, it can be seen that, compared with the organic electroluminescent devices of Comparative Examples 6 and 7, the organic electroluminescent devices of Examples 18 to 23 using the compound of the present disclosure in the mixed host material for the red light-emitting layer have a life span extended by at least 15% under similar driving voltage and luminous efficiency.

Therefore, when the novel compound of the present disclosure is used to produce a red organic electroluminescent device with a mixed host material, it can effectively improve the life span of the organic electroluminescent device.

What is claimed is:

1. An organic compound having structures shown in Chemical formula 1 and Chemical formula 2:

Chemical formula 1

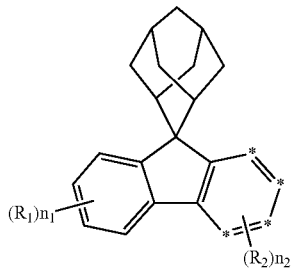

Chemical formula 2

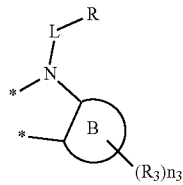

wherein two * in Chemical formula 2 are attached to any two adjacent * of four * in Chemical formula 1 to form a fused ring;

Ring B is a benzene ring or a naphthalene ring;

L is selected from the group consisting of a single bond and the following groups:

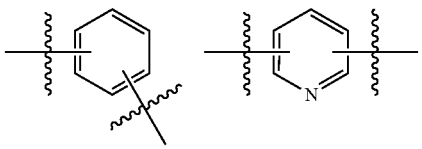

-continued

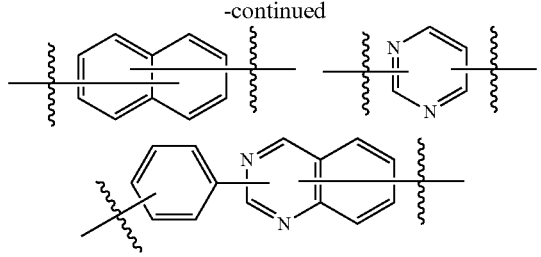

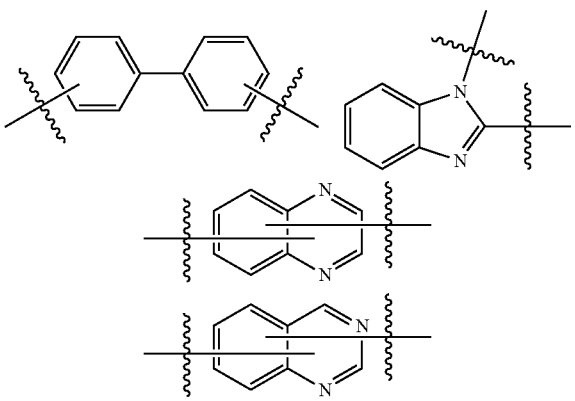

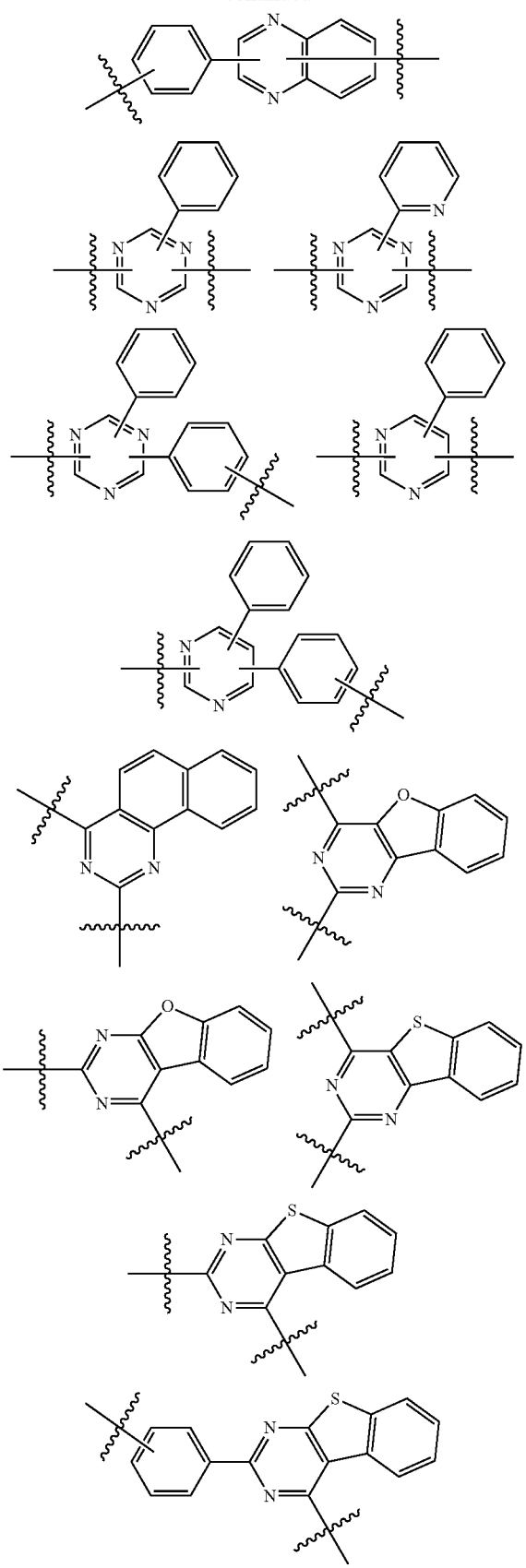
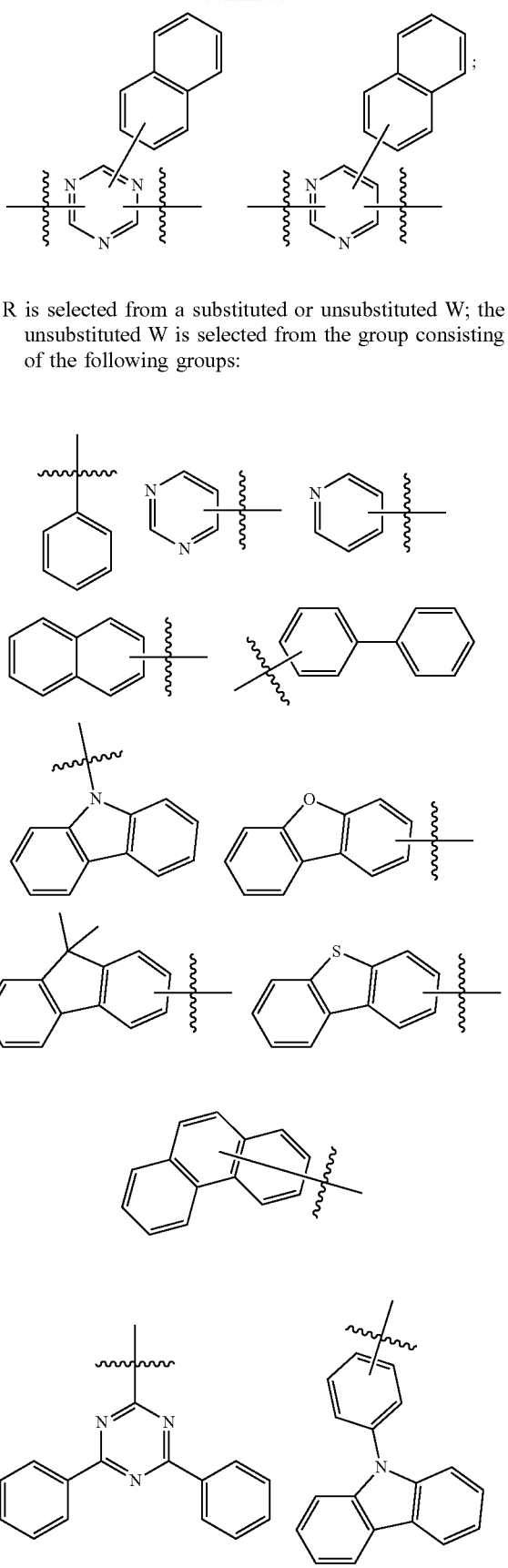
R is selected from a substituted or unsubstituted W; the unsubstituted W is selected from the group consisting of the following groups:

-continued

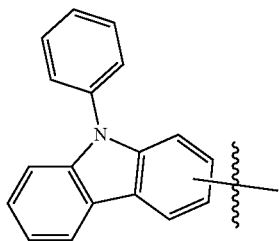

when W is substituted, the substituents of W are selected from hydrogen, deuterium, a fluorine, a chlorine, a cyano, an alkyl with 1 to 5 carbon atoms, a haloalkyl with 1 to 4 carbon atoms, an aryl with 6 to 12 carbon atoms, or a heteroaryl with 3 to 12 carbon atoms; and when W is substituted by a plurality of substituents, the plurality of substituents are the same or different; or R is selected from

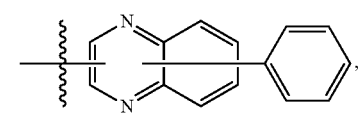,

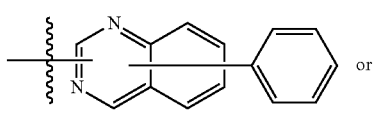 or

;

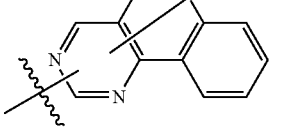

$R_1$, $R_2$, and $R_3$ are respectively independently selected from hydrogen, deuterium, or an alkyl with 1 to 5 carbon atoms;

$n_t$ is the number of substituents $R_t$, wherein t is any integer from 1 to 3; when t is 1, $n_t$ is selected from 1, 2, 3, or 4; when t is 2, $n_t$ is selected from 1 or 2; when t is 3, $n_t$ is selected from 1, 2, 3, 4, 5, or 6; and when $n_t$ is greater than 1, any two substituents $R_t$ are the same or different.

2. The organic compound according to claim 1, wherein Chemical formula 2 is any one of Chemical formula 2-1, Chemical formula 2-2, Chemical formula 2-3, and Chemical formula 2-4:

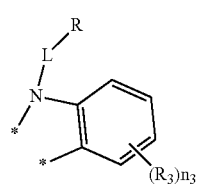 2-1

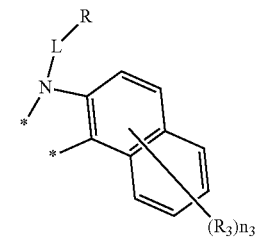 2-2

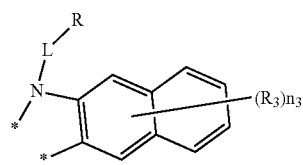 2-3

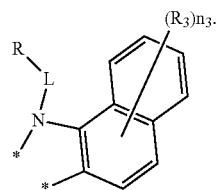 2-4

3. The organic compound according to claim 1, wherein L is selected from the group consisting of a single bond and the following groups:

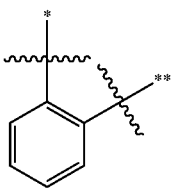 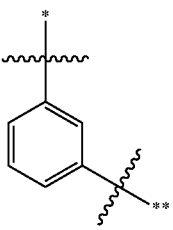

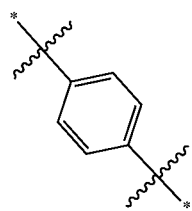 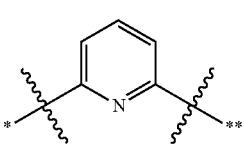

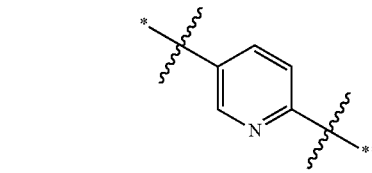

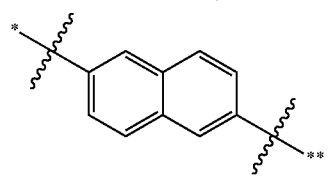

171
-continued
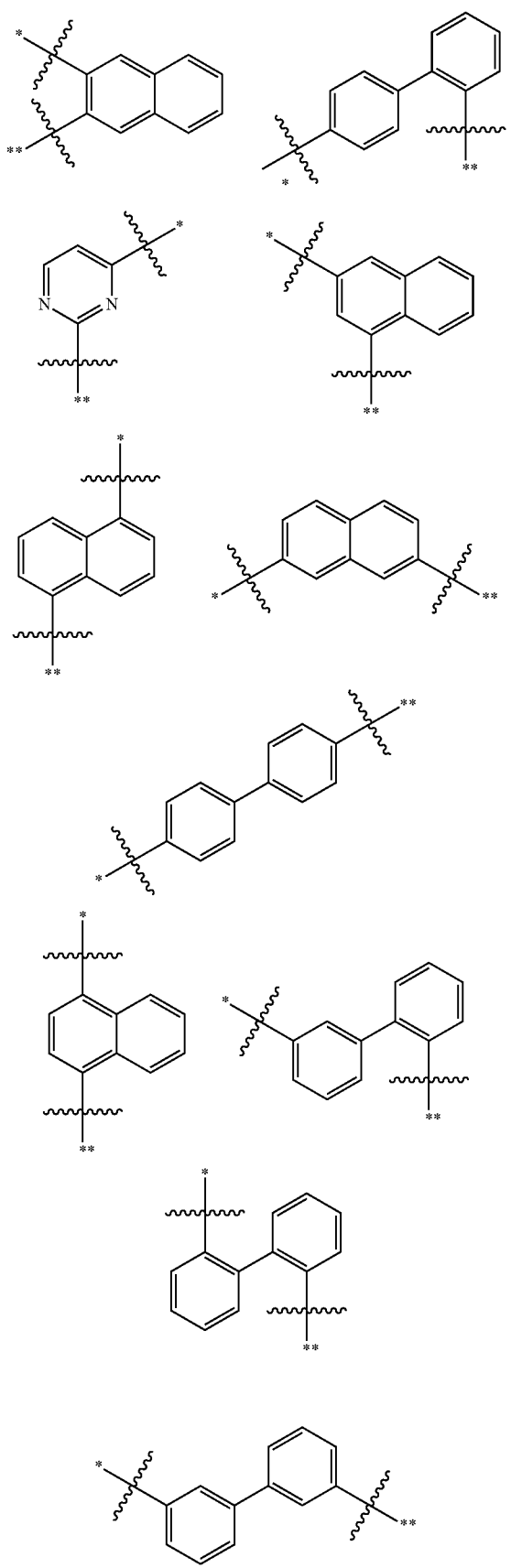
172
-continued
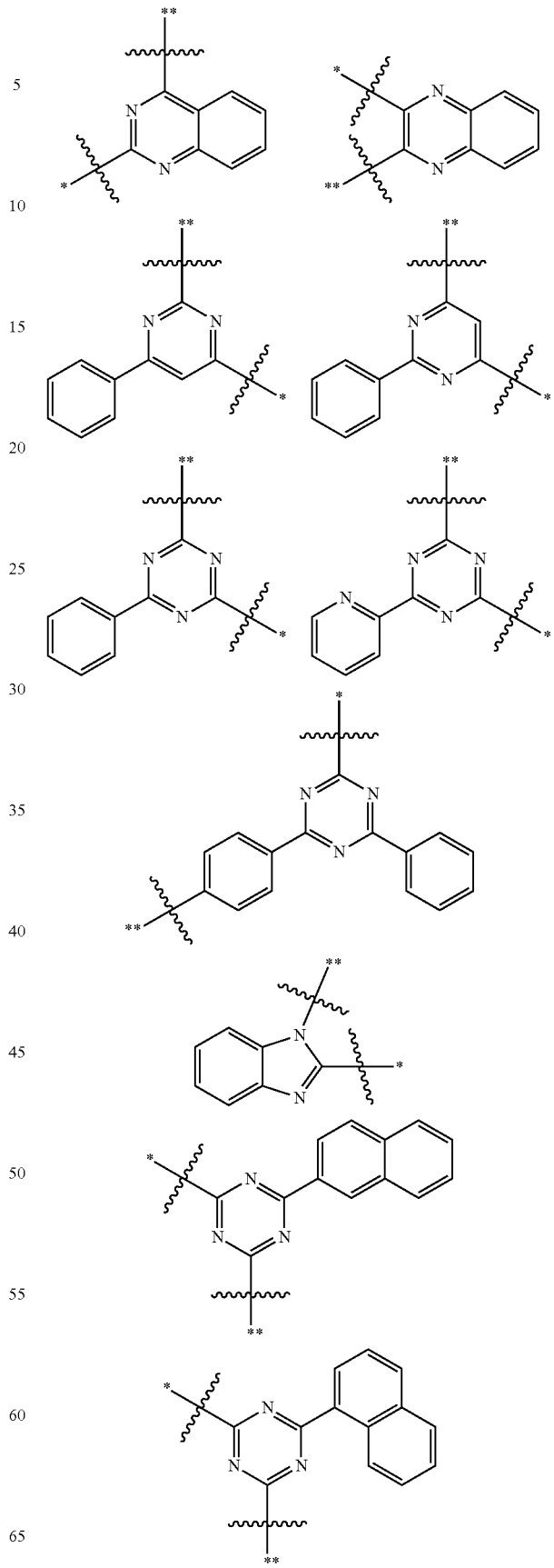

173
-continued
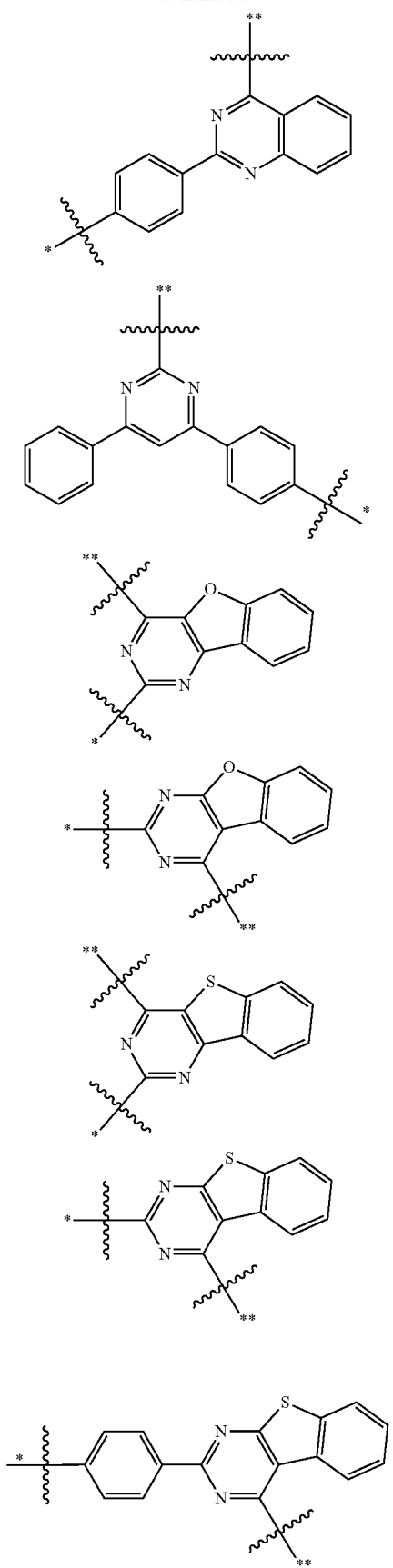
174
-continued
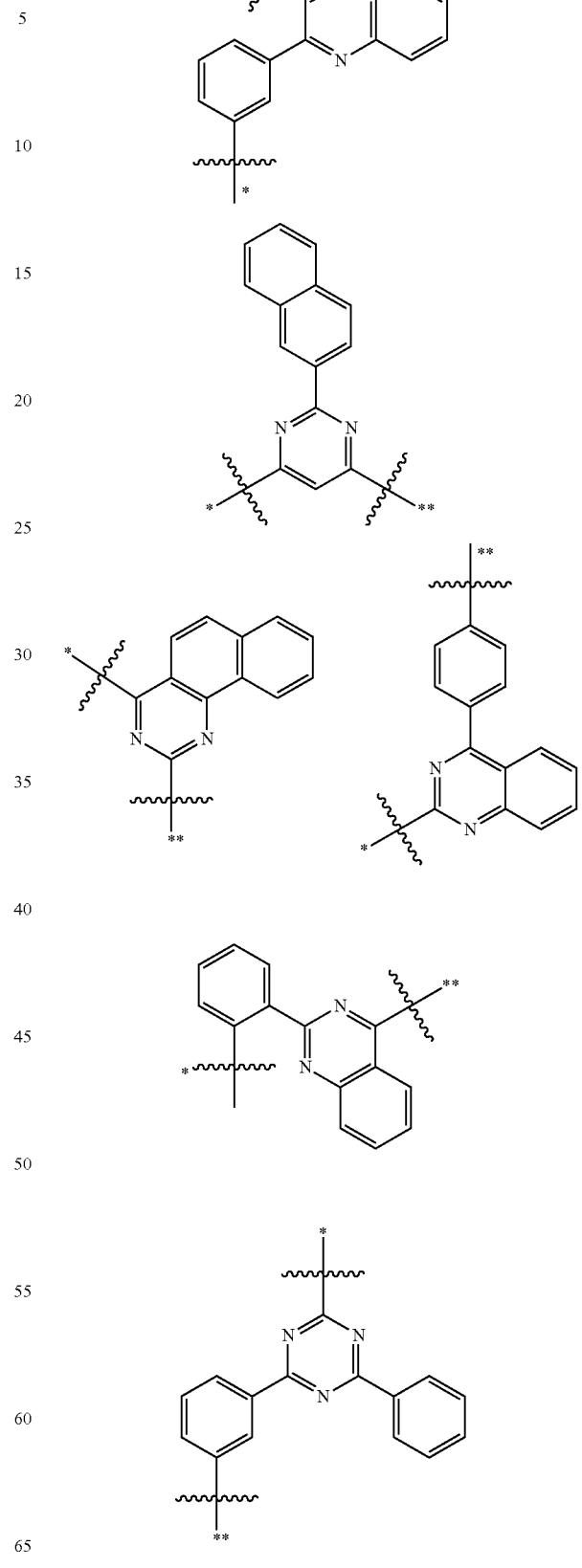

-continued

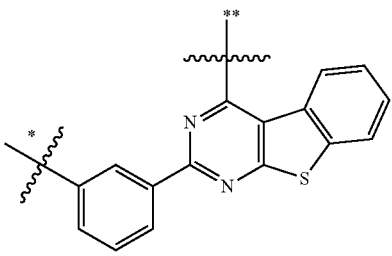

where * represents a point connected with

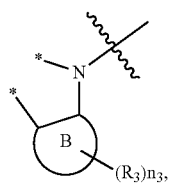

and ** represents a point connected with R.

4. The organic compound according to claim 1, wherein L is selected from the group consisting of a single bond and the following groups:

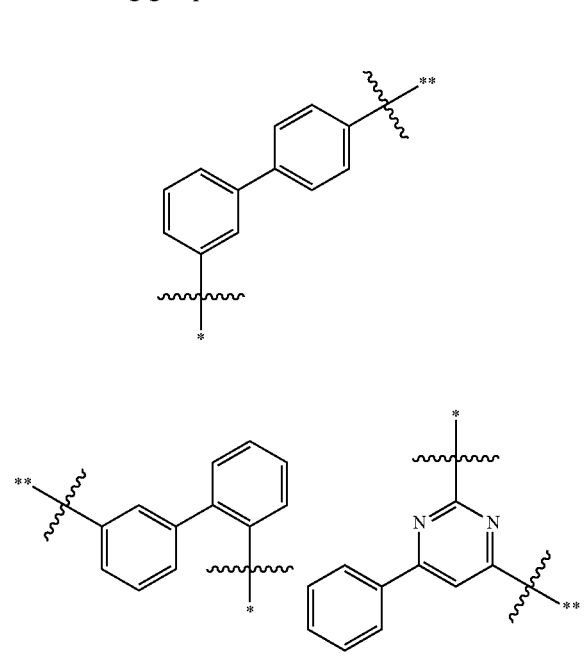

-continued

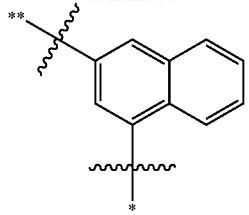

where * represents a point connected with

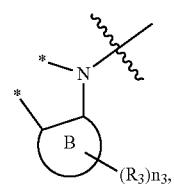

and ** represents a point connected with R.

5. The organic compound according to claim 1, wherein R is selected from the group consisting of the following groups:

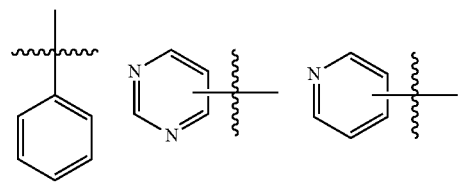
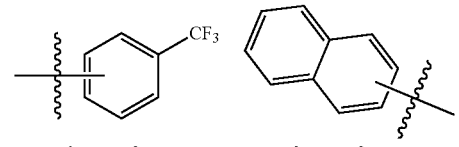
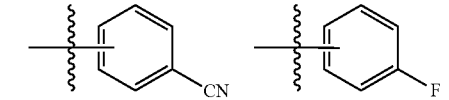
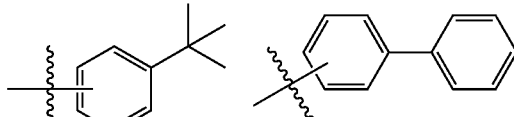
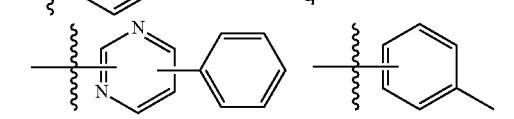
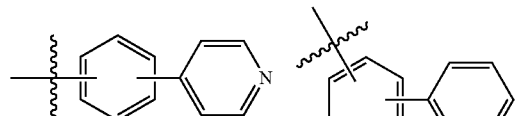
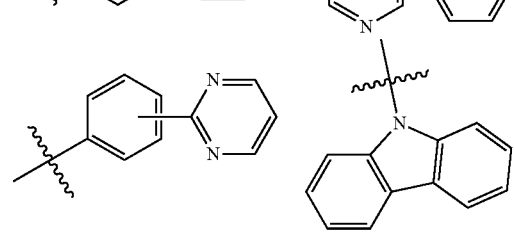

-continued
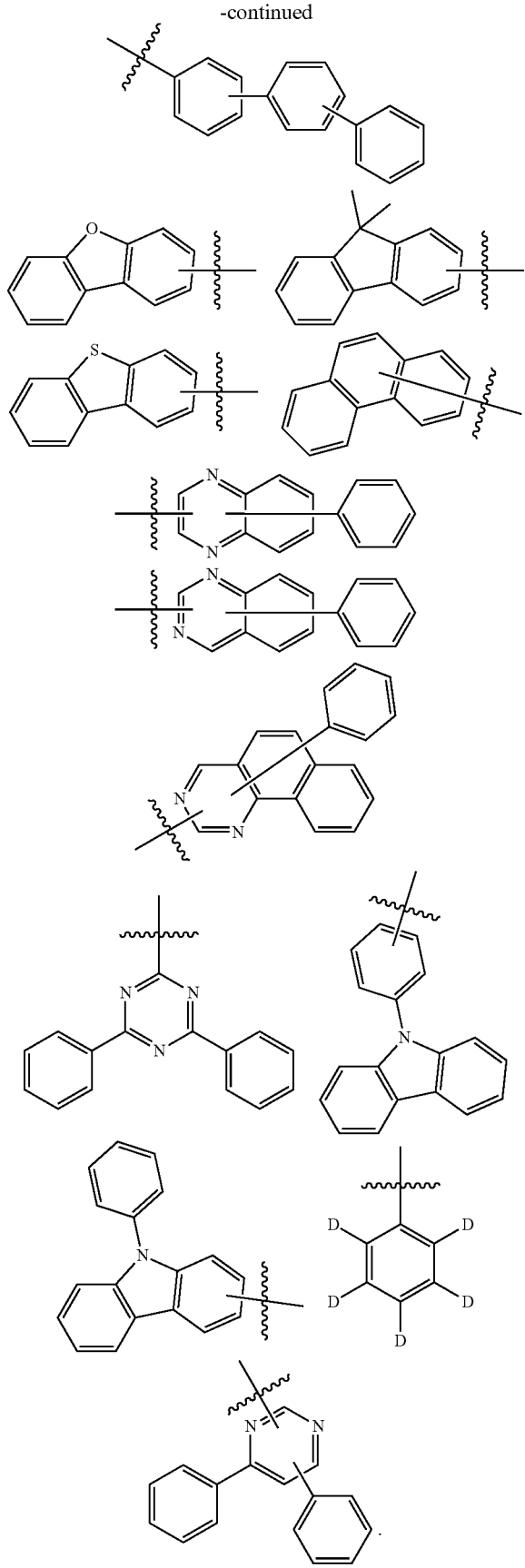
6. The organic compound according to claim 1, wherein R is selected from the group consisting of the following groups:
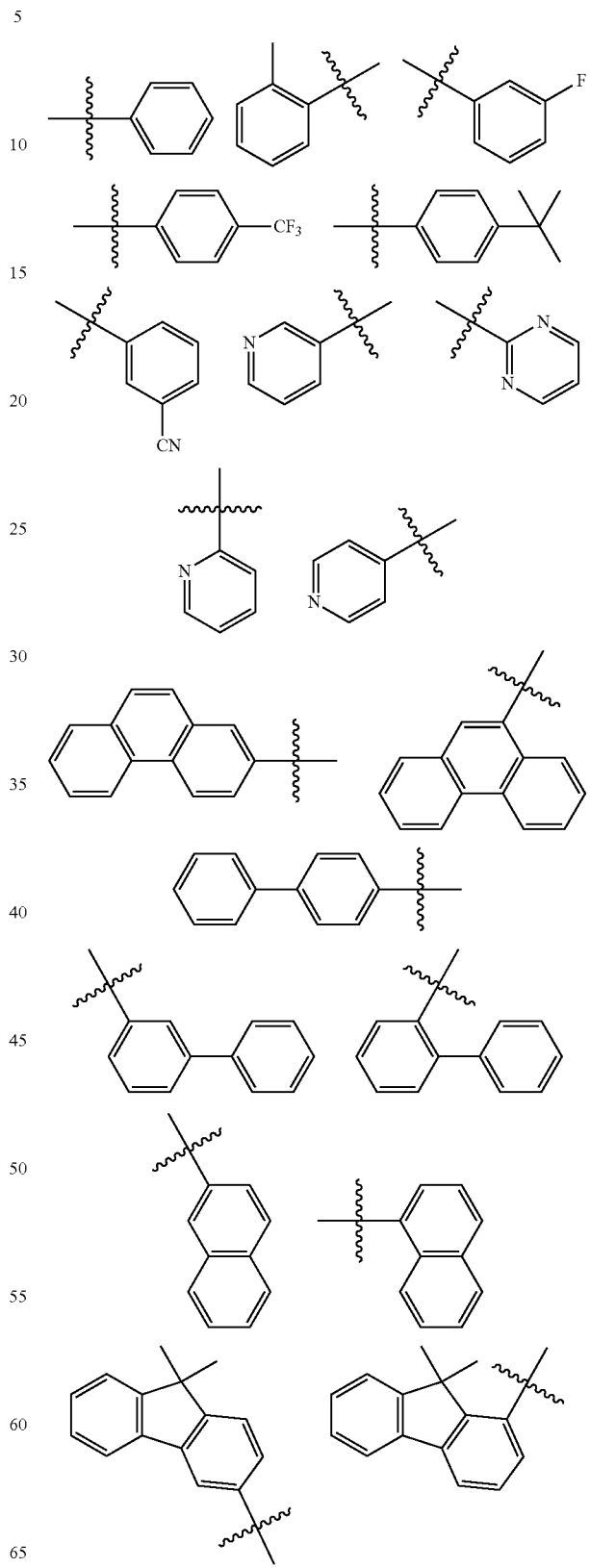

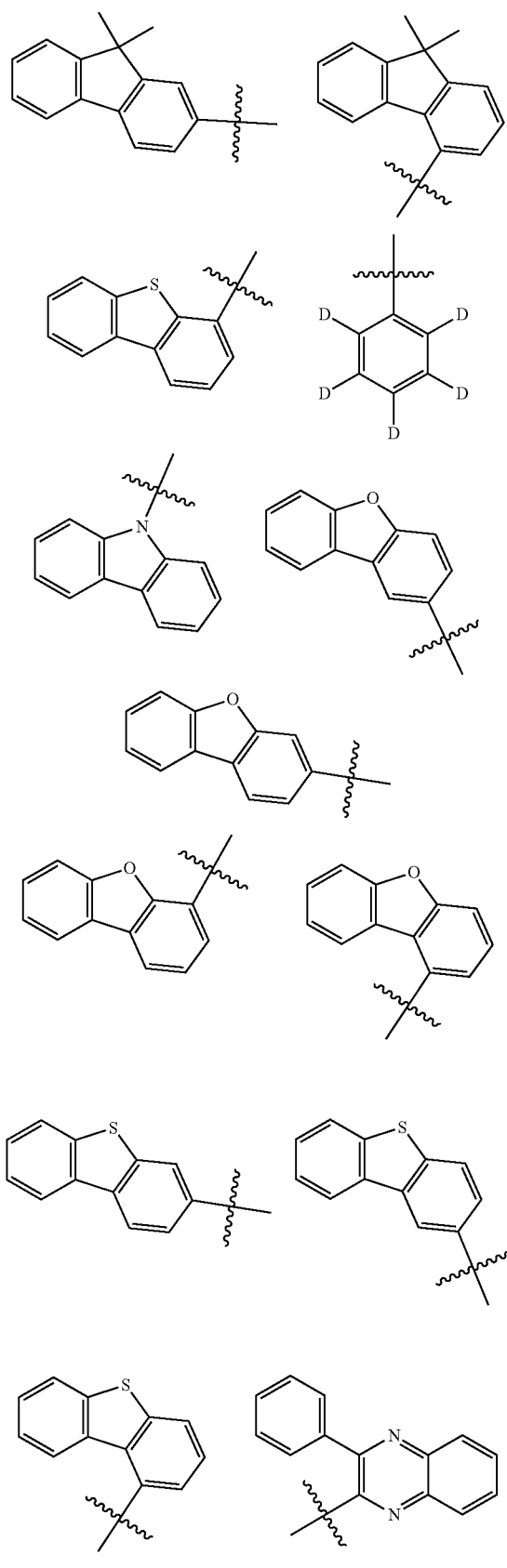
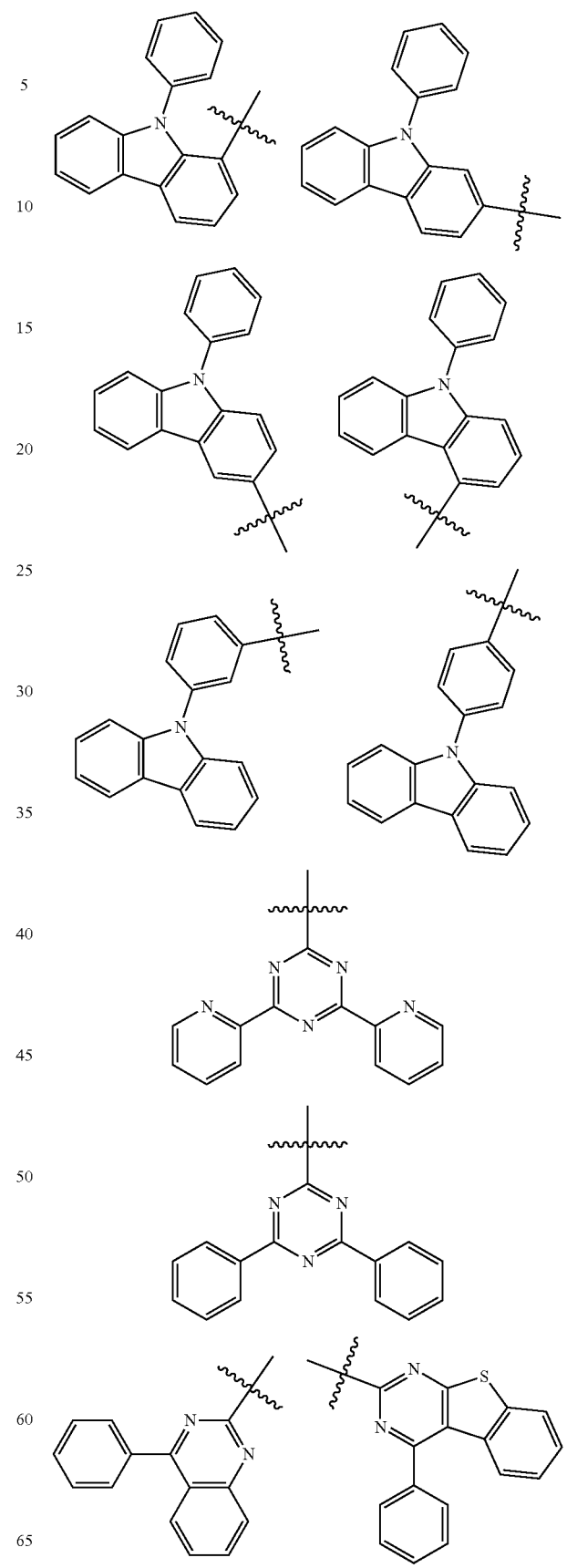

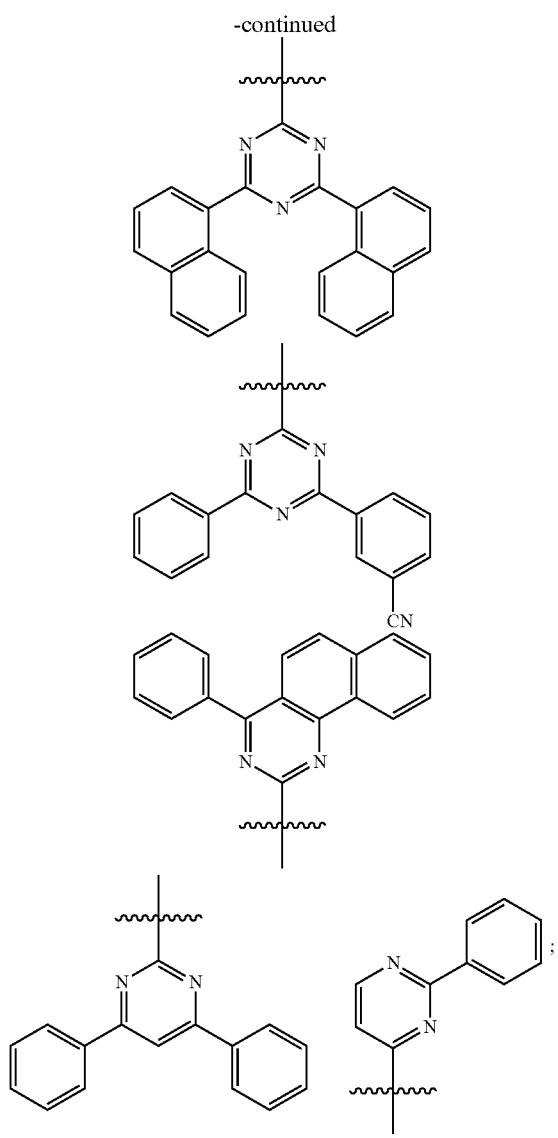
and
R₁, R₂, and R₃ are selected from hydrogen, deuterium, a methyl, an ethyl, an isopropyl, a tert-butyl.
7. The organic compound according to claim 1, wherein the organic compound is selected from the group consisting of the following compounds:
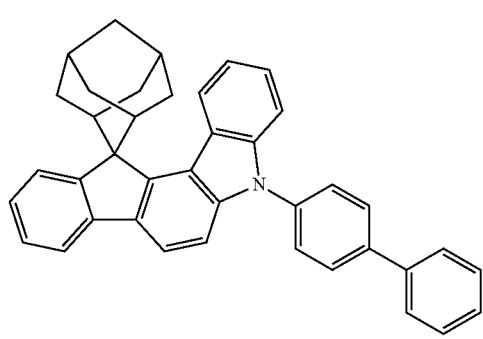
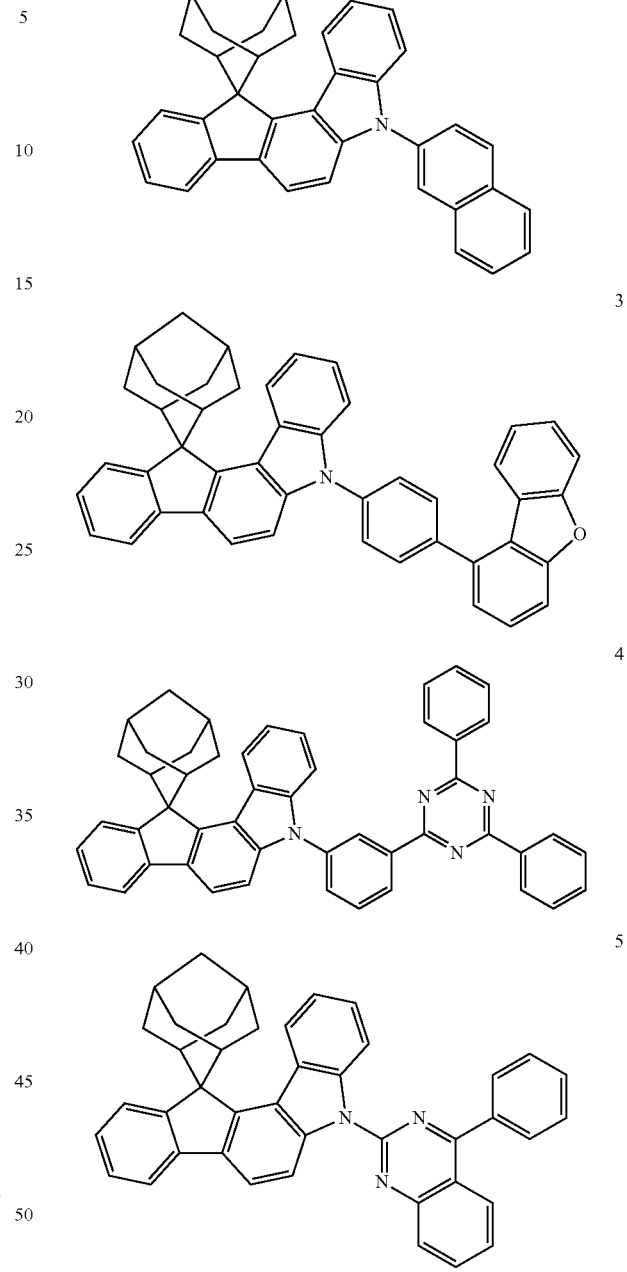
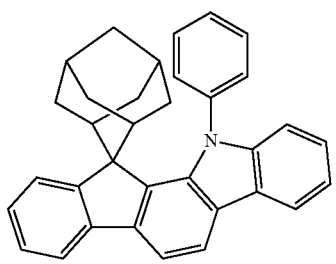

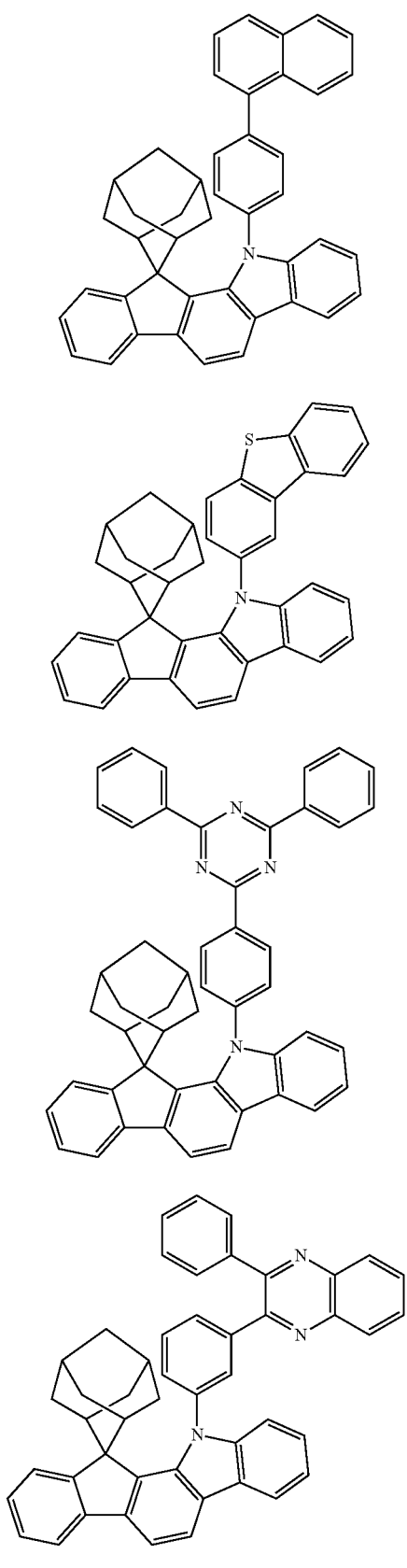
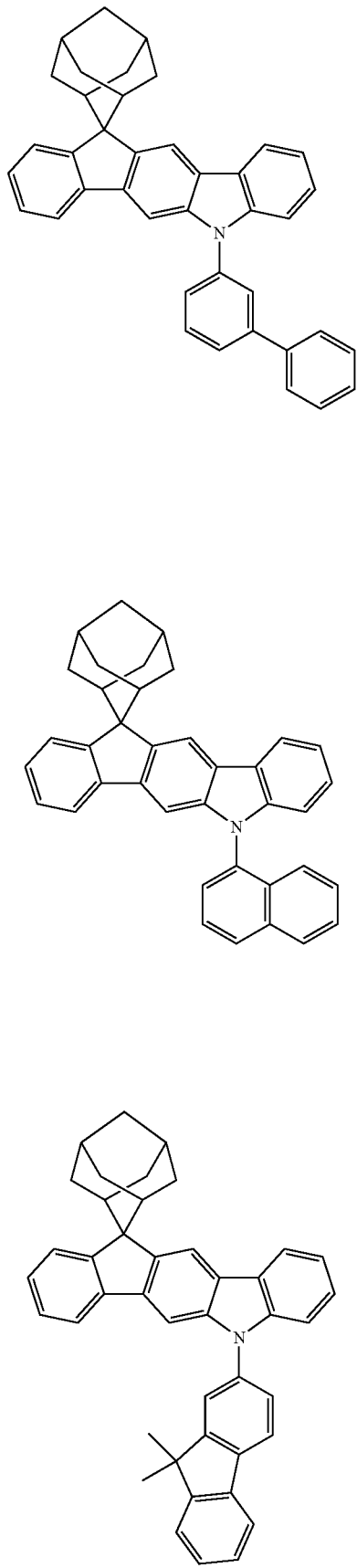

14
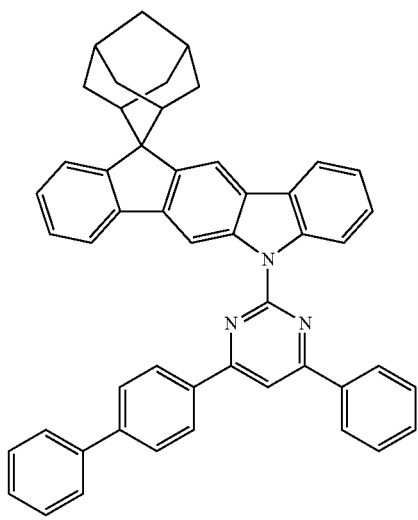
15
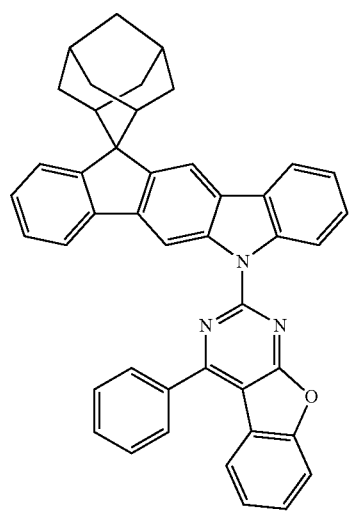
16
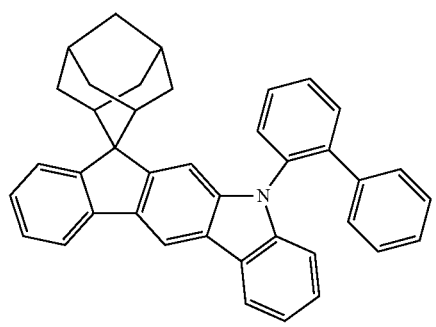
17
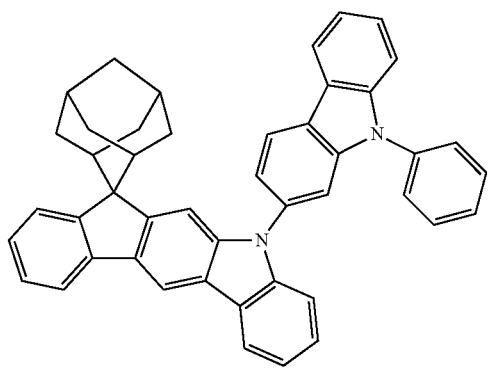
18
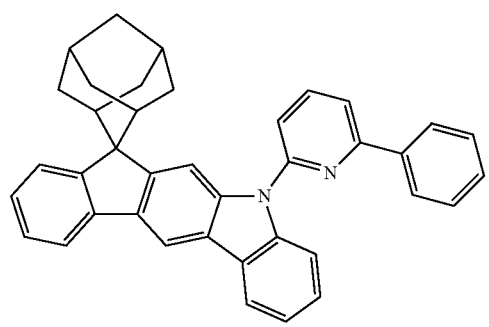
19
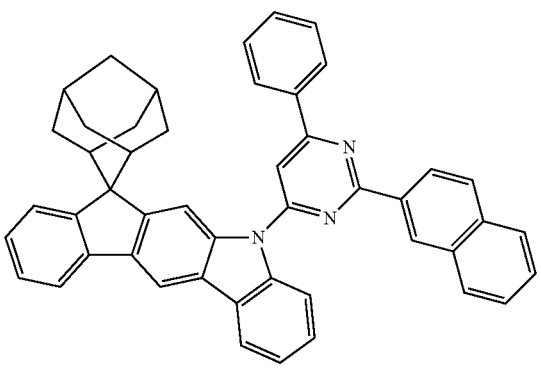
20
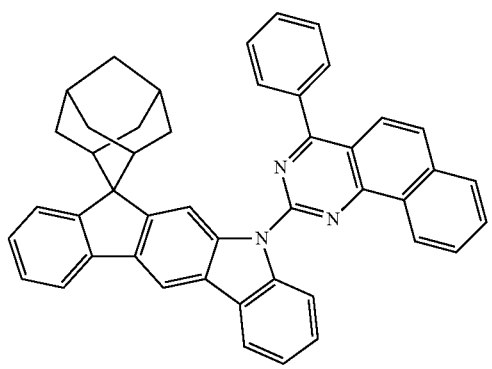

187
-continued
21
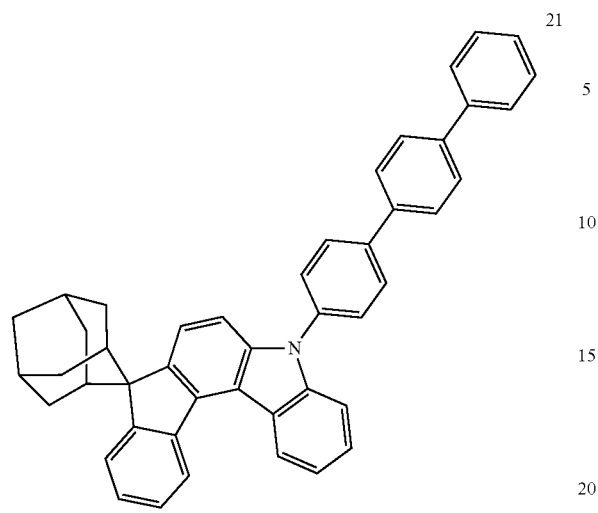
22
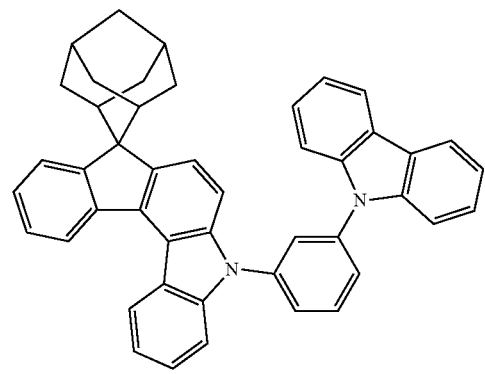
23
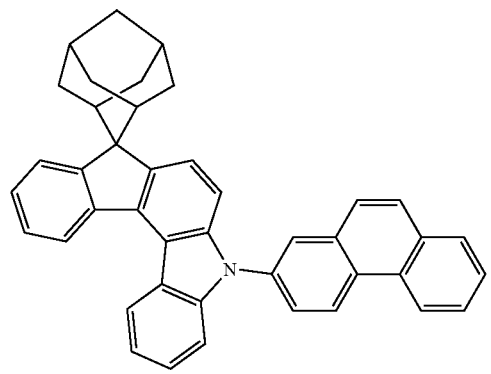
24
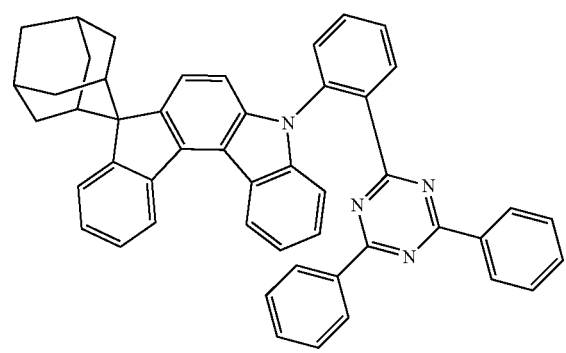
188
-continued
25
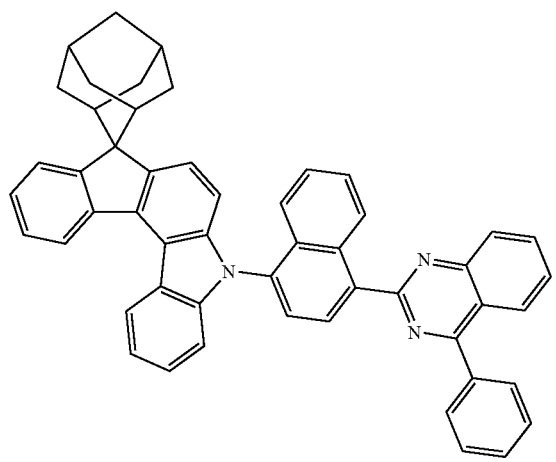
26
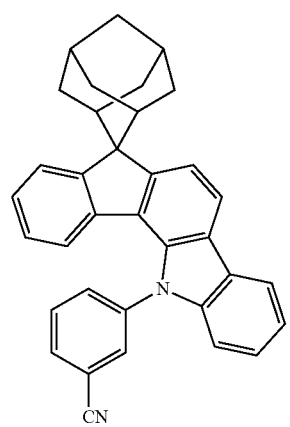
27
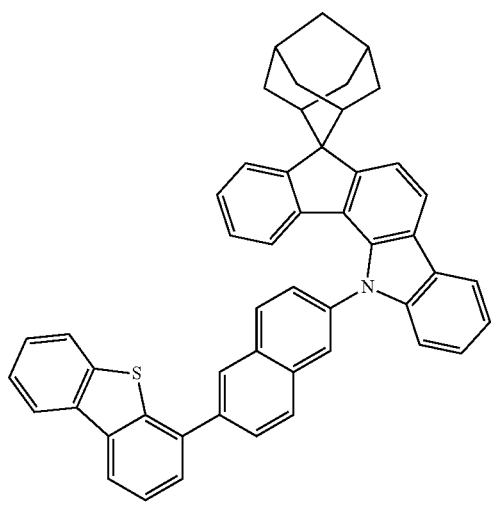

189
-continued
28
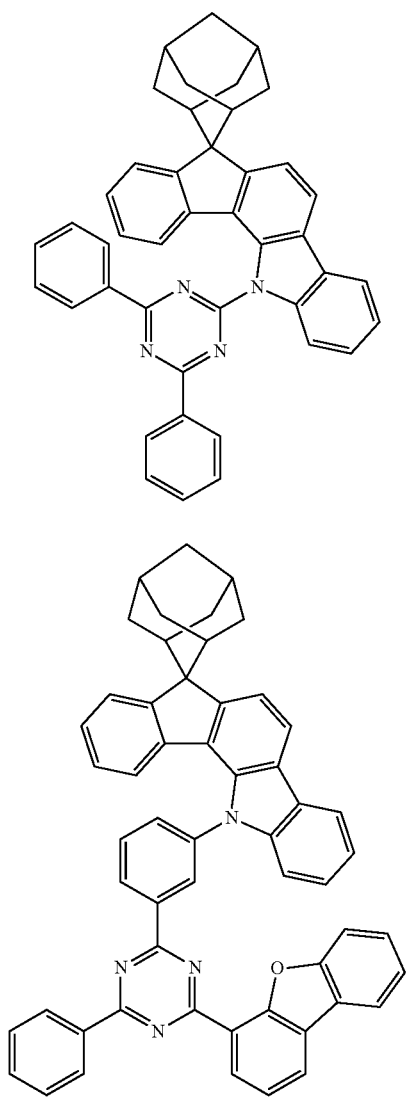
29
30
190
-continued
31
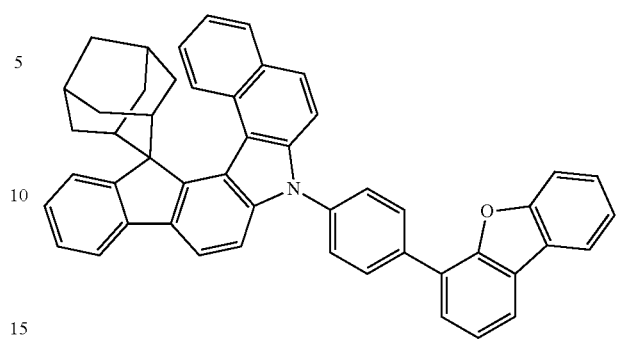
32
33
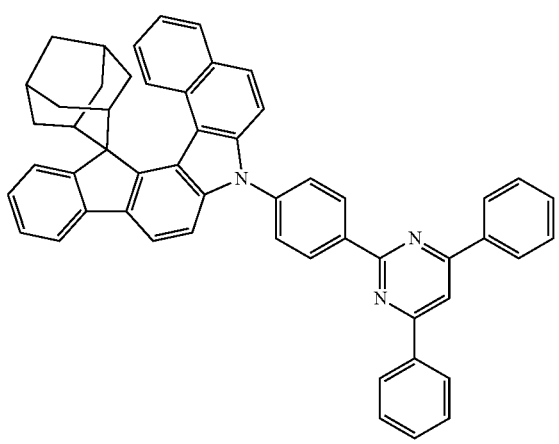
34

35
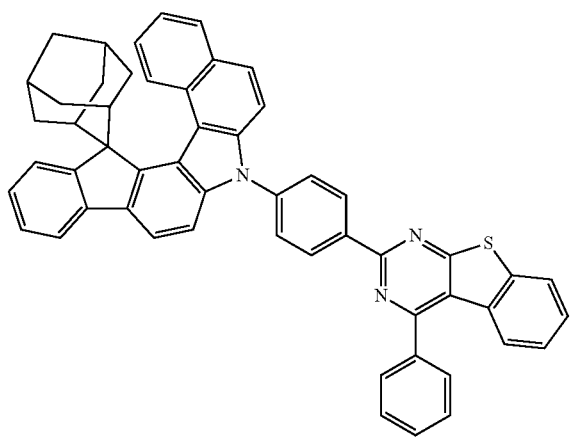
36
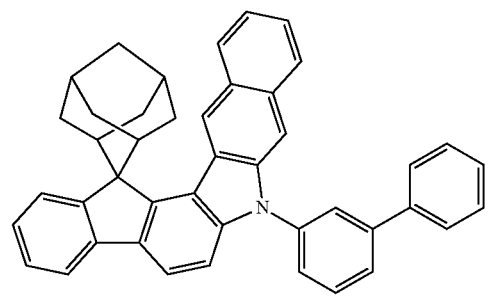
37
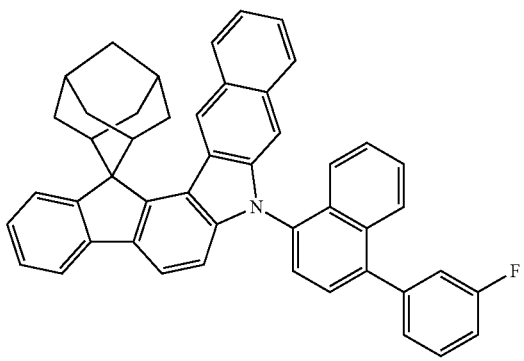
38
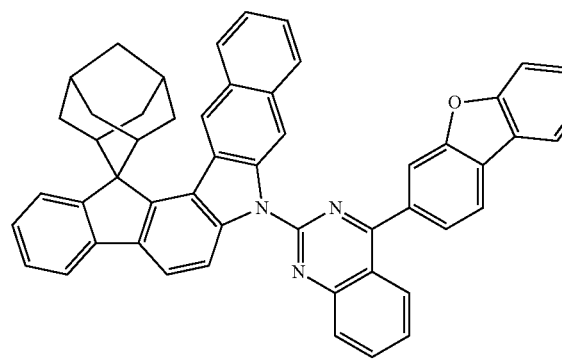
39
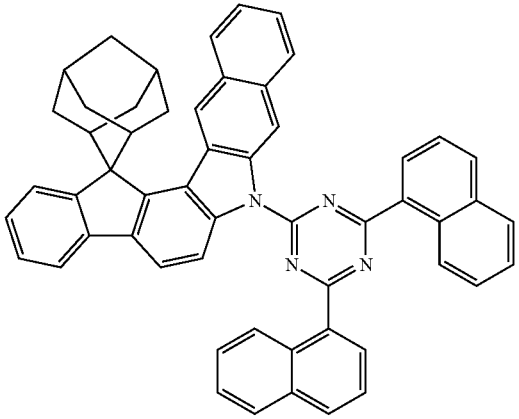
40
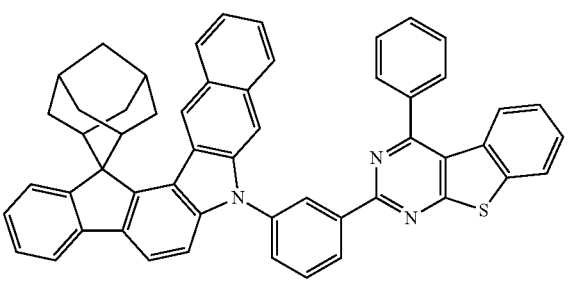
41
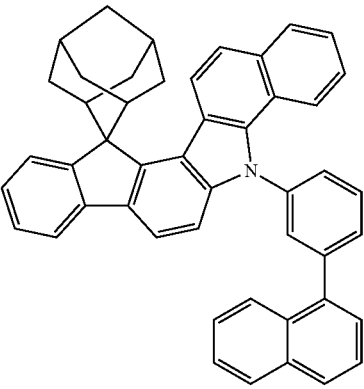
42
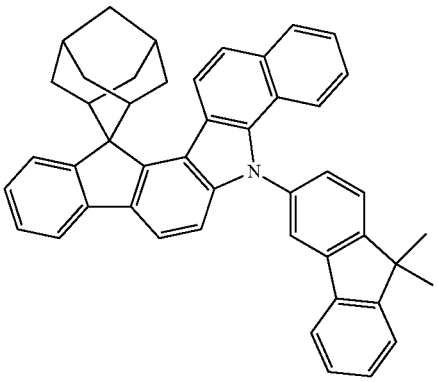

43
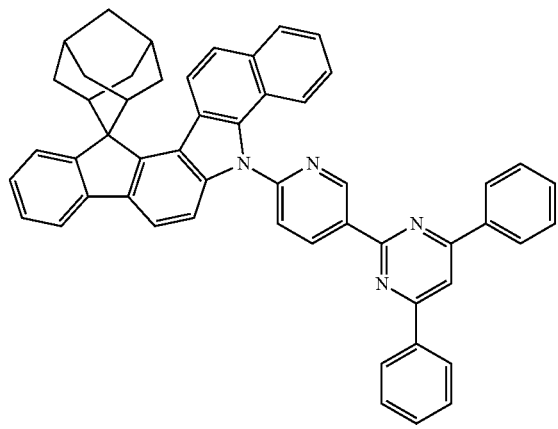
44
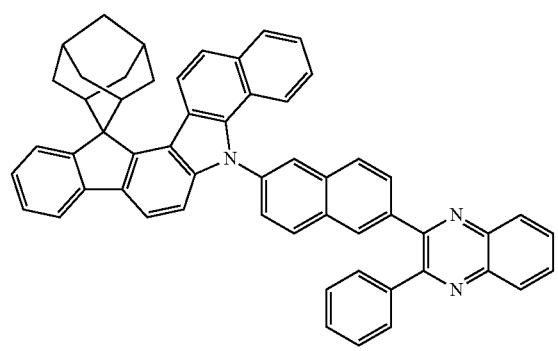
45
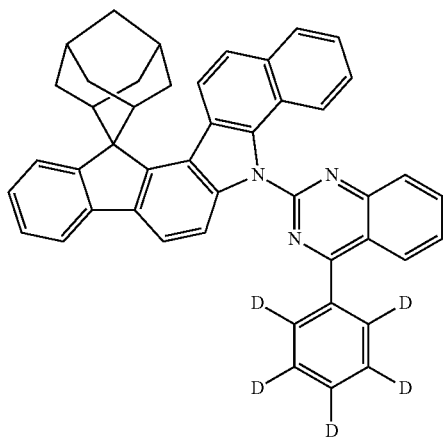
46
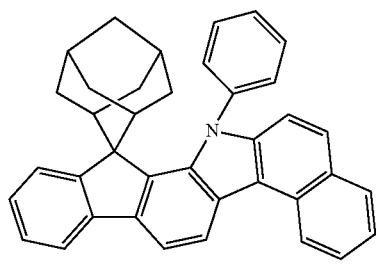
47
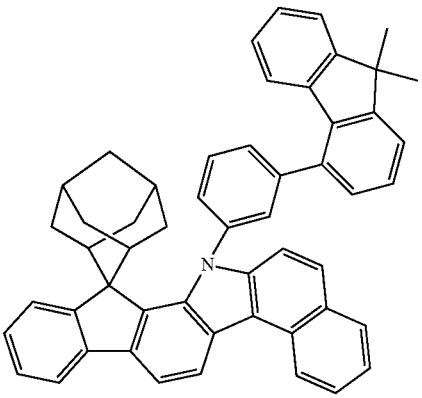
48
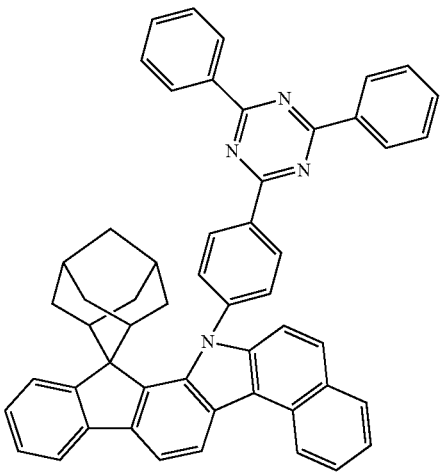
49
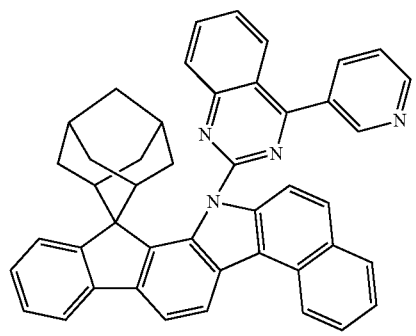
50
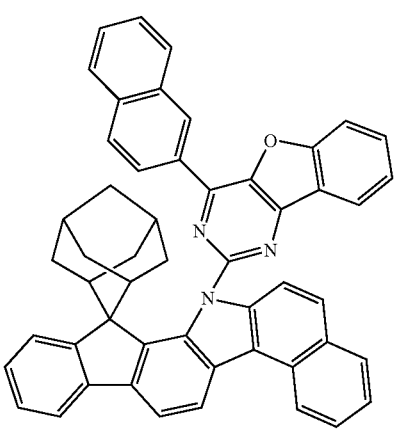

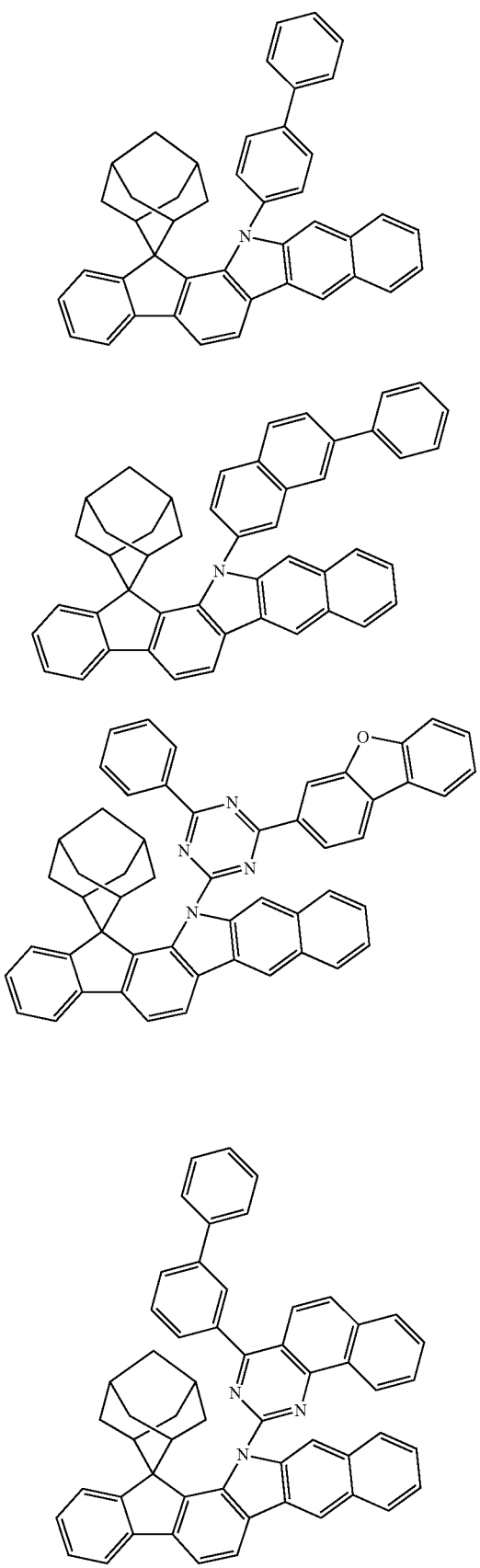
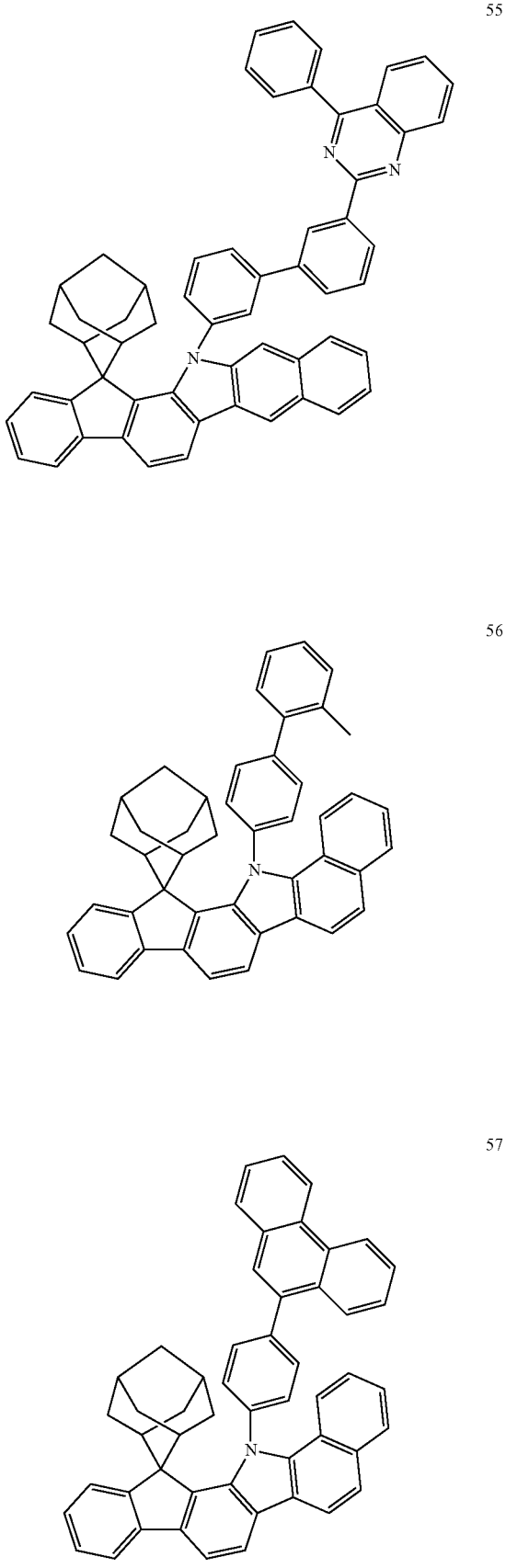

197
-continued
58
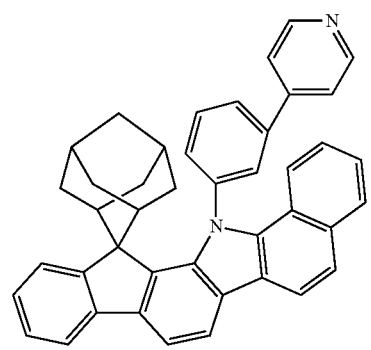
59
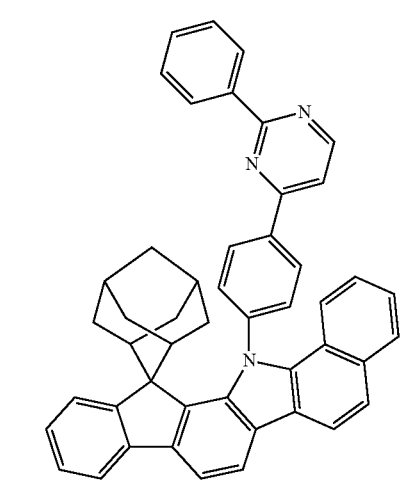
60
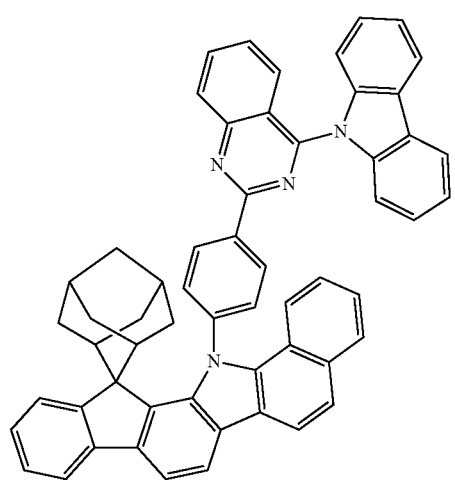
198
-continued
61
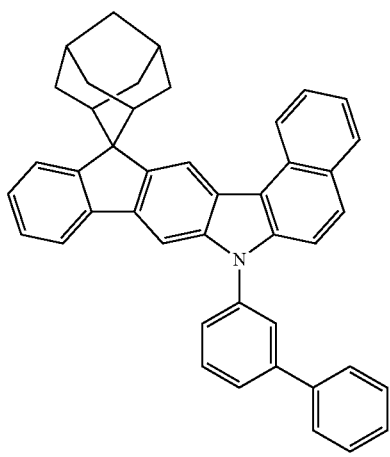
62
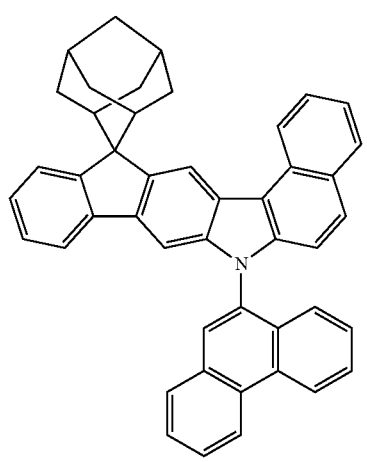
63
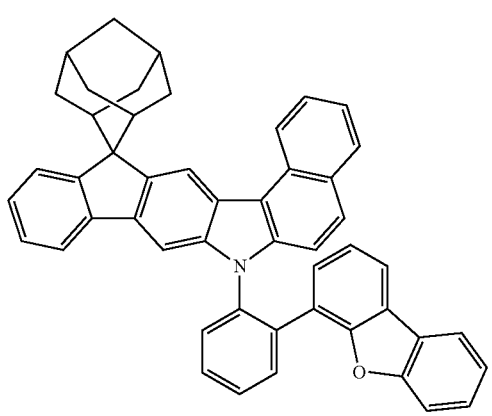

64
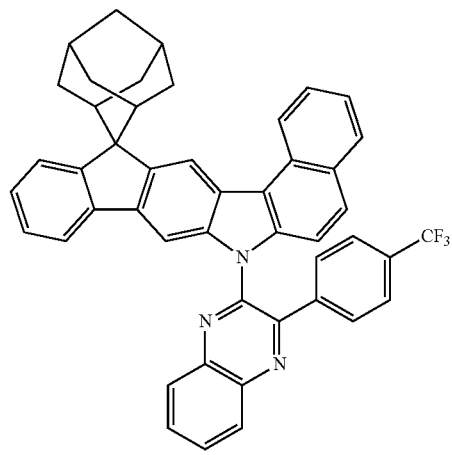
65
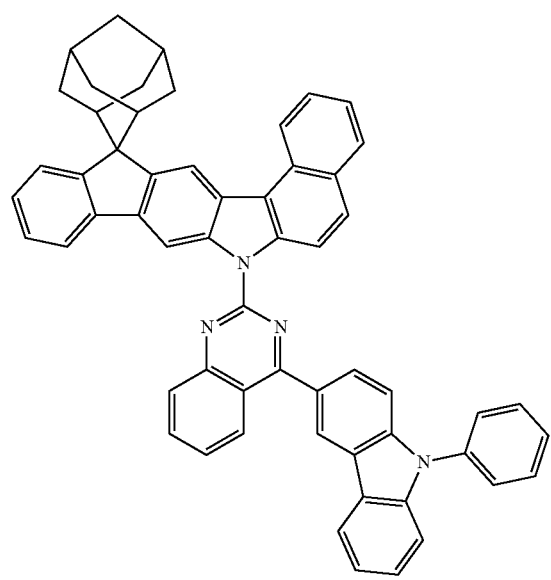
66
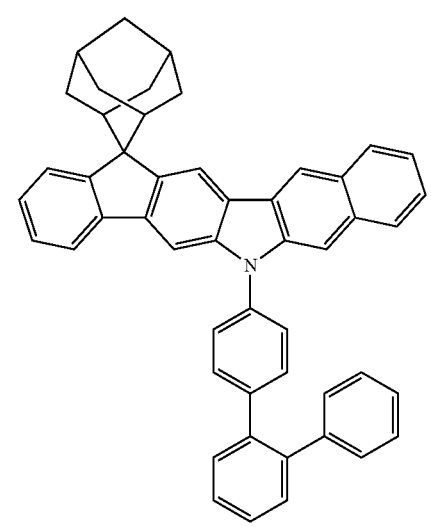
67
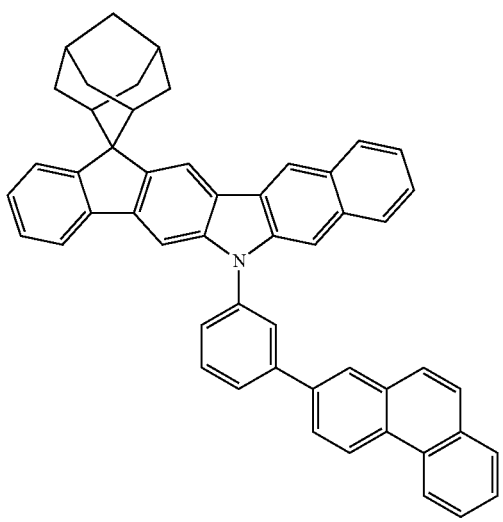
68
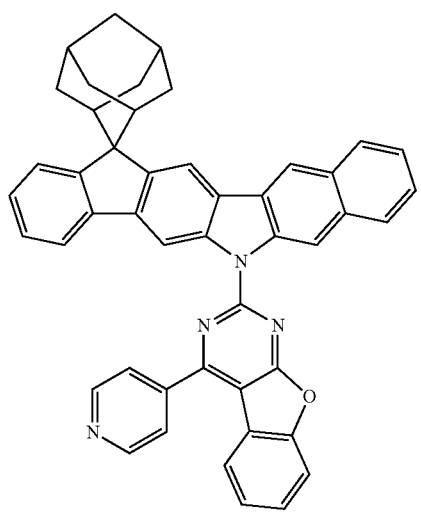
69

201
-continued
70
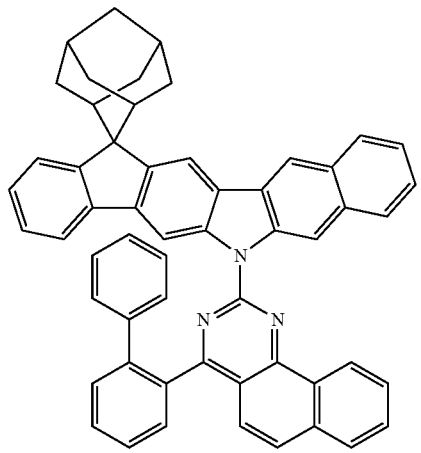
71
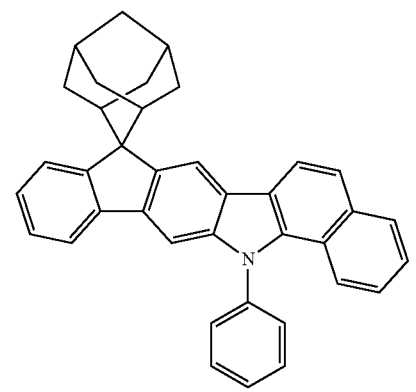
72
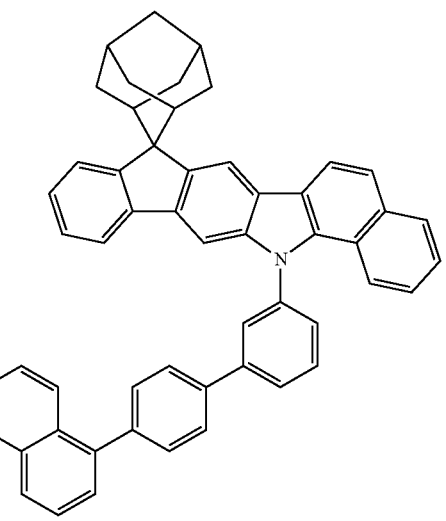
202
-continued
73
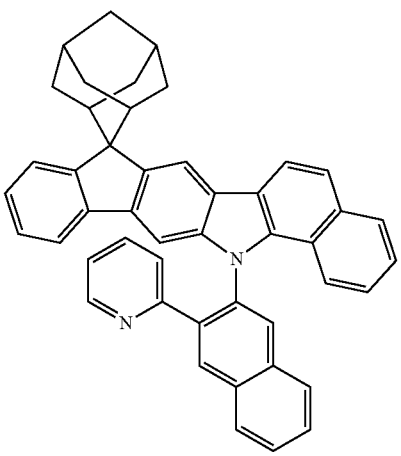
74
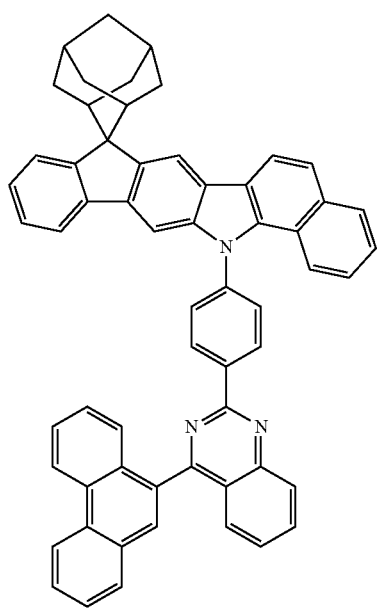
75
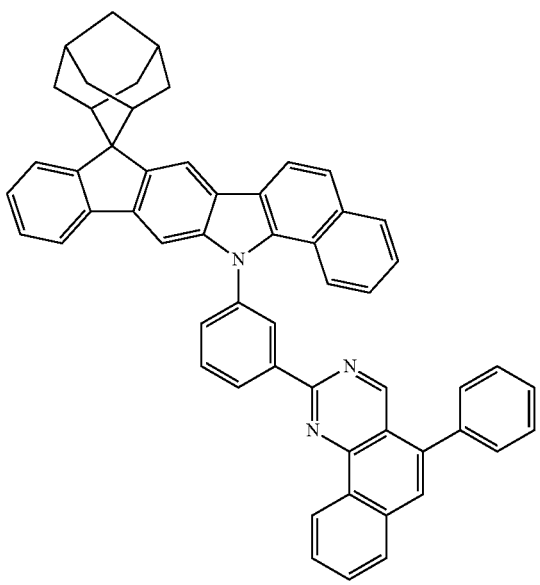

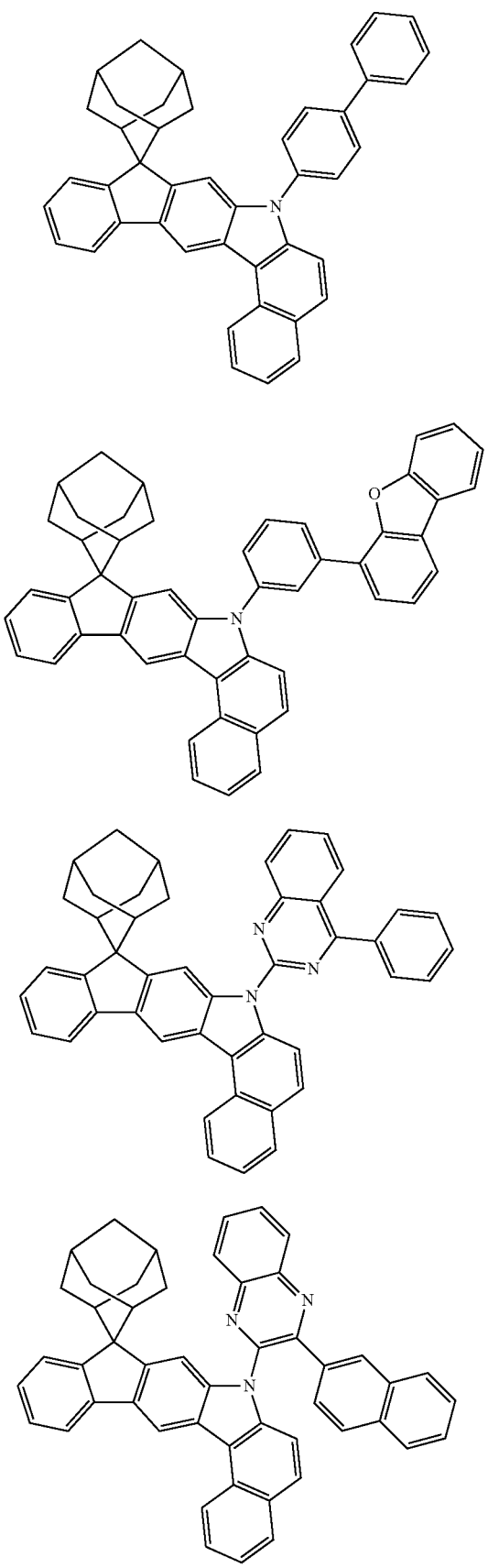
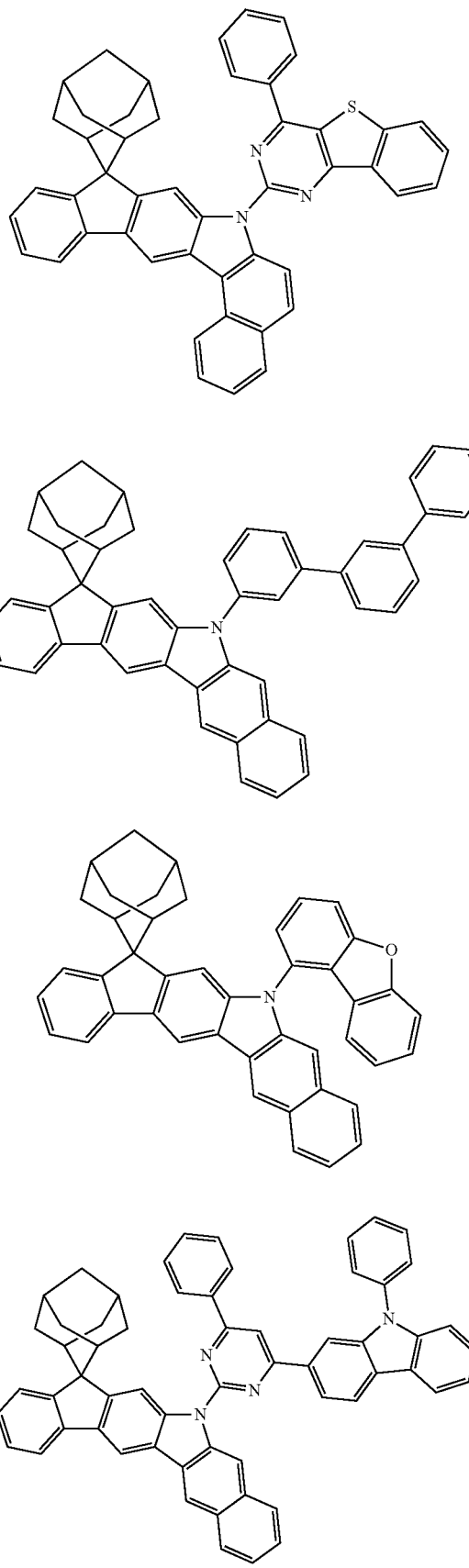

-continued
84
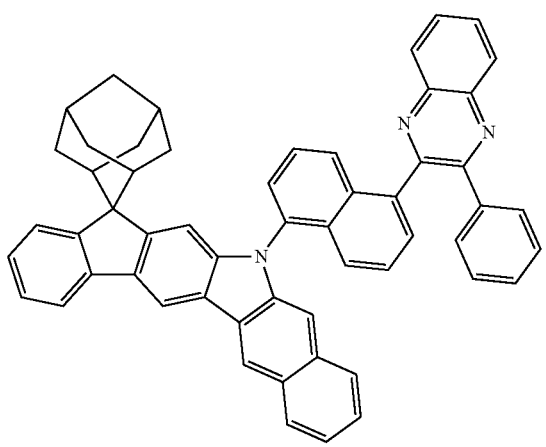
85
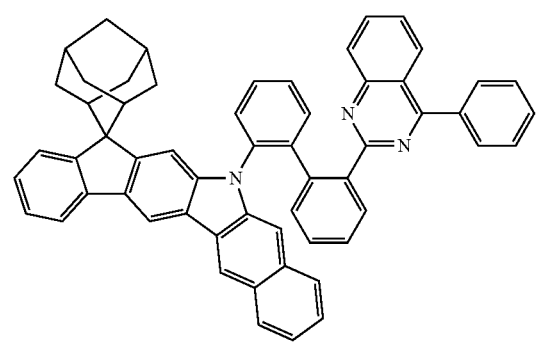
86
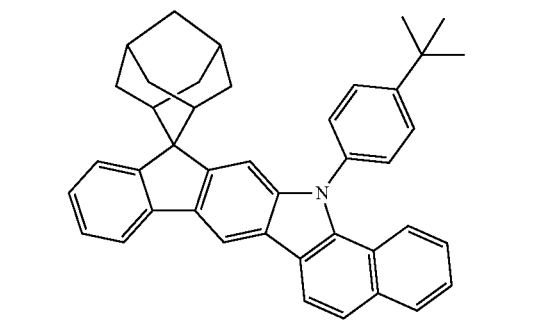
81
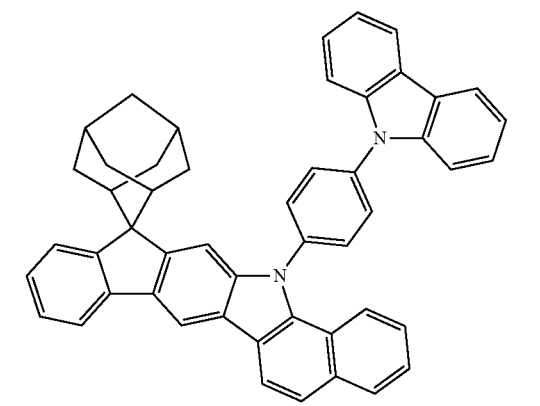
-continued
88
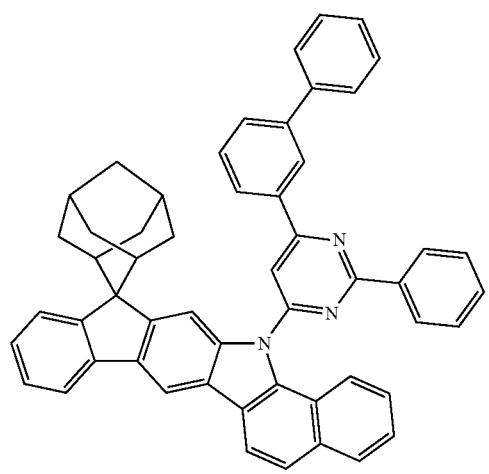
89
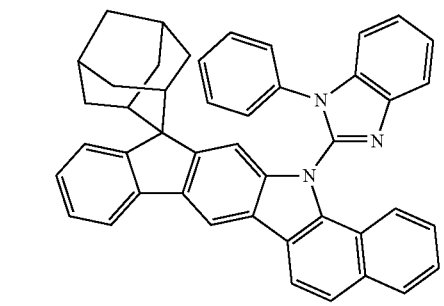
90
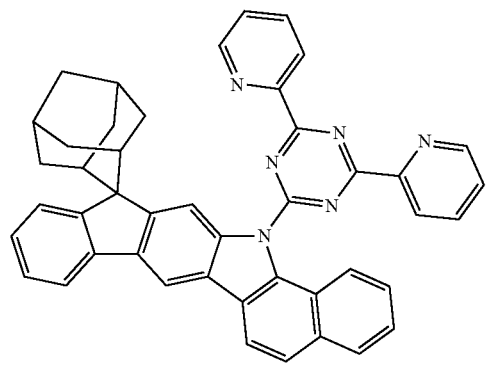
91
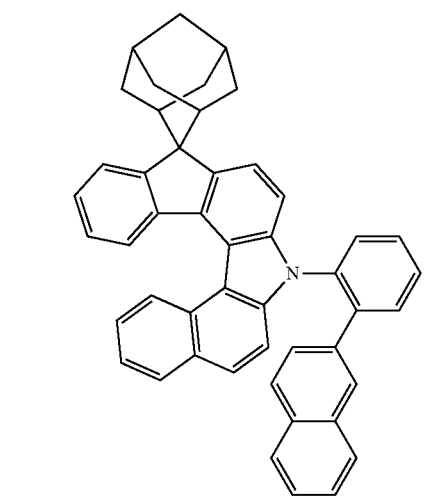

207
-continued
92
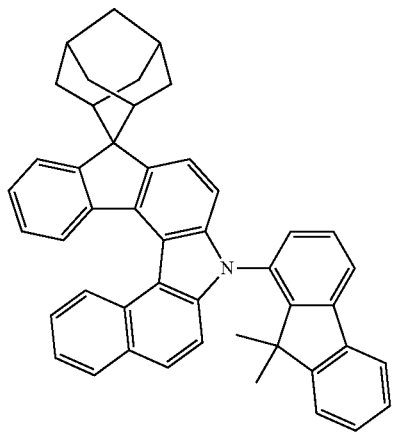
94
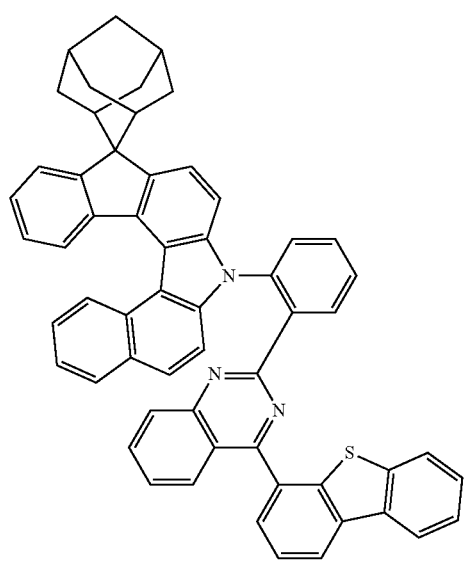
95
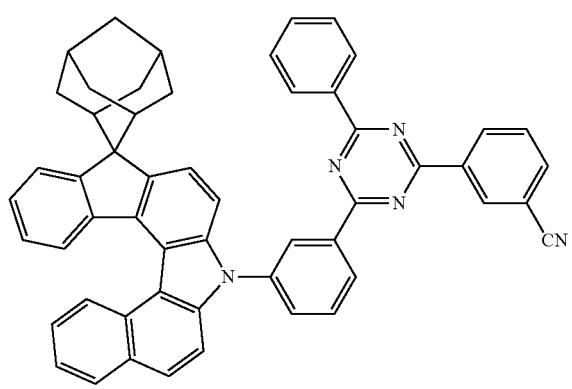
208
-continued
96
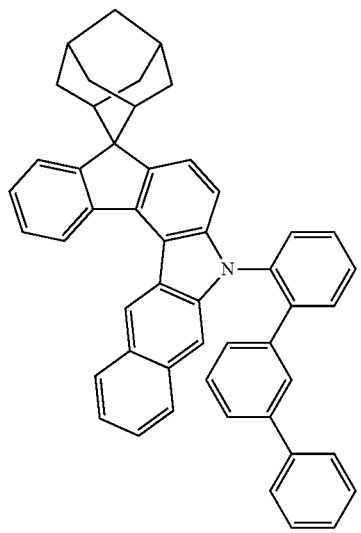
97
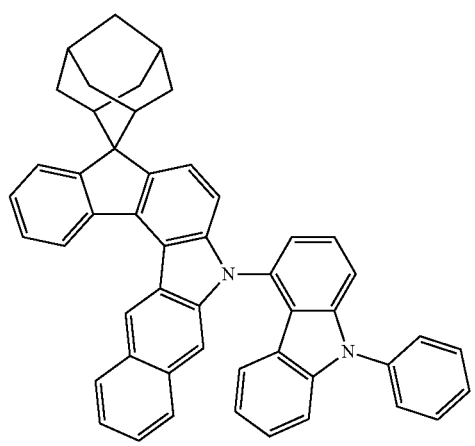
98
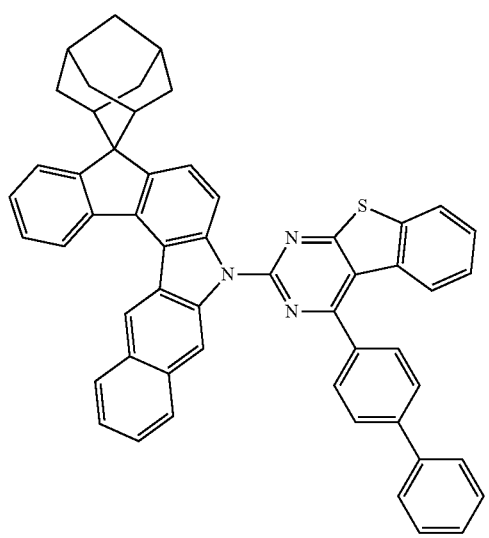

99
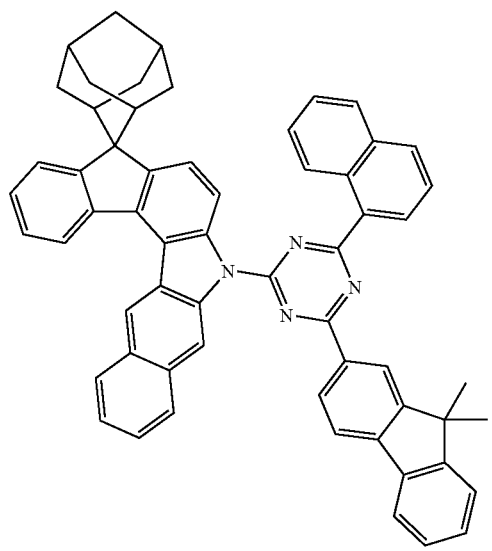
100
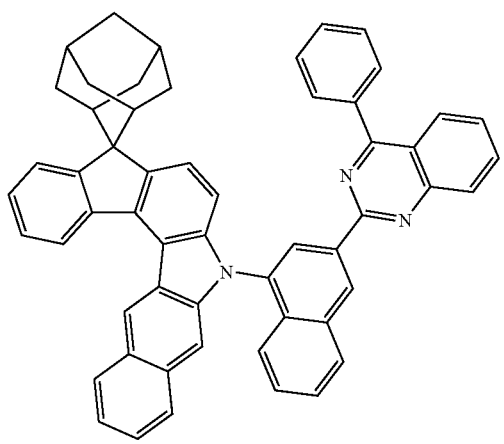
102
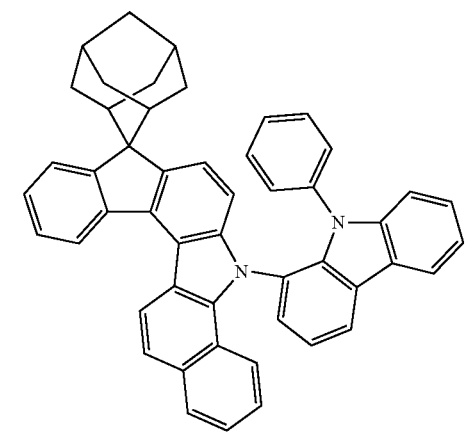
103
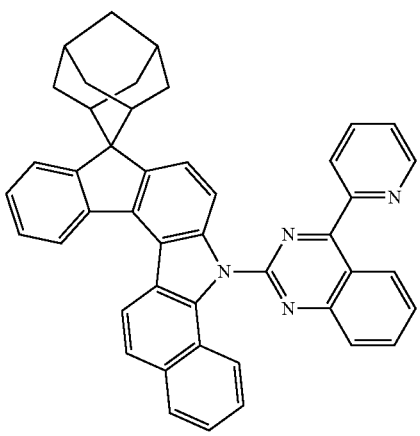
104
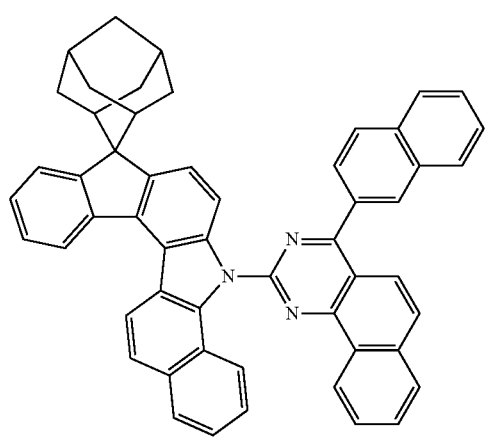
105
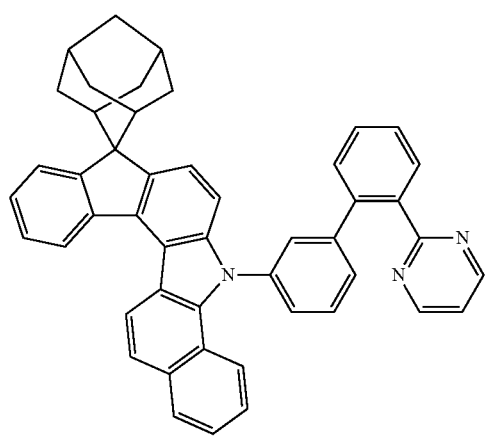

106
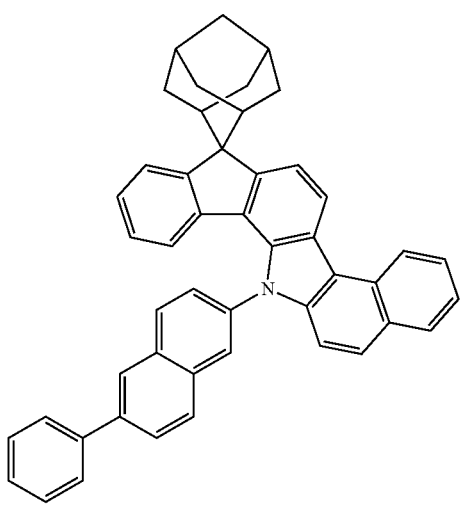
107
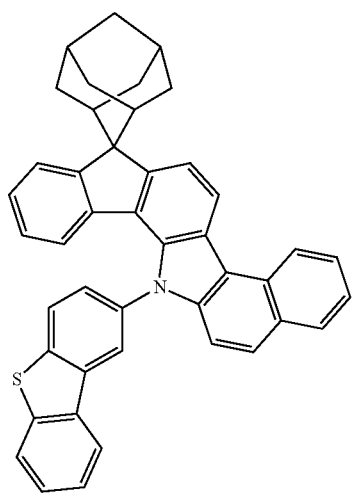
108
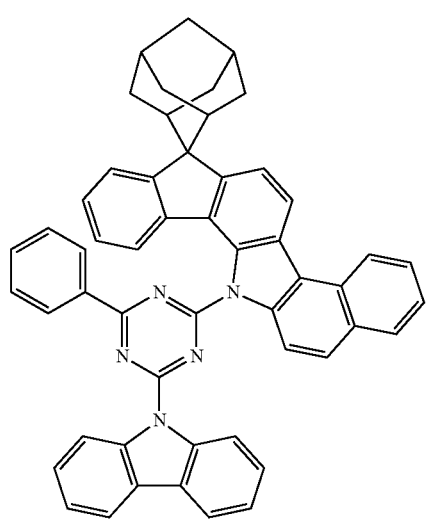
109
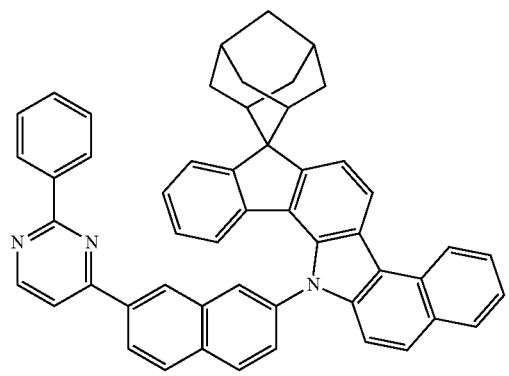
110
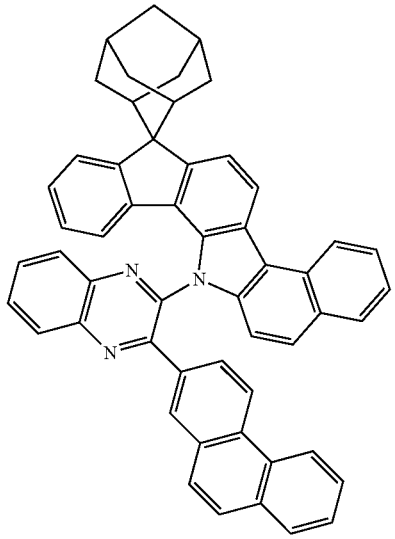
111
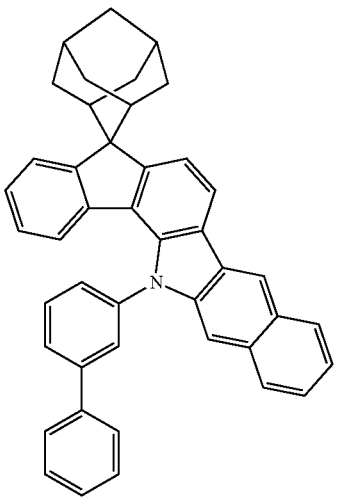

213
-continued
112
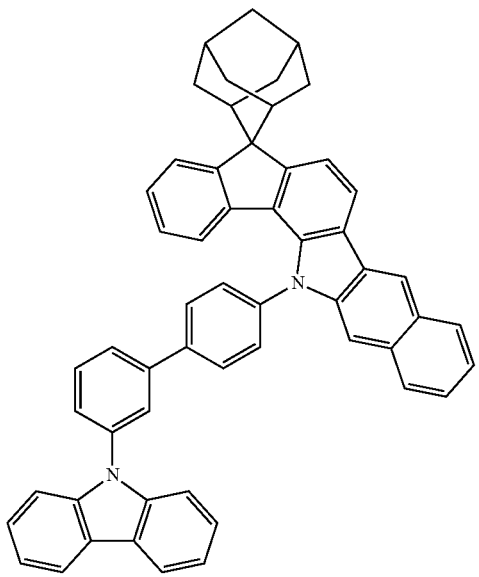
113
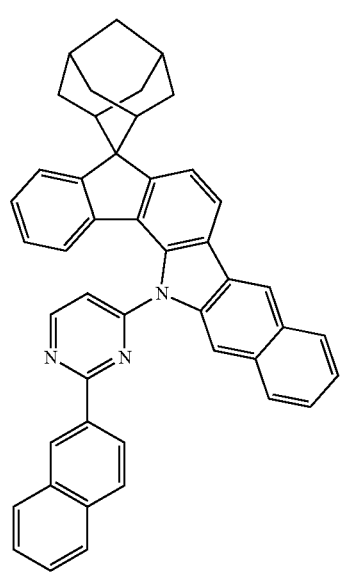
114
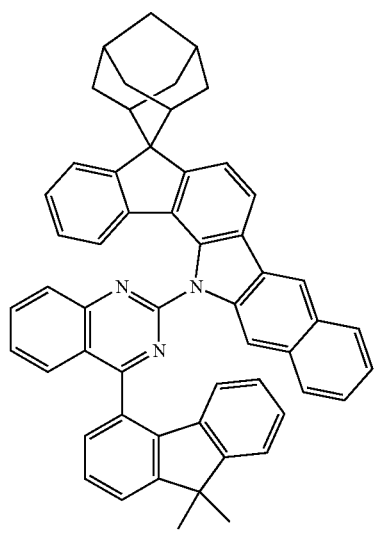
214
-continued
115
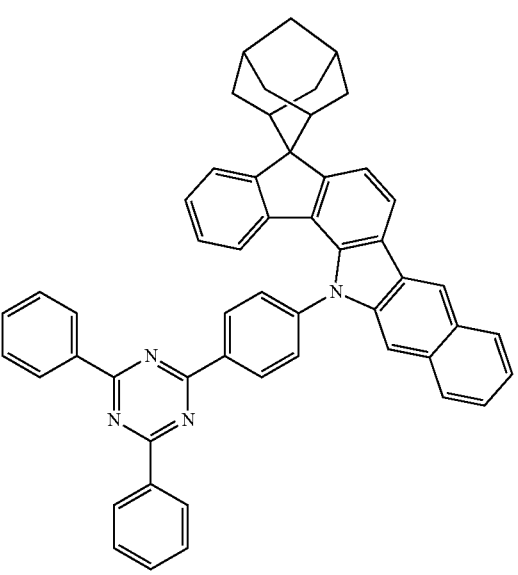
116
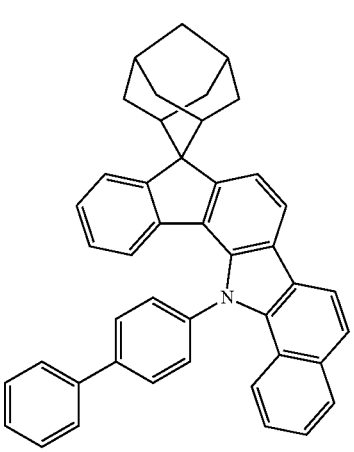
117
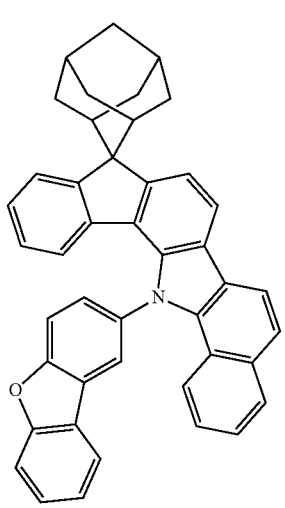

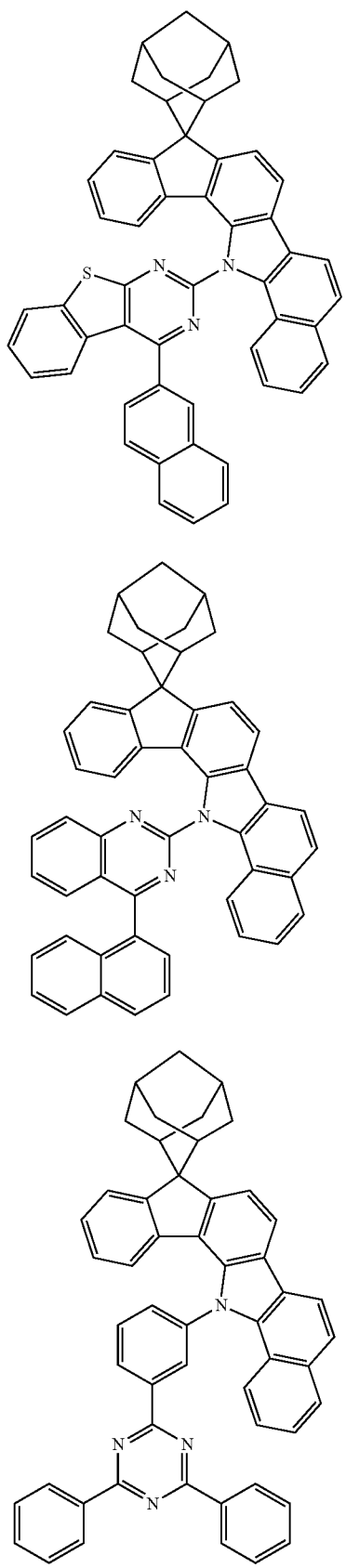
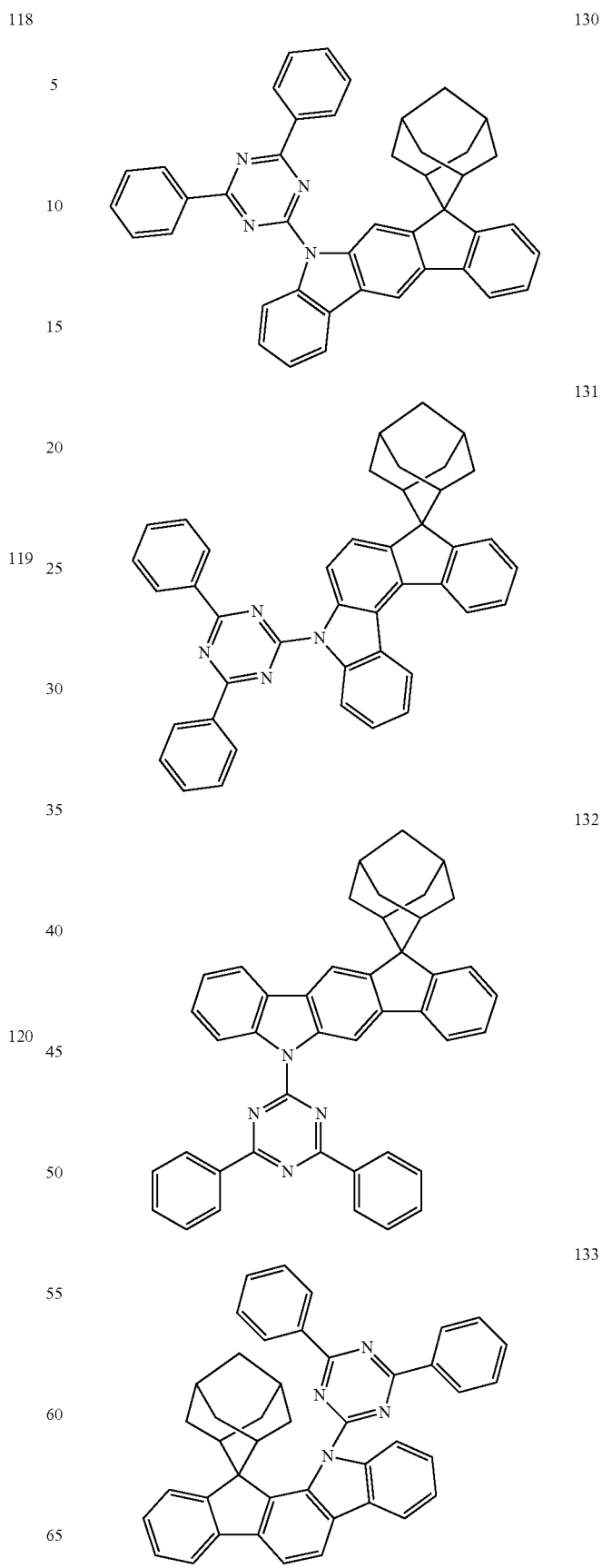

217
-continued
134
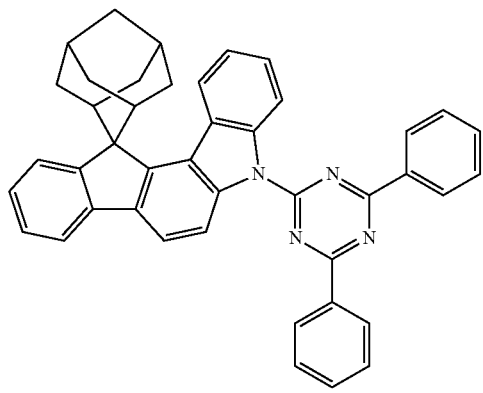
135
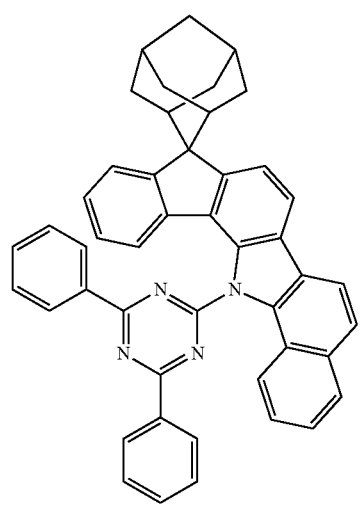
136
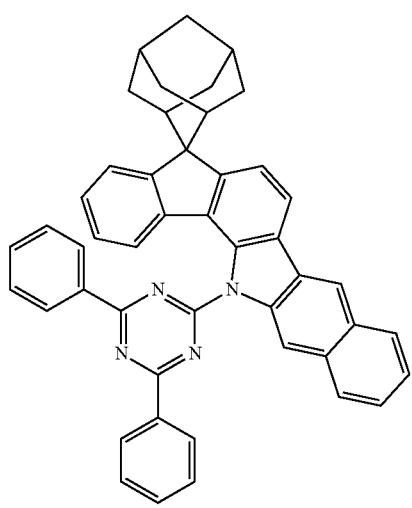
218
-continued
137
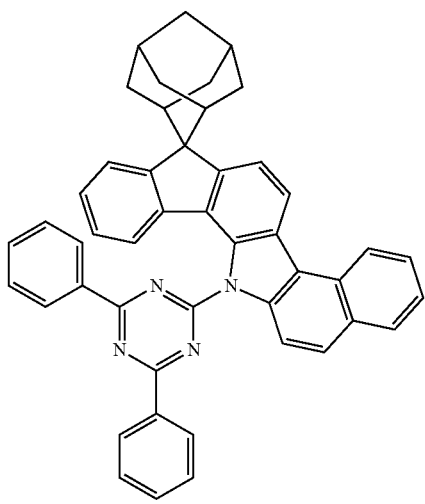
138
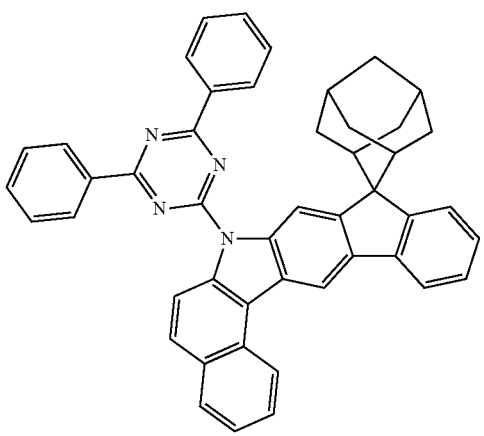
139
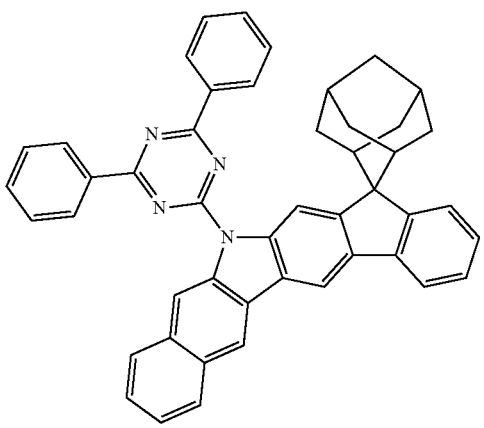

-continued
140
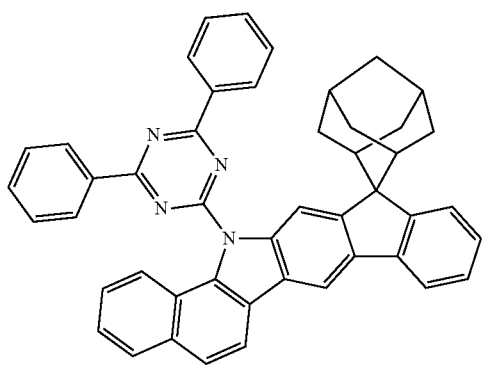
141
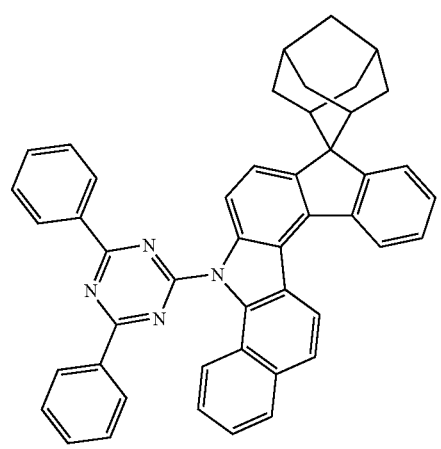
142
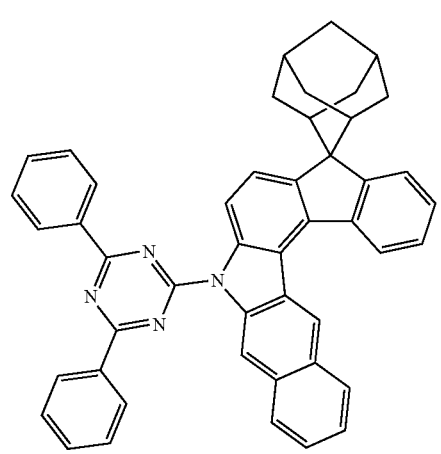
-continued
143
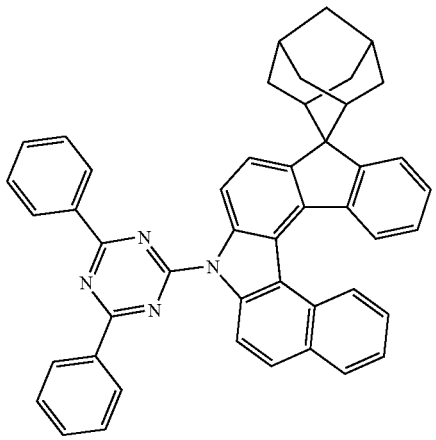
144
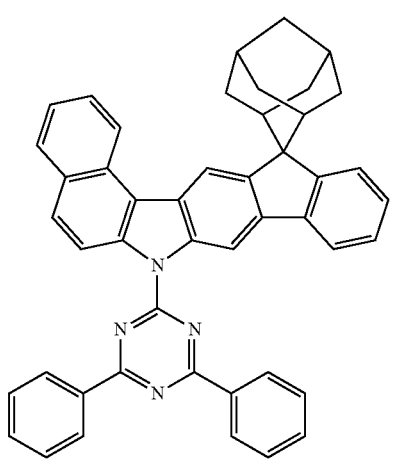
145
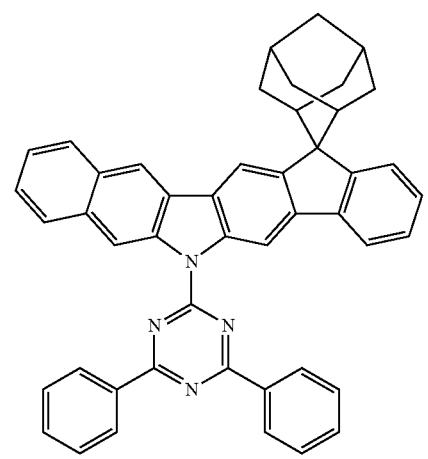

-continued
146
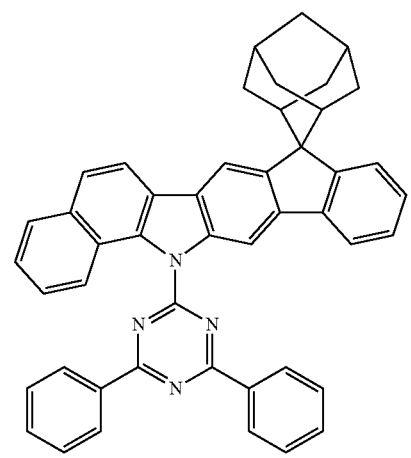
147
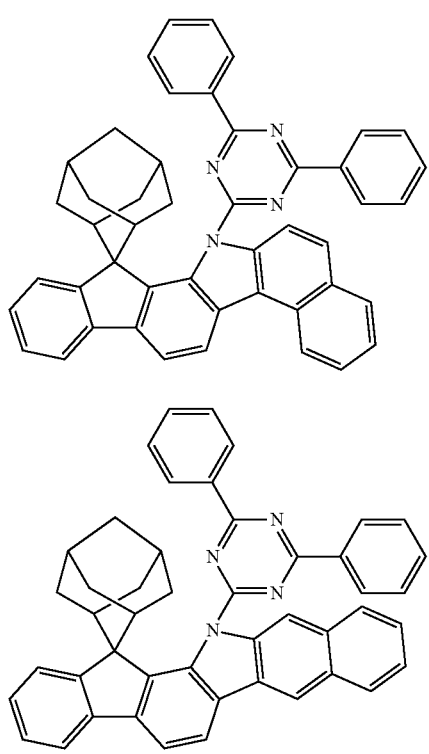
148
149
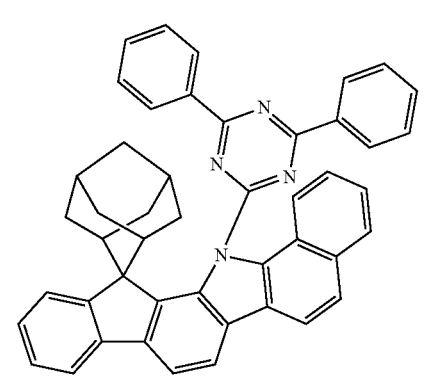
-continued
150
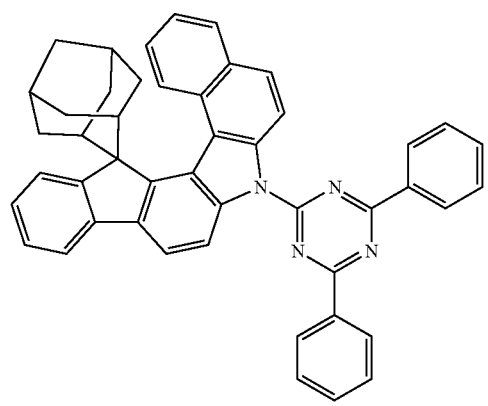
151
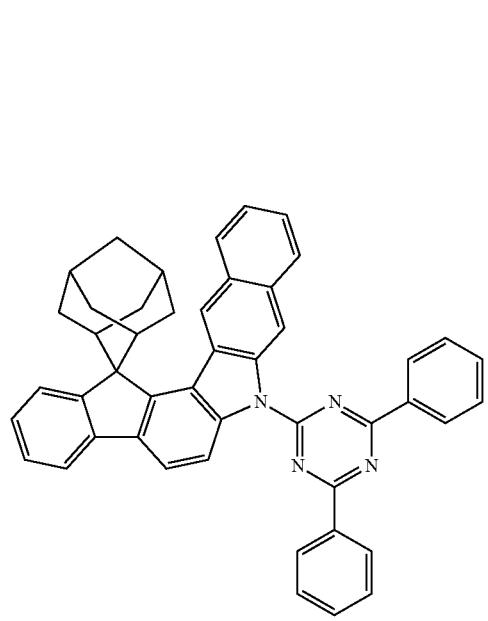
152
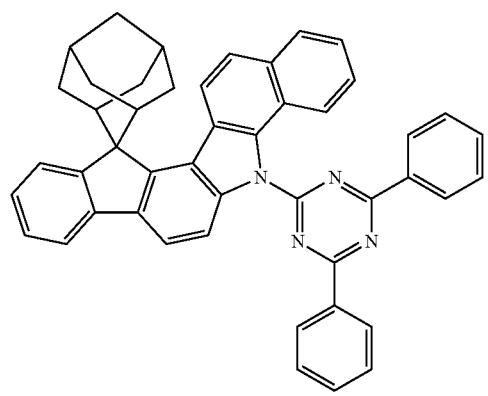

-continued
153
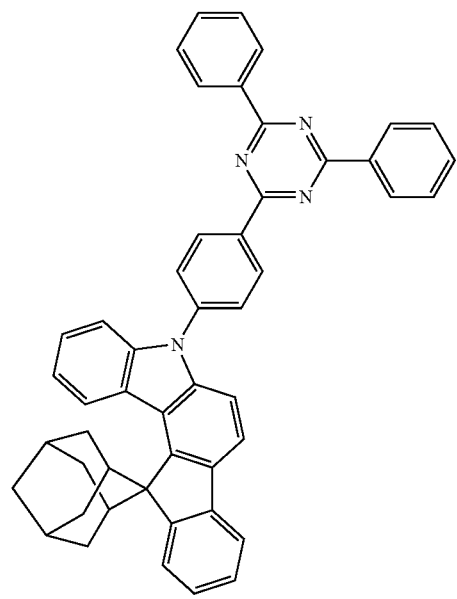
154
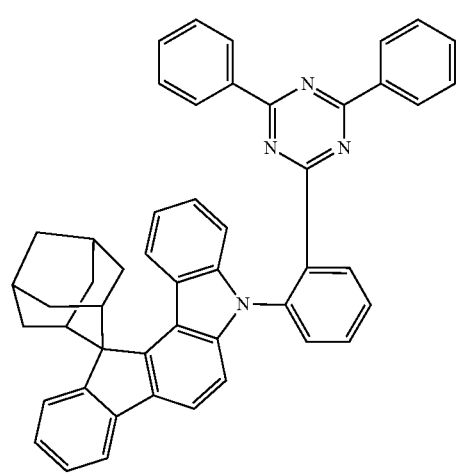
155
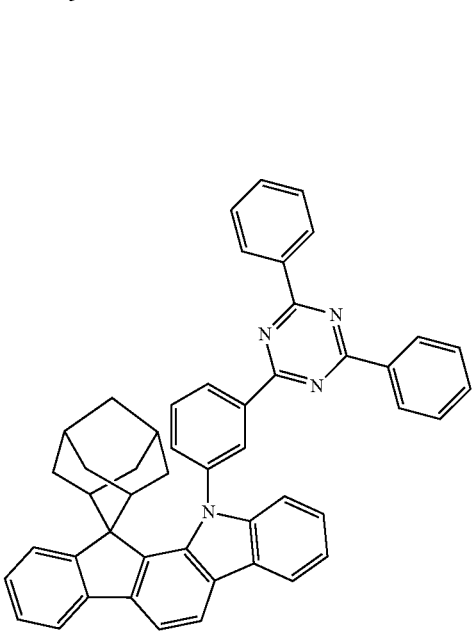
-continued
156
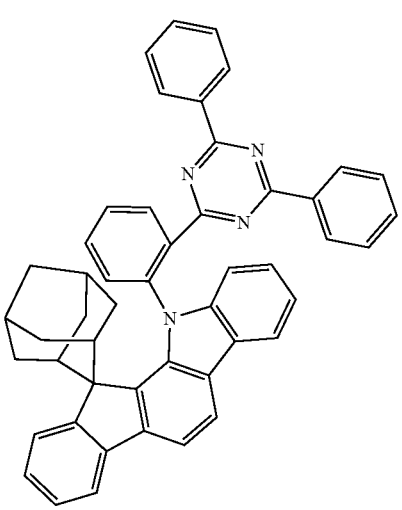
157
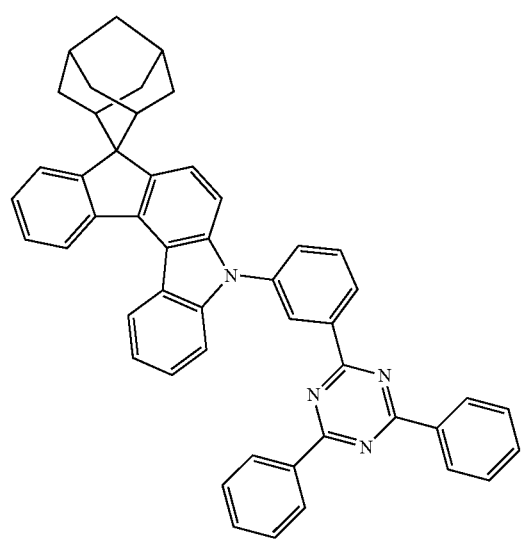
158
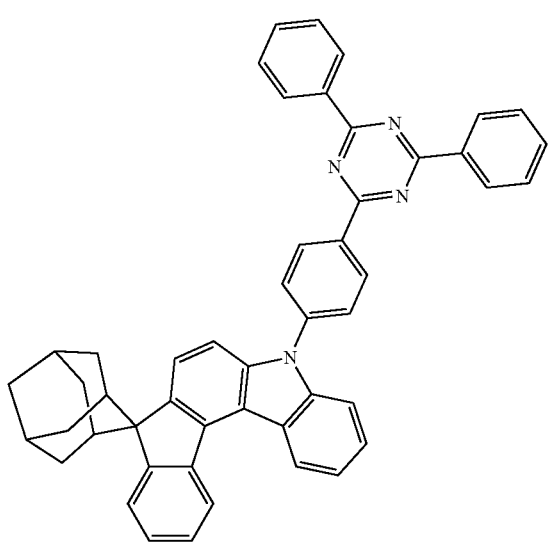

159
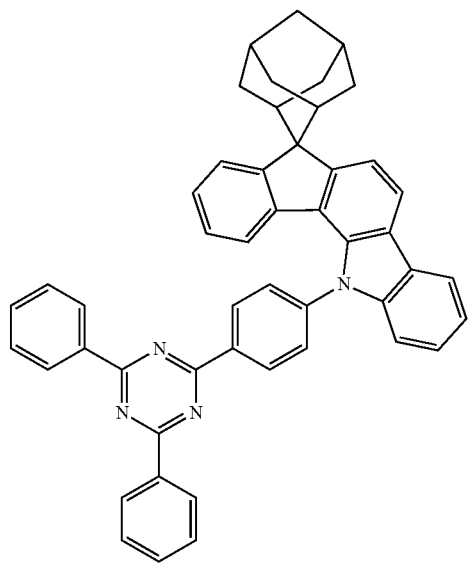
160
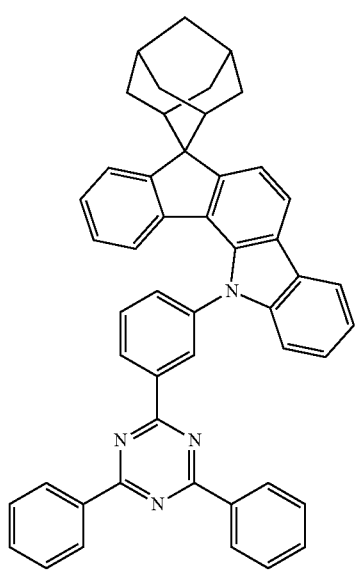
161
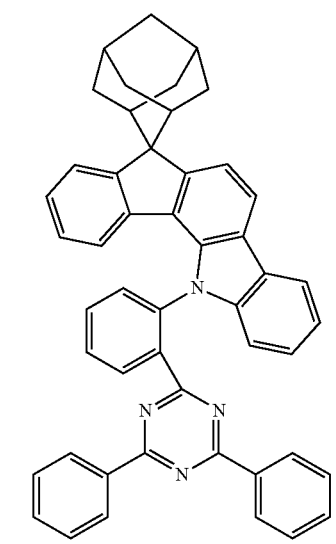
162
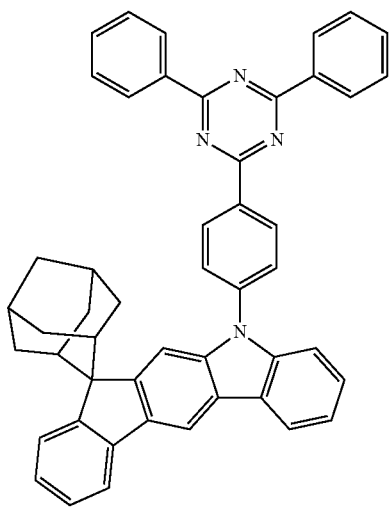
163
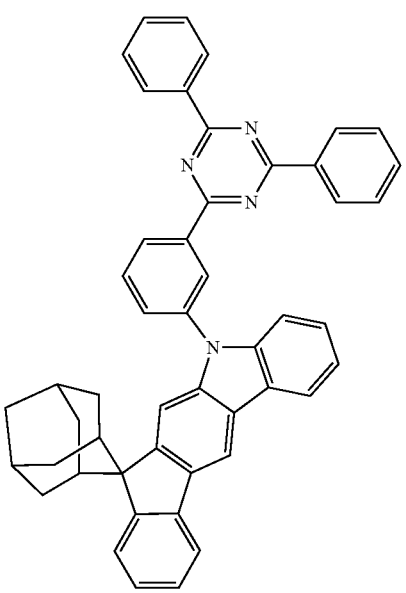
164
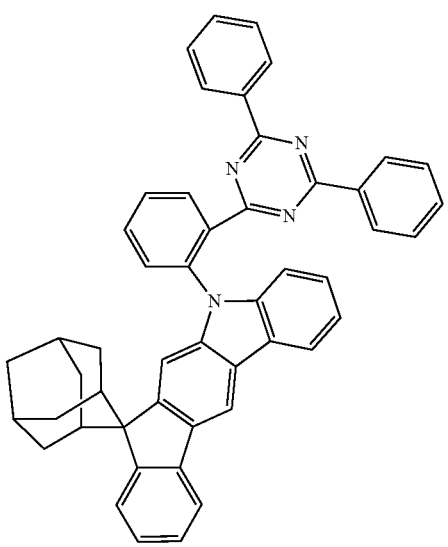

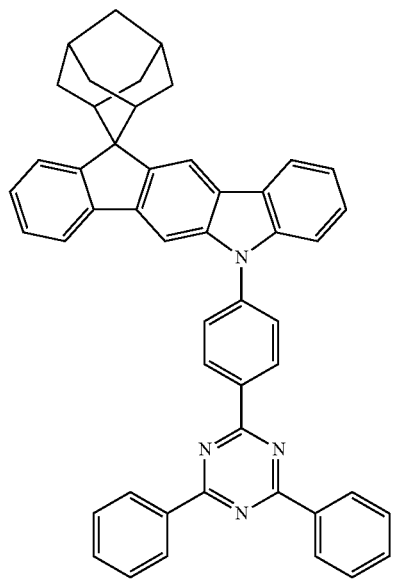

165

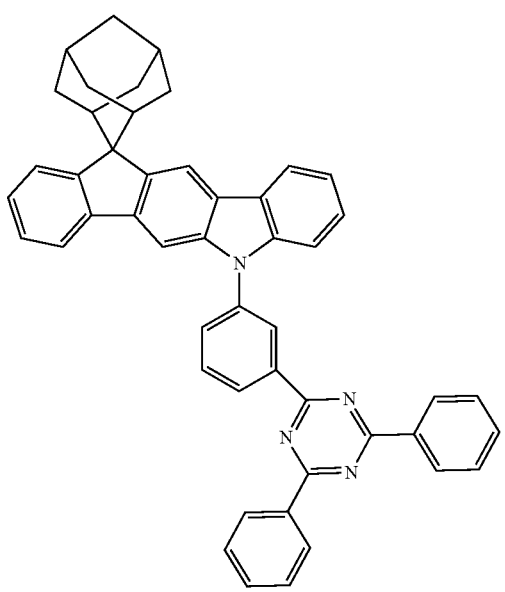

166

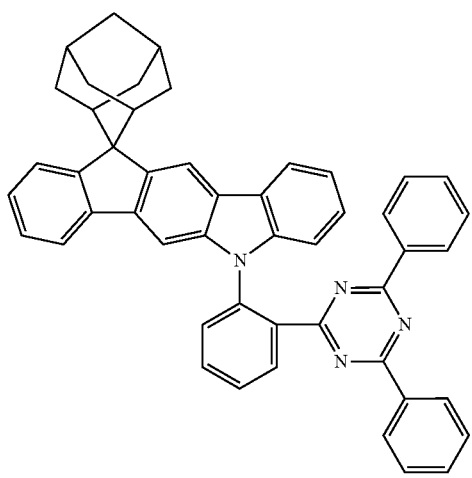

167

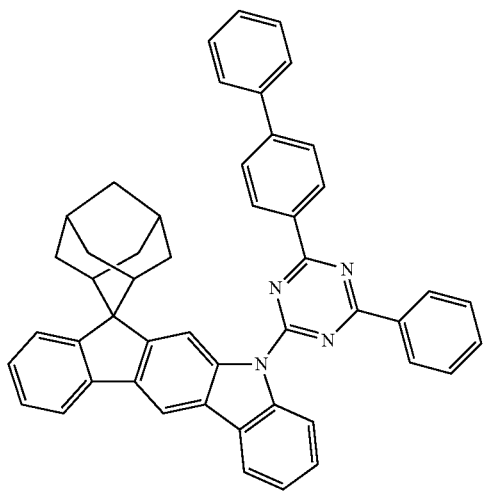

168

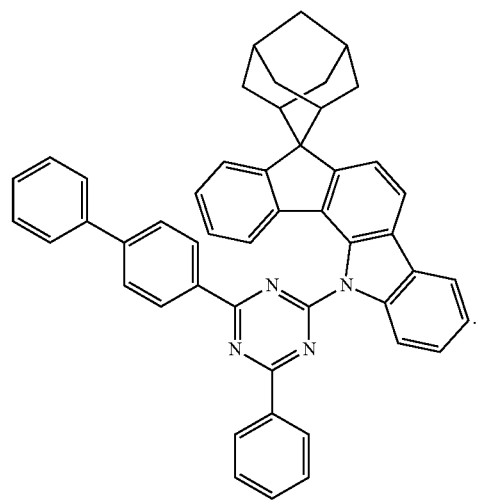

169

8. An electronic component, comprising an anode and a cathode arranged oppositely, and a functional layer arranged between the anode and the cathode,
wherein the functional layer comprises the organic compound according to claim 1.

9. The electronic component according to claim 8, wherein the functional layer comprises a light-emitting layer, and the light-emitting layer comprises the organic compound.

10. The electronic component according to claim 9, wherein the electronic component is an organic electroluminescent device.

11. An electronic device, comprising the electronic component according to claim 8.

12. An electronic device, comprising the electronic component according to claim 9.

13. An electronic device, comprising the electronic component according to claim 10.

\* \* \* \* \*